US012582788B2

(12) United States Patent
Scheiner

(10) Patent No.: US 12,582,788 B2
(45) Date of Patent: Mar. 24, 2026

(54) MODULAR PATIENT INTERFACE INCLUDING A JOINT COUPLING MOUTH AND NASAL CUSHIONS

(71) Applicant: ResMed Pty Ltd, Bella Vista (AU)

(72) Inventor: Rupert Christian Scheiner, Sydney (AU)

(73) Assignee: ResMed Pty Ltd, Bella Vista (AU)

( * ) Notice: Subject to any disclaimer, the term of this patent is extended or adjusted under 35 U.S.C. 154(b) by 912 days.

(21) Appl. No.: 17/773,546

(22) PCT Filed: Oct. 30, 2020

(86) PCT No.: PCT/AU2020/051180
§ 371 (c)(1),
(2) Date: Apr. 29, 2022

(87) PCT Pub. No.: WO2021/081596
PCT Pub. Date: May 6, 2021

(65) Prior Publication Data
US 2022/0395660 A1      Dec. 15, 2022

Related U.S. Application Data

(60) Provisional application No. 62/928,185, filed on Oct. 30, 2019, provisional application No. 62/928,228,
(Continued)

(51) Int. Cl.
*A61M 16/06*       (2006.01)
*A61M 16/08*       (2006.01)
*A61M 16/20*       (2006.01)

(52) U.S. Cl.
CPC .... *A61M 16/0666* (2013.01); *A61M 16/0605* (2014.02); *A61M 16/0616* (2014.02);
(Continued)

(58) Field of Classification Search
CPC .............. A61M 16/06; A61M 16/0605; A61M 16/0611; A61M 16/0616; A61M 16/0622;
(Continued)

(56) References Cited

U.S. PATENT DOCUMENTS 4,782,832 A      11/1988   Trimble et al.
4,944,310 A       7/1990   Sullivan
(Continued)

FOREIGN PATENT DOCUMENTS

CN      216124987 U      3/2022
CN      216366212 U      4/2022
(Continued)

OTHER PUBLICATIONS

Extended European Search Report for Application No. 20883570.2 mailed Sep. 28, 2023.
(Continued)

*Primary Examiner* — Joseph D. Boecker
(74) *Attorney, Agent, or Firm* — Nixon & Vanderhye P.C.

(57) ABSTRACT

A patient interface kit to deliver a flow of air at a positive pressure with respect to ambient air pressure to an entrance to a patients airways including at least the entrance of a patients nares while the patient is sleeping. The patient interface comprising: a nasal cushion having a nasal cushion opening; a mouth cushion having a mouth cushion opening, the mouth cushion including a flexible joint, positioned above the mouth opening, to selectively connect the nasal cushion to the mouth cushion; and a positioning and stabilizing structure to provide a force to hold the nasal and/or mouth seal-forming structures in a therapeutically effective position on a patient's head, the positioning an stabilizing structure including a nasal headgear including upper straps
(Continued)

or conduits and a mouth headgear including lower straps, the mouth headgear being selectively connected to the nasal headgear.

40 Claims, 54 Drawing Sheets

Related U.S. Application Data filed on Oct. 30, 2019, provisional application No. 62/928,213, filed on Oct. 30, 2019.

(52) U.S. Cl.
CPC .... *A61M 16/0683* (2013.01); *A61M 16/0816* (2013.01); *A61M 16/0875* (2013.01); *A61M 16/208* (2013.01)

(58) Field of Classification Search
CPC .......... A61M 16/0666; A61M 16/0683; A61M 16/0816; A61M 16/0875; A61M 16/208
See application file for complete search history.

(56) References Cited

U.S. PATENT DOCUMENTS

| | | | | |
|---|---|---|---|---|
| 5,560,354 | A | * | 10/1996 | Berthon-Jones ...... A61M 16/06 128/205.24 |
| 6,532,959 | B1 | | 3/2003 | Berthon-Jones |
| 6,581,594 | B1 | | 6/2003 | Drew et al. |
| 7,866,944 | B2 | | 1/2011 | Kenyon et al. |
| 8,636,479 | B2 | | 1/2014 | Kenyon et al. |
| 8,638,014 | B2 | | 1/2014 | Sears et al. |
| 8,733,349 | B2 | | 5/2014 | Bath et al. |
| 2009/0044808 | A1 | | 2/2009 | Guney et al. |
| 2009/0050156 | A1 | | 2/2009 | Ng et al. |
| 2009/0133696 | A1 | * | 5/2009 | Remmers .......... A61M 16/0493 128/204.26 |
| 2010/0000534 | A1 | | 1/2010 | Kooij et al. |
| 2013/0133646 | A1 | | 5/2013 | Rose et al. |
| 2013/0199537 | A1 | * | 8/2013 | Formica ............ A61M 16/0816 128/205.25 |
| 2014/0290668 | A1 | | 10/2014 | Thornton et al. |
| 2016/0074613 | A1 | | 3/2016 | Davidson et al. |
| 2016/0158475 | A1 | * | 6/2016 | Harrison ............. A61M 16/105 128/205.12 |
| 2016/0271354 | A1 | | 9/2016 | Grashow et al. |
| 2017/0274167 | A1 | | 9/2017 | Huddart et al. |
| 2018/0207385 | A1 | | 7/2018 | Freestone et al. |
| 2019/0091431 | A1 | | 3/2019 | Formica et al. |

FOREIGN PATENT DOCUMENTS

| | | | | |
|---|---|---|---|---|
| CN | 216366241 | U | 4/2022 | |
| EP | 0549299 | A2 * | 6/1993 | ........... A61M 16/06 |
| WO | WO 98/004310 | A1 | 2/1998 | |
| WO | WO 98/034665 | A1 | 8/1998 | |
| WO | WO 2000/078381 | A1 | 12/2000 | |
| WO | WO 2004/073778 | A1 | 9/2004 | |
| WO | WO 2005/063328 | A1 | 7/2005 | |
| WO | 2005/099801 | | 10/2005 | |
| WO | WO 2006/074513 | A1 | 7/2006 | |
| WO | 2006/096924 | | 9/2006 | |
| WO | WO 2006/130903 | A1 | 12/2006 | |
| WO | 2008/011682 | | 1/2008 | |
| WO | WO 2009/052560 | A1 | 4/2009 | |
| WO | WO 2010/135785 | A1 | 12/2010 | |
| WO | WO 2012/171072 | A1 | 12/2012 | |
| WO | WO 2013/020167 | A1 | 2/2013 | |
| WO | 2013/142909 | | 10/2013 | |
| WO | 2014/183167 | | 11/2014 | |
| WO | 2015/187995 | | 12/2015 | |
| WO | 2016/201358 | | 12/2016 | |
| WO | WO 2018/176094 | A1 | 4/2018 | |
| WO | WO 2019/119058 | A1 | 6/2019 | |
| WO | WO 2019/159063 | A1 | 8/2019 | |
| WO | WO 2021/035306 | A1 | 3/2021 | |
| WO | WO 2021/046605 | A1 | 3/2021 | |

OTHER PUBLICATIONS

"*Respiratory Physiology*", by John B. West, Lippincott Williams & Wilkins, 9th edition published 2012 (8 pages).
First Office Action mailed May 16, 2025 in Chinese Application No. 202080089950.X, with English translation, 15 pages.

* cited by examiner

Nasal cavity

Oral cavity

Larynx

Vocal folds

Oesophagus

Trachea

Bronchus

Lung

Heart

Diaphragm

Alveolar sacs

Nasal cavity

Nasal bone

Lateral nasal cartilage

Greater alar cartilage

Nostril

Lip superior

Lip inferior

Hard palate

Soft palate

Oropharynx

Tongue

Epiglottis

Vocal folds

Esophagus

Trachea

Larynx

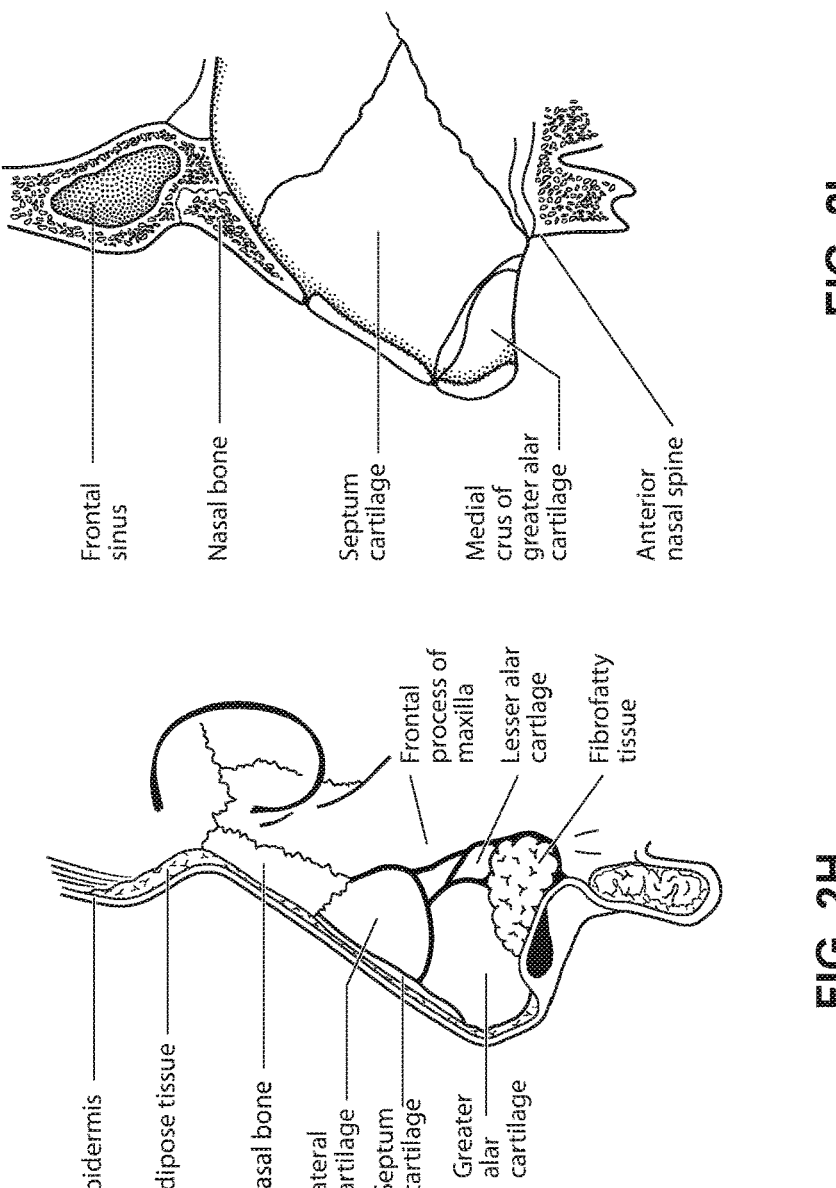
Frontal sinus
Nasal bone
Septum cartilage
Medial crus of greater alar cartilage
Anterior nasal spine
FIG. 2I
Frontal process of maxilla
Lesser alar cartilage
Fibrofatty tissue
Epidermis
Adipose tissue
Nasal bone
Lateral cartilage
Septum cartilage
Greater alar cartilage
FIG. 2H
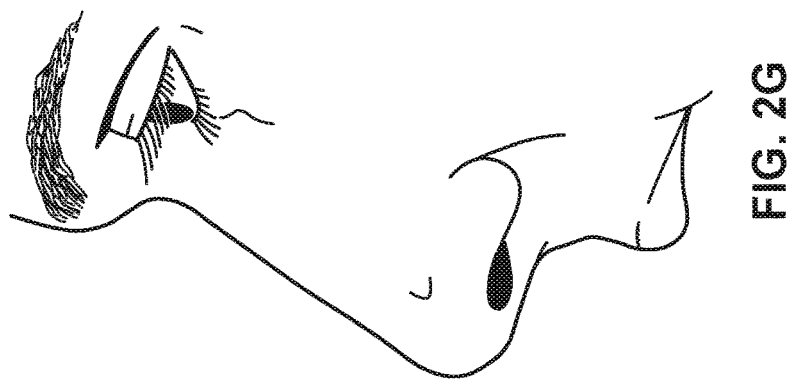
FIG. 2G

Parietal bone

Temporal bone

Occipital bone

Trapezius m.

Frontal bone

Sphenoid bone

Nasal bone

Zygomatic bone

Maxilla

Masseter m.

Mandible

Mental protuberance

Digastricus m.

Sternocleidomastoid m.

Concha

Frontal bone

Supraorbital foramen

Nasal bones

Septal cartilage

Lateral cartilage

Sesamoid cartilage

Greater alar cartilage

Medial crus of greater alar cartilage

Anterior nasal spine

Infraorbital foramen

Lesser nasal cartilage

Alar fibrofatty tissue

Septal cartilage

Nose - Anterolateral view

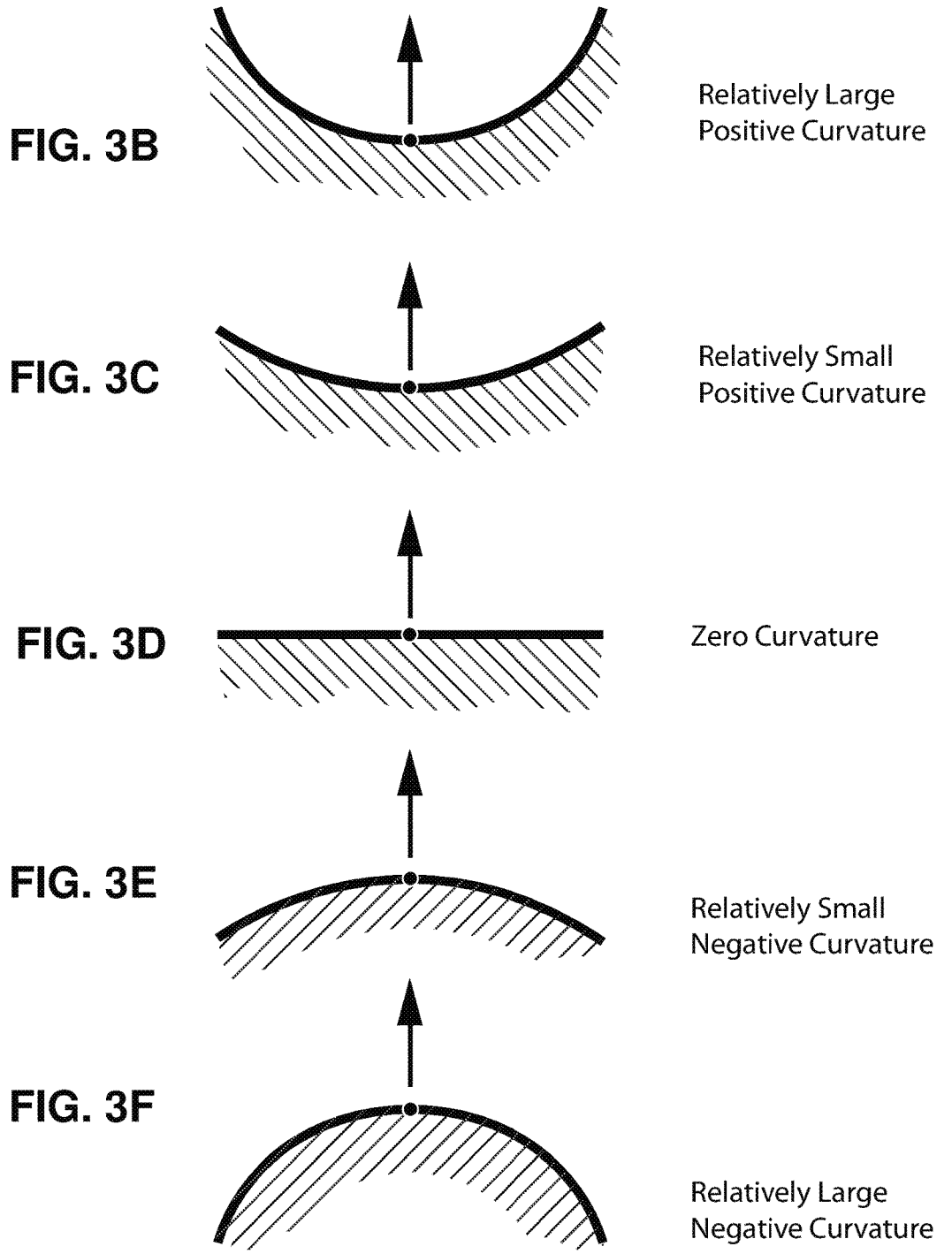
FIG. 3B     Relatively Large Positive Curvature
FIG. 3C     Relatively Small Positive Curvature
FIG. 3D     Zero Curvature
FIG. 3E     Relatively Small Negative Curvature
FIG. 3F     Relatively Large Negative Curvature + = Positive Curvature =
— = Negative Curvature =
◄ = Outward Normal Exterior Surface A Path on Surface Edge of Surface Straight Line Distance

B

A

Dome Region

Saddle Region

—

—

—

+

Saddle Region

—

+

—

Saddle Region

—

+

+ = Positive Curvature =
— = Negative Curvature =
◄ = Outward Normal

Edge of Surface

Saddle Region

—

+

Dome Region

—

Exterior Surface

Dome Region

—

—

Saddle Region

—

+

—

Curve

Surface

Surface

Interior surface

Interior surface

Left-hand rule
Binormal(B)
Osculating plane
Tangent(T)
Normal(N)
FIG. 3O
Right-hand rule
Binormal(B)
Osculating plane
Tangent(T)
Normal(N)
FIG. 3P
Left ear helix
FIG. 3Q
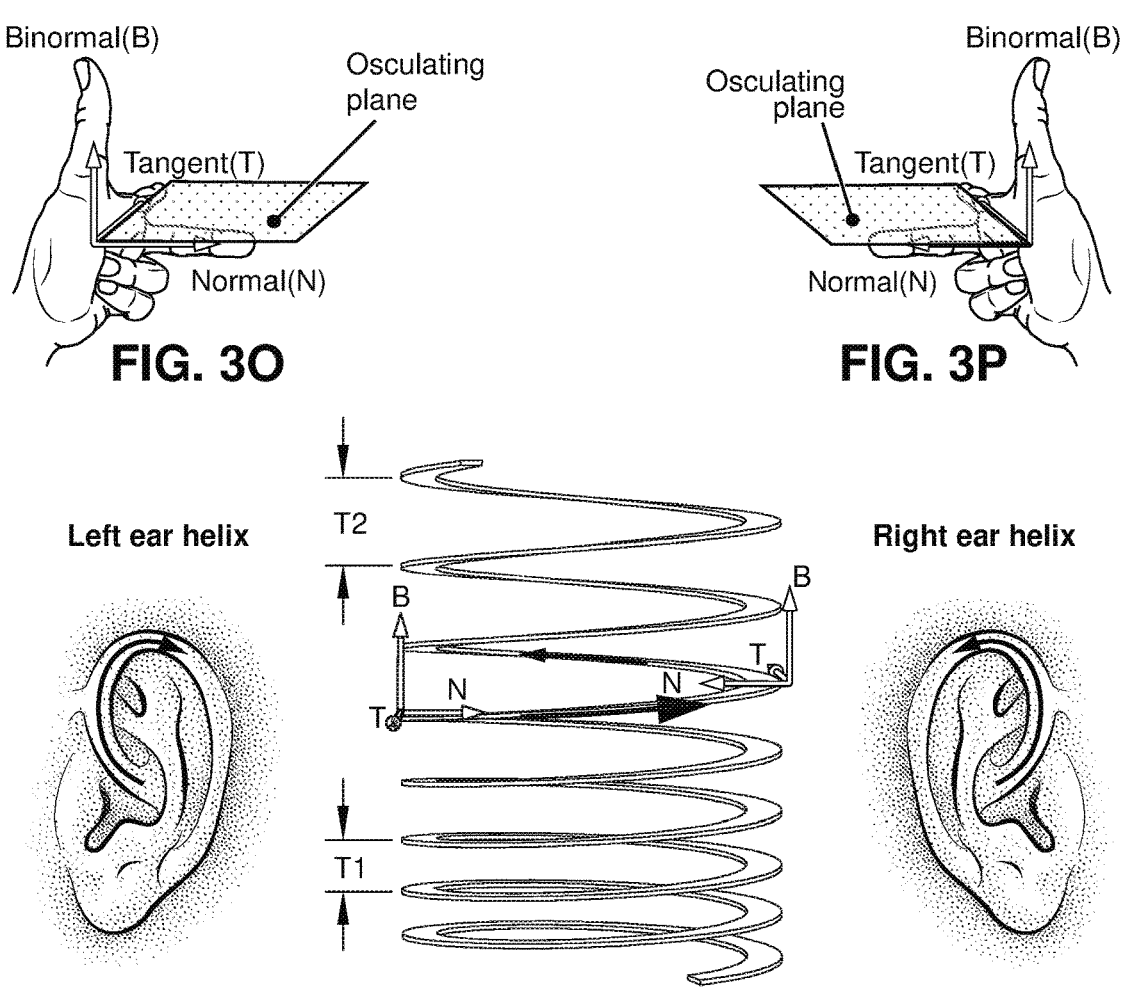
T2
B
N    N    T
T
T1
**Right-hand helix
Right-hand positive**
FIG. 3S
Right ear helix
FIG. 3R
Right-hand negative
(=left-hand positive)
Right-hand positive
Right-hand negative
Right-hand positive
FIG. 3T
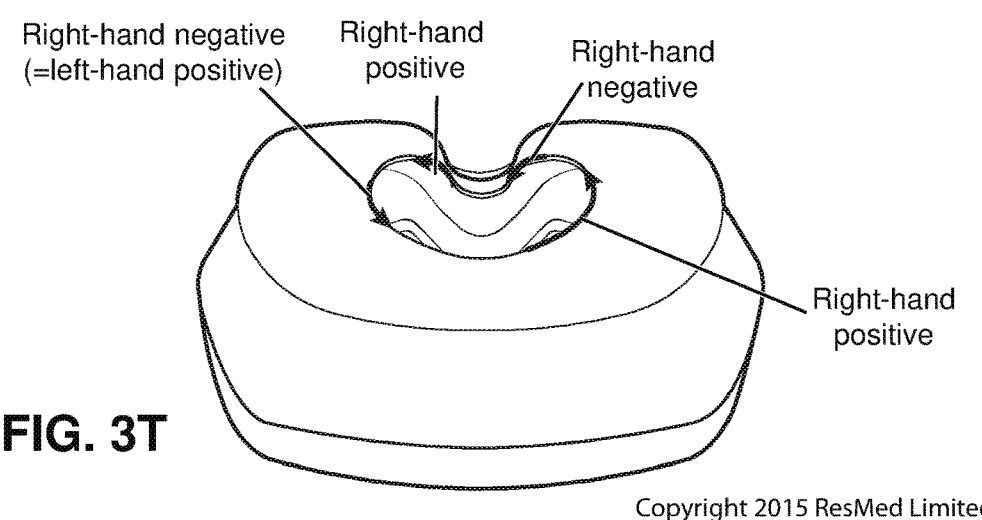

3000

3300

3310

3050

3052

3600

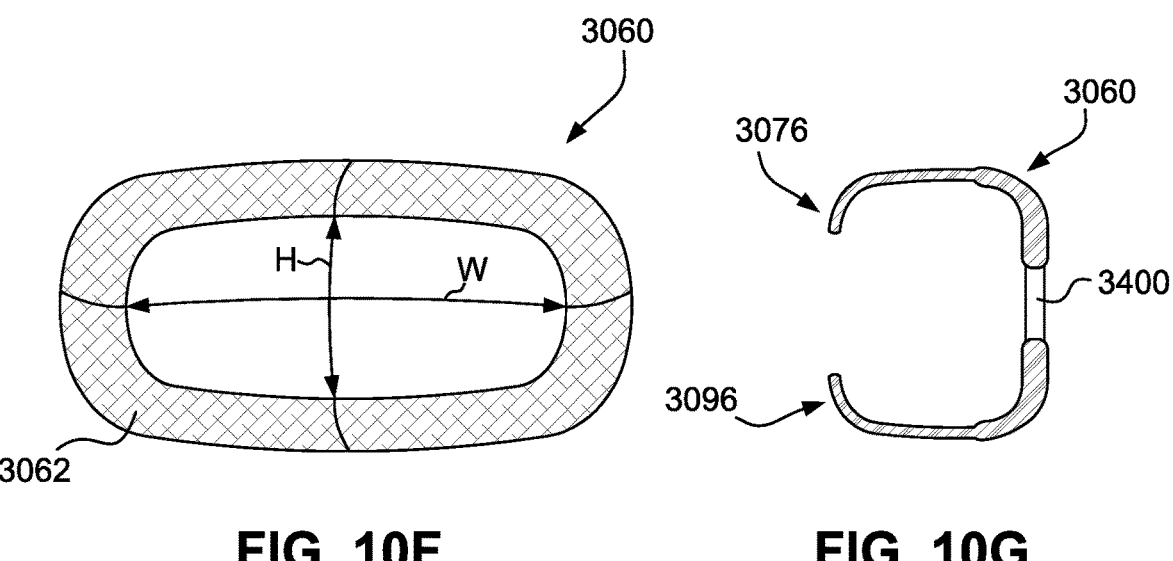
FIG. 10F          FIG. 10G
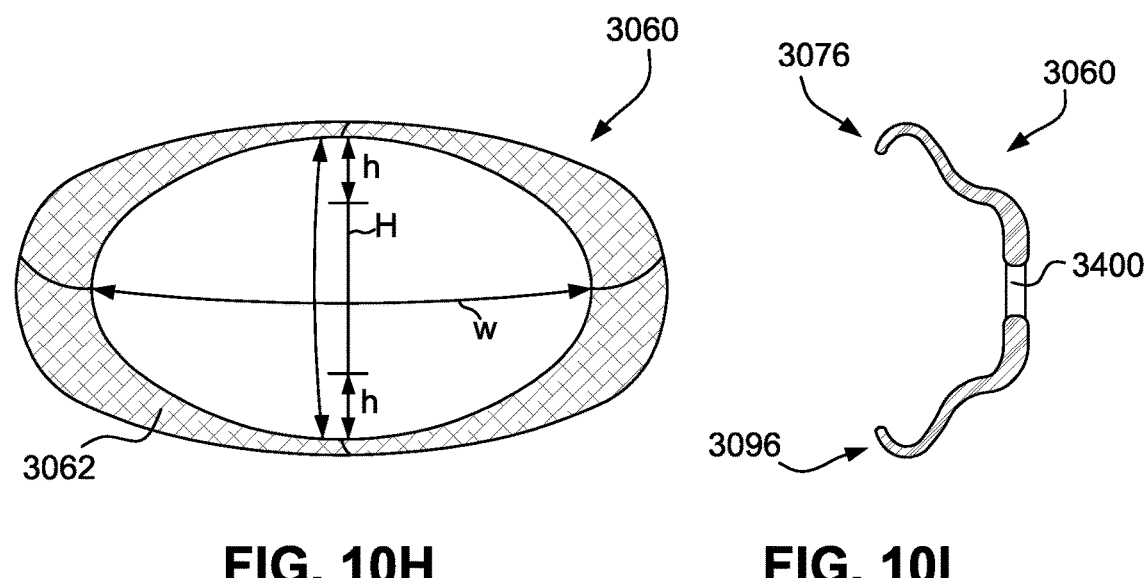
FIG. 10H          FIG. 10I

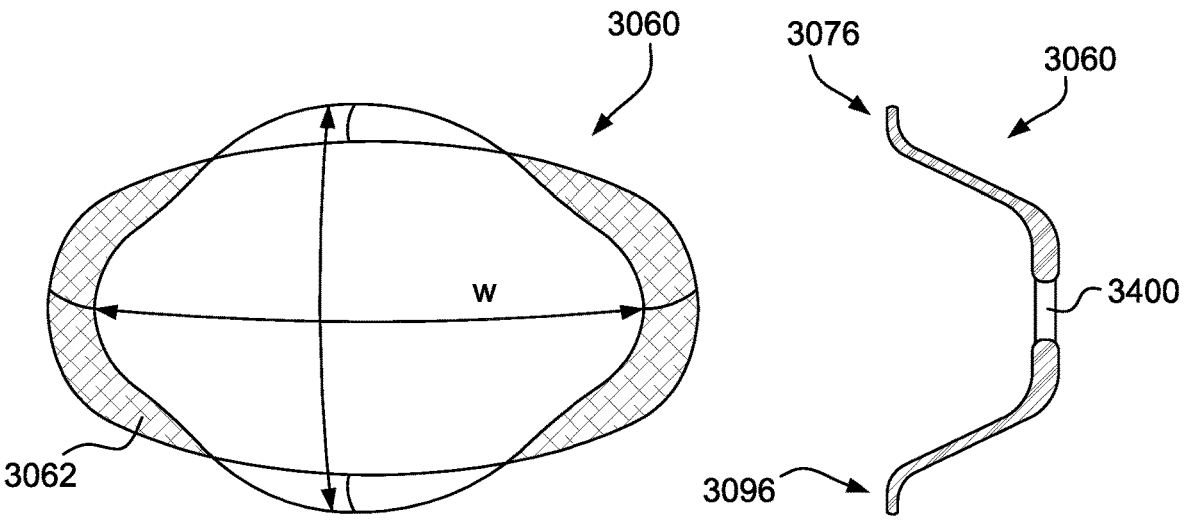
FIG. 10J            FIG. 10K

3050

3165

3060

3066-3

3068

3600

4170

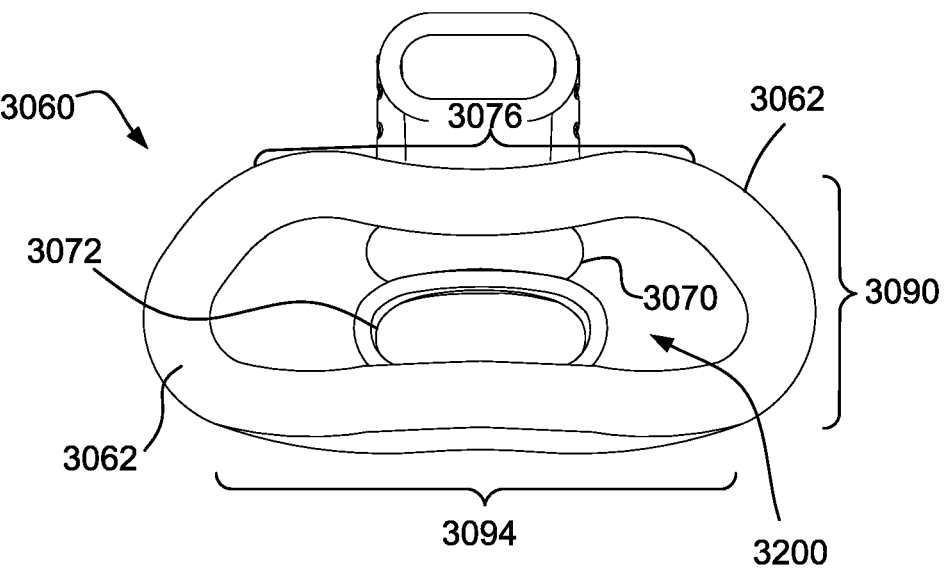
FIG. 13D
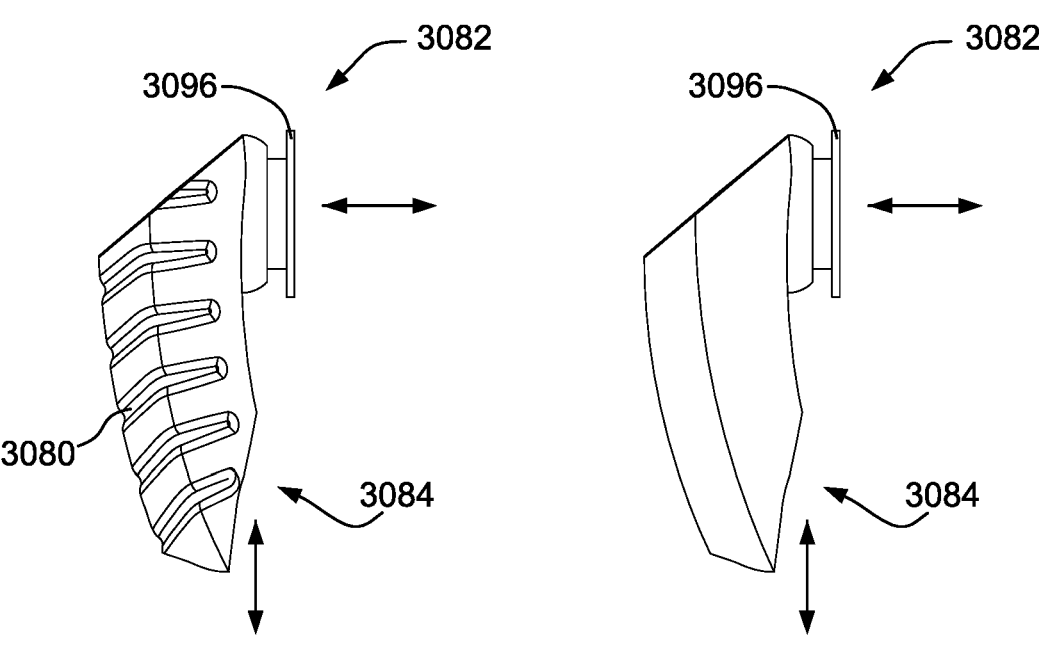
FIG. 14A          FIG. 14B

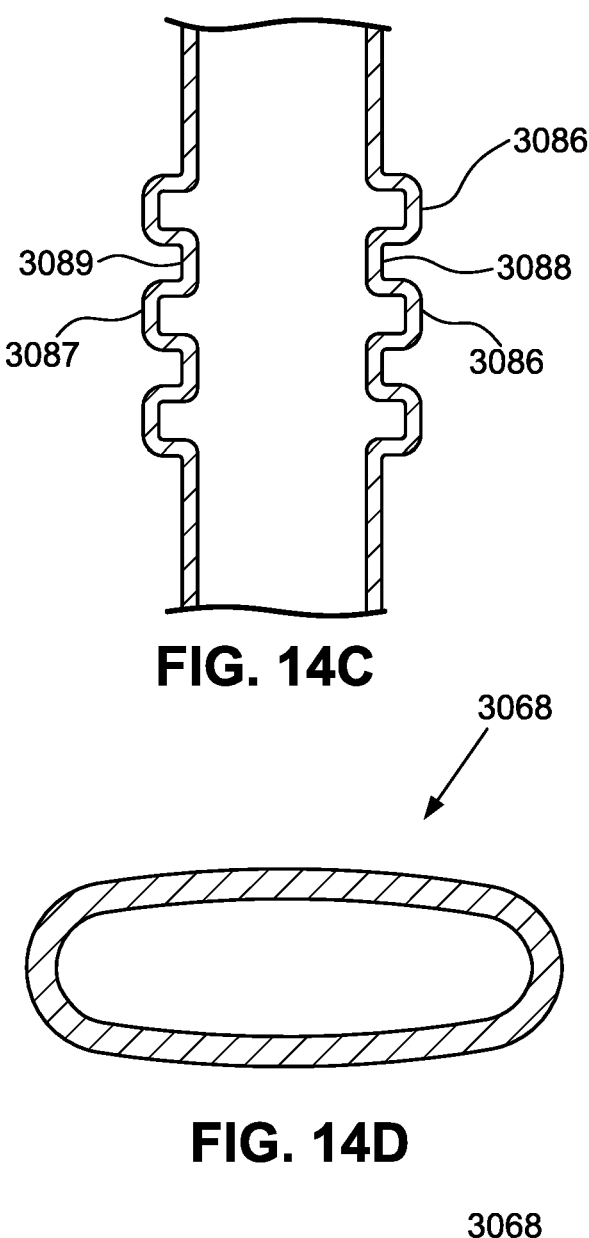
FIG. 14C
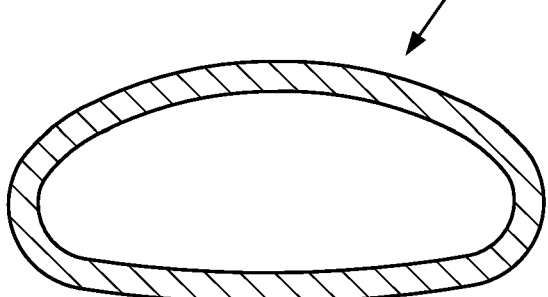
FIG. 14D
FIG. 14E

MODULAR PATIENT INTERFACE INCLUDING A JOINT COUPLING MOUTH AND NASAL CUSHIONS

1 CROSS-REFERENCE TO RELATED APPLICATIONS

This application is the U.S. national phase of International Application No. PCT/AU2020/051180 filed Oct. 30, 2020 which designated the U.S. and claims priority to U.S. Provisional Application No. 62/928,228, filed Oct. 30, 2019; U.S. Provisional Application No. 62/928,213, filed Oct. 30, 2019; and U.S. Provisional Application No. 62/928,185, filed Oct. 30, 2019, which are hereby incorporated herein by reference in their entirety.

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

2 BACKGROUND OF THE TECHNOLOGY

2.1 Field of the Technology

The present technology relates to one or more of the screening, diagnosis, monitoring, treatment, prevention and amelioration of respiratory-related disorders. The present technology also relates to medical devices or apparatus, and their use.

2.2 Description of the Related Art 2.2.1 Human Respiratory System and its Disorders The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the inhaled air into the venous blood and carbon dioxide to move in the opposite direction. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See "Respiratory Physiology", by John B. West, Lippincott Williams & Wilkins, 9th edition published 2012.

A range of respiratory disorders exist. Certain disorders may be characterised by particular events, e.g. apneas, hypopneas, and hyperpneas.

Examples of respiratory disorders include Obstructive Sleep Apnea (OSA), Cheyne-Stokes Respiration (CSR), respiratory insufficiency, Obesity Hyperventilation Syndrome (OHS), Chronic Obstructive Pulmonary Disease (COPD), Neuromuscular Disease (NMD) and Chest wall disorders.

Obstructive Sleep Apnea (OSA), a form of Sleep Disordered Breathing (SDB), is characterised by events including occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds in duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Cheyne-Stokes Respiration (CSR) is another form of sleep disordered breathing. CSR is a disorder of a patient's respiratory controller in which there are rhythmic alternating periods of waxing and waning ventilation known as CSR cycles. CSR is characterised by repetitive de-oxygenation and re-oxygenation of the arterial blood. It is possible that CSR is harmful because of the repetitive hypoxia. In some patients CSR is associated with repetitive arousal from sleep, which causes severe sleep disruption, increased sympathetic activity, and increased afterload. See U.S. Pat. No. 6,532,959 (Berthon-Jones).

Respiratory failure is an umbrella term for respiratory disorders in which the lungs are unable to inspire sufficient oxygen or exhale sufficient $CO_2$ to meet the patient's needs. Respiratory failure may encompass some or all of the following disorders.

A patient with respiratory insufficiency (a form of respiratory failure) may experience abnormal shortness of breath on exercise.

Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common. These include increased resistance to air movement, extended expiratory phase of respiration, and loss of the normal elasticity of the lung. Examples of COPD are emphysema and chronic bronchitis. COPD is caused by chronic tobacco smoking (primary risk factor), occupational exposures, air pollution and genetic factors. Symptoms include: dyspnea on exertion, chronic cough and sputum production.

Neuromuscular Disease (NMD) is a broad term that encompasses many diseases and ailments that impair the functioning of the muscles either directly via intrinsic muscle pathology, or indirectly via nerve pathology. Some NMD patients are characterised by progressive muscular impairment leading to loss of ambulation, being wheelchair-bound, swallowing difficulties, respiratory muscle weakness and, eventually, death from respiratory failure. Neuromuscular disorders can be divided into rapidly progressive and slowly progressive: (i) Rapidly progressive disorders: Characterised by muscle impairment that worsens over months and results in death within a few years (e.g. Amyotrophic lateral sclerosis (ALS) and Duchenne muscular dystrophy (DMD) in teenagers); (ii) Variable or slowly progressive disorders: Characterised by muscle impairment that worsens over years and only mildly reduces life expectancy (e.g. Limb girdle, Facioscapulohumeral and Myotonic muscular dystrophy). Symptoms of respiratory failure in NMD include: increasing generalised weakness, dysphagia, dyspnea on exertion and at rest, fatigue, sleepiness, morning headache, and difficulties with concentration and mood changes.

Chest wall disorders are a group of thoracic deformities that result in inefficient coupling between the respiratory muscles and the thoracic cage. The disorders are usually characterised by a restrictive defect and share the potential of long term hypercapnic respiratory failure. Scoliosis and/or kyphoscoliosis may cause severe respiratory failure. Symptoms of respiratory failure include: dyspnea on exertion, peripheral oedema, orthopnea, repeated chest infections, morning headaches, fatigue, poor sleep quality and loss of appetite.

A range of therapies have been used to treat or ameliorate such conditions. Furthermore, otherwise healthy individuals may take advantage of such therapies to prevent respiratory disorders from arising. However, these have a number of shortcomings.

2.2.2 Therapy

Various therapies, such as Continuous Positive Airway Pressure (CPAP) therapy, Non-invasive ventilation (NIV) and Invasive ventilation (IV) have been used to treat one or more of the above respiratory disorders.

Continuous Positive Airway Pressure (CPAP) therapy has been used to treat Obstructive Sleep Apnea (OSA). The mechanism of action is that continuous positive airway pressure acts as a pneumatic splint and may prevent upper airway occlusion, such as by pushing the soft palate and tongue forward and away from the posterior oropharyngeal wall. Treatment of OSA by CPAP therapy may be voluntary, and hence patients may elect not to comply with therapy if they find devices used to provide such therapy one or more of: uncomfortable, difficult to use, expensive and aesthetically unappealing.

Non-invasive ventilation (NIV) provides ventilatory support to a patient through the upper airways to assist the patient breathing and/or maintain adequate oxygen levels in the body by doing some or all of the work of breathing. The ventilatory support is provided via a non-invasive patient interface. NIV has been used to treat CSR and respiratory failure, in forms such as OHS, COPD, NMD and Chest Wall disorders. In some forms, the comfort and effectiveness of these therapies may be improved.

Invasive ventilation (IV) provides ventilatory support to patients that are no longer able to effectively breathe themselves and may be provided using a tracheostomy tube. In some forms, the comfort and effectiveness of these therapies may be improved.

2.2.3 Treatment Systems

These therapies may be provided by a treatment system or device. Such systems and devices may also be used to screen, diagnose, or monitor a condition without treating it.

A treatment system may comprise a Respiratory Pressure Therapy Device (RPT device), an air circuit, a humidifier, a patient interface, and data management.

Another form of treatment system is a mandibular repositioning device.

2.2.3.1 Patient Interface

A patient interface may be used to interface respiratory equipment to its wearer, for example by providing a flow of air to an entrance to the airways. The flow of air may be provided via a mask to the nose and/or mouth, a tube to the mouth or a tracheostomy tube to the trachea of a patient. Depending upon the therapy to be applied, the patient interface may form a seal, e.g., with a region of the patient's face, to facilitate the delivery of gas at a pressure at sufficient variance with ambient pressure to effect therapy, e.g., at a positive pressure of about 10 cmH$_2$O relative to ambient pressure. For other forms of therapy, such as the delivery of oxygen, the patient interface may not include a seal sufficient to facilitate delivery to the airways of a supply of gas at a positive pressure of about 10 cmH$_2$O.

Certain other mask systems may be functionally unsuitable for the present field. For example, purely ornamental masks may be unable to maintain a suitable pressure. Mask systems used for underwater swimming or diving may be configured to guard against ingress of water from an external higher pressure, but not to maintain air internally at a higher pressure than ambient.

Certain masks may be clinically unfavourable for the present technology e.g. if they block airflow via the nose and only allow it via the mouth.

Certain masks may be uncomfortable or impractical for the present technology if they require a patient to insert a portion of a mask structure in their mouth to create and maintain a seal via their lips.

Certain masks may be impractical for use while sleeping, e.g. for sleeping while lying on one's side in bed with a head on a pillow.

The design of a patient interface presents a number of challenges. The face has a complex three-dimensional shape. The size and shape of noses and heads varies considerably between individuals. Since the head includes bone, cartilage and soft tissue, different regions of the face respond differently to mechanical forces. The jaw or mandible may move relative to other bones of the skull. The whole head may move during the course of a period of respiratory therapy.

As a consequence of these challenges, some masks suffer from being one or more of obtrusive, aesthetically undesirable, costly, poorly fitting, difficult to use, and uncomfortable especially when worn for long periods of time or when a patient is unfamiliar with a system. Wrongly sized masks can give rise to reduced compliance, reduced comfort and poorer patient outcomes. Masks designed solely for aviators, masks designed as part of personal protection equipment (e.g. filter masks), SCUBA masks, or for the administration of anaesthetics may be tolerable for their original application, but nevertheless such masks may be undesirably uncomfortable to be worn for extended periods of time, e.g., several hours. This discomfort may lead to a reduction in patient compliance with therapy. This is even more so if the mask is to be worn during sleep.

CPAP therapy is highly effective to treat certain respiratory disorders, provided patients comply with therapy. If a mask is uncomfortable, or difficult to use a patient may not comply with therapy. Since it is often recommended that a patient regularly wash their mask, if a mask is difficult to clean (e.g., difficult to assemble or disassemble), patients may not clean their mask and this may impact on patient compliance.

While a mask for other applications (e.g. aviators) may not be suitable for use in treating sleep disordered breathing, a mask designed for use in treating sleep disordered breathing may be suitable for other applications.

For these reasons, patient interfaces for delivery of CPAP during sleep form a distinct field.

2.2.3.1.1 Seal-Forming Structure

Patient interfaces may include a seal-forming structure. Since it is in direct contact with the patient's face, the shape and configuration of the seal-forming structure can have a direct impact the effectiveness and comfort of the patient interface.

A patient interface may be partly characterised according to the design intent of where the seal-forming structure is to engage with the face in use. In one form of patient interface, a seal-forming structure may comprise a first sub-portion to form a seal around the left naris and a second sub-portion to form a seal around the right naris. In one form of patient interface, a seal-forming structure may comprise a single element that surrounds both nares in use. Such single element may be designed to for example overlay an upper lip region and a nasal bridge region of a face. In one form of patient interface a seal-forming structure may comprise an element that surrounds a mouth region in use, e.g. by forming a seal on a lower lip region of a face. In one form of patient interface, a seal-forming structure may comprise a single element that surrounds both nares and a mouth region in use. These different types of patient interfaces may be known by a variety of names by their manufacturer including nasal masks, full-face masks, nasal pillows, nasal puffs and oro-nasal masks.

A seal-forming structure that may be effective in one region of a patient's face may be inappropriate in another region, e.g. because of the different shape, structure, variability and sensitivity regions of the patient's face. For example, a seal on swimming goggles that overlays a patient's forehead may not be appropriate to use on a patient's nose.

Certain seal-forming structures may be designed for mass manufacture such that one design fit and be comfortable and effective for a wide range of different face shapes and sizes. To the extent to which there is a mismatch between the shape of the patient's face, and the seal-forming structure of the mass-manufactured patient interface, one or both must adapt in order for a seal to form.

One type of seal-forming structure extends around the periphery of the patient interface, and is intended to seal against the patient's face when force is applied to the patient interface with the seal-forming structure in confronting engagement with the patient's face. The seal-forming structure may include an air or fluid filled cushion, or a moulded or formed surface of a resilient seal element made of an elastomer such as a rubber. With this type of seal-forming structure, if the fit is not adequate, there will be gaps between the seal-forming structure and the face, and additional force will be required to force the patient interface against the face in order to achieve a seal.

Another type of seal-forming structure incorporates a flap seal of thin material positioned about the periphery of the mask so as to provide a self-sealing action against the face of the patient when positive pressure is applied within the mask Like the previous style of seal forming portion, if the match between the face and the mask is not good, additional force may be required to achieve a seal, or the mask may leak. Furthermore, if the shape of the seal-forming structure does not match that of the patient, it may crease or buckle in use, giving rise to leaks.

Another type of seal-forming structure may comprise a friction-fit element, e.g. for insertion into a naris, however some patients find these uncomfortable.

Another form of seal-forming structure may use adhesive to achieve a seal. Some patients may find it inconvenient to constantly apply and remove an adhesive to their face.

A range of patient interface seal-forming structure technologies are disclosed in the following patent applications, assigned to ResMed Limited: WO 1998/004,310; WO 2006/074,513; WO 2010/135,785.

One form of nasal pillow is found in the Adam Circuit manufactured by Puritan Bennett. Another nasal pillow, or nasal puff is the subject of U.S. Pat. No. 4,782,832 (Trimble et al.), assigned to Puritan-Bennett Corporation.

ResMed Limited has manufactured the following products that incorporate nasal pillows: SWIFT™ nasal pillows mask, SWIFT™ II nasal pillows mask, SWIFT™ LT nasal pillows mask, SWIFT™ FX nasal pillows mask and MIRAGE LIBERTY™ full-face mask. The following patent applications, assigned to ResMed Limited, describe examples of nasal pillows masks: International Patent Application WO2004/073,778 (describing amongst other things aspects of the ResMed Limited SWIFT™ nasal pillows), US Patent Application 2009/0044808 (describing amongst other things aspects of the ResMed Limited SWIFT™ LT nasal pillows); International Patent Applications WO 2005/063,328 and WO 2006/130,903 (describing amongst other things aspects of the ResMed Limited MIRAGE LIBERTY™ full-face mask); International Patent Application WO 2009/052,560 (describing amongst other things aspects of the ResMed Limited SWIFT™ FX nasal pillows).

2.2.3.1.2 Positioning and Stabilising

A seal-forming structure of a patient interface used for positive air pressure therapy is subject to the corresponding force of the air pressure to disrupt a seal. Thus a variety of techniques have been used to position the seal-forming structure, and to maintain it in sealing relation with the appropriate portion of the face.

One technique is the use of adhesives. See for example US Patent Application Publication No. US 2010/0000534. However, the use of adhesives may be uncomfortable for some.

Another technique is the use of one or more straps and/or stabilising harnesses. Many such harnesses suffer from being one or more of ill-fitting, bulky, uncomfortable and awkward to use.

2.2.3.2 Respiratory Pressure Therapy (RPT) Device

A respiratory pressure therapy (RPT) device may be used individually or as part of a system to deliver one or more of a number of therapies described above, such as by operating the device to generate a flow of air for delivery to an interface to the airways. The flow of air may be pressurised. Examples of RPT devices include a CPAP device and a ventilator.

Air pressure generators are known in a range of applications, e.g. industrial-scale ventilation systems. However, air pressure generators for medical applications have particular requirements not fulfilled by more generalised air pressure generators, such as the reliability, size and weight requirements of medical devices. In addition, even devices designed for medical treatment may suffer from shortcomings, pertaining to one or more of: comfort, noise, ease of use, efficacy, size, weight, manufacturability, cost, and reliability.

An example of the special requirements of certain RPT devices is acoustic noise.

Table of noise output levels of prior RPT devices (one specimen only, measured using test method specified in ISO 3744 in CPAP mode at 10 cmH$_2$O).

| RPT Device name | A-weighted sound pressure level dB(A) | Year (approx.) |
|---|---|---|
| C-Series Tango ™ | 31.9 | 2007 |
| C-Series Tango ™ with Humidifier | 33.1 | 2007 |
| S8 Escape ™ II | 30.5 | 2005 |
| S8 Escape ™ II with H4i ™ Humidifier | 31.1 | 2005 |
| S9 AutoSet ™ | 26.5 | 2010 |
| S9 AutoSet ™ with H5i Humidifier | 28.6 | 2010 |

One known RPT device used for treating sleep disordered breathing is the S9 Sleep Therapy System, manufactured by ResMed Limited. Another example of an RPT device is a ventilator. Ventilators such as the ResMed Stellar™ Series of Adult and Paediatric Ventilators may provide support for invasive and non-invasive non-dependent ventilation for a range of patients for treating a number of conditions such as but not limited to NMD, OHS and COPD.

The ResMed Elisée™ 150 ventilator and ResMed VS III™ ventilator may provide support for invasive and non-invasive dependent ventilation suitable for adult or paediatric patients for treating a number of conditions. These ventilators provide volumetric and barometric ventilation modes with a single or double limb circuit. RPT devices typically comprise a pressure generator, such as a motor-driven blower or a compressed gas reservoir, and are configured to supply a flow of air to the airway of a patient. In some cases, the flow of air may be supplied to the airway of the patient at positive pressure. The outlet of the RPT device is connected via an air circuit to a patient interface such as those described above.

The designer of a device may be presented with an infinite number of choices to make. Design criteria often conflict, meaning that certain design choices are far from routine or inevitable. Furthermore, the comfort and efficacy of certain aspects may be highly sensitive to small, subtle changes in one or more parameters.

2.2.3.3 Humidifier

Delivery of a flow of air without humidification may cause drying of airways. The use of a humidifier with an RPT device and the patient interface produces humidified gas that minimizes drying of the nasal mucosa and increases patient airway comfort. In addition in cooler climates, warm air applied generally to the face area in and about the patient interface is more comfortable than cold air.

A range of artificial humidification devices and systems are known, however they may not fulfil the specialised requirements of a medical humidifier.

Medical humidifiers are used to increase humidity and/or temperature of the flow of air in relation to ambient air when required, typically where the patient may be asleep or resting (e.g. at a hospital). A medical humidifier for bedside placement may be small. A medical humidifier may be configured to only humidify and/or heat the flow of air delivered to the patient without humidifying and/or heating the patient's surroundings. Room-based systems (e.g. a sauna, an air conditioner, or an evaporative cooler), for example, may also humidify air that is breathed in by the patient, however those systems would also humidify and/or heat the entire room, which may cause discomfort to the occupants. Furthermore medical humidifiers may have more stringent safety constraints than industrial humidifiers While a number of medical humidifiers are known, they can suffer from one or more shortcomings. Some medical humidifiers may provide inadequate humidification, some are difficult or inconvenient to use by patients.

2.2.3.4 Data Management

There may be clinical reasons to obtain data to determine whether the patient prescribed with respiratory therapy has been "compliant", e.g. that the patient has used their RPT device according to one or more "compliance rules". One example of a compliance rule for CPAP therapy is that a patient, in order to be deemed compliant, is required to use the RPT device for at least four hours a night for at least 21 of 30 consecutive days. In order to determine a patient's compliance, a provider of the RPT device, such as a health care provider, may manually obtain data describing the patient's therapy using the RPT device, calculate the usage over a predetermined time period, and compare with the compliance rule. Once the health care provider has determined that the patient has used their RPT device according to the compliance rule, the health care provider may notify a third party that the patient is compliant.

There may be other aspects of a patient's therapy that would benefit from communication of therapy data to a third party or external system.

Existing processes to communicate and manage such data can be one or more of costly, time-consuming, and error-prone.

2.2.3.5 Mandibular Repositioning

A mandibular repositioning device (MRD) or mandibular advancement device (MAD) is one of the treatment options for sleep apnea and snoring. It is an adjustable oral appliance available from a dentist or other supplier that holds the lower jaw (mandible) in a forward position during sleep. The MRD is a removable device that a patient inserts into their mouth prior to going to sleep and removes following sleep. Thus, the MRD is not designed to be worn all of the time. The MRD may be custom made or produced in a standard form and includes a bite impression portion designed to allow fitting to a patient's teeth. This mechanical protrusion of the lower jaw expands the space behind the tongue, puts tension on the pharyngeal walls to reduce collapse of the airway and diminishes palate vibration.

In certain examples a mandibular advancement device may comprise an upper splint that is intended to engage with or fit over teeth on the upper jaw or maxilla and a lower splint that is intended to engage with or fit over teeth on the upper jaw or mandible. The upper and lower splints are connected together laterally via a pair of connecting rods. The pair of connecting rods are fixed symmetrically on the upper splint and on the lower splint.

In such a design the length of the connecting rods is selected such that when the MRD is placed in a patient's mouth the mandible is held in an advanced position. The length of the connecting rods may be adjusted to change the level of protrusion of the mandible. A dentist may determine a level of protrusion for the mandible that will determine the length of the connecting rods.

Some MRDs are structured to push the mandible forward relative to the maxilla while other MADs, such as the ResMed Narval CC™ MRD are designed to retain the mandible in a forward position. This device also reduces or minimises dental and temporo-mandibular joint (TMJ) side effects. Thus, it is configured to minimises or prevent any movement of one or more of the teeth.

2.2.3.6 Vent Technologies

Some forms of treatment systems may include a vent to allow the washout of exhaled carbon dioxide. The vent may allow a flow of gas from an interior space of a patient interface, e.g., the plenum chamber, to an exterior of the patient interface, e.g., to ambient.

The vent may comprise an orifice and gas may flow through the orifice in use of the mask. Many such vents are noisy. Others may become blocked in use and thus provide insufficient washout. Some vents may be disruptive of the sleep of a bed partner 1100 of the patient 1000, e.g. through noise or focussed airflow.

ResMed Limited has developed a number of improved mask vent technologies. See International Patent Application Publication No. WO 1998/034,665; International Patent Application Publication No. WO 2000/078,381; U.S. Pat. No. 6,581,594; US Patent Application Publication No. US 2009/0050156; US Patent Application Publication No. 2009/0044808.

Table of noise of prior masks (ISO 17510-2:2007, 10 cmH₂O pressure at 1 m)

| Mask name | Mask type | A-weighted sound power level dB(A) (uncertainty) | A-weighted sound pressure dB(A) (uncertainty) | Year (approx.) |
|---|---|---|---|---|
| Glue-on (*) | nasal | 50.9 | 42.9 | 1981 |
| ResCare standard (*) | nasal | 31.5 | 23.5 | 1993 |
| ResMed Mirage ™ (*) | nasal | 29.5 | 21.5 | 1998 |
| ResMed UltraMirage ™ | nasal | 36 (3) | 28 (3) | 2000 |
| ResMed Mirage Activa ™ | nasal | 32 (3) | 24 (3) | 2002 |
| ResMed Mirage Micro ™ | nasal | 30 (3) | 22 (3) | 2008 |
| ResMed Mirage ™ SoftGel | nasal | 29 (3) | 22 (3) | 2008 |
| ResMed Mirage ™ FX | nasal | 26 (3) | 18 (3) | 2010 |
| ResMed Mirage Swift ™ (*) | nasal pillows | 37 | 29 | 2004 |
| ResMed Mirage Swift ™ II | nasal pillows | 28 (3) | 20 (3) | 2005 |
| ResMed Mirage Swift ™ LT | nasal pillows | 25 (3) | 17 (3) | 2008 |
| ResMed AirFit P10 | nasal pillows | 21 (3) | 13 (3) | 2014 |

(* one specimen only, measured using test method specified in ISO 3744 in CPAP mode at 10 cmH$_2$O)

Sound pressure values of a variety of objects are listed below

| Object | A-weighted sound pressure dB(A) | Notes |
|---|---|---|
| Vacuum cleaner: Nilfisk Walter Broadly Litter Hog: B+ Grade | 68 | ISO 3744 at 1 m distance |
| Conversational speech | 60 | 1 m distance |
| Average home | 50 | |
| Quiet library | 40 | |
| Quiet bedroom at night | 30 | |
| Background in TV studio | 20 | |

2.2.4 Screening, Diagnosis, and Monitoring Systems

Polysomnography (PSG) is a conventional system for diagnosis and monitoring of cardio-pulmonary disorders, and typically involves expert clinical staff to apply the system. PSG typically involves the placement of 15 to 20 contact sensors on a patient in order to record various bodily signals such as electroencephalography (EEG), electrocardiography (ECG), electrooculograpy (EOG), electromyography (EMG), etc. PSG for sleep disordered breathing has involved two nights of observation of a patient in a clinic, one night of pure diagnosis and a second night of titration of treatment parameters by a clinician. PSG is therefore expensive and inconvenient. In particular it is unsuitable for home screening/diagnosis/monitoring of sleep disordered breathing.

Screening and diagnosis generally describe the identification of a condition from its signs and symptoms. Screening typically gives a true/false result indicating whether or not a patient's SDB is severe enough to warrant further investigation, while diagnosis may result in clinically actionable information. Screening and diagnosis tend to be one-off processes, whereas monitoring the progress of a condition can continue indefinitely. Some screening/diagnosis systems are suitable only for screening/diagnosis, whereas some may also be used for monitoring.

Clinical experts may be able to screen, diagnose, or monitor patients adequately based on visual observation of PSG signals. However, there are circumstances where a clinical expert may not be available, or a clinical expert may not be affordable. Different clinical experts may disagree on a patient's condition. In addition, a given clinical expert may apply a different standard at different times.

3 BRIEF SUMMARY OF THE TECHNOLOGY

The present technology is directed towards providing medical devices used in the screening, diagnosis, monitoring, amelioration, treatment, or prevention of respiratory disorders having one or more of improved comfort, cost, efficacy, ease of use and manufacturability.

A first aspect of the present technology relates to apparatus used in the screening, diagnosis, monitoring, amelioration, treatment or prevention of a respiratory disorder.

Another aspect of the present technology relates to methods used in the screening, diagnosis, monitoring, amelioration, treatment or prevention of a respiratory disorder.

An aspect of certain forms of the present technology is to provide methods and/or apparatus that improve the compliance of patients with respiratory therapy.

Another aspect of one form of the present technology is a patient interface that is moulded or otherwise constructed with a perimeter shape which is complementary to that of an intended wearer.

An aspect of one form of the present technology is a method of manufacturing apparatus.

An aspect of certain forms of the present technology is a medical device that is easy to use, e.g. by a person who does not have medical training, by a person who has limited dexterity, vision or by a person with limited experience in using this type of medical device.

An aspect of one form of the present technology is a patient interface that may be washed in a home of a patient, e.g., in soapy water, without requiring specialised cleaning equipment.

An aspect of the present technology relates to a patient interface including a cushion assembly including a seal-forming structure constructed and arranged to form a seal with the patient's nasal and/or oral airways, and a positioning and stabilizing structure to maintain the cushion in place on the patient's head during therapy.

An aspect of the present technology relates to a patient interface configured to deliver a flow of breathable gas to a patient's airways. The patient interface being configurable between a nasal mask configuration including a nasal cushion, and an oro-nasal mask configuration including a nasal cushion and a mouth cushion coupled to the nasal cushion by a flexible joint. The patient interface comprising a positioning and stabilizing structure to provide a force to hold the nasal cushion and/or the mouth cushion in a therapeutically effective position on a patient's head.

An aspect of the present technology relates to a patient interface configured to deliver a flow of breathable gas to a patient's airways. The patient interface including a nasal cushion, a mouth cushion, a flexible joint connecting the nasal cushion to the mouth cushion; and a positioning and stabilizing structure to provide a force to hold the nasal cushion and the mouth cushion in a therapeutically effective position on a patient's head.

An aspect of the present technology relates to a patient interface configured to deliver a flow of breathable gas to a patient's airways, to ameliorate sleep disordered breathing. The patient interface comprising: a nasal cushion forming at least part of a nasal cushion plenum chamber pressurizable to a therapeutic pressure; a mouth cushion forming at least part of a mouth cushion plenum chamber pressurizable to the therapeutic pressure; a flexible joint connecting the nasal cushion to the mouth cushion; and a positioning and stabilizing structure to provide a force to hold a nasal and mouth seal-forming structures in a therapeutically effective position on a patient's head.

Another aspect of the present technology relates to a patient interface kit to deliver a flow of air at a positive pressure with respect to ambient air pressure to an entrance to a patient's airways including at least the entrance of a patient's nares while the patient is sleeping, to ameliorate sleep disordered breathing. The patient interface comprising:

a nasal cushion forming at least part of a nasal cushion plenum chamber pressurizable to a therapeutic pressure, wherein the nasal cushion comprises a nasal seal-forming structure constructed and arranged to form a seal with a region of a patient's face surrounding the entrance to a patient's nares, the nasal cushion having a nasal cushion opening;

a mouth cushion forming at least part of a mouth cushion plenum chamber pressurizable to the therapeutic pressure, wherein the mouth cushion comprises a seal-forming structure constructed and arranged to form a seal with a region of a patient's face surrounding the entrance to a patient's mouth, the mouth cushion having a mouth cushion opening, the mouth cushion including a flexible joint, positioned above the mouth opening, to selectively connect the nasal cushion to the mouth cushion; and a positioning and stabilizing structure to provide a force to hold the nasal and/or mouth seal-forming structures in a therapeutically effective position on a patient's head, the positioning an stabilizing structure including a nasal headgear including upper straps or conduits and a mouth headgear including lower straps, the mouth headgear being selectively connected to the nasal headgear, wherein each of the nasal opening and the mouth opening is configured to receive a vent insert with one or more gas washout vents, and in the alternative, a tube connector adapted to connect to an air delivery tube, the nasal opening and the mouth opening having the same size, wherein the nasal opening is additional and alternatively configured to receive a nasal cushion end of the flexible joint, wherein the patient interface kit is configured to allow the patient to select a nasal cushion therapy mode or a combined nasal cushion and mouth cushion therapy mode, the nasal cushion therapy mode including a nasal assembly having the nasal cushion and the nasal headgear and not the mouth cushion or the mouth headgear, the nasal cushion including the vent insert and/or the tube connection received in the nasal cushion opening, the combined nasal cushion and mouth cushion therapy mode including an oro-nasal assembly including the nasal cushion and the mouth cushion being connected by inserting the nasal cushion end of the flexible joint into the nasal cushion opening, the nasal headgear connected to nasal connectors of the nasal cushion, the mouth headgear connected to mouth connectors of the mouth cushion, the mouth headgear being detachably connected to the nasal headgear, the mouth cushion including the vent insert or the tube connector received in the mouth cushion opening.

In examples, the patient interface kit can include one or more of the following features: (a) the nasal headgear includes the upper conduits to deliver flow of breathable gas to the nasal cushion; (b) in the nasal cushion therapy mode, the nasal cushion opening includes the vent insert, and wherein in the oro-nasal cushion therapy mode the mouth cushion opening includes the vent insert; (c) the nasal headgear includes the upper straps to connect with the nasal cushion; (d) in the nasal cushion therapy mode, the nasal cushion opening includes the tube connector, and wherein in the oro-nasal cushion therapy mode, the mouth cushion opening includes the tube connector; (e) the nasal cushion includes ports to receive pressurized gas, the nasal cushion including plugs to close the ports, the plugs including connectors to connect to the upper straps; (f) the tube connector includes at least one vent hole for gas washout; (g) the flexible joint comprises a concertina section having at least one fold; (h) the concertina allows the mouth cushion to move relative to the nasal cushion in an axial direction, as well as a curved direction to accommodate the patient's supramenton angle; (i) the flexible joint and/or the mouth cushion are configured to move towards the patient's supramenton due to a spring bias of the flexible joint and/or introduction of the flow of breathable gas through the mouth cushion and/or the flexible joint; (j) the flexible joint has a neutral position and a curved position oriented towards the patient's supramenton, and wherein the flexible joint resists movement from the neutral position to a position away from the patient's face; (k) the nasal cushion end is configured to direct or receive the flow of pressurized breathable gas into or from the nasal plenum chamber in a direction that is substantially parallel to the patient's Frankfurt horizontal; (l) the mouth cushion end is attached to the mouth cushion at a position that is above a horizontal medial plane of the mouth cushion; (m) the nasal cushion includes a pair of upper headgear connectors, the mouth cushion includes a pair of lower headgear connectors, the nasal headgear is configured to connect to the upper headgear connectors, and the mouth headgear is configured to connect to the lower headgear connectors; (n) each of the lower headgear connectors includes a magnetic connection element; (o) the lower headgear connectors each include a pair of arms having a wish-bone shape, each of the lower headgear connectors having an upper arm and a lower arm connected to a front face of the mouth cushion, the upper arm being spaced from the lower arm; (p) the upper arm and the lower arm distribute support forces, respectively, to a mid-zone and a lower zone of the mouth cushion; (q) each of the pair of arms is flexible and has a U-shape; (r) the U-shape is similar in size and/or shape to lateral side portions of the mouth cushion; (s) each of the pair of arms is made of silicone or a material that is more rigid than silicone; (t) each of the pair of arms is connected to a front face of the mouth cushion made of silicone; (u) each of the arms is attached to the front face of the mouth cushion at a position that is spaced inwards from the lateral edge of the mouth cushion; (v) each of the arms is dimensioned and configured to straddle opposite sides of the patient's cheilion, thus applying forces against corners of the patient's mouth when worn by the patient and supported by the positioning and stabilizing structure; (w) each of the arms is movable or flexible to lie flush against the front face of the mouth cushion; (x) the arms apply a force to the front face of the mouth cushion due to tension applied to the lower straps coupled to the arms, to anchor the mouth cushion into the corners surrounding the patient's mouth; (y) the mouth cushion and/or the nasal cushion includes a textile sealing surface mounted on a silicone body; (z) the mouth cushion includes a front face, a sealing lip and a wall connecting the front face and the sealing lip, all made of silicone, wherein the wall and/or the sealing lip at a superior part of the corner-of-mouth portions of the mouth cushion is more rigid than an inferior part of the corner-of-mouth portions of the mouth cushion; (aa) the mouth cushion has a depth configured so as not to extend beyond the nasal cushion and/or the pronasale of the patient's nose; (ab) the mouth seal-forming structure includes an upper lip membrane configured to allow the mouth cushion to expand upwards when the patient's jaw opens; (ac) the upper lip membrane includes a central portion that is curved inwardly towards the mouth cushion plenum chamber; (ad) the upper lip membrane includes a central portion that is substantially linear or curved outwardly away from the mouth cushion plenum chamber; (ae) the mouth seal-forming structure includes a lower lip membrane configured to allow the mouth cushion to expand downwards when the patient's jaw opens; (af) the mouth cushion is configured to expand due to the flow of pressurized gas to hold upper portion and/or lower portion of the mouth cushion outwards from lateral sides of the mouth cushion; (ag) the flexible joint includes an anti-asphyxia valve; (ah) the mouth cushion is made of a first type of material and the nasal cushion is made of a second type of material different from the first type of material; (ai) the mouth cushion includes a sealing surface made of a first type of material and the nasal cushion includes a sealing surface of second type of material different from the first type of material; (aj) one of the first type of material and the second type of material is silicone and the other one of the first type of material and the second type of material is textile; and/or (ak) further comprising a pair of vent connectors including a plurality of holes, the pair of vent connectors configured to couple the nasal headgear to the nasal connectors of the nasal cushion.

Another aspect of the present technology relates to patient interface kit to deliver a flow of air at a positive pressure with respect to ambient air pressure to an entrance to a patient's airways including at least the entrance of a patient's nares while the patient is sleeping, to ameliorate sleep disordered breathing. The patient interface comprising:

a nasal cushion forming at least part of a nasal cushion plenum chamber pressurizable to a therapeutic pressure, wherein the nasal cushion comprises a nasal seal-forming structure constructed and arranged to form a seal with a region of a patient's face surrounding the entrance to a patient's nares, the nasal cushion having a nasal cushion opening;

a mouth cushion forming at least part of a mouth cushion plenum chamber pressurizable to the therapeutic pressure, wherein the mouth cushion comprises a seal-forming structure constructed and arranged to form a seal with a region of a patient's face surrounding the entrance to a patient's mouth, the mouth cushion having a mouth cushion opening, the mouth cushion including a flexible joint, positioned above the mouth opening, to selectively connect the nasal cushion to the mouth cushion; and a positioning and stabilizing structure to provide a force to hold the nasal and/or mouth seal-forming structures in a therapeutically effective position on a patient's head, the positioning an stabilizing structure including a nasal headgear including upper conduits and a mouth headgear including lower straps, the mouth headgear being selectively connected to the nasal headgear, wherein each of the nasal opening and the mouth opening is configured to receive a vent insert with one or more gas washout vents, and in the alternative, a tube connector adapted to connect to an air delivery tube, the nasal opening and the mouth opening having the same size, wherein the nasal opening is additional and alternatively configured to receive a nasal cushion end of the flexible joint, wherein the patient interface kit is configured to allow the patient to select a nasal cushion therapy mode or a combined nasal cushion and mouth cushion therapy mode, the nasal cushion therapy mode including a nasal assembly having the nasal cushion and the upper conduits and not the mouth cushion, the mouth headgear or the tube connector, the nasal cushion including the vent insert received in the nasal cushion opening, the combined nasal cushion and mouth cushion therapy mode including an oro-nasal assembly including the nasal cushion and the mouth cushion being connected by inserting the nasal cushion end of the flexible joint into the nasal cushion opening, the upper conduits being connected to hollow nasal connectors of the nasal cushion, the mouth headgear connected to mouth connectors of the mouth cushion, the mouth headgear being detachably connected to the nasal headgear, the mouth cushion including the vent insert received in the mouth cushion opening.

In examples, the patient interface kit can include one or more of the following features: (a) the tube connector includes at least one vent hole for gas washout; (b) the flexible joint comprises a concertina section having at least one fold; (c) the concertina allows the mouth cushion to move relative to the nasal cushion in an axial direction, as well as a curved direction to accommodate the patient's supramenton angle; (d) the flexible joint and/or the mouth cushion are configured to move towards the patient's supramenton due to a spring bias of the flexible joint and/or introduction of the flow of breathable gas through the mouth cushion and/or the flexible joint; (e) the flexible joint has a neutral position and a curved position oriented towards the patient's supramenton, and wherein the flexible joint resists movement from the neutral position to a position away from the patient's face; (f) the nasal cushion end is configured to direct or receive the flow of pressurized breathable gas into or from the nasal plenum chamber in a direction that is substantially parallel to the patient's Frankfurt horizontal; (g) the mouth cushion end is attached to the mouth cushion at a position that is above a horizontal medial plane of the mouth cushion; (h) the mouth connectors each include a pair of arms having a wish-bone shape, each of the mouth connectors having an upper arm and a lower arm connected to a front face of the mouth cushion, the upper arm being spaced from the lower arm; (i) the upper arm and the lower arm distribute support forces, respectively, to a mid-zone and a lower zone of the mouth cushion; (j) each of the pair of arms is flexible and has a U-shape; (k) the U-shape is similar in size and/or shape to lateral side portions of the mouth cushion; (m) each of the pair of arms is made of silicone or a material that is more rigid than silicone; (n) each of the pair of arms is connected to a front face of the mouth cushion made of silicone; (o) each of the arms is attached to the front face of the mouth cushion at a position that is spaced inwards from the lateral edge of the mouth cushion; (p) each of the arms is dimensioned and configured to straddle opposite sides of the patient's cheilion, thus applying forces against corners of the patient's mouth when worn by the patient and supported by the positioning and stabilizing structure; (q) each of the arms is movable or flexible to lie flush against the front face of the mouth cushion; (r) the arms apply a force to the front face of the mouth cushion due to tension applied to the lower straps coupled to the arms, to anchor the mouth cushion into the corners surrounding the patient's mouth; (s) the mouth cushion includes a front face, a sealing lip and a wall connecting the front face and the sealing lip, all made of silicone, wherein the wall and/or the sealing lip at a superior part of the corner-of-mouth portions of the mouth cushion is more rigid than an inferior part of the corner-of-mouth portions of the mouth cushion; (t) the mouth cushion has a depth configured so as not to extend beyond the nasal cushion and/or the pronasale of the patient's nose; (u) the mouth seal-forming structure includes an upper lip membrane configured to allow the mouth cushion to expand upwards when the patient's jaw opens; (v) the upper lip membrane includes a central portion that is curved inwardly towards the mouth cushion plenum chamber; (w) the upper lip membrane includes a central portion that is substantially linear or curved outwardly away from the mouth cushion plenum chamber; (x) the mouth seal-forming structure includes a lower lip membrane configured to allow the mouth cushion to expand downwards when the patient's jaw opens; (y) the mouth cushion is configured to expand due to the flow of pressurized gas to hold upper portion and/or lower portion of the mouth cushion outwards from lateral sides of the mouth cushion; (z) the flexible joint includes an anti-asphyxia valve; (aa) the mouth cushion includes a sealing surface made of a first type of material and the nasal cushion includes a sealing surface of second type of material different from the first type of material; (ab) one of the first type of material and the second type of material is silicone and the other one of the first type of material and the second type of material is textile; and/or (ac) further comprising a pair of vent connectors including a plurality of holes, the pair of vent connectors configured to couple the upper conduits to the hollow nasal connectors of the nasal cushion.

Another aspect of the present technology relates to a method of fitting an oro-nasal mask on a patient, the oro-nasal mask configured to deliver a flow of air at a positive pressure with respect to ambient air pressure to the patient's while the patient is sleeping, to ameliorate sleep disordered breathing. The method comprising: providing a nasal cushion forming at least part of a nasal cushion plenum chamber pressurizable to a therapeutic pressure, wherein the nasal cushion comprises a nasal seal-forming structure constructed and arranged to form a seal with a region of a patient's face surrounding an entrance to a patient's nares; providing a mouth cushion forming at least part of a mouth cushion plenum chamber pressurizable to the therapeutic pressure, wherein the mouth cushion comprises a seal-forming structure constructed and arranged to form a seal with a region of a patient's face surrounding the entrance to a patient's mouth; connecting the nasal cushion and the mouth cushion with a flexible joint; and holding the nasal and mouth seal-forming structures in a therapeutically effective position on a patient's head by: placing the nasal cushion under the patient's nose and engaging a superior portion of the patient's upper lip, whilst the mouth cushion is connected to the nasal cushion, securing the nasal cushion on the patient's head using upper headgear conduits or straps, adjusting the length and/or position of the upper headgear conduits or straps, positioning an upper membrane of the mouth cushion on an inferior portion of the patient's upper lip, below the nasal cushion, allowing engagement between the mouth cushion and the nasal cushion, securing the mouth cushion on the patient's head using lower headgear straps, adjusting the length and/or position of the lower headgear straps, wherein the adjustment of the upper headgear conduits or straps is substantially independent of adjustment of the lower headgear straps.

Another aspect of the present technology relates to a patient interface to deliver a flow of breathable gas at a positive pressure with respect to ambient air pressure to an entrance to a patient's airways while the patient is sleeping, to ameliorate sleep disordered breathing, the patient interface comprising: a mouth cushion forming at least part of a mouth cushion plenum chamber pressurizable to the therapeutic pressure, wherein the mouth cushion comprises a mouth seal-forming structure constructed and arranged to form a seal with a region of a patient's face below the patient's nose and surrounding the entrance to the patient's mouth, a flexible front face including a first opening for flow of breathable gas into and/or out of the mouth cushion plenum chamber, and a pair of lower headgear connectors attached to the flexible front face; and a positioning and stabilizing structure configured to connect the pair of lower headgear connectors and provide a force to hold the mouth seal-forming structures in a therapeutically effective position on a patient's head.

In examples, the patient interface can include one or more of the following features: (a) the mouth cushion includes a sealing lip and a wall connecting the front face and the sealing lip, all made of silicone; (b) each of the lower headgear connectors include an upper arm and a lower arm attached to the front face of the mouth cushion at a position that is spaced inwards from lateral edges of the mouth cushion, the upper arm being spaced from the lower arm; (c) each of the arms is dimensioned and configured to straddle opposite sides of the patient's cheilion, thus applying forces against corners of the patient's mouth when worn by the patient and supported by the positioning and stabilizing structure; (d) each of the lower headgear connectors includes a magnetic connection element; (e) each of the arms is dimensioned and configured to straddle opposite sides of the flexible front face and apply a force towards corners of the mouth seal-forming structure; (f) the upper arm and the lower arm are provided in a wish-bone shape; (g) the upper arm and the lower arm distribute support forces, respectively, to a mid-zone and a lower zone of the mouth cushion; (h) the upper arm and the lower arm are flexible and have a U-shape; (i) the U-shape is similar in size and/or shape to lateral side portions of the mouth cushion; (j) the ends of the U-shape are connected to the front face of the mouth cushion and the mid portion of the U-shape includes a magnetic connection element; (k) the upper arm and the lower arm are made of silicone or a material that is more rigid than silicone; (l) each of the arms is movable or flexible to lie flush against the front face of the mouth cushion; (m) the arms apply a force to the front face of the mouth cushion due to tension applied to a lower headgear strap coupled to the arms, to anchor the mouth cushion into the corners surrounding the patient's mouth; (n) the mouth cushion includes a sealing lip and a wall connecting the front face and the sealing lip, and the wall and/or the sealing lip at a superior part of the corner-of-mouth portions of the mouth cushion is more rigid than an inferior part of the corner-of-mouth portions of the mouth cushion; (o) the lateral sides of the mouth cushion are flexible to allow the patient's jaw to drop while maintaining a seal; (p) a width of the mouth seal-forming structure configured to seal against the patient's face above the mouth is smaller than a width of the mouth seal-forming structure configured to seal against the patient's face below the mouth; (g) the mouth cushion and/or the mouth seal-forming structure has a width to seal around the mouth between the patient's cheilion and naso-labial sulcus; (r) the mouth cushion and/or the mouth seal-forming structure has a height to seal around the mouth on an inferior part of the upper lip and a junction between the supramenton and the lower lip; (s) the mouth cushion has a depth configured so as not to extend beyond the pronasale of the patient's nose; (t) the mouth seal forming structure includes an upper lip membrane configured to allow the mouth cushion to expand upwards when the patient's jaw opens; (u) the upper lip membrane includes a central portion that is curved inwardly towards the mouth cushion plenum chamber; (v) the upper lip membrane includes a central portion that is substantially linear or curved outwardly away from the mouth cushion plenum chamber; (w) the mouth seal forming structure includes a lower lip membrane configured to allow the mouth cushion to expand downwards when the patient's jaw opens; (x) the mouth seal forming structure includes an upper lip membrane and a lower lip membrane, wherein a width of the upper lip membrane is smaller than a width of the lower lip membrane; (y) the mouth cushion is configured to expand due to the flow of pressurized gas to hold upper portion and/or lower portion of the mouth cushion outwards from lateral sides of the mouth cushion; (z) the mouth cushion further comprises a tube connector configured to provide breathable gas to the mouth cushion; (aa) the mouth cushion further comprises a second opening configured to receive a tube connector or a removable vent; (ab) the second opening is on the front face of the mouth cushion and below the first opening; and/or (ac) a region of the front face around the second opening is more rigid than other portions of the mouth cushion.

Another aspect of the present technology relates to a patient interface to deliver a flow of breathable gas at a positive pressure with respect to ambient air pressure to an entrance to a patient's airways while the patient is sleeping, to ameliorate sleep disordered breathing, the patient interface comprising: a mouth cushion forming at least part of a mouth cushion plenum chamber pressurizable to the therapeutic pressure, wherein the mouth cushion comprises a mouth seal-forming structure constructed and arranged to form a seal with a region of a patient's face surrounding the entrance to a patient's mouth, the mouth cushion comprising a first opening on a front face of the mouth cushion for flow of breathable gas into and/or out of the mouth cushion plenum chamber, and a pair of lower headgear connectors, each of the lower headgear connectors having an upper arm and a lower arm attached to the front face of the mouth cushion at a position that is spaced inwards from lateral edges of the mouth cushion, the upper arm being spaced from the lower arm; and a positioning and stabilizing structure configured to connect the pair of lower headgear connectors and provide a force to hold the mouth seal-forming structures in a therapeutically effective position on a patient's head.

In examples, the patient interface can include one or more of the following features: (a) a flexible joint connecting to the first opening; (b) a nasal cushion forming at least part of a nasal cushion plenum chamber pressurizable to a therapeutic pressure, wherein the nasal cushion comprises a nasal seal-forming structure constructed and arranged to form a seal with a region of a patient's face surrounding the entrance to a patient's nares; (c) the nasal cushion comprises a nasal joint opening configured to receive one end of the flexible joint, and the flexible joint connects the nasal cushion to the mouth cushion; (d) the flexible joint comprises a concertina section having at least one fold; (e) the concertina allows the mouth cushion to move relative to the nasal cushion in an axial direction, as well as a curved direction to accommodate the patient's supramenton angle; (f) the flexible joint is configured to allow the mouth cushion to move relative to the nasal cushion to adjust for the patient's supramenton angle; (g) the mouth cushion is configured to flex away from the nasal cushion so as to not interfere with an initial positioning of the nasal cushion on the patient's face; (h) the flexible joint and/or the mouth cushion are configured to move towards the patient's supramenton due to a spring bias of the flexible joint and/or introduction of the flow of pressurized breathable gas through the mouth cushion and/or the flexible joint; (i) the mouth cushion includes a gusset that causes the mouth cushion to move towards the patient's mouth upon application of the flow of pressurized gas; (j) the flexible joint has a neutral position and a curved position oriented towards the patient's supramenton, and wherein the flexible joint resists movement from the neutral position to a position away from the patient's face; (k) the flexible joint has an oval cross section; (l) the flexible joint has a nasal cushion end detachably connected to the nasal cushion, and a mouth cushion end permanently connected to the mouth cushion; (m) the flexible joint and the mouth cushion form a one piece construction made of the same material; (n) the nasal cushion includes a nasal cushion opening to receive the nasal cushion end of the flexible joint, and the mouth cushion includes a mouth cushion opening to receive the mouth cushion end, the mouth cushion end directing or receiving the flow of pressurized gas into or from the mouth cushion plenum chamber in a direction that is substantially perpendicular to the patient's Frankfurt horizontal; (o) the nasal cushion end is configured to direct or receive the flow of pressurized breathable gas into or from the nasal plenum chamber in a direction that is substantially parallel to the patient's Frankfurt horizontal; (p) the mouth cushion end is attached to the mouth cushion at a position that is above a horizontal medial plane of the mouth cushion; (q) the nasal cushion includes pillows, nasal puffs or a nasal cradle; (r) the nasal cushion includes a pair of upper headgear connectors; (s) the positioning and stabilizing structure includes a pair of upper headgear straps or conduits connected to the upper headgear connectors and a pair of lower headgear straps connected to the lower headgear connectors; (t) the headgear straps or conduits, in combination with the nasal cushion, provides support for the mouth cushion; (u) each of the lower headgear connectors includes a magnetic connection element; (v) the upper arm and the lower arm are provided in a wish-bone shape; (w) the upper arm and the lower arm distribute support forces, respectively, to a mid-zone and a lower zone of the mouth cushion; (x) the upper arm and the lower arm are flexible and have a U-shape; (y) the U-shape is similar in size and/or shape to lateral side portions of the mouth cushion; (z) the ends of the U-shape are connected to the front face of the mouth cushion and the mid portion of the U-shape includes a magnetic connection element; (aa) the upper arm and the lower arm are made of silicone or a material that is more rigid than silicone; (ab) wherein each of the arms extends from the attached location towards the lateral edges of the mouth cushion; (ac) each of the arms is dimensioned and configured to straddle opposite sides of the patient's cheilion, thus applying forces against corners of the patient's mouth when worn by the patient and supported by the positioning and stabilizing structure; (ad) each of the arms is movable or flexible to lie flush against the front face of the mouth cushion; (ae) the arms apply a force to the front face of the mouth cushion due to tension applied to a lower headgear strap coupled to the arms, to anchor the mouth cushion into the corners surrounding the patient's mouth; (af) the mouth cushion and/or the nasal cushion includes a textile sealing surface mounted on a silicone body; (ag) the mouth cushion includes a front face, a sealing lip and a wall connecting the front face and the sealing lip, all made of silicone; (ah) the wall and/or the sealing lip at a superior part of the corner-of-mouth portions of the mouth cushion is more rigid than an inferior part of the corner-of-mouth portions of the mouth cushion; (ai) the lateral sides of the mouth cushion are flexible to allow the patient's jaw to drop while maintaining a seal; (aj) the mouth cushion has a width to seal around the mouth between the patient's cheilion and naso-labial sulcus; (ak) the mouth cushion has a height to seal around the mouth on an inferior part of the upper lip and a junction between the supramenton and the lower lip; (al) the nasal cushion is a nasal cradle and is configured to be anchored on the superior part of the patient's upper lip, at or below the subnasale; (am) the mouth cushion has a depth configured so as not to extend beyond the nasal cushion and/or the pronasale of the patient's nose; (an) the mouth seal forming structure includes an upper lip membrane configured to allow the mouth cushion to expand upwards when the patient's jaw opens; (ao) the upper lip membrane includes a central portion that is curved inwardly towards the mouth cushion plenum chamber; (ap) the upper lip membrane includes a central portion that is substantially linear or curved outwardly away from the mouth cushion plenum chamber; (aq) the mouth seal forming structure includes a lower lip membrane configured to allow the mouth cushion to expand downwards when the patient's jaw opens; (ar) the mouth cushion is configured to expand due to the flow of pressurized gas to hold upper portion and/or lower portion of the mouth cushion outwards from lateral sides of the mouth cushion; (as) the flexible joint includes an anti-asphyxia valve; (at) the mouth cushion further comprises a tube connector configured to provide breathable gas to the mouth cushion; (au) the mouth cushion further comprises a second opening configured to receive a tube connector; (av) the second opening is on the front face of the mouth cushion and below the first opening; (aw) and/or (ax) a region of the front face around the second opening is more rigid than other portions of the mouth cushion.

An aspect of the present technology relates to a patient interface to deliver a flow of breathable gas at a positive pressure with respect to ambient air pressure to an entrance to a patient's airways including at least the entrance of a patient's nares while the patient is sleeping, to ameliorate sleep disordered breathing. The patient interface comprising:

a nasal cushion forming at least part of a nasal cushion plenum chamber pressurizable to a therapeutic pressure, wherein the nasal cushion comprises a nasal seal-forming structure constructed and arranged to form a seal with a region of a patient's face surrounding the entrance to a patient's nares;

a mouth cushion forming at least part of a mouth cushion plenum chamber pressurizable to the therapeutic pressure, wherein the mouth cushion comprises a mouth seal-forming structure constructed and arranged to form a seal with a region of a patient's face surrounding the entrance to a patient's mouth;

a flexible joint connecting the nasal cushion to the mouth cushion; and a positioning and stabilizing structure to provide a force to the nasal and mouth seal-forming structures to hold the nasal and mouth seal-forming structures in a therapeutically effective position on a patient's head.

In examples, the patient interface can include one or more of the following features: (a) the flexible joint comprises a concertina section having at least one fold; (b) the concertina allows the mouth cushion to move relative to the nasal cushion in an axial direction, as well as a curved direction to accommodate the patient's supramenton angle; (c) the flexible joint is configured to allow the mouth cushion to move relative to the nasal cushion to adjust for the patient's supramenton angle; (d) the mouth cushion is configured to flex away from the nasal cushion so as to not interfere with an initial positioning of the nasal cushion on the patient's face; (e) the flexible joint and/or the mouth cushion are configured to move towards the patient's supramenton due to a spring bias of the flexible joint and/or introduction of the flow of pressurized breathable gas through the mouth cushion and/or the flexible joint; (f) the mouth cushion includes a gusset that causes the mouth cushion to move towards the patient's mouth upon application of the flow of pressurized gas; (g) the flexible joint has a neutral position and a curved position oriented towards the patient's supramenton, and wherein the flexible joint resists movement from the neutral position to a position away from the patient's face; (h) the flexible joint has an oval cross section; (i) the flexible joint has a nasal cushion end detachably connected to the nasal cushion, and a mouth cushion end permanently connected to the mouth cushion; (j) the flexible joint and the mouth cushion form a one piece construction made of the same material; (k) the nasal cushion includes a nasal cushion opening to receive the nasal cushion end of the flexible joint, and the mouth cushion includes a mouth cushion opening to receive the mouth cushion end, the mouth cushion end directing or receiving the flow of pressurized gas into or from the mouth cushion plenum chamber in a direction that is substantially perpendicular to the patient's Frankfurt horizontal; (l) the nasal cushion end is configured to direct or receive the flow of pressurized breathable gas into or from the nasal plenum chamber in a direction that is substantially parallel to the patient's Frankfurt horizontal; (m) the mouth cushion end is attached to the mouth cushion at a position that is above a horizontal medial plane of the mouth cushion; (n) the nasal cushion includes pillows, nasal puffs or a nasal cradle; (o) the nasal cushion includes a pair of upper headgear connectors, and the mouth cushion includes a pair of lower headgear connectors; (p) the positioning and stabilizing structure includes a pair of upper headgear straps or conduits connected to the upper headgear connectors and a pair of lower headgear straps connected to the lower headgear connectors; (q) the headgear straps or conduits, in combination with the nasal cushion, provides support for the mouth cushion; (r) each of the lower headgear connectors includes a magnetic connection element; (s) the lower headgear connectors each include a pair of arms having a wish-bone shape, each of the lower headgear connectors having an upper arm and a lower arm connected to a front face of the mouth cushion, the upper arm being spaced from the lower arm; (t) the upper arm and the lower arm distribute support forces, respectively, to a mid-zone and a lower zone of the mouth cushion; (u) each of the pair of arms is flexible and has a U-shape; (v) the U-shape is similar in size and/or shape to lateral side portions of the mouth cushion; (w) each of the pair of arms is made of silicone or a material that is more rigid than silicone; (x) each of the pair of arms is connected to a front face of the mouth cushion made of silicone; (y) each of the arms is attached to the front face of the mouth cushion at a position that is spaced inwards from the lateral edge of the mouth cushion; (z) each of the arms is dimensioned and configured to straddle opposite sides of the patient's cheilion, thus applying forces against corners of the patient's mouth when worn by the patient and supported by the positioning and stabilizing structure; (aa) each of the arms is movable or flexible to lie flush against the front face of the mouth cushion; (ab) the arms apply a force to the front face of the mouth cushion due to tension applied to a lower headgear strap coupled to the arms, to anchor the mouth cushion into the corners surrounding the patient's mouth; (ac) the mouth cushion and/or the nasal cushion includes a textile sealing surface mounted on a silicone body; (ad) the mouth cushion includes a front face, a sealing lip and a wall connecting the front face and the sealing lip, all made of silicone; (ae) the wall and/or the sealing lip at a superior part of the corner-of-mouth portions of the mouth cushion is more rigid than an inferior part of the corner-of-mouth portions of the mouth cushion; (af) the lateral sides of the mouth cushion are flexible to allow the patient's jaw to drop while maintaining a seal; (ag) the mouth cushion has a width to seal around the mouth between the patient's cheilion and naso-labial sulcus; (ah) the mouth cushion has a height to seal around the mouth on an inferior part of the upper lip and a junction between the supramenton and the lower lip; (al) the nasal cushion is a nasal cradle and is configured to be anchored on the superior part of the patient's upper lip, at or below the subnasale; (aj) the mouth cushion has a depth configured so as not to extend beyond the nasal cushion and/or the pronasale of the patient's nose; (ak) the mouth seal forming structure includes an upper lip membrane configured to allow the mouth cushion to expand upwards when the patient's jaw opens; (al) the upper lip membrane includes a central portion that is curved inwardly towards the mouth cushion plenum chamber; (am) the upper lip membrane includes a central portion that is substantially linear or curved outwardly away from the mouth cushion plenum chamber; (an) the mouth seal forming structure includes a lower lip membrane configured to allow the mouth cushion to expand downwards when the patient's jaw opens; (ao) the mouth cushion is configured to expand due to the flow of pressurized gas to hold upper portion and/or lower portion of the mouth cushion outwards from lateral sides of the mouth cushion; (ap) the flexible joint includes an anti-asphyxia valve; (aq) further comprising a tube connector configured to provide breathable gas to the nasal cushion and to allow the patient, in use, to position the tube in a superior position or an inferior position relative to the patient's head; (ar) the mouth cushion is made of a first type of material and the nasal cushion is made of a second type of material different from the first type of material; (as) the mouth cushion includes a sealing surface made of a first type of material and the nasal cushion includes a sealing surface of second type of material different from the first type of material; one of the first type of material and the second type of material is silicone and the other one of the first type of material and the second type of material is textile; and/or (at) further comprising a pair of vent connectors including a plurality of holes, the pair of vent connectors configured to couple a nasal headgear to a pair of nasal connectors disposed on the nasal cushion.

Another aspect of the present technology relates to a method of fitting an oro-nasal mask on a patient, the oro-nasal mask configured to deliver a flow of air at a positive pressure with respect to ambient air pressure to the patient's while the patient is sleeping, to ameliorate sleep disordered breathing. The method comprising: providing a nasal cushion forming at least part of a nasal cushion plenum chamber pressurizable to a therapeutic pressure, wherein the nasal cushion comprises a nasal seal-forming structure constructed and arranged to form a seal with a region of a patient's face surrounding an entrance to a patient's nares; providing a mouth cushion forming at least part of a mouth cushion plenum chamber pressurizable to the therapeutic pressure, wherein the mouth cushion comprises a seal-forming structure constructed and arranged to form a seal with a region of a patient's face surrounding the entrance to a patient's mouth; connecting the nasal cushion and the mouth cushion with a flexible joint; and holding the nasal and mouth seal-forming structures in a therapeutically effective position on a patient's head by: placing the nasal cushion under the patient's nose and engaging a superior portion of the patient's upper lip, whilst the mouth cushion is connected to the nasal cushion, securing the nasal cushion on the patient's head using upper headgear conduits or straps, adjusting the length and/or position of the upper headgear conduits or straps, positioning an upper membrane of the mouth cushion on an inferior portion of the patient's upper lip, below the nasal cushion, allowing engagement between the mouth cushion and the nasal cushion, securing the mouth cushion on the patient's head using lower headgear straps, adjusting the length and/or position of the lower headgear straps, wherein the adjustment of the upper headgear conduits or straps is substantially independent of adjustment of the lower headgear straps.

An aspect of the present technology relates to a flexible joint including a nasal cushion end configured to connect to a front surface of a nasal cushion and a mouth cushion end configured to connect to a front surface of a mouth cushion.

In examples, (a) the flexible joint comprises a concertina section having at least one fold; (b) allows the mouth cushion to move relative to the nasal cushion in an axial direction, as well as a curved direction to accommodate the patient's supramenton angle; (c) the flexible joint is configured to allow the mouth cushion to move relative to the nasal cushion to adjust for the patient's supramenton; (d) the flexible joint is configured to move towards the patient's supramenton due to a spring bias of the flexible joint and/or introduction of the flow of pressurized breathable gas through the mouth cushion and/or the flexible joint; (e) the flexible joint has an oval cross section; (f) the nasal cushion end is detachably connected to the nasal cushion, and the mouth cushion end is permanently connected to the mouth cushion; (g) the flexible joint and the mouth cushion form a one piece construction made of the same material; (h) the nasal cushion end is configured to direct or receive the flow of pressurized breathable gas into or from the nasal plenum chamber in a direction that is substantially parallel to the patient's Frankfurt horizontal; (i) the mouth cushion end is attached to the mouth cushion at a position that is above a horizontal medial plane of the mouth cushion; (j) the flexible joint includes an anti-asphyxia valve; and/or (k) anti-asphyxia valve is provided on a front surface of the flexible joint.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

4 BRIEF DESCRIPTION OF THE DRAWINGS

The present technology is illustrated by way of example, and not by way of limitation, in the figures of the accompanying drawings, in which like reference numerals refer to similar elements including:

4.1 Treatment Systems

FIG. 1A shows a system including a patient 1000 wearing a patient interface 3000, in the form of nasal pillows, receiving a supply of air at positive pressure from an RPT device 4000. Air from the RPT device 4000 is humidified in a humidifier 5000, and passes along an air circuit 4170 to the patient 1000. A bed partner 1100 is also shown. The patient is sleeping in a supine sleeping position.

FIG. 1B shows a system including a patient 1000 wearing a patient interface 3000, in the form of a nasal mask, receiving a supply of air at positive pressure from an RPT device 4000. Air from the RPT device is humidified in a humidifier 5000, and passes along an air circuit 4170 to the patient 1000.

FIG. 1C shows a system including a patient 1000 wearing a patient interface 3000, in the form of a full-face mask, receiving a supply of air at positive pressure from an RPT device 4000. Air from the RPT device is humidified in a humidifier 5000, and passes along an air circuit 4170 to the patient 1000. The patient is sleeping in a side sleeping position.

4.2 Respiratory System and Facial Anatomy

Figure 2A:
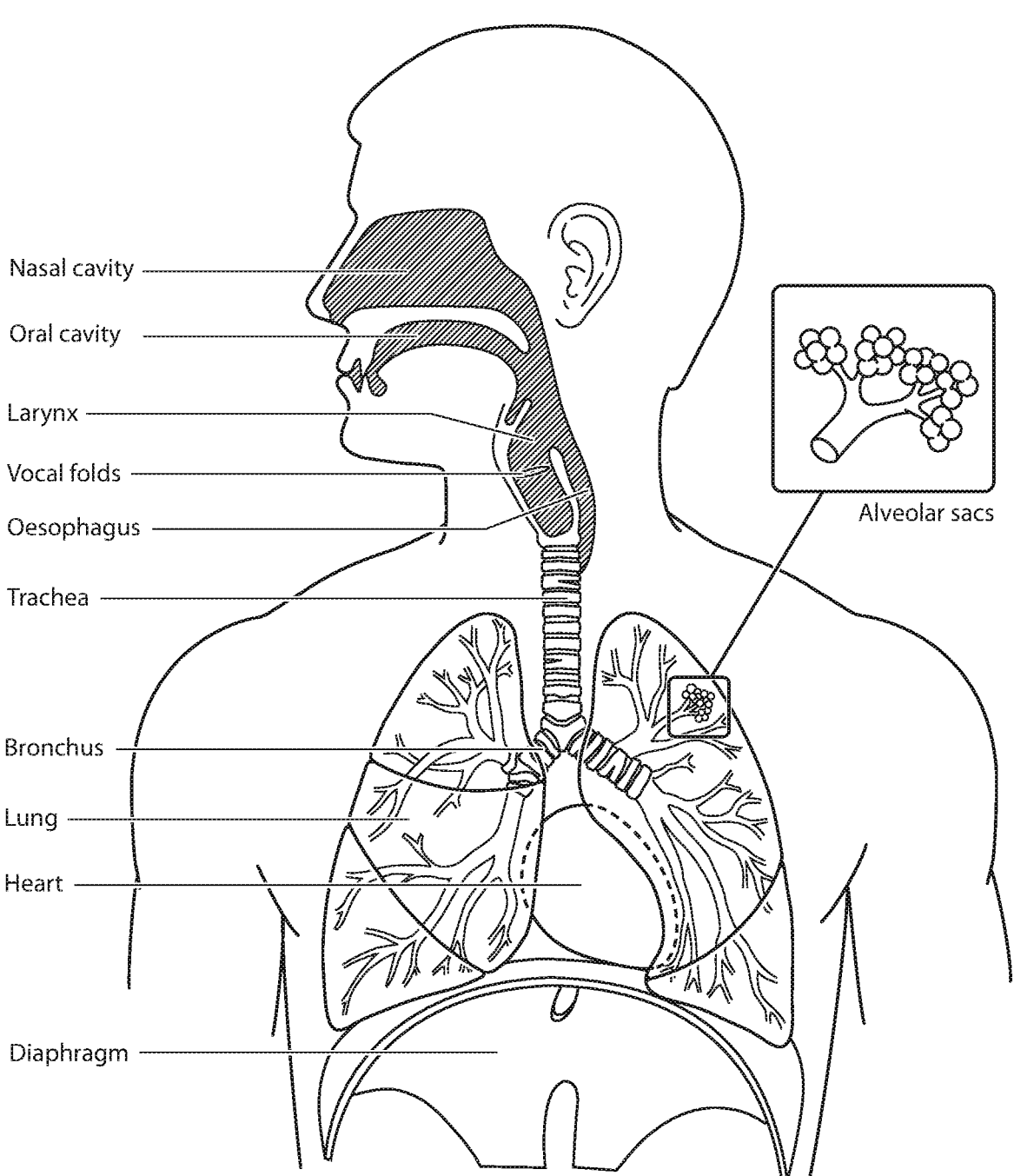
FIG. 2A shows an overview of a human respiratory system including the nasal and oral cavities, the larynx, vocal folds, oesophagus, trachea, bronchus, lung, alveolar sacs, heart and diaphragm.
Figure 2B:
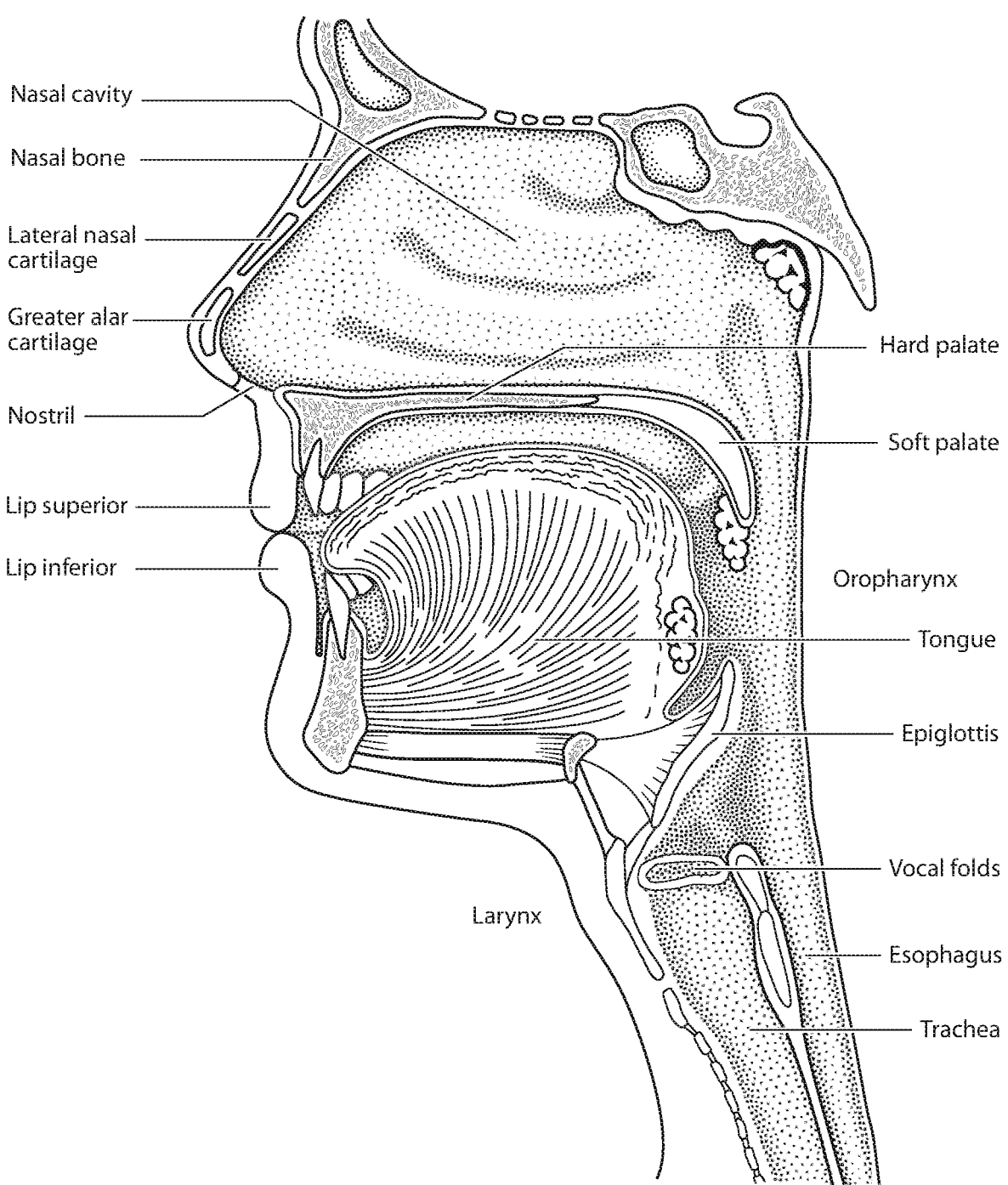
FIG. 2B shows a view of a human upper airway including the nasal cavity, nasal bone, lateral nasal cartilage, greater alar cartilage, nostril, lip superior, lip inferior, larynx, hard palate, soft palate, oropharynx, tongue, epiglottis, vocal folds, oesophagus and trachea.
Figure 2C:
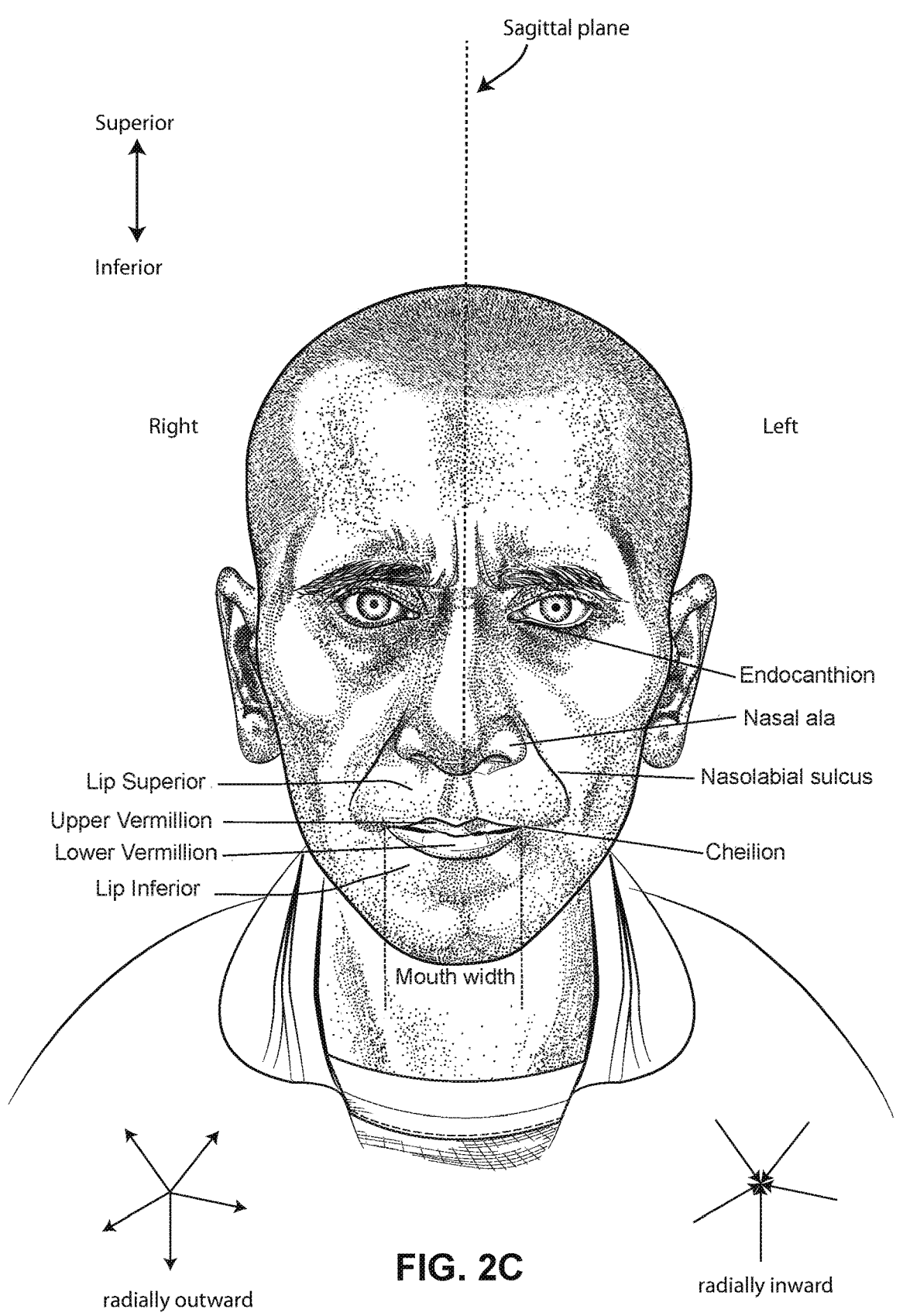
FIG. 2C is a front view of a face with several features of surface anatomy identified including the lip superior, upper vermilion, lower vermilion, lip inferior, mouth width, endocanthion, a nasal ala, nasolabial sulcus and cheilion. Also indicated are the directions superior, inferior, radially inward and radially outward.
Figure 2D:
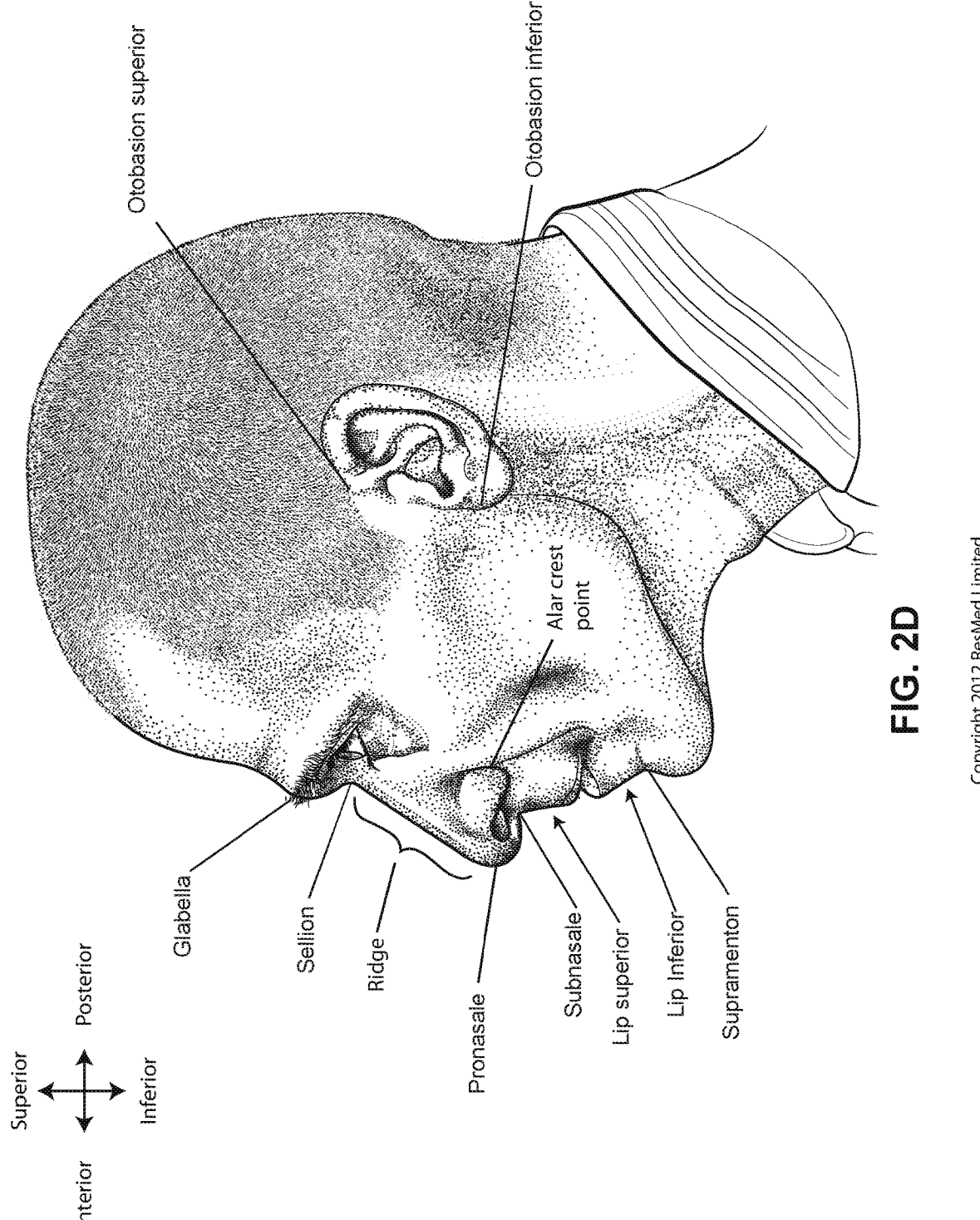
FIG. 2D is a side view of a head with several features of surface anatomy identified including glabella, sellion, pronasale, subnasale, lip superior, lip inferior, supramenton, nasal ridge, alar crest point, otobasion superior and otobasion inferior. Also indicated are the directions superior & inferior, and anterior & posterior.
Figure 2E:
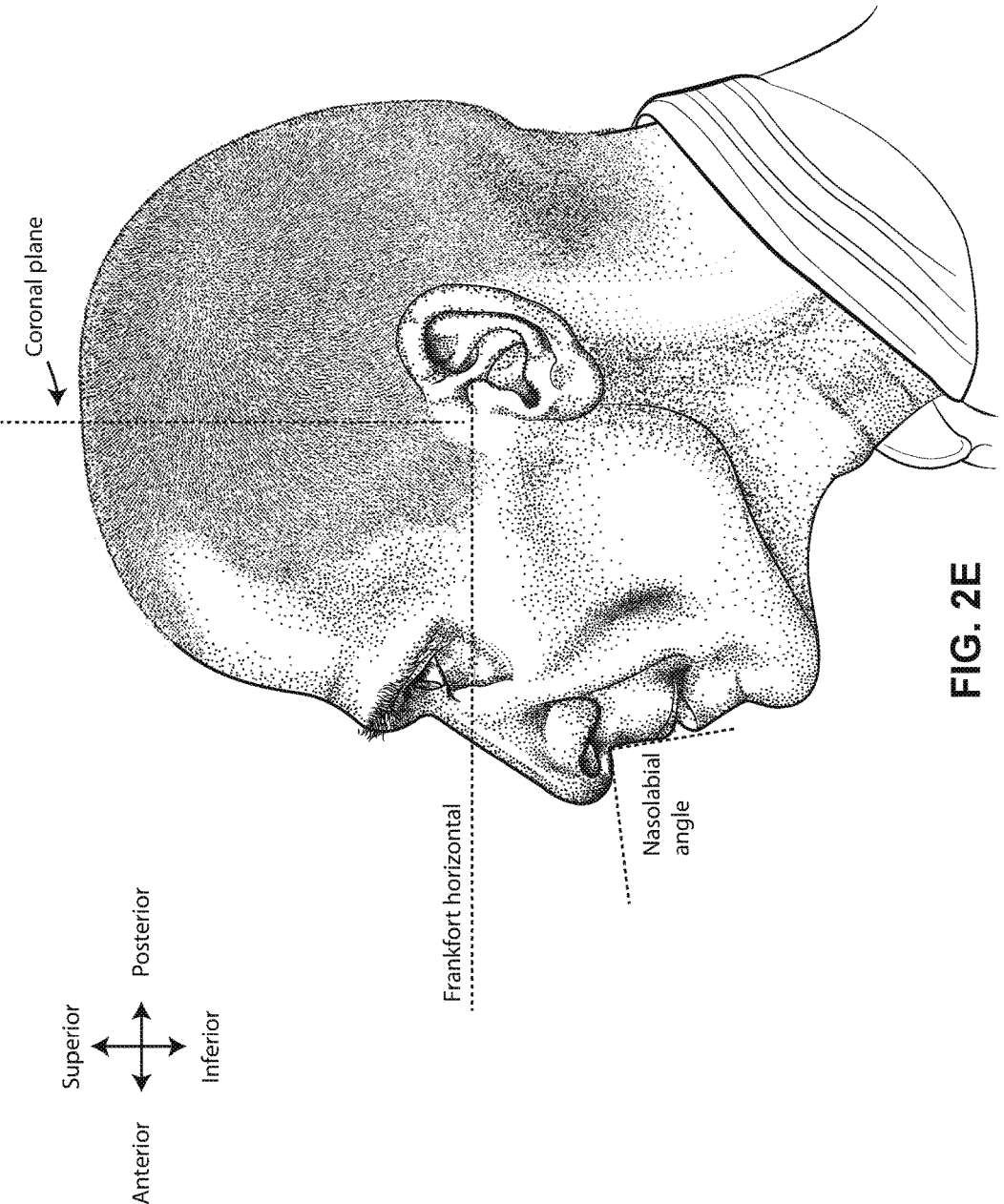

FIG. 2E is a further side view of a head. The approximate locations of the Frankfort horizontal and nasolabial angle are indicated. The coronal plane is also indicated.

Figure 2F:
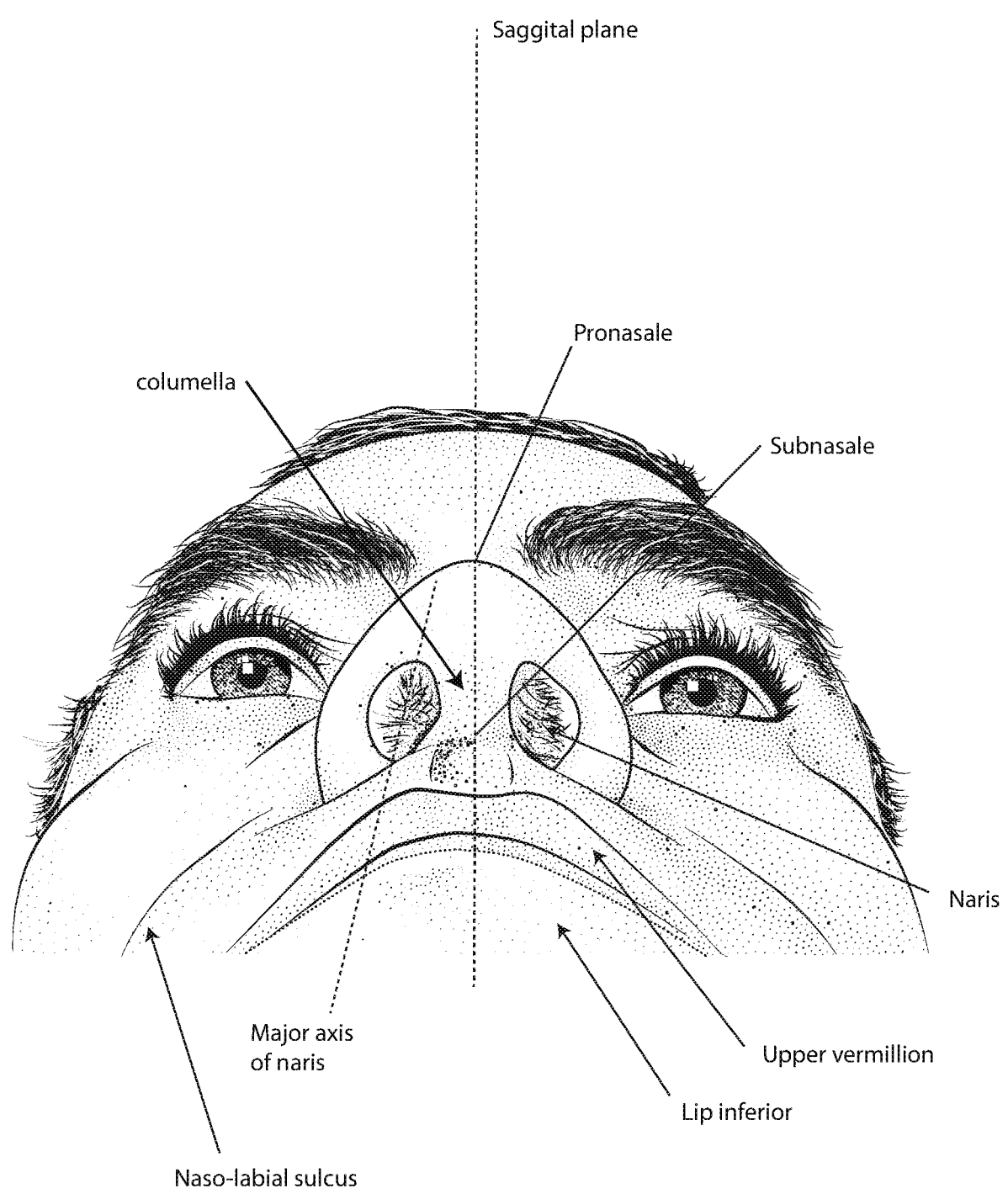

FIG. 2F shows a base view of a nose with several features identified including naso-labial sulcus, lip inferior, upper Vermilion, naris, subnasale, columella, pronasale, the major axis of a naris and the midsagittal plane.

FIG. 2G shows a side view of the superficial features of a nose.

FIG. 2H shows subcutaneal structures of the nose, including lateral cartilage, septum cartilage, greater alar cartilage, lesser alar cartilage, sesamoid cartilage, nasal bone, epidermis, adipose tissue, frontal process of the maxilla and fibrofatty tissue.

FIG. 2I shows a medial dissection of a nose, approximately several millimeters from the midsagittal plane, amongst other things showing the septum cartilage and medial crus of greater alar cartilage.

Figures 2J, 2K:
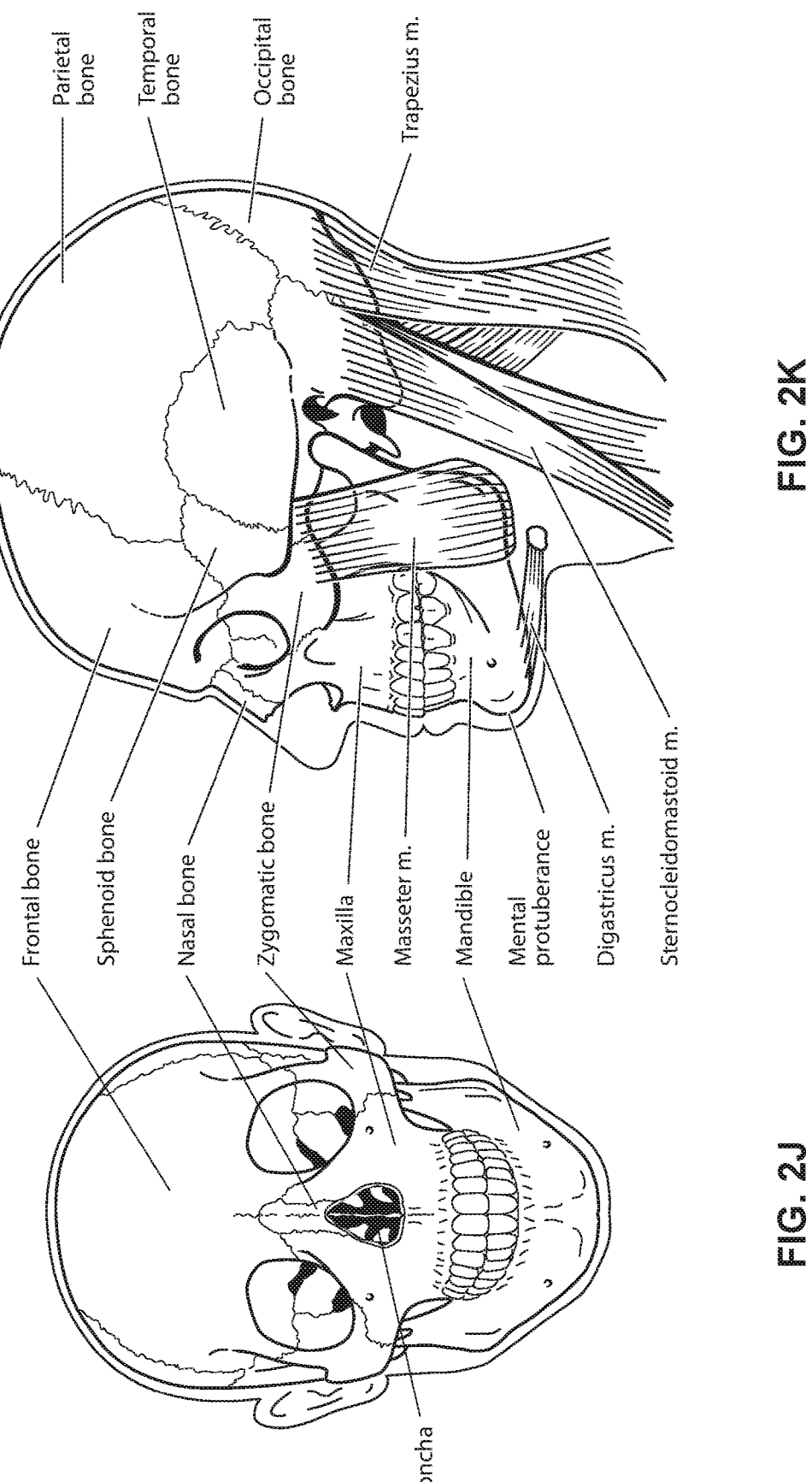

FIG. 2J shows a front view of the bones of a skull including the frontal, nasal and zygomatic bones. Nasal concha are indicated, as are the maxilla, and mandible.

FIG. 2K shows a lateral view of a skull with the outline of the surface of a head, as well as several muscles. The following bones are shown: frontal, sphenoid, nasal, zygomatic, maxilla, mandible, parietal, temporal and occipital. The mental protuberance is indicated. The following muscles are shown: digastricus, masseter, sternocleidomastoid and trapezius.

Figure 2L:
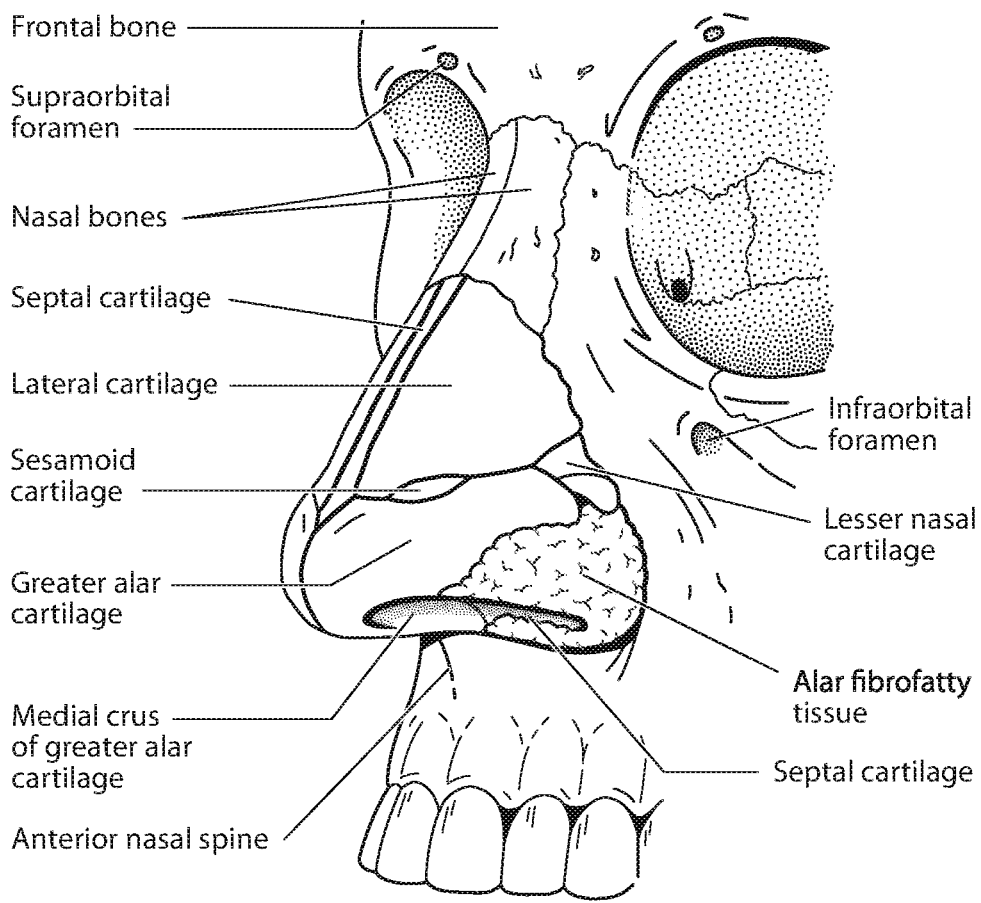

FIG. 2L shows an anterolateral view of a nose.

4.3 Patient Interface

Figure 3A:
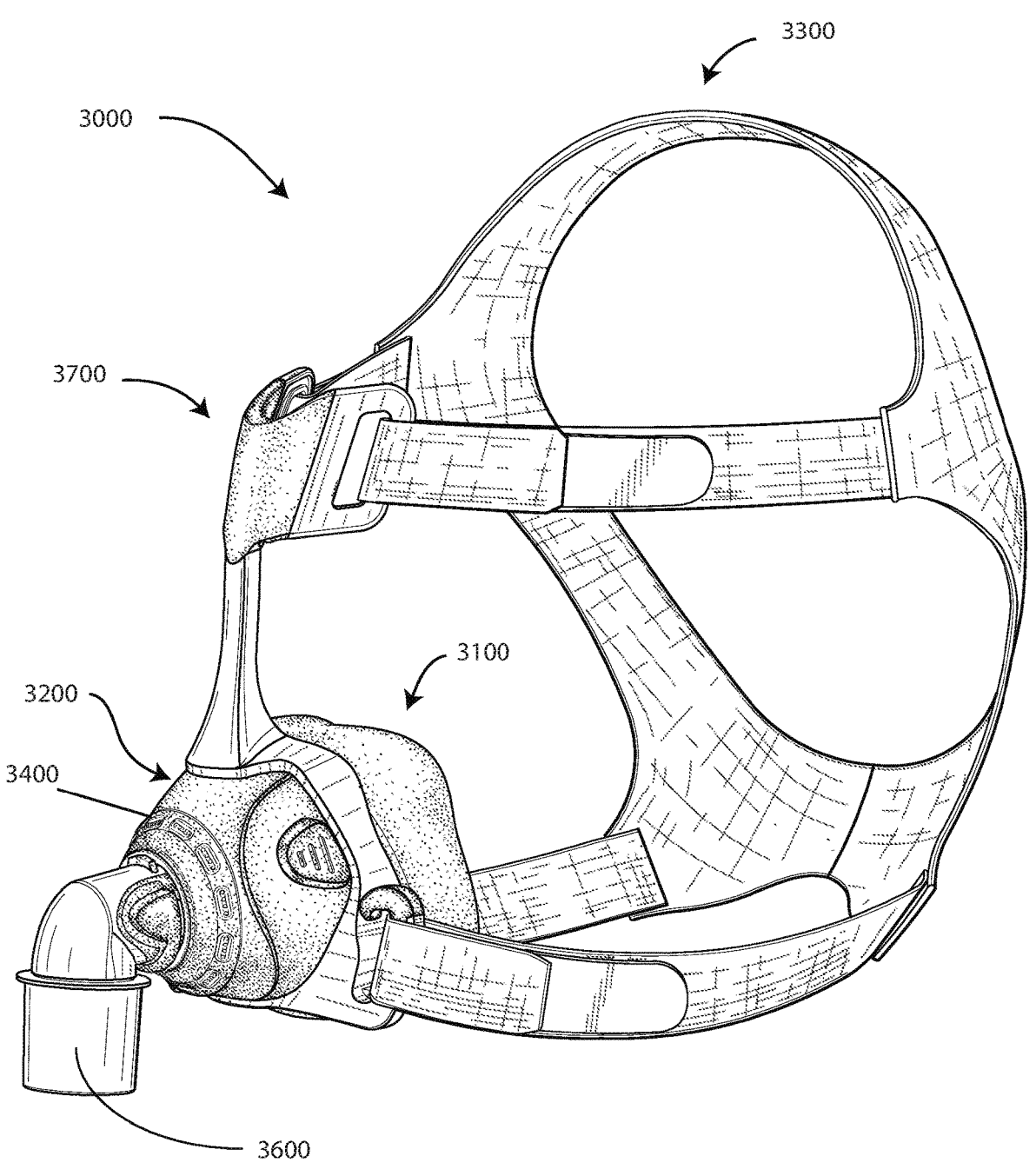

FIG. 3A shows a patient interface in the form of a nasal mask in accordance with one form of the present technology.

FIG. 3B shows a schematic of a cross-section through a structure at a point. An outward normal at the point is indicated. The curvature at the point has a positive sign, and a relatively large magnitude when compared to the magnitude of the curvature shown in FIG. 3C.

FIG. 3C shows a schematic of a cross-section through a structure at a point. An outward normal at the point is indicated. The curvature at the point has a positive sign, and a relatively small magnitude when compared to the magnitude of the curvature shown in FIG. 3B.

FIG. 3D shows a schematic of a cross-section through a structure at a point. An outward normal at the point is indicated. The curvature at the point has a value of zero.

FIG. 3E shows a schematic of a cross-section through a structure at a point. An outward normal at the point is indicated. The curvature at the point has a negative sign, and a relatively small magnitude when compared to the magnitude of the curvature shown in FIG. 3F.

FIG. 3F shows a schematic of a cross-section through a structure at a point. An outward normal at the point is indicated. The curvature at the point has a negative sign, and a relatively large magnitude when compared to the magnitude of the curvature shown in FIG. 3E.

Figures 3G, 3H:
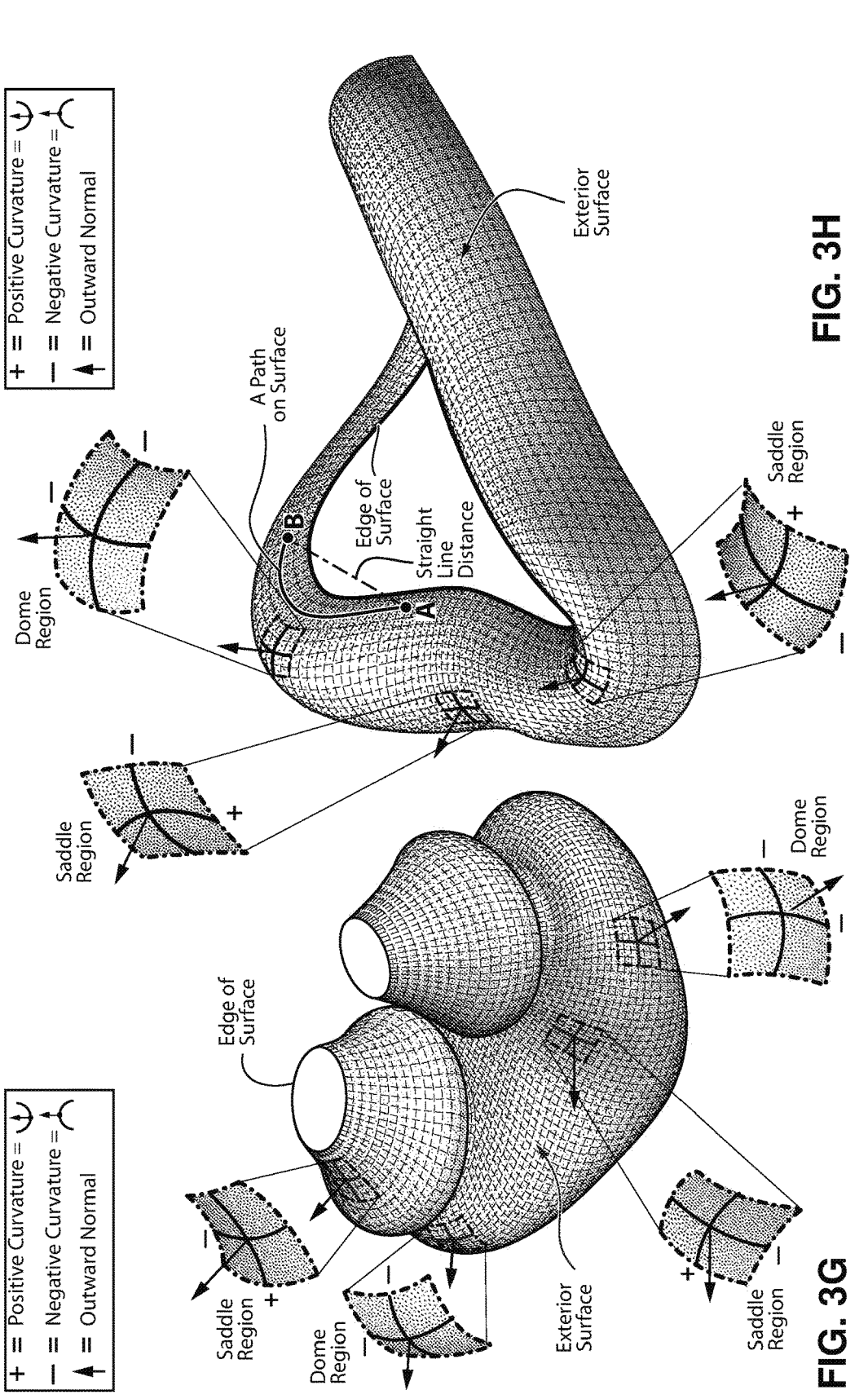

FIG. 3G shows a cushion for a mask that includes two pillows. An exterior surface of the cushion is indicated. An edge of the surface is indicated. Dome and saddle regions are indicated.

FIG. 3H shows a cushion for a mask. An exterior surface of the cushion is indicated. An edge of the surface is indicated. A path on the surface between points A and B is indicated. A straight line distance between A and B is indicated. Two saddle regions and a dome region are indicated.

Figures 3I, 3J, 3K, 3L, 3M, 3N:
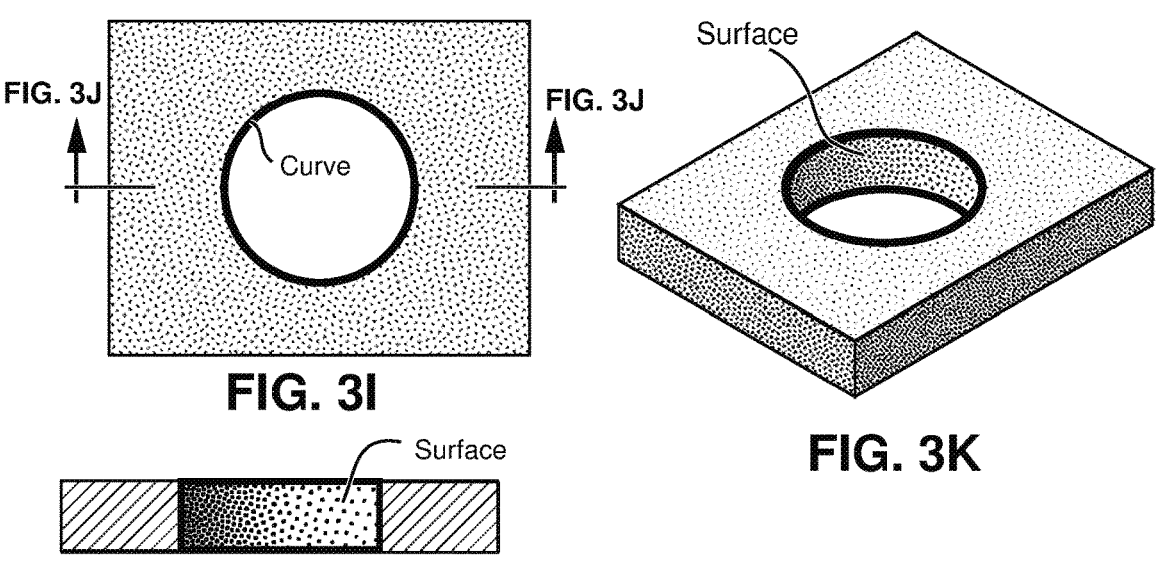

FIG. 3I shows the surface of a structure, with a one dimensional hole in the surface. The illustrated plane curve forms the boundary of a one dimensional hole.

FIG. 3J shows a cross-section through the structure of FIG. 3I. The illustrated surface bounds a two dimensional hole in the structure of FIG. 3I.

FIG. 3K shows a perspective view of the structure of FIG. 3I, including the two dimensional hole and the one dimensional hole. Also shown is the surface that bounds a two dimensional hole in the structure of FIG. 3I.

FIG. 3L shows a mask having an inflatable bladder as a cushion.

FIG. 3M shows a cross-section through the mask of FIG. 3L, and shows the interior surface of the bladder. The interior surface bounds the two dimensional hole in the mask.

FIG. 3N shows a further cross-section through the mask of FIG. 3L. The interior surface is also indicated.

FIG. 3O illustrates a left-hand rule.

FIG. 3P illustrates a right-hand rule.

FIG. 3Q shows a left ear, including the left ear helix.

FIG. 3R shows a right ear, including the right ear helix.

FIG. 3S shows a right-hand helix.

FIG. 3T shows a view of a mask, including the sign of the torsion of the space curve defined by the edge of the sealing membrane in different regions of the mask.

Figures 3U, 3V, 3W, 3X:
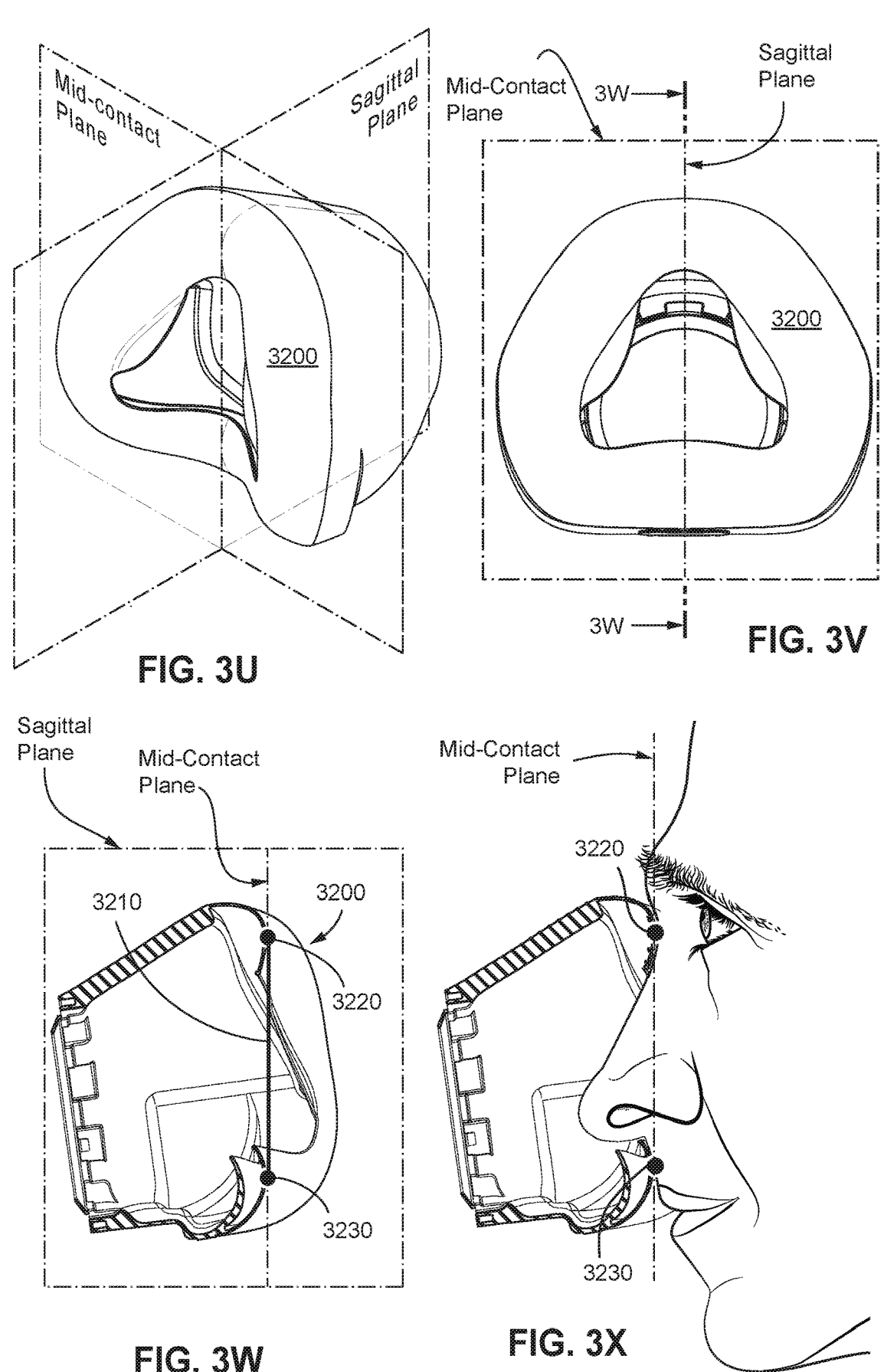

FIG. 3U shows a view of a plenum chamber 3200 showing a sagittal plane and a mid-contact plane.

FIG. 3V shows a view of a posterior of the plenum chamber of FIG. 3U. The direction of the view is normal to the mid-contact plane. The sagittal plane in FIG. 3V bisects the plenum chamber into left-hand and right-hand sides.

FIG. 3W shows a cross-section through the plenum chamber of FIG. 3V, the cross-section being taken at the sagittal plane shown in FIG. 3V. A 'mid-contact' plane is shown. The mid-contact plane is perpendicular to the sagittal plane. The orientation of the mid-contact plane corresponds to the orientation of a chord 3210 which lies on the sagittal plane and just touches the cushion of the plenum chamber at two points on the sagittal plane: a superior point 3220 and an inferior point 3230. Depending on the geometry of the cushion in this region, the mid-contact plane may be a tangent at both the superior and inferior points.

FIG. 3X shows the plenum chamber 3200 of FIG. 3U in position for use on a face. The sagittal plane of the plenum chamber 3200 generally coincides with the midsagittal plane of the face when the plenum chamber is in position for use. The mid-contact plane corresponds generally to the 'plane of the face' when the plenum chamber is in position for use. In FIG. 3X the plenum chamber 3200 is that of a nasal mask, and the superior point 3220 sits approximately on the sellion, while the inferior point 3230 sits on the lip superior.

4.4 Patient Interface According to the Present Technology

Figure 4A:
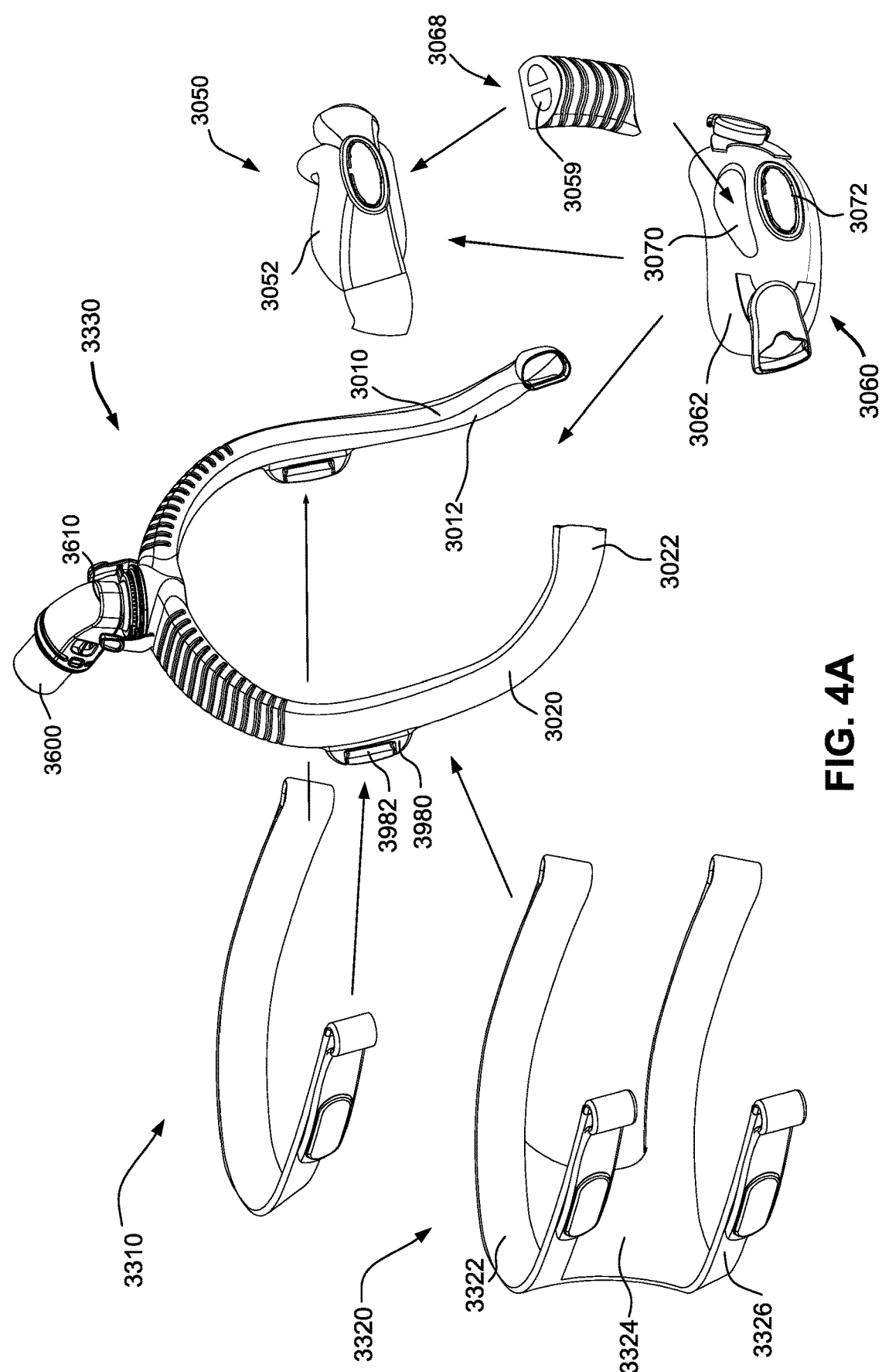

FIG. 4A shows a configurable patient interface according to an example of the present technology.

Figure 4B:
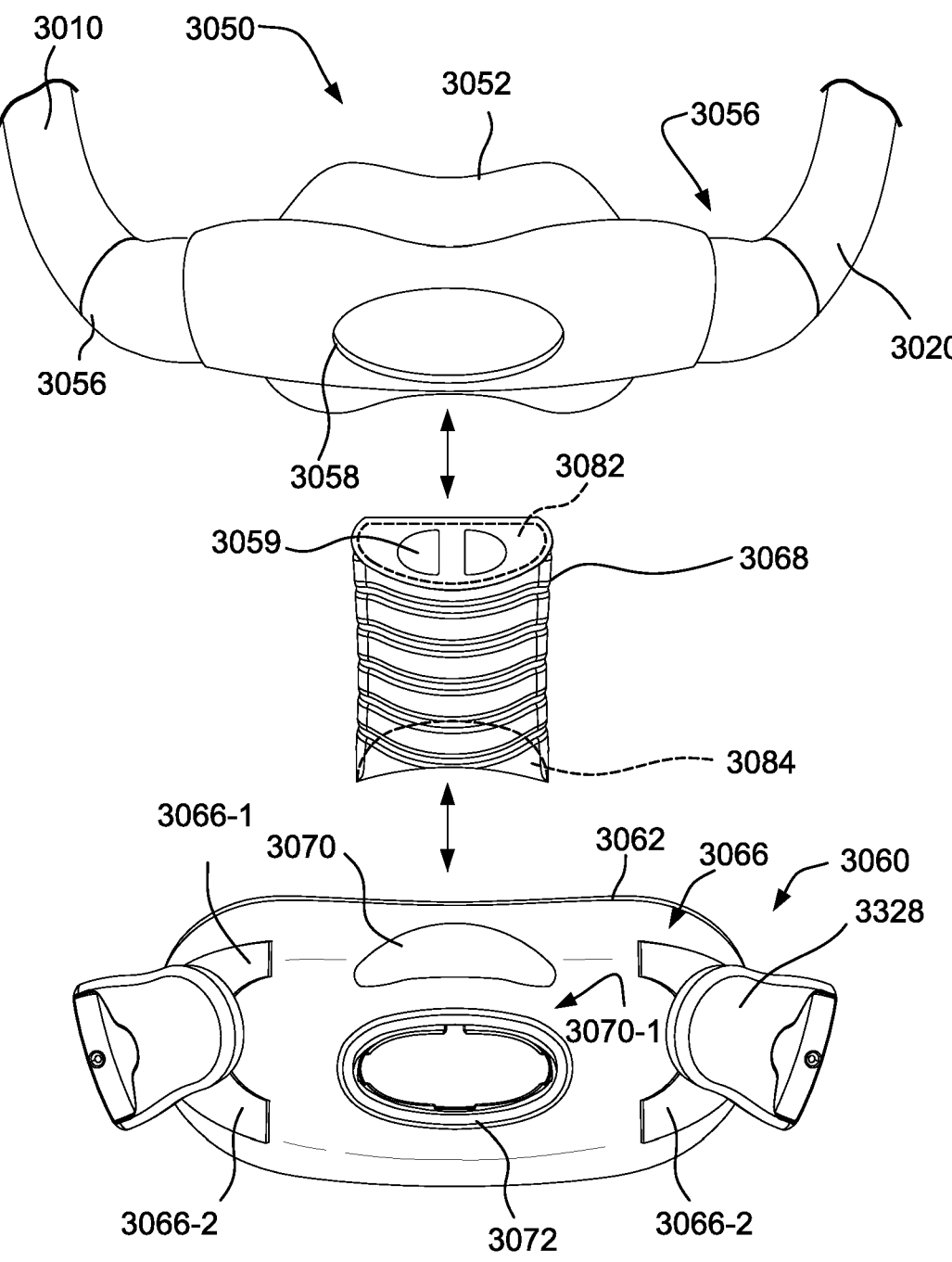

FIG. 4B shows a configurable patient interface using conduits to provide breathable gas to a nasal cushion according to an example of the present technology.

Figure 4C:
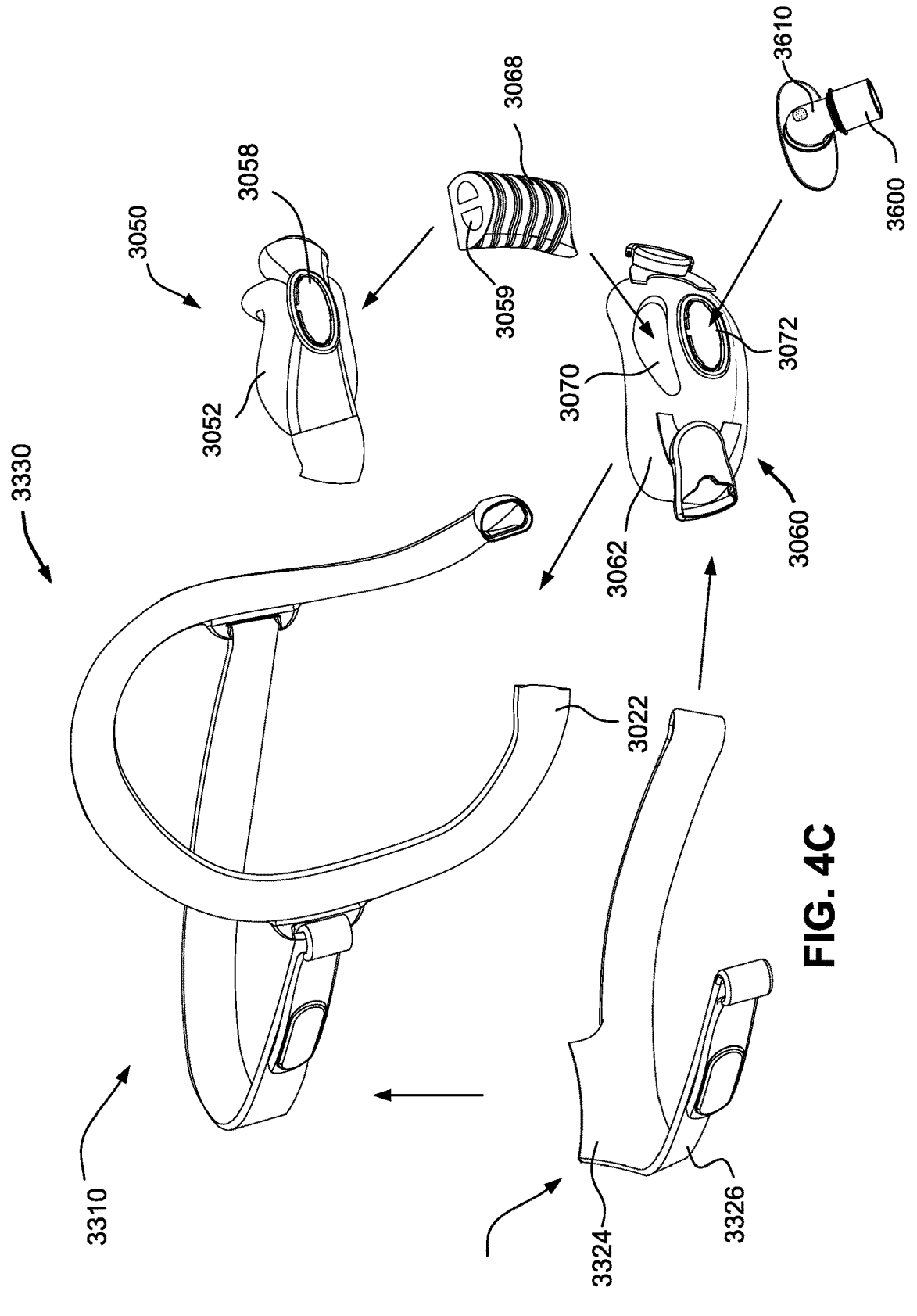

FIG. 4C shows a configurable patient interface according to another example of the present technology.

Figure 4D:
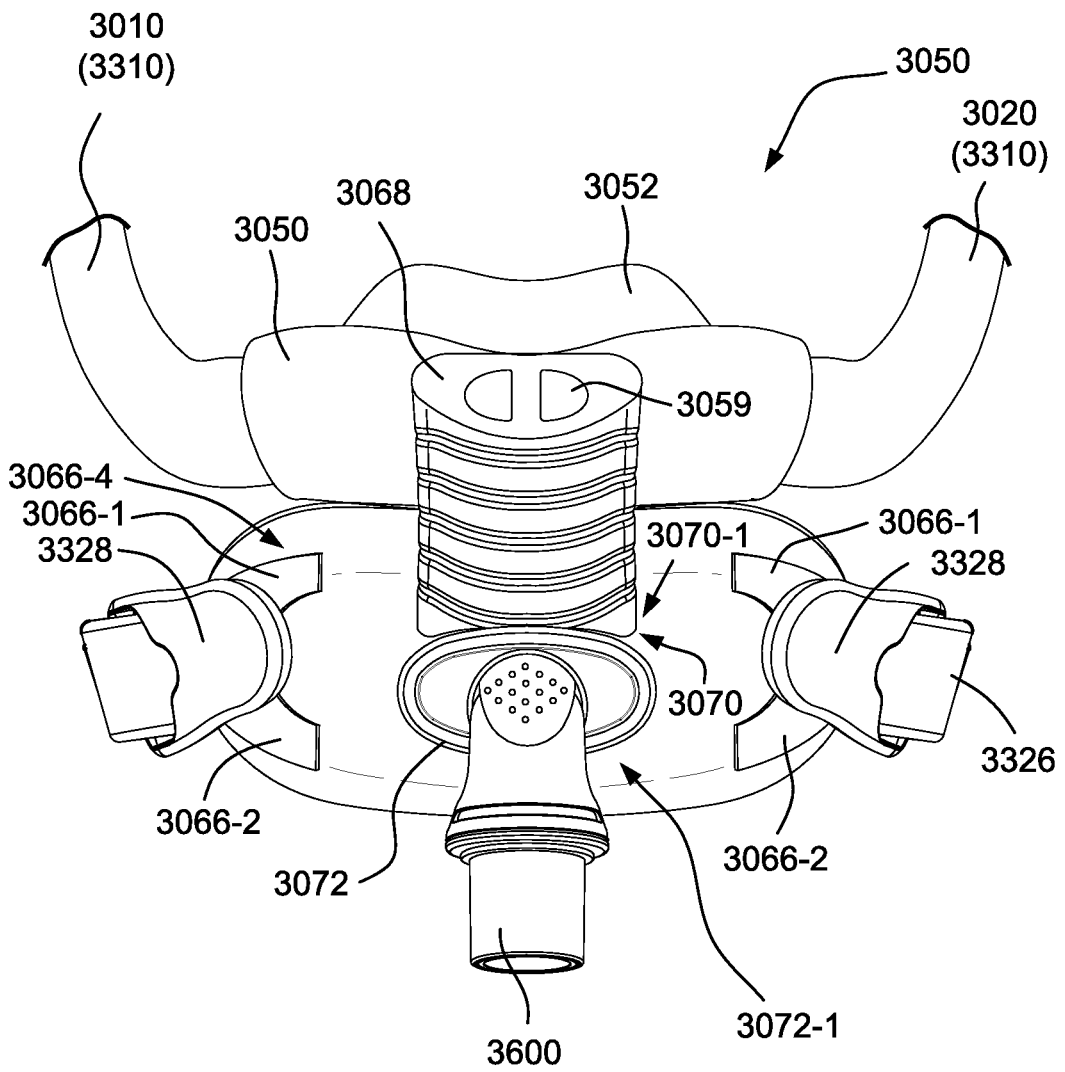

FIG. 4D shows a configurable patient interface to which breathable gas is provided via a tube coupled to a front surface of a mouth cushion according to an example of the present technology.

Figure 5A:
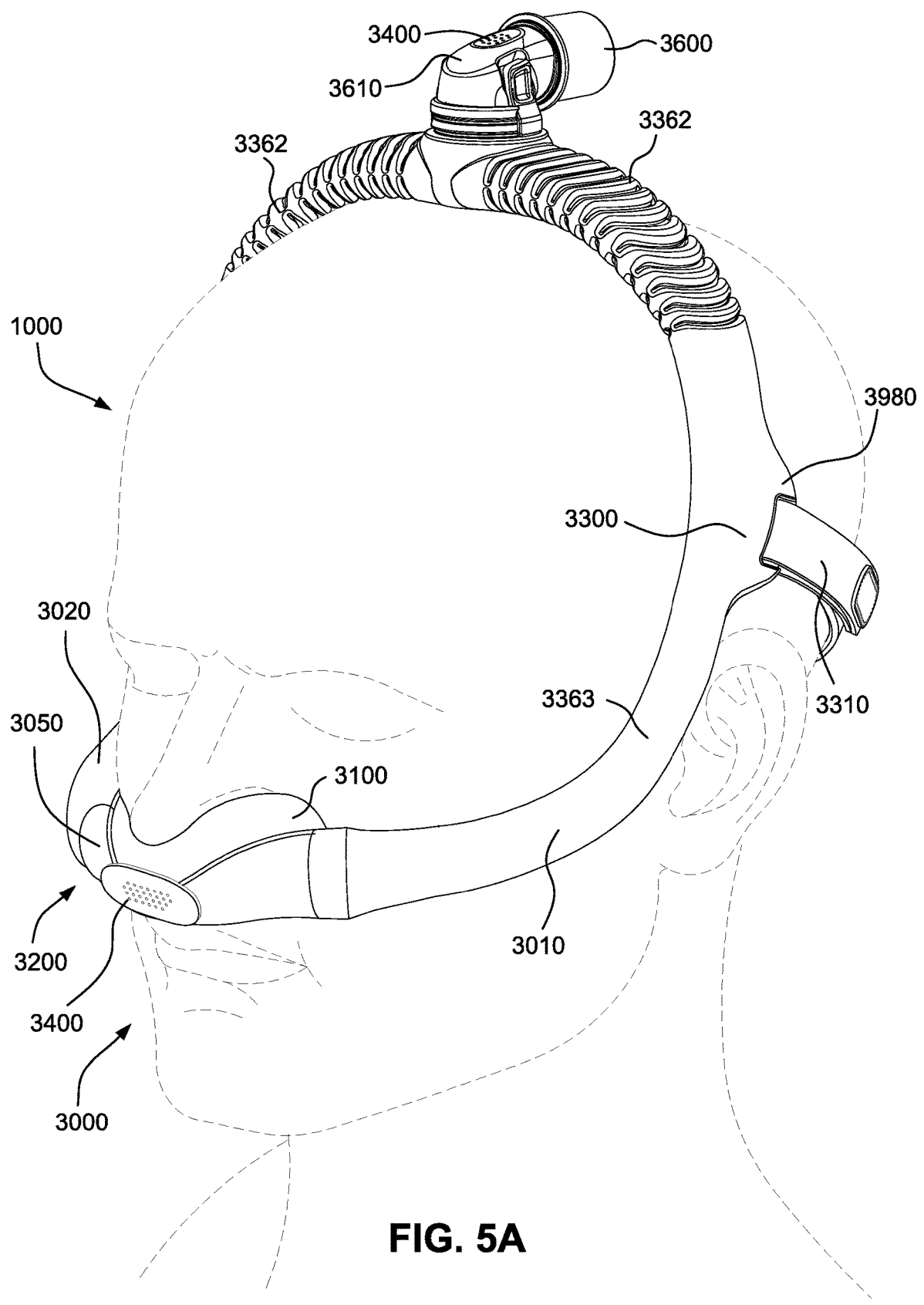

FIG. 5A shows a perspective view of a nasal mask configuration using conduits according to an example of the present technology.

Figure 5B:
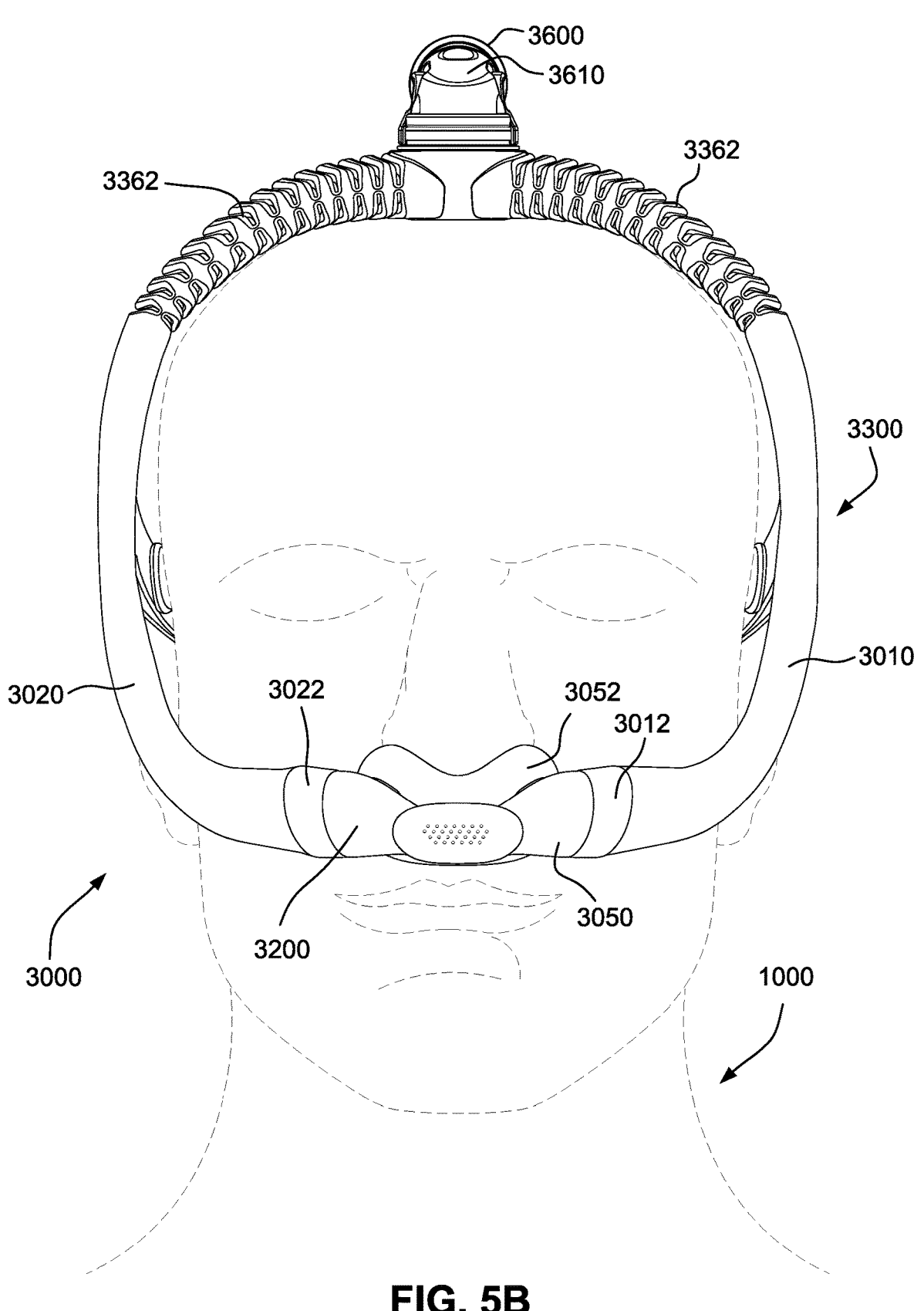

FIG. 5B shows a front view of a nasal mask configuration using conduits according to an example of the present technology.

Figure 5C:
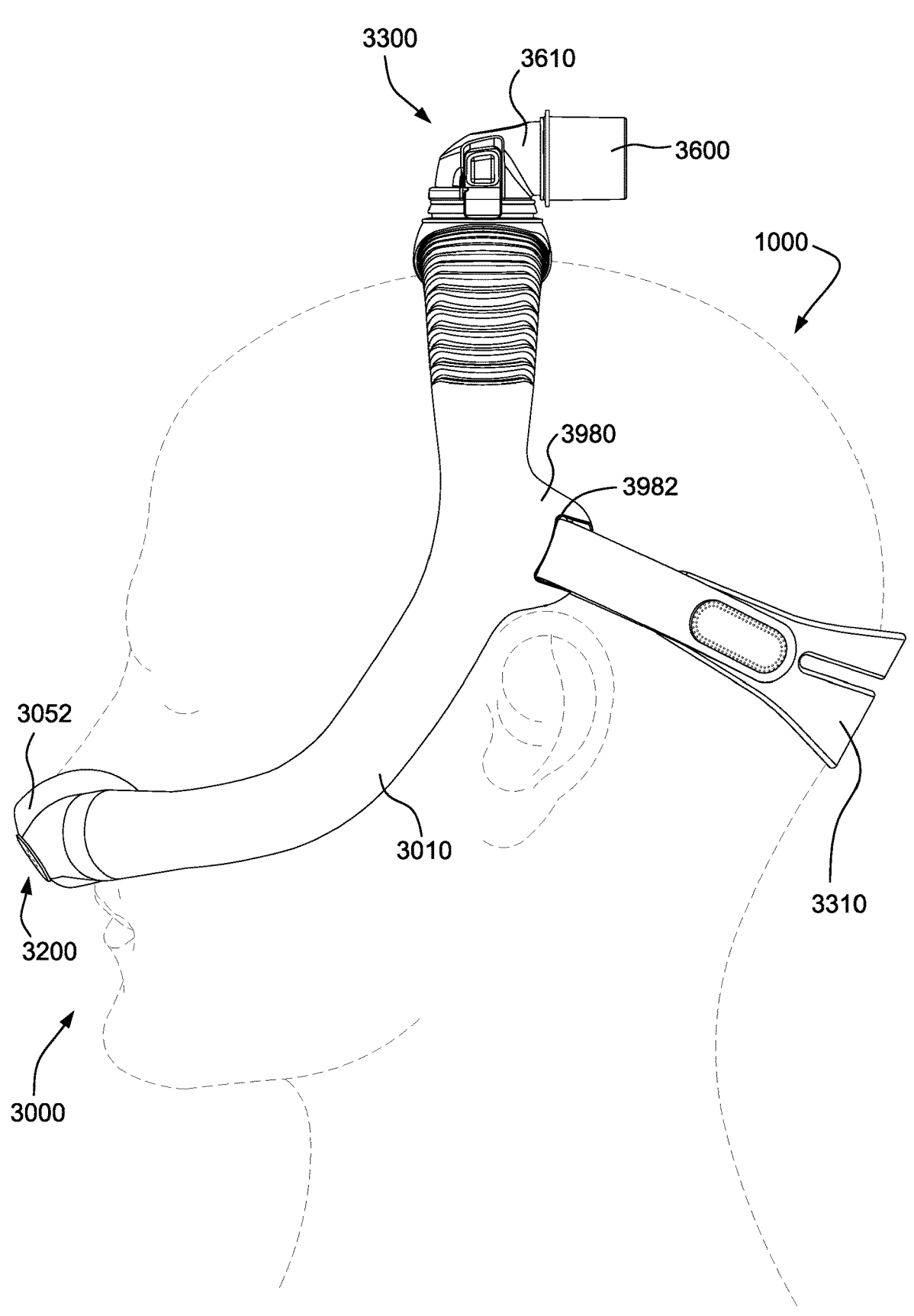

FIG. 5C shows a side view of a nasal mask configuration using conduits according to an example of the present technology.

Figure 5D:
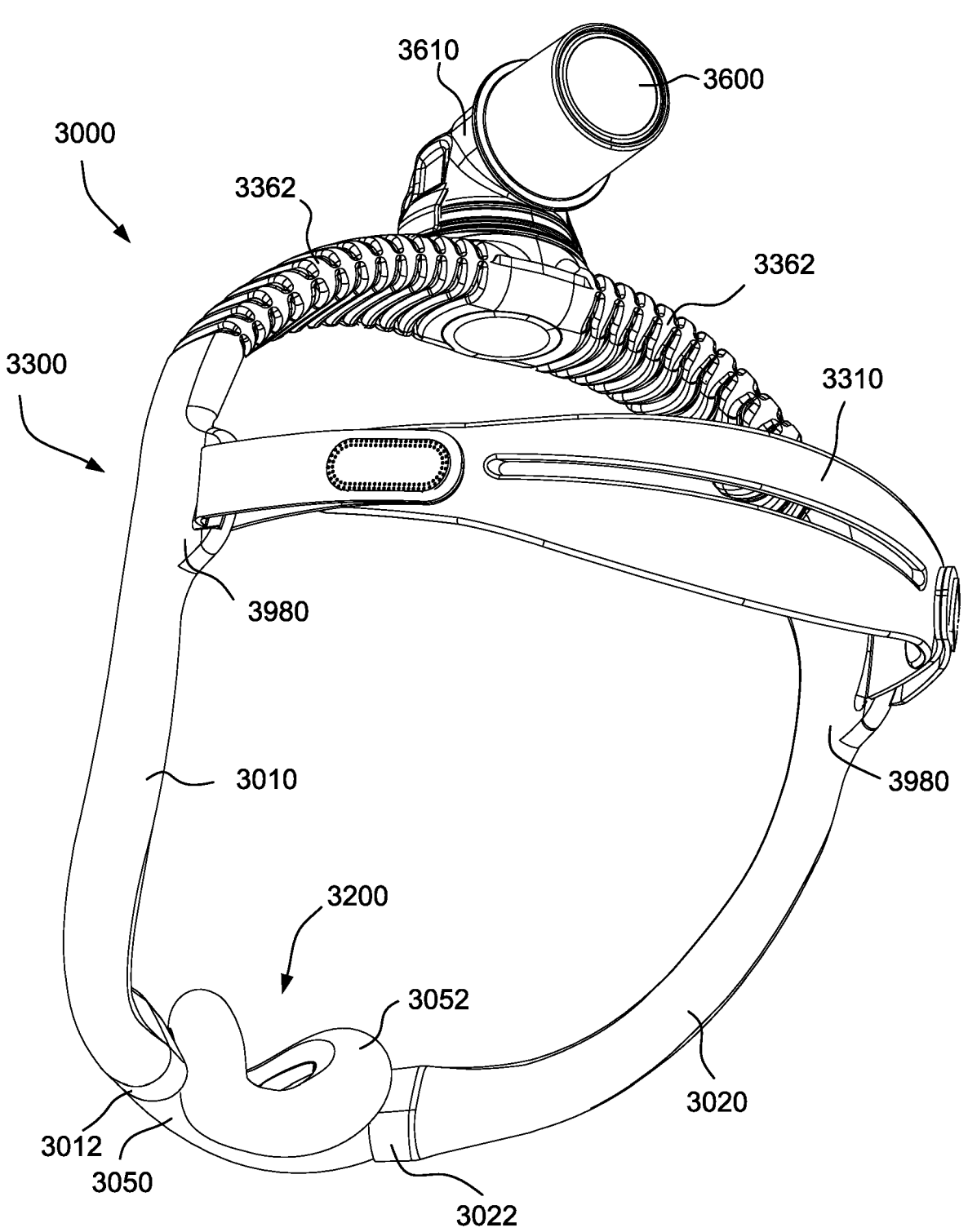

FIG. 5D shows a back view of a nasal mask configuration using conduits according to an example of the present technology.

Figure 6A:
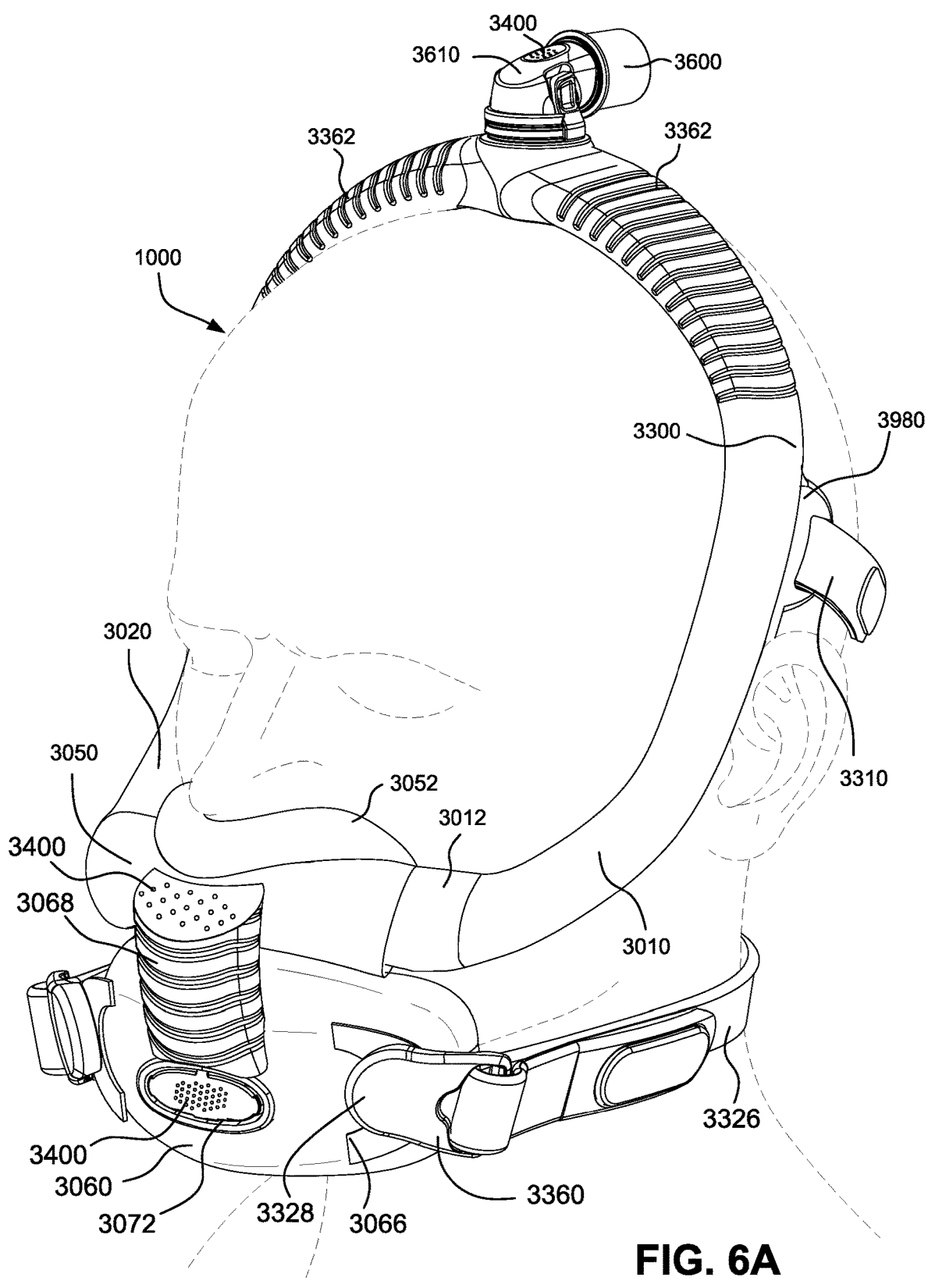

FIG. 6A shows a perspective view of an oro-nasal mask configuration using conduits according to an example of the present technology.

Figure 6B:
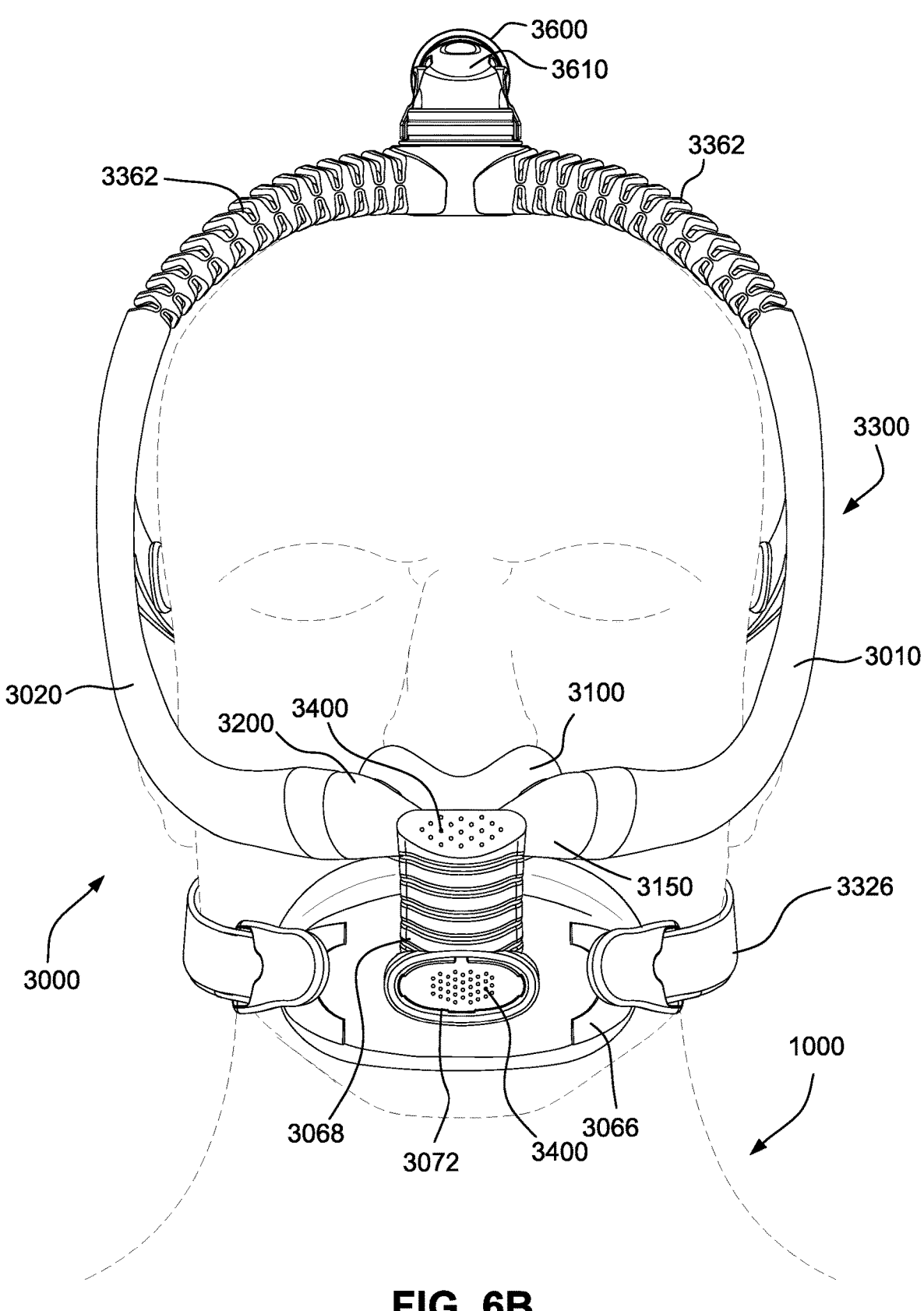

FIG. 6B shows a front view of an oro-nasal mask configuration using conduits according to an example of the present technology.

Figure 6C:
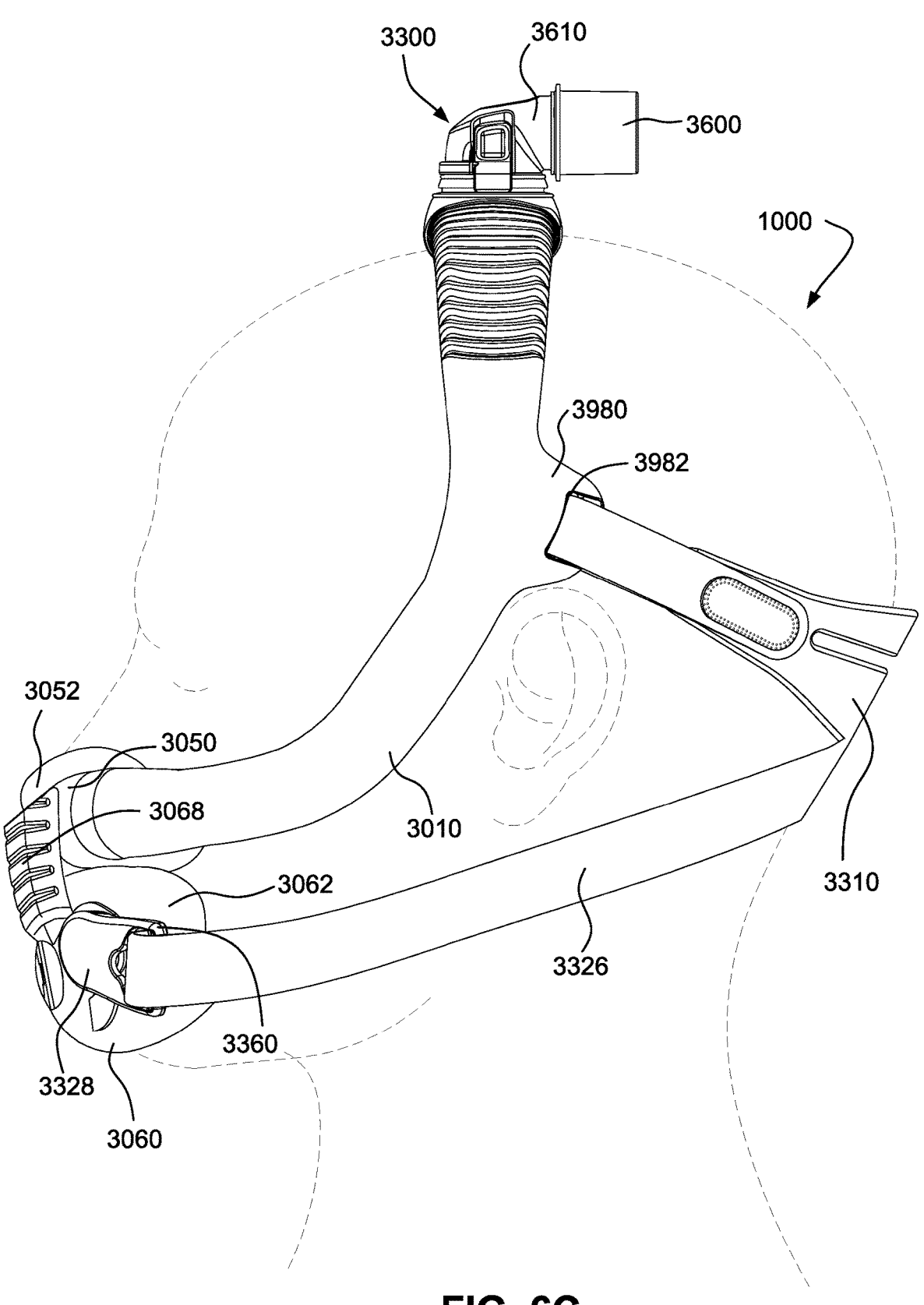

FIG. 6C shows a side view of an oro-nasal mask configuration using conduits according to an example of the present technology.

Figure 6D:
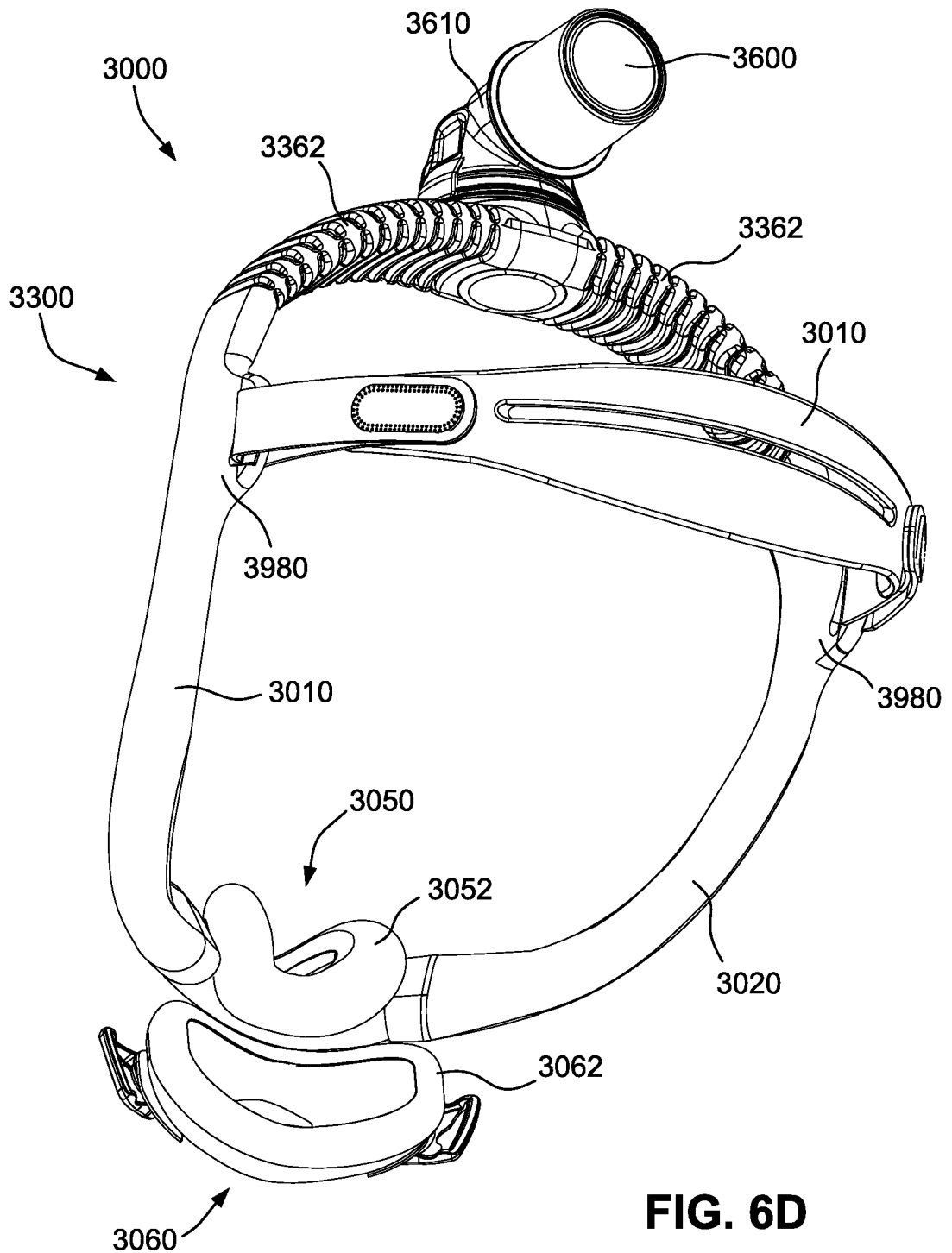

FIG. 6D shows a back view of an oro-nasal mask configuration using conduits according to an example of the present technology.

Figure 7A:
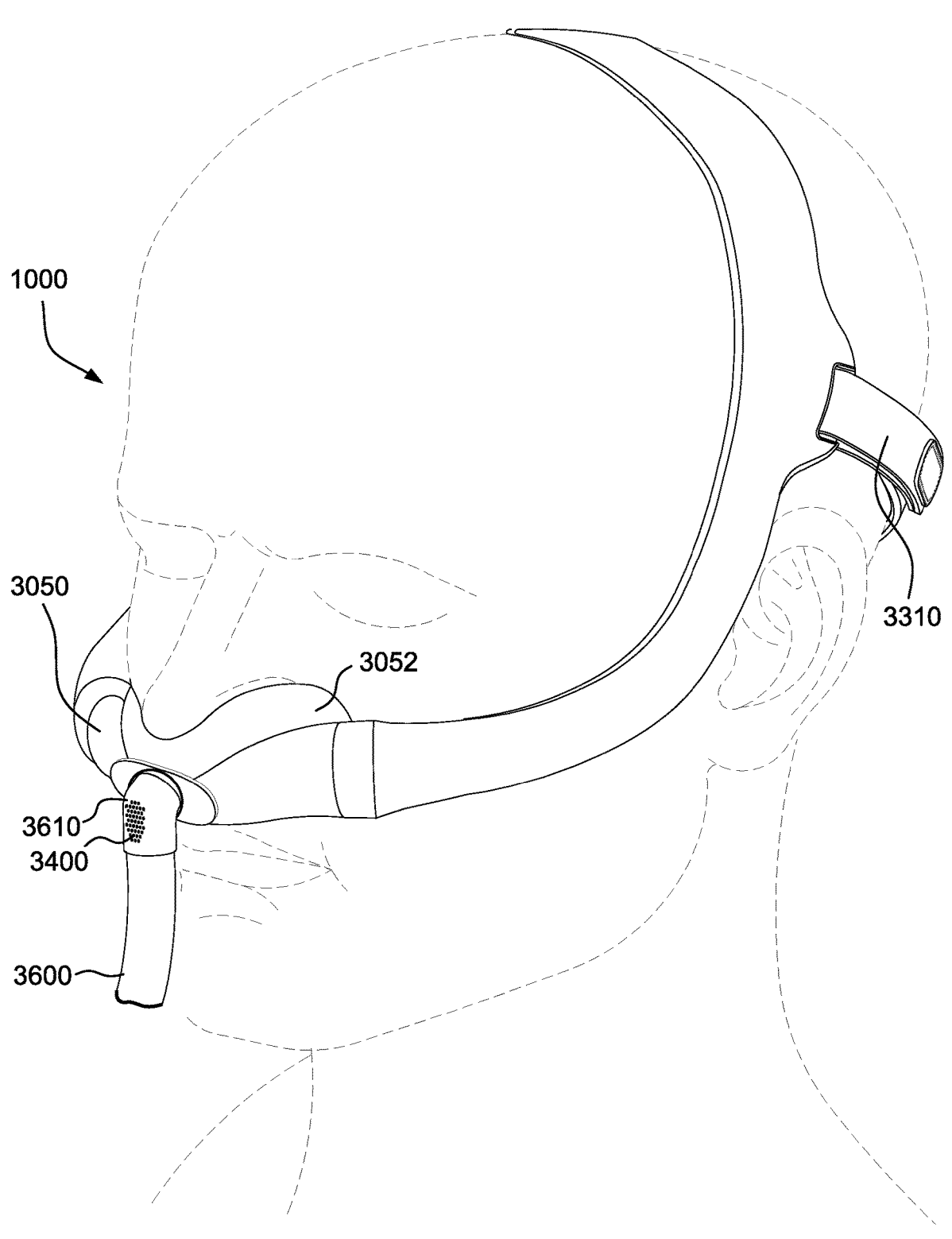

FIG. 7A shows a perspective view of a nasal mask configuration using a tube connected to a surface of a nasal cushion according to an example of the present technology.

Figure 7B:
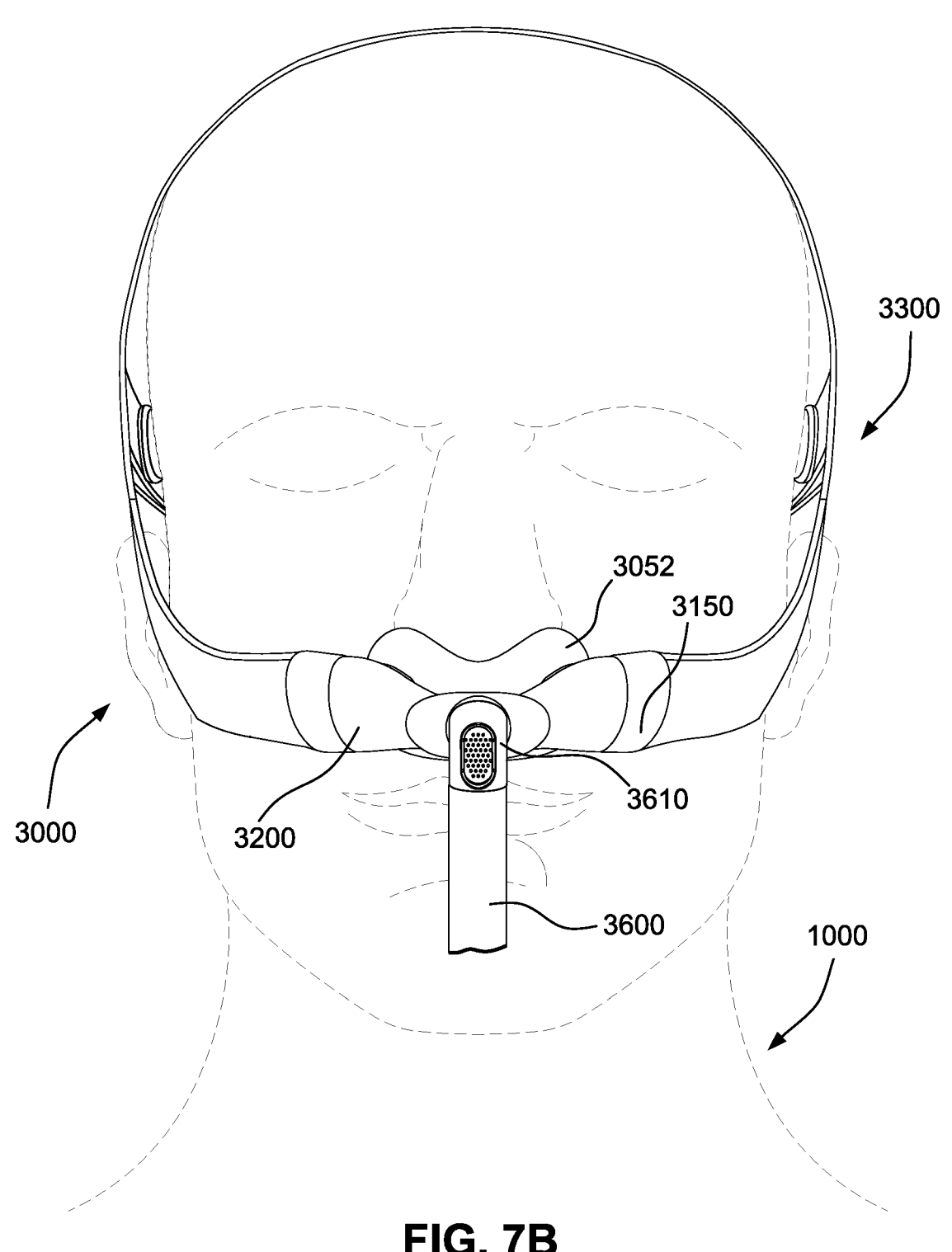

FIG. 7B shows a front view of a nasal mask configuration using a tube connected to a surface of a nasal cushion according to an example of the present technology.

Figure 7C:
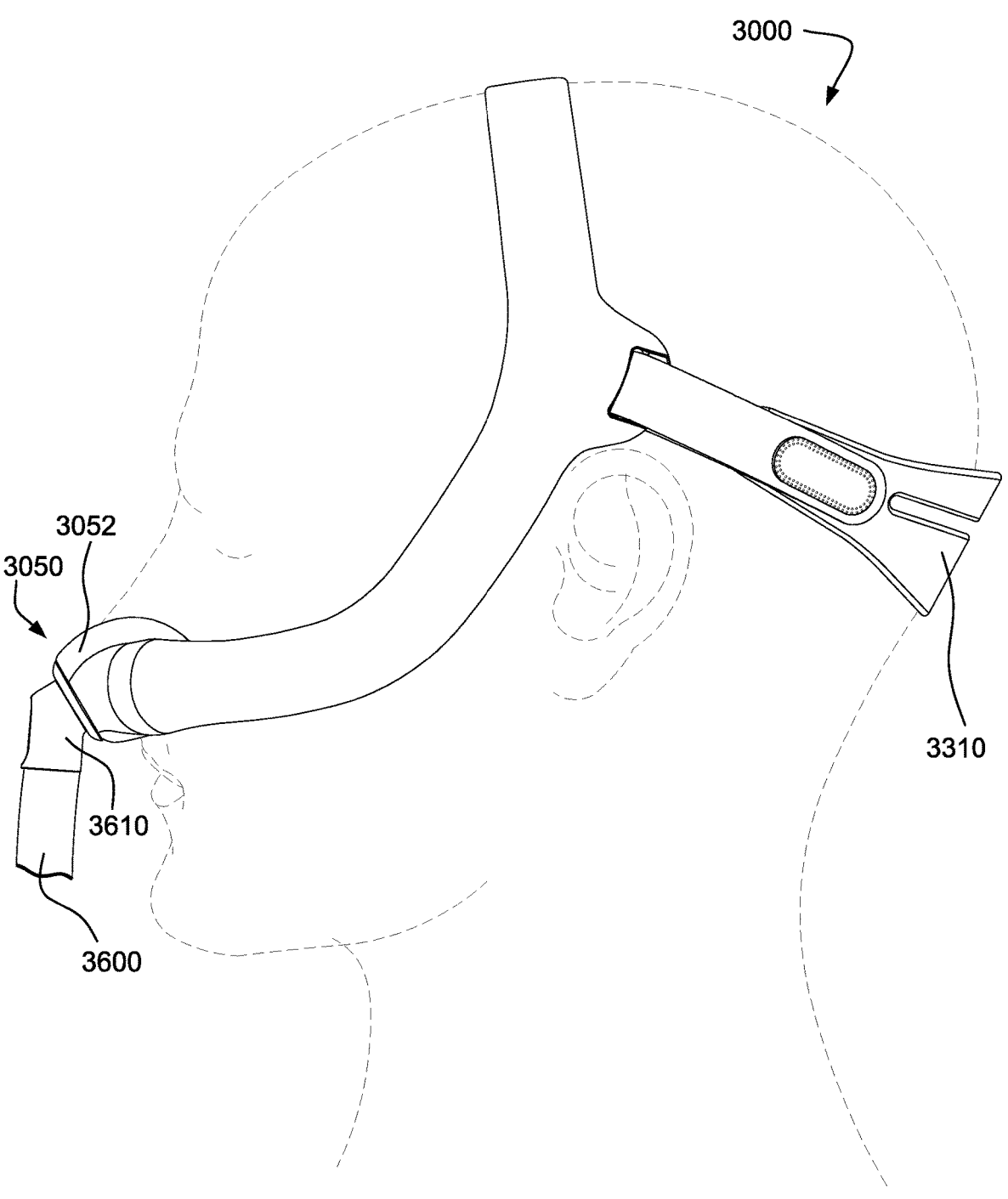

FIG. 7C shows a side view of a nasal mask configuration using a tube connected to a surface of a nasal cushion according to an example of the present technology.

Figure 7D:
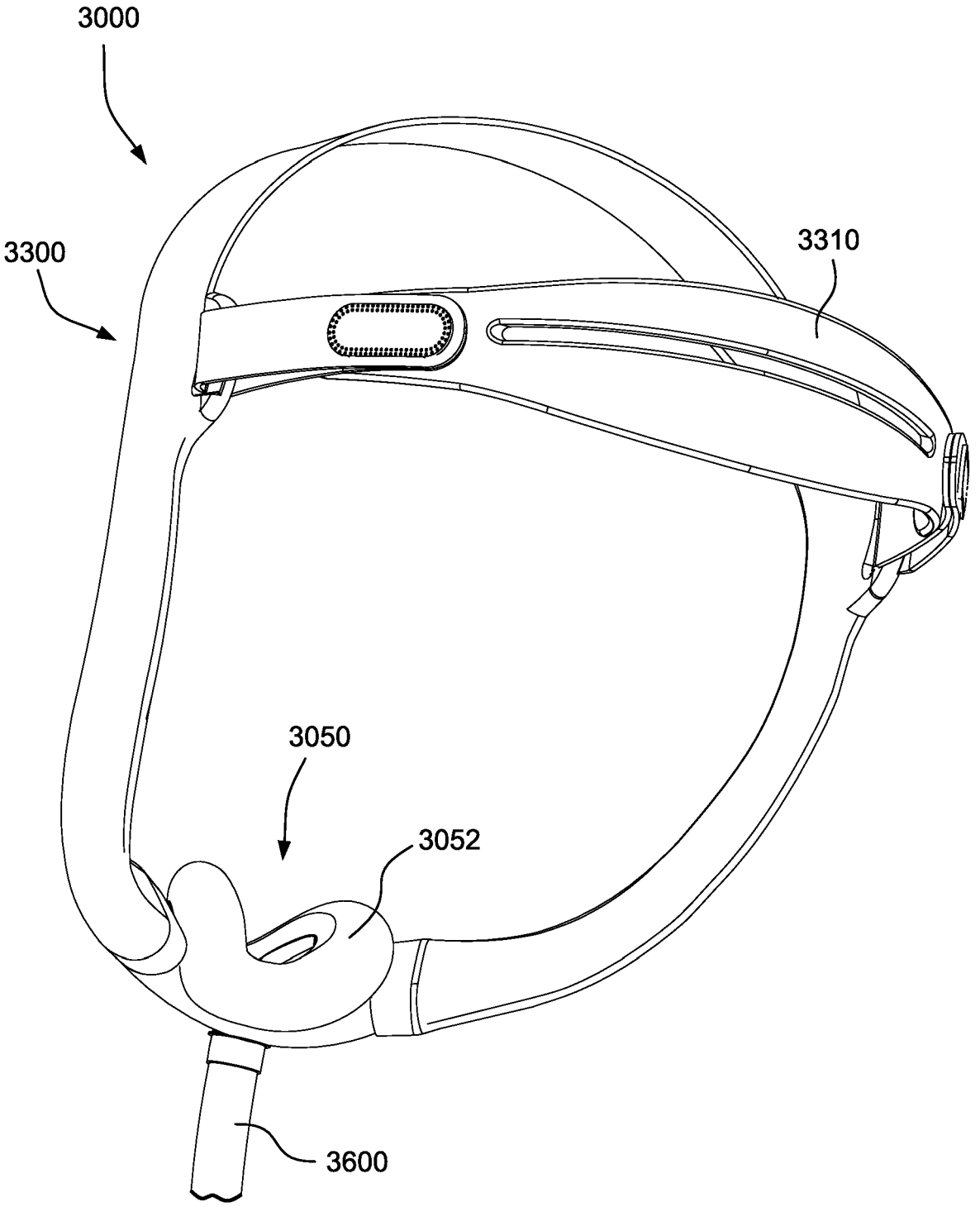

FIG. 7D shows a back view of a nasal mask configuration using a tube connected to a surface of a nasal cushion according to an example of the present technology.

Figure 8A:
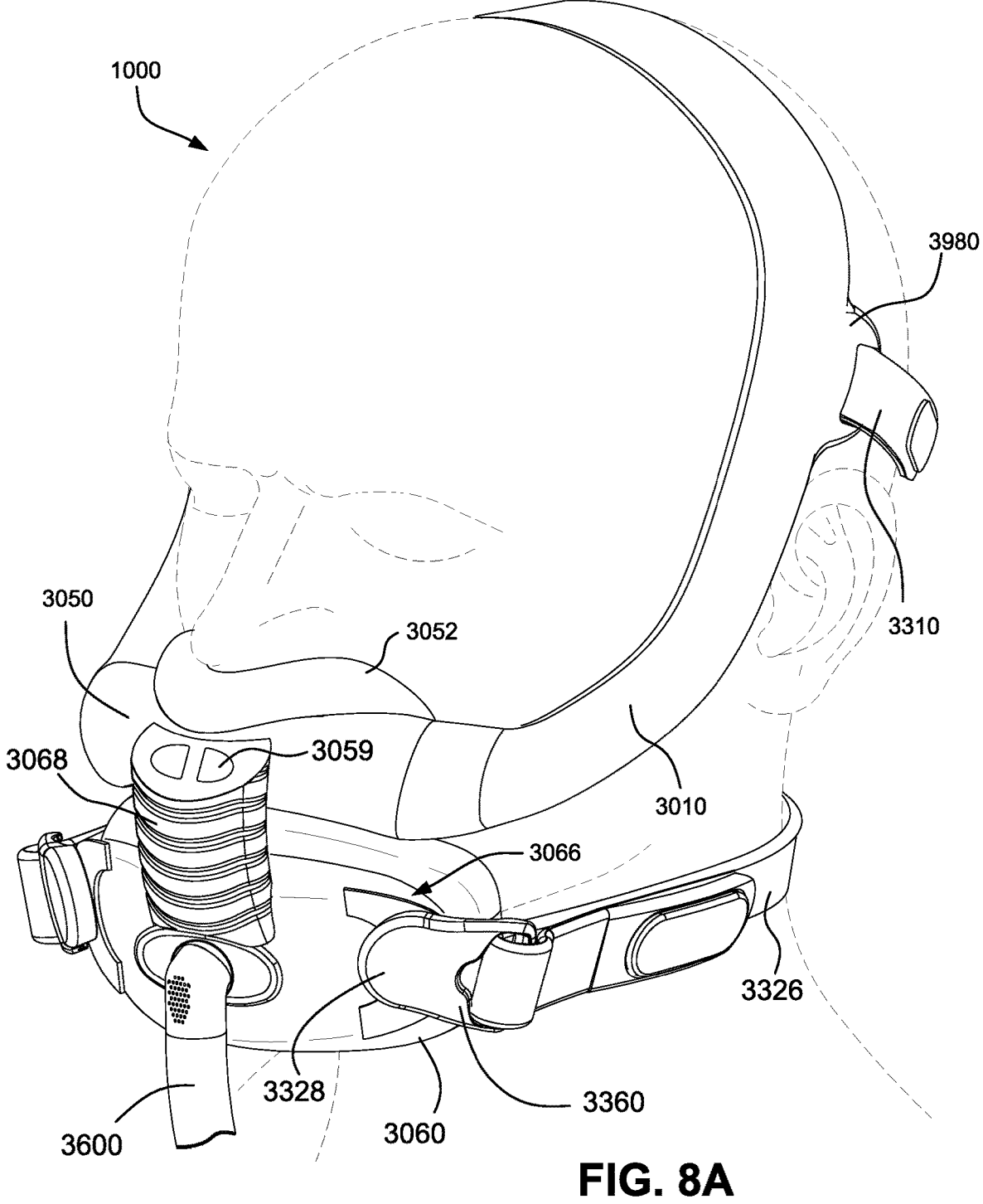

FIG. 8A shows a perspective view of an oro-nasal mask configuration using a tube connected to a surface of a mouth cushion according to an example of the present technology.

Figure 8B:
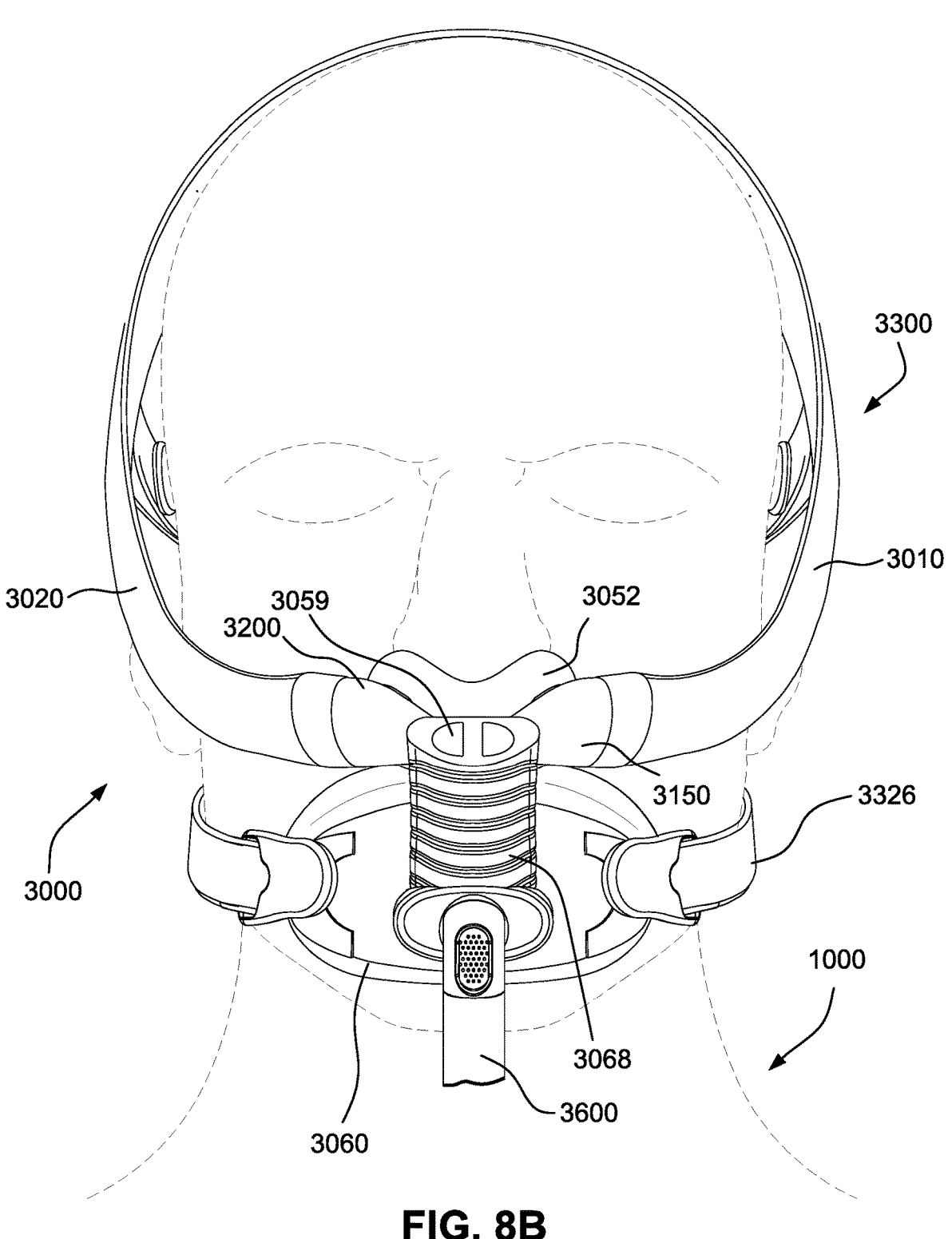

FIG. 8B shows a front view of an oro-nasal mask configuration using a tube connected to a surface of a mouth cushion according to an example of the present technology.

Figure 8C:
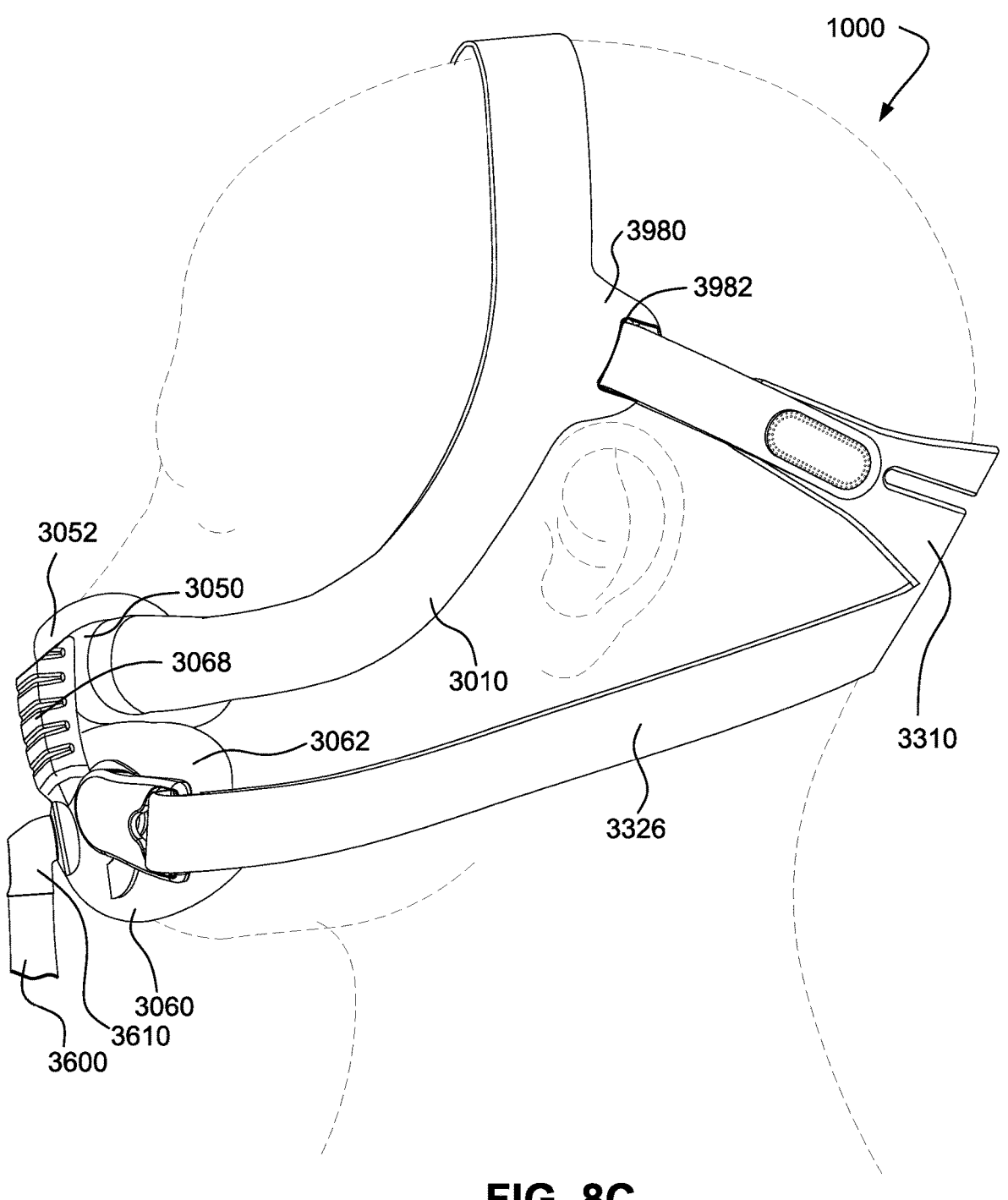

FIG. 8C shows a side view of an oro-nasal mask configuration using a tube connected to a surface of a mouth cushion according to an example of the present technology.

Figure 9A:
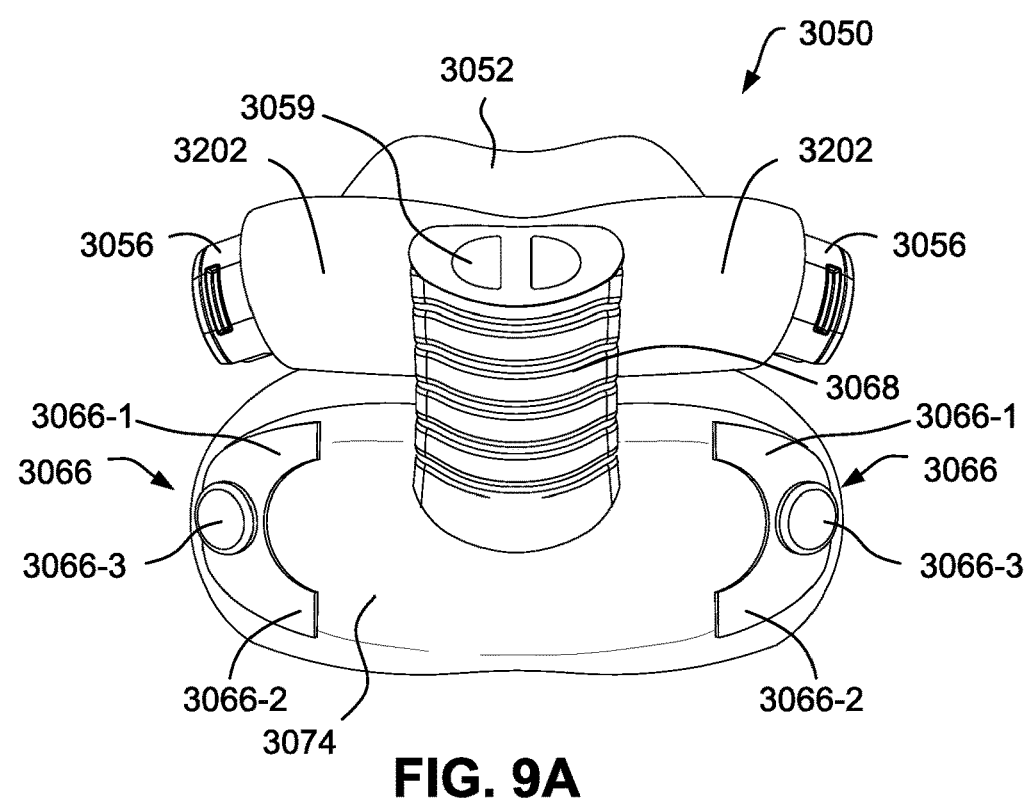

FIG. 9A shows a front view of a joint connecting a mouth cushion to a nasal cushion according to an example of the present technology.

Figure 9B:
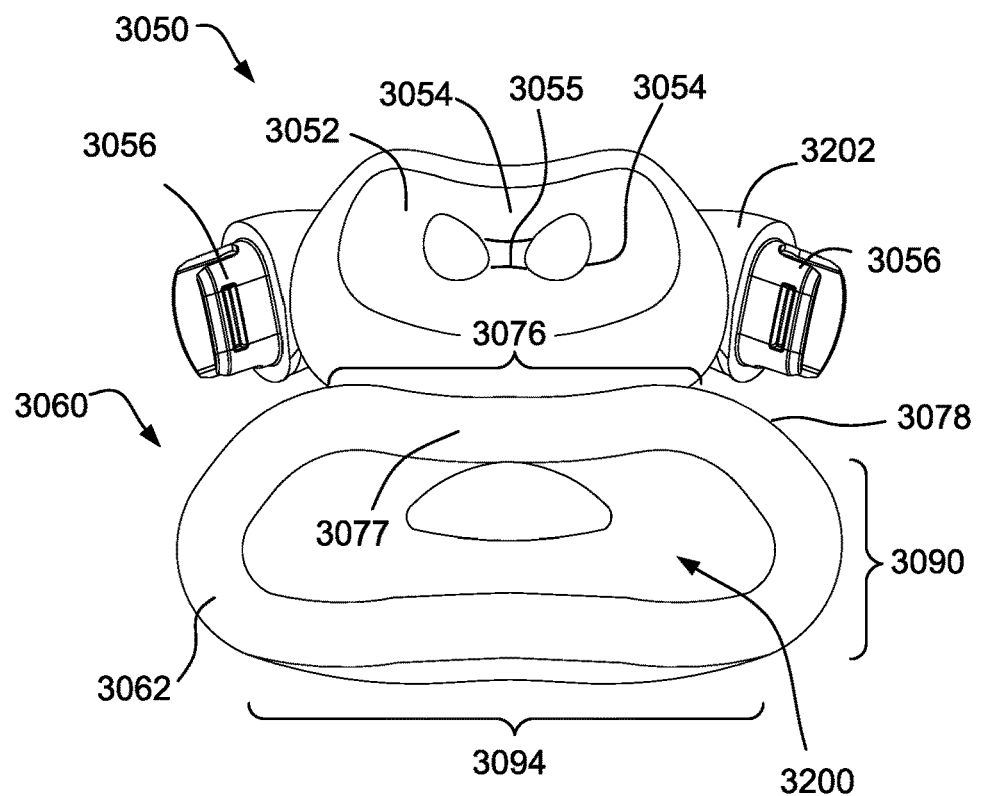

FIG. 9B shows a back view of a joint connecting a mouth cushion to a nasal cushion according to an example of the present technology.

Figure 9C:
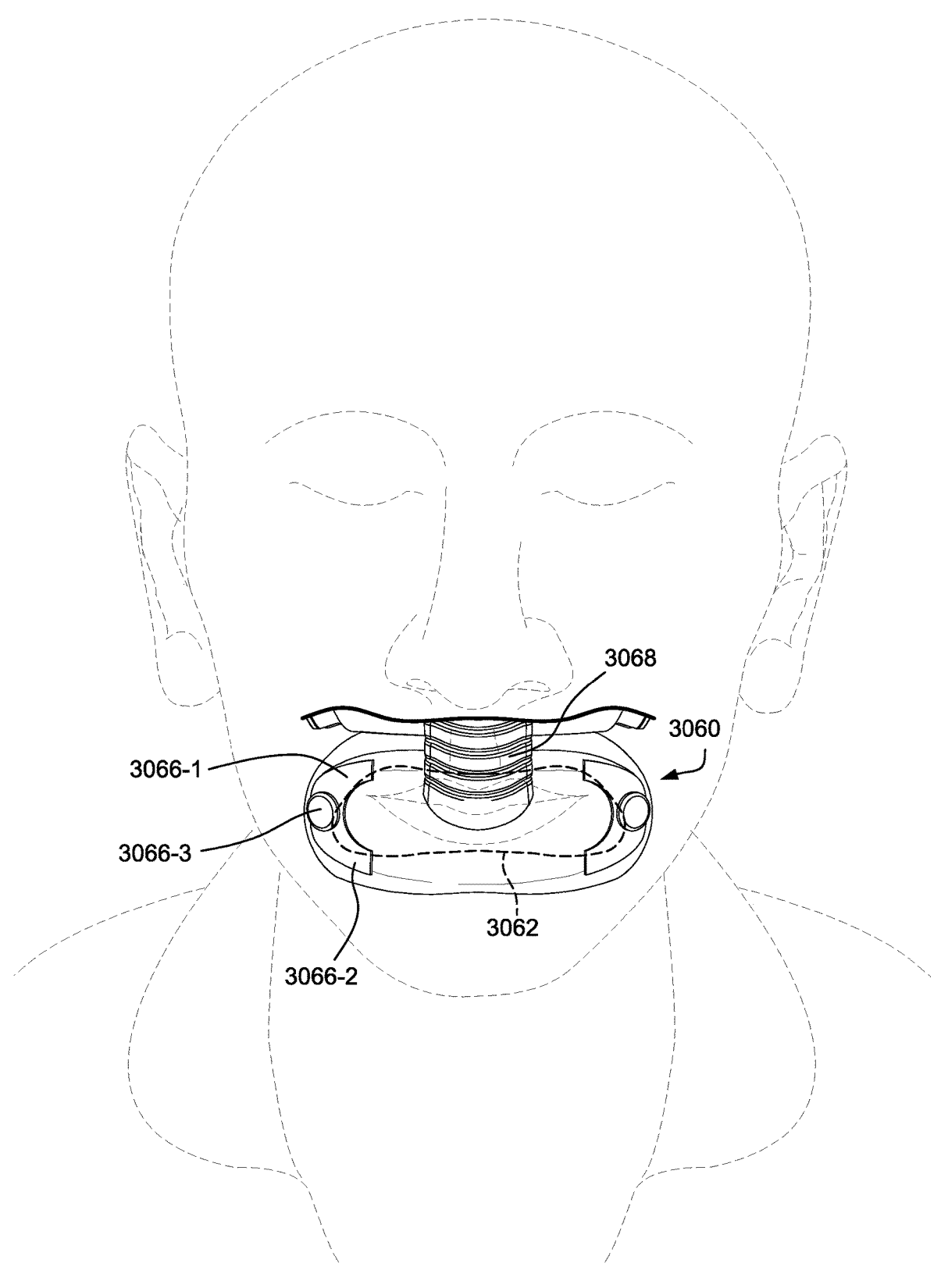

FIG. 9C shows a front view of a seal formed by a mouth cushion shown in FIGS. 9A and 9B on a patient's face according to an example of the present technology.

Figure 9D:
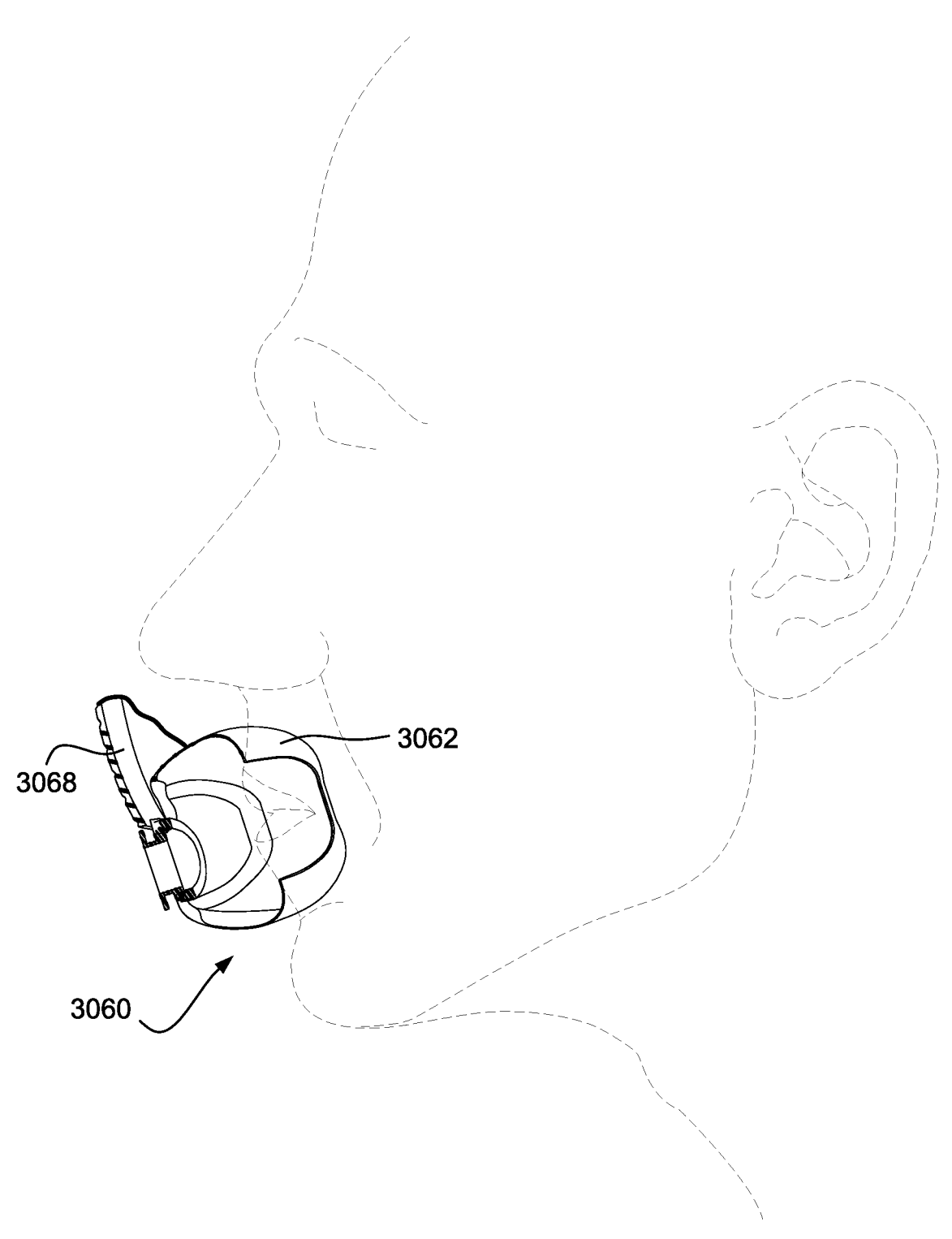

FIG. 9D shows a side view of seal formed by a mouth cushion shown in FIGS. 9A and 9B on a patient's face according to an example of the present technology.

Figure 10A:
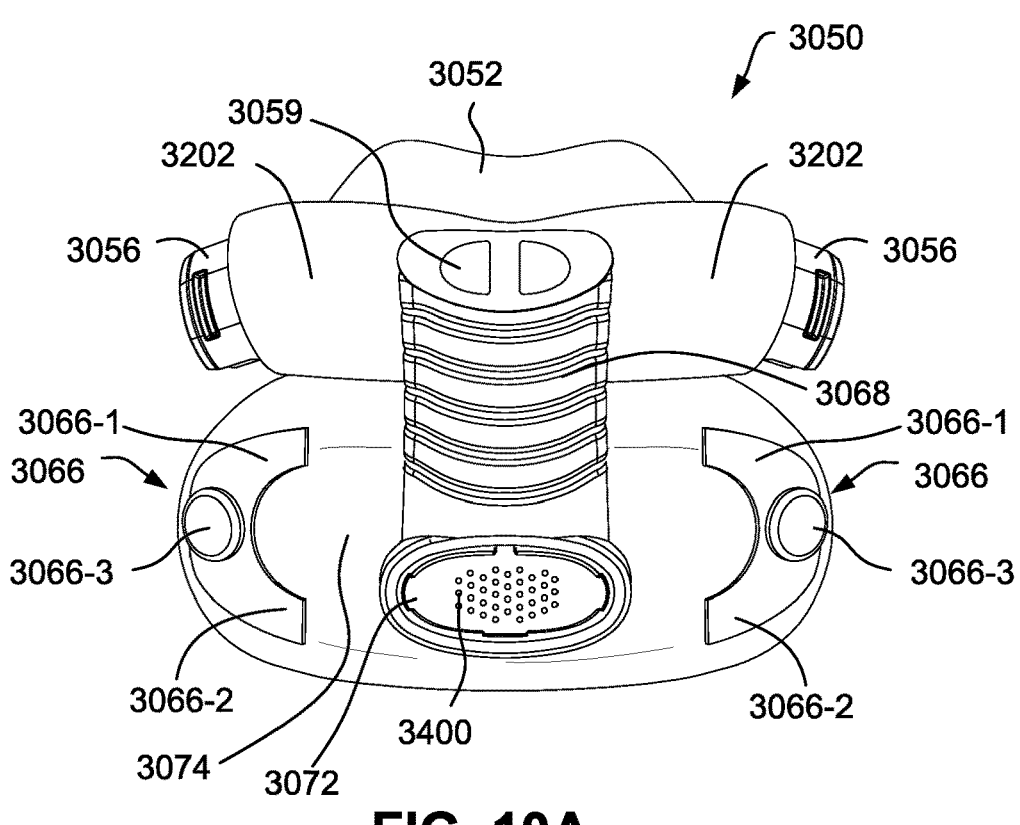

FIG. 10A shows a front view of a joint connecting a nasal cushion to a mouth cushion including a mouth cushion opening for an air circuit according to an example of the present technology.

Figure 10B:
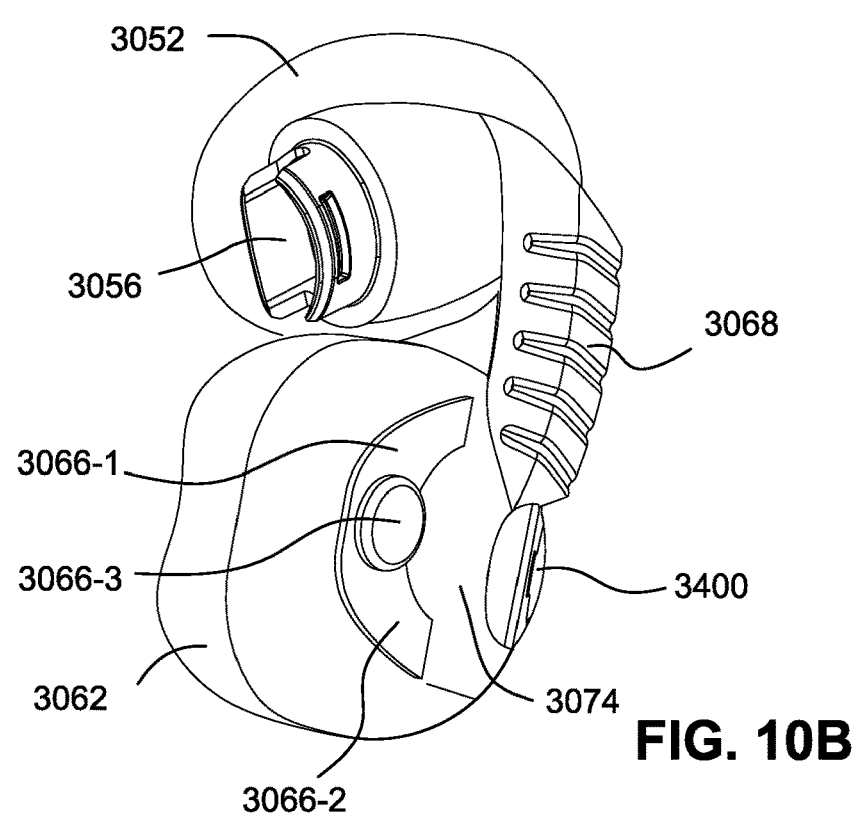

FIG. 10B shows a side view of a joint connecting a nasal cushion to a mouth cushion including a mouth cushion opening for an air circuit according to an example of the present technology.

Figure 10C:
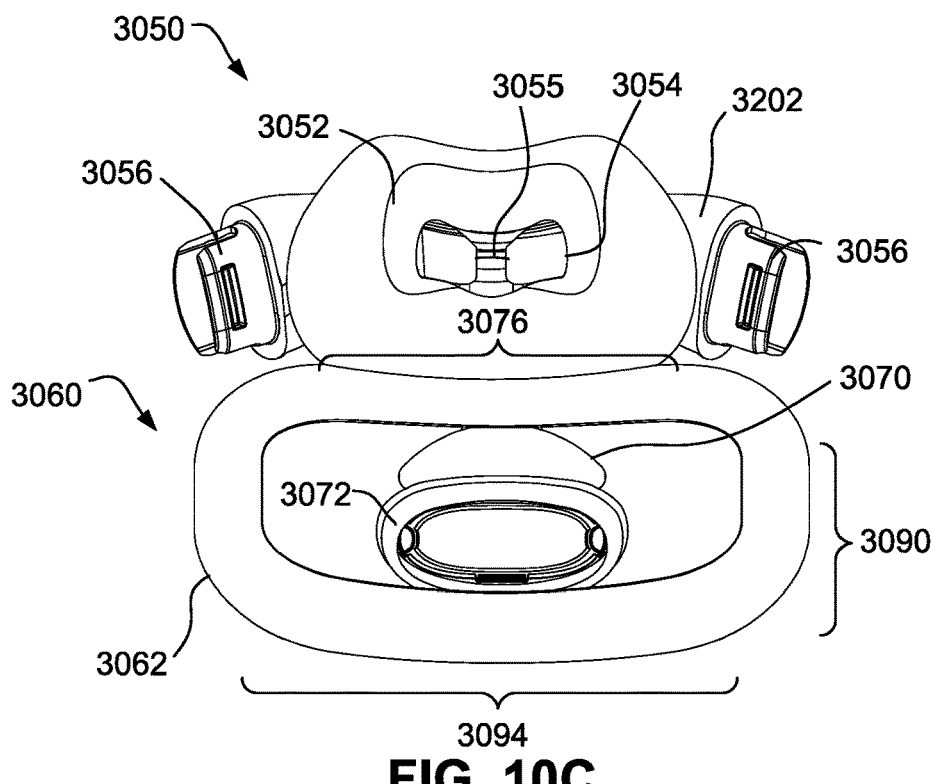

FIG. 10C shows a back view of a joint connecting a nasal cushion to a mouth cushion including a mouth cushion opening for an air circuit to according to an example of the present technology.

Figure 10D:
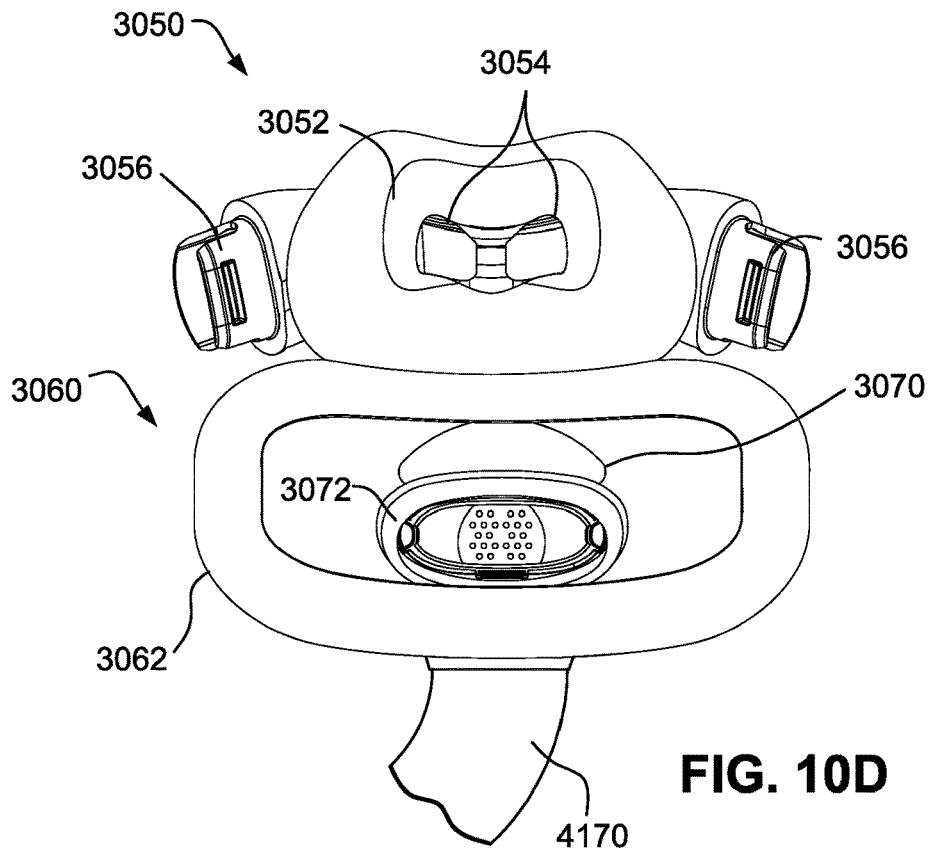

FIG. 10D shows a back view of a joint connecting a nasal cushion to a mouth cushion connected to an air circuit according to an example of the present technology.

Figure 10E:
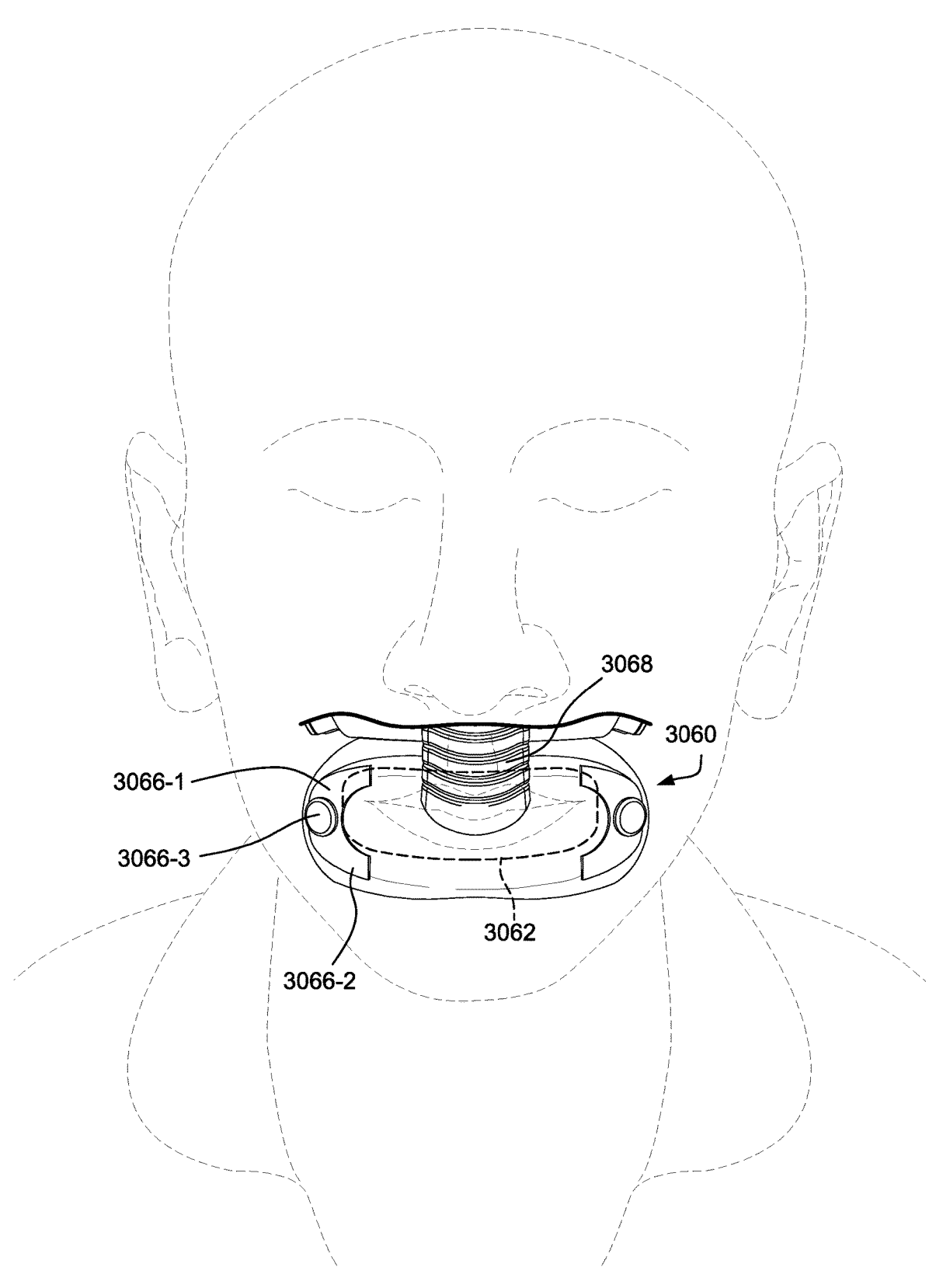

FIG. 10E shows a front view of a mouth cushion shown in FIGS. 10A-10D on a patient's face according to an example of the present technology.

FIG. 10F shows a back view of a mouth cushion in a relaxed position according to an example of the present technology.

FIG. 10G shows a cross sectional view of the mouth cushion of FIG. 10F in the relaxed position according to an example of the present technology.

FIG. 10H shows a back view of a mouth cushion in a first use position according to an example of the present technology.

FIG. 10I shows a cross sectional view of the mouth cushion of FIG. 10H in the first use position according to an example of the present technology.

FIG. 10J shows a back view of a mouth cushion in a second use position according to an example of the present technology.

FIG. 10K shows a cross sectional view of the mouth cushion of FIG. 10J in the second use position according to an example of the present technology.

Figure 10L:
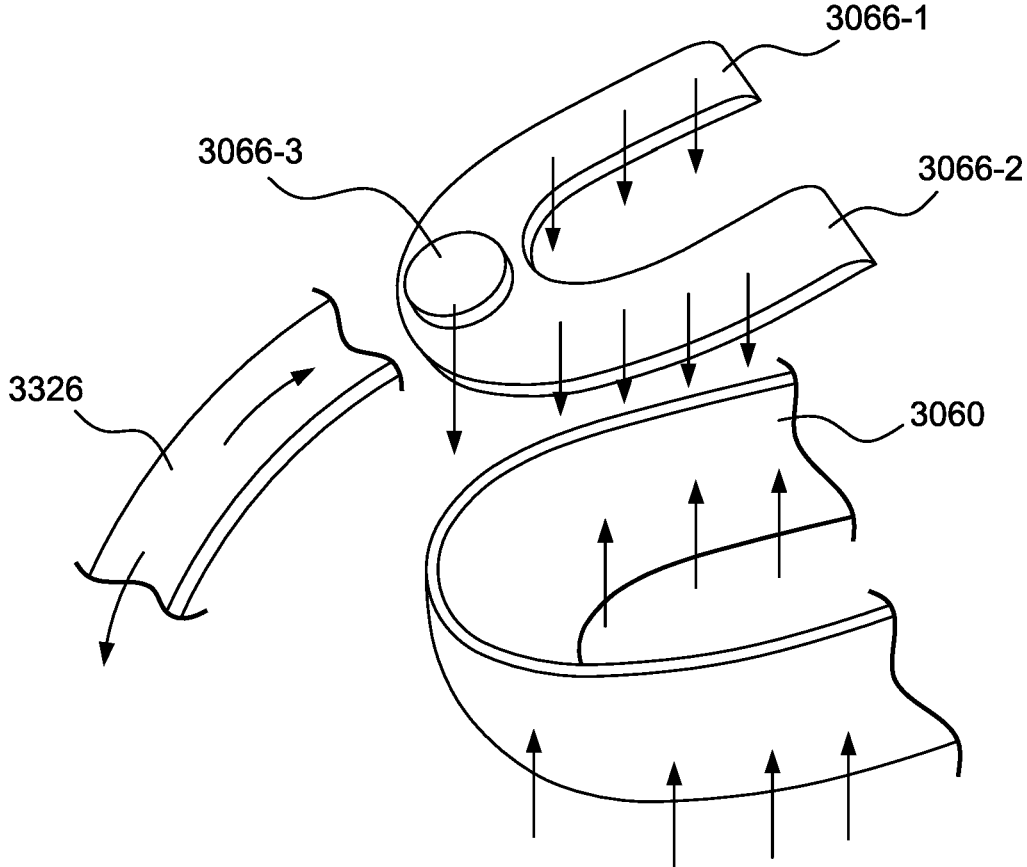

FIG. 10L shows exemplary vector forces that may be distributed by a mouth cushion connector according to an example of the present technology.

Figures 11A, 11B:
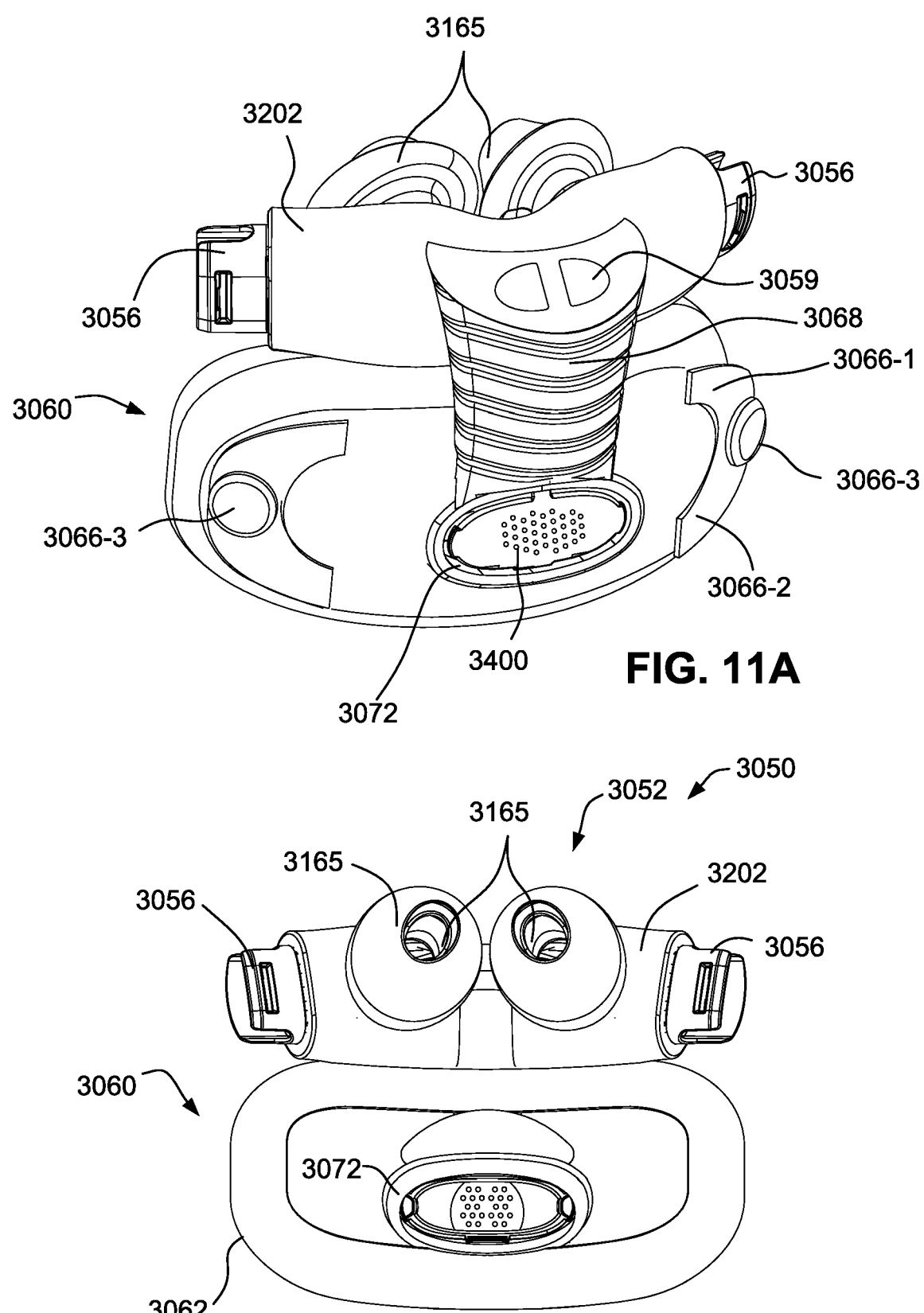

FIG. 11A shows a perspective view of a joint connecting a nasal cushion with nasal pillows to a mouth cushion including a mouth cushion opening for an air circuit according to an example of the present technology.

FIG. 11B shows a side view of a joint connecting a nasal cushion with nasal pillows to a mouth cushion including a mouth cushion opening for an air circuit according to an example of the present technology.

Figure 11C:
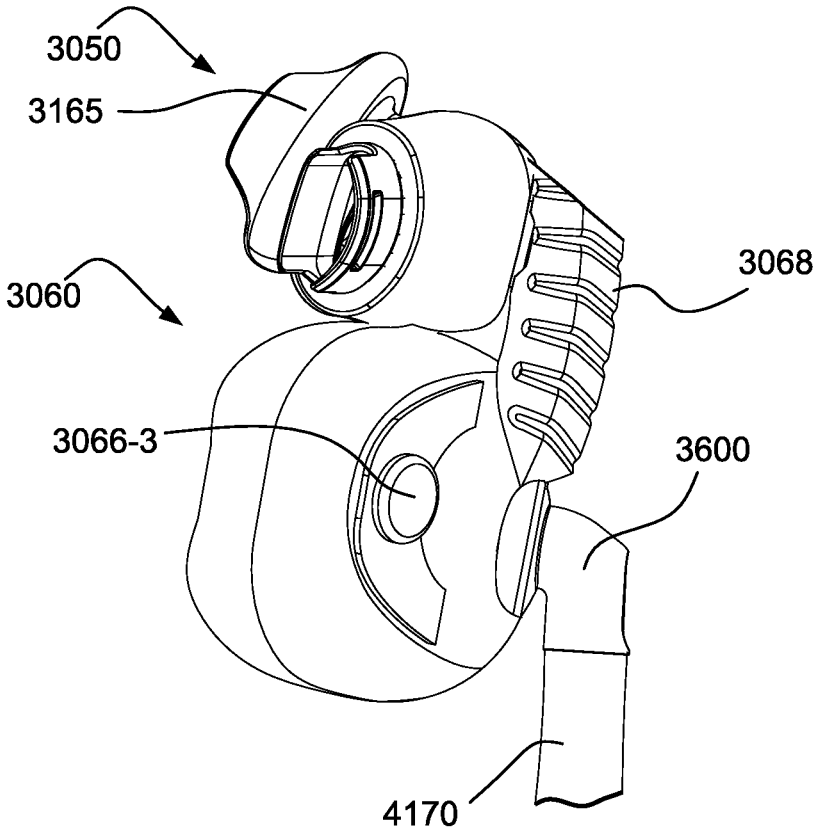

FIG. 11C shows a back view of a joint connecting a nasal cushion with nasal pillows to a mouth cushion connected to an air circuit according to an example of the present technology.

Figure 12:
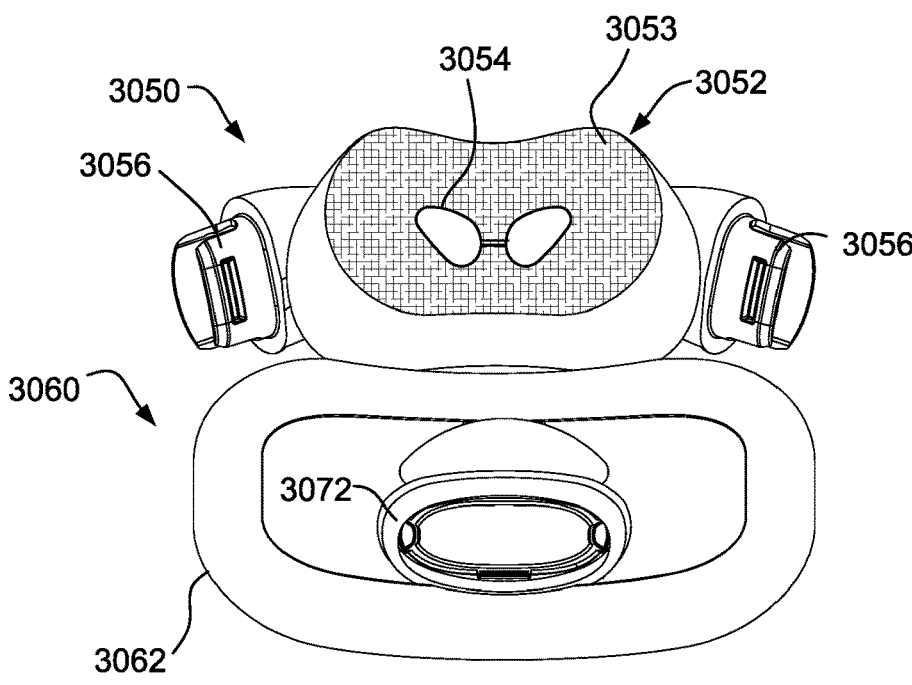

FIG. 12 shows a back view of a joint connecting a nasal cushion with textured surface to a mouth cushion according to an example of the present technology.

Figure 13A:
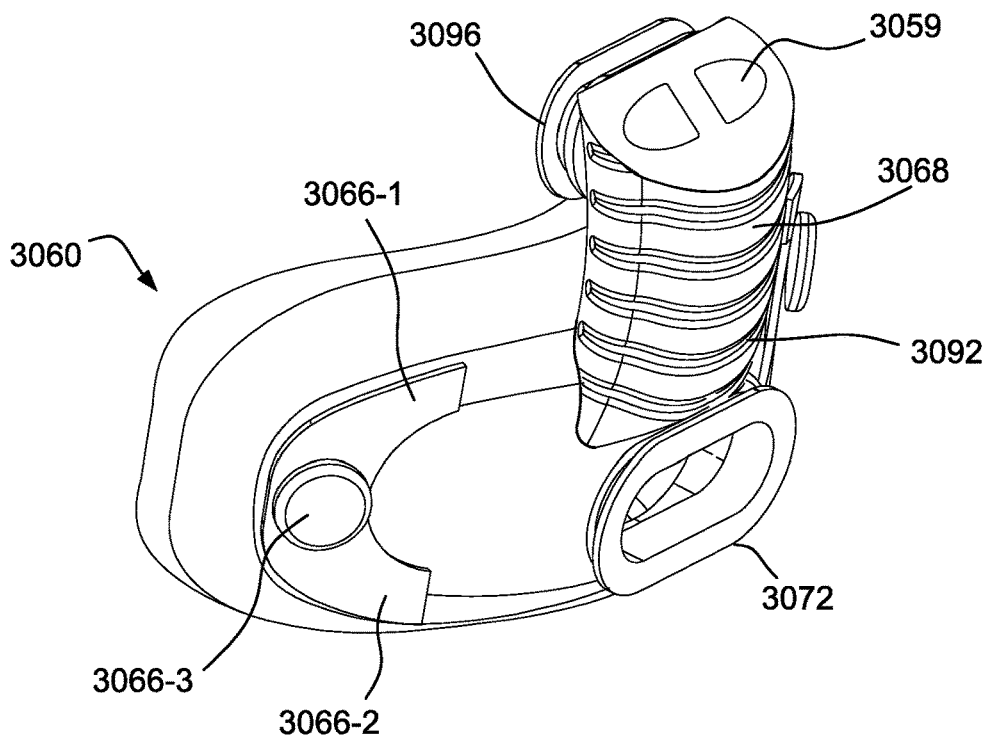

FIG. 13A shows a perspective view of a joint connected to a mouth cushion according to an example of the present technology.

Figure 13B:
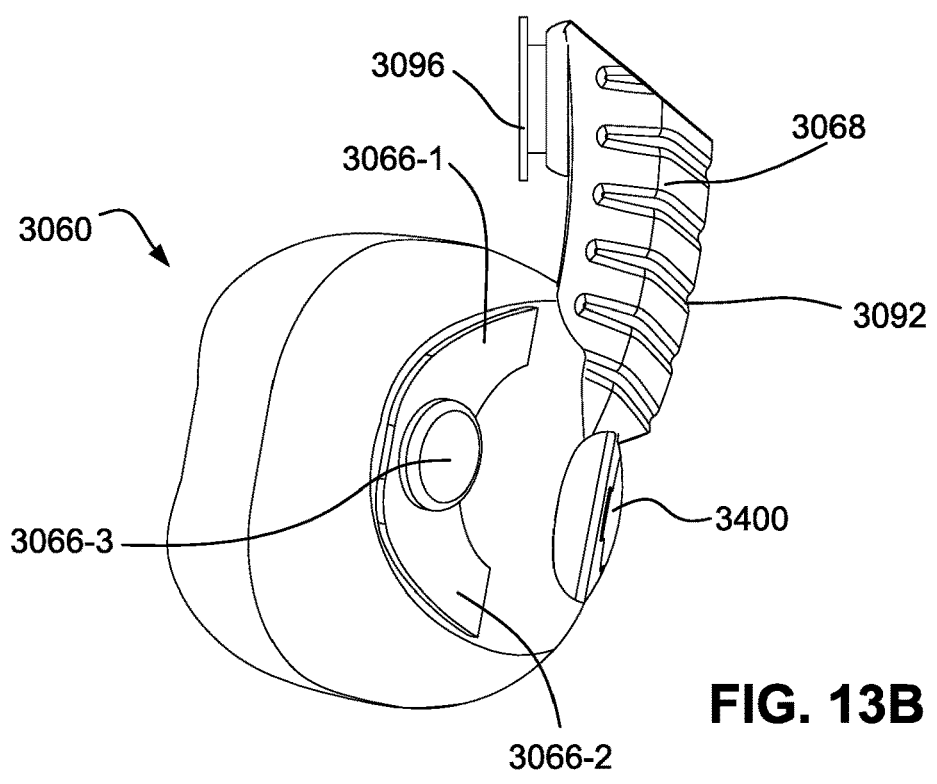

FIG. 13B shows a side view of a joint connected to a mouth cushion according to an example of the present technology.

Figure 13C:
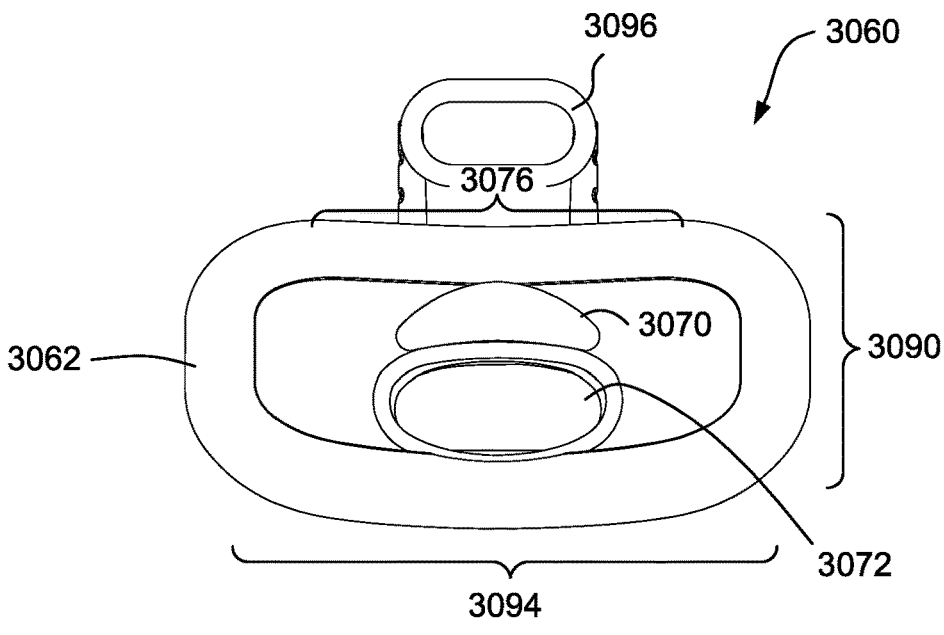

FIG. 13C shows a back view of a joint connected to a mouth cushion according to an example of the present technology.

FIG. 13D shows a back view of a joint connected to a mouth cushion according to another example of the present technology.

FIG. 14A shows a side view of a joint including a concertina section according to an example of the present technology.

FIG. 14B shows a side view of a joint without a concertina section according to an example of the present technology.

FIG. 14C shows a side cross section of a joint according to an example of the present technology.

FIG. 14D shows a top cross section of a joint according to an example of the present technology.

FIG. 14E shows a top cross section of a joint according to another example of the present technology.

Figure 14F:
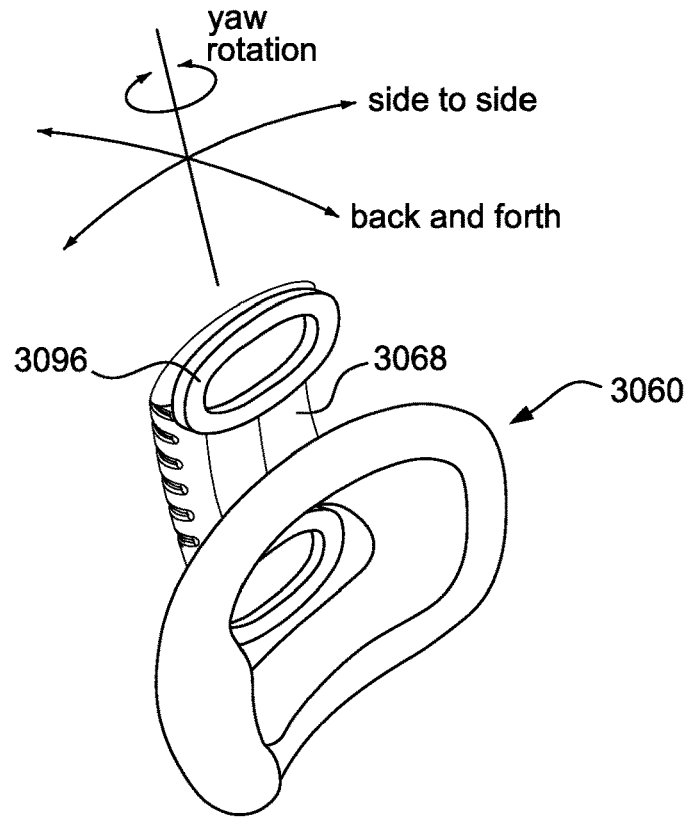

FIG. 14F shows flexibility provided by a joint according to an example of the present technology.

Figure 15:
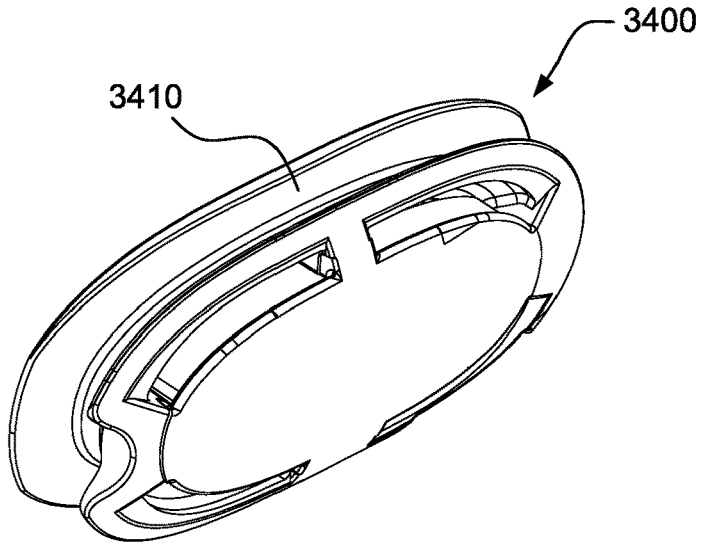

FIG. 15 shows a vent according to an example of the present technology.

Figure 16:
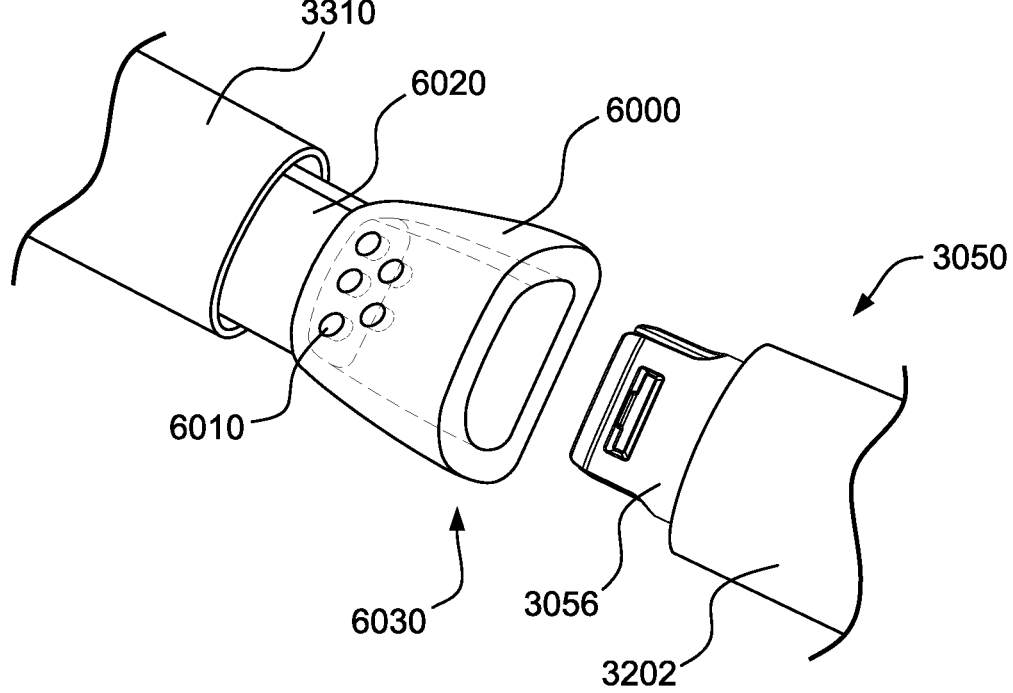

FIG. 16 shows a vent connector including vent holes according to an example of the present technology.

5 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

5.1 Therapy

In one form, the present technology comprises a method for treating a respiratory disorder comprising the step of applying positive pressure to the entrance of the airways of a patient 1000.

In certain examples of the present technology, a supply of air at positive pressure is provided to the nasal passages of the patient via one or both nares.

In certain examples of the present technology, mouth breathing is limited, restricted or prevented.

5.2 Treatment Systems

Figure 1A:
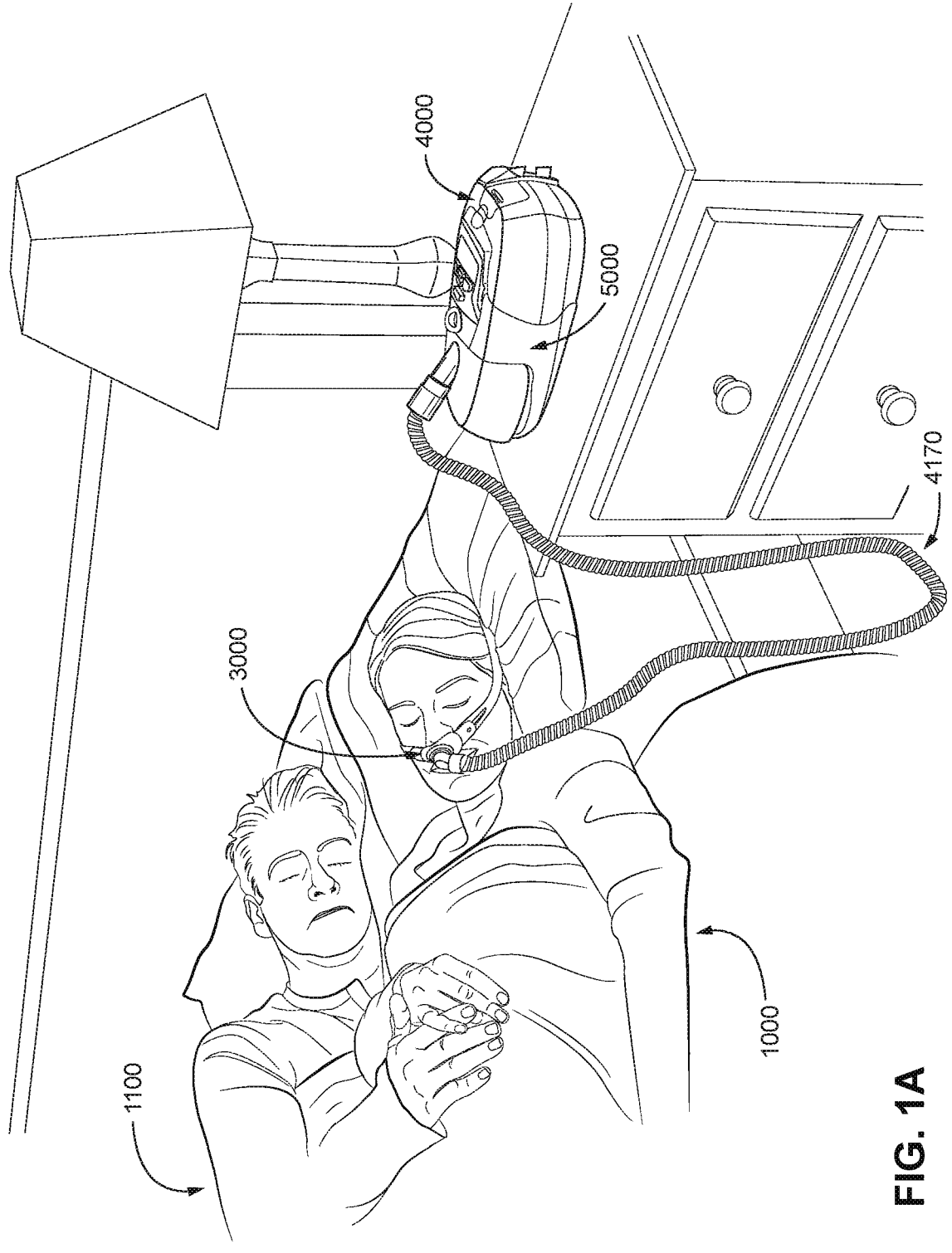
Figure 1B:
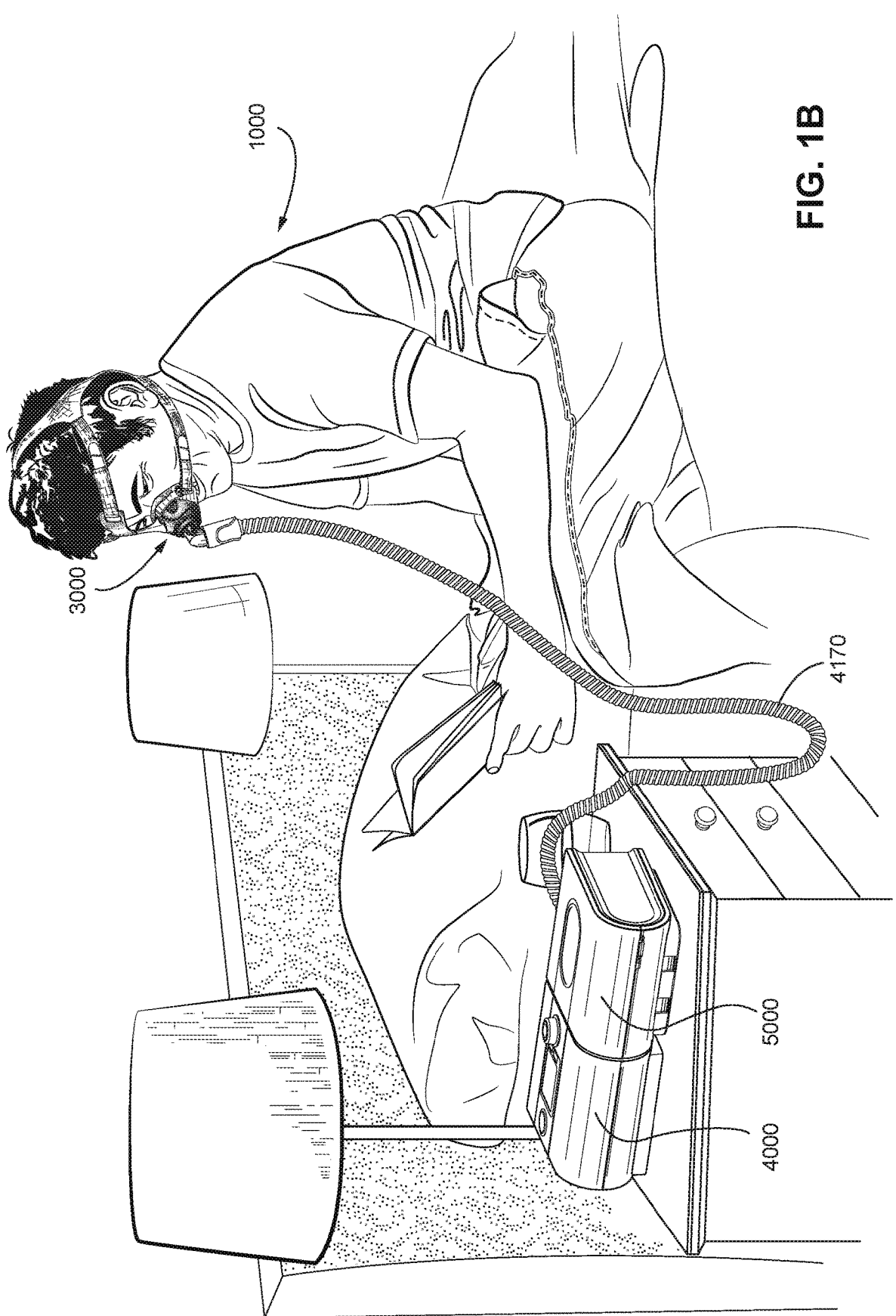
Figure 1C:

In one form, the present technology comprises an apparatus or device for treating a respiratory disorder. The apparatus or device may comprise an RPT device 4000 for supplying pressurised air to the patient 1000 via an air circuit 4170 to a patient interface 3000, e.g., see FIGS. 1A to 1C.

5.3 Patient Interface

FIGS. 3A and 4A-12 shows a non-invasive patient interface 3000 in accordance various aspects of the present technology. With reference to FIG. 3A, a non-invasive patient interface 3000 in accordance with one aspect of the present technology comprises the following functional aspects: a seal-forming structure 3100, a plenum chamber 3200, a positioning and stabilising structure 3300, a vent 3400, one form of connection port 3600 for connection to air circuit 4170, and a forehead support 3700. In some forms a functional aspect may be provided by one or more physical components. In some forms, one physical component may provide one or more functional aspects. In use the seal-forming structure 3100 is arranged to surround an entrance to the airways of the patient so as to maintain positive pressure at the entrance(s) to the airways of the patient 1000. The sealed patient interface 3000 is therefore suitable for delivery of positive pressure therapy.

FIGS. 4A-12 show a patient interface 3000 providing a modular configuration in accordance with aspects of the present technology. The patient interface 3000 may be convertible between a nasal "under the nose" seal mask and an oro-nasal mask (e.g., a full face mask configuration). As shown in FIG. 4A, the patient interface 3000 may include a common connecting element 3330 forming a part of the stabilising structure 3300 to which various components may be removably coupled to provide the nasal mask (shown in FIGS. 5A-5D and 7A-7D) or the oro-nasal mask (shown in FIGS. 6A-6D and 8A-8D).

If a patient interface is unable to comfortably deliver a minimum level of positive pressure to the airways, the patient interface may be unsuitable for respiratory pressure therapy.

The patient interface 3000 in accordance with one form of the present technology is constructed and arranged to be able to provide a supply of air at a positive pressure of at least 6 cmH$_2$O with respect to ambient.

The patient interface 3000 in accordance with one form of the present technology is constructed and arranged to be able to provide a supply of air at a positive pressure of at least 10 cmH$_2$O with respect to ambient.

The patient interface 3000 in accordance with one form of the present technology is constructed and arranged to be able to provide a supply of air at a positive pressure of at least 20 cmH$_2$O with respect to ambient.

5.3.1 Seal-Forming Structure

In one form of the present technology, a seal-forming structure 3100, which may include a nasal seal-forming structure 3052 and/or a mouth seal-forming structure 3062, provides a target seal-forming region, and may additionally provide a cushioning function. The target seal-forming region is a region on the seal-forming structure 3100 where sealing may occur. The region where sealing actually occurs—the actual sealing surface—may change within a given treatment session, from day to day, and from patient to patient, depending on a range of factors including for example, where the patient interface was placed on the face, tension in the positioning and stabilising structure and the shape of a patient's face.

In one form the target seal-forming region is located on an outside surface of the seal-forming structure 3100.

In certain forms of the present technology, the seal-forming structure 3100 is constructed from a biocompatible material, e.g. silicone rubber.

A seal-forming structure 3100 in accordance with the present technology may be constructed from a soft, flexible, resilient material such as silicone.

In certain forms of the present technology, a system is provided comprising more than one a seal-forming structure 3100, each being configured to correspond to a different size and/or shape range. For example the system may comprise one form of a seal-forming structure 3100 suitable for a large sized head, but not a small sized head and another suitable for a small sized head, but not a large sized head.

5.3.1.1 Sealing Mechanisms

In one form, the seal-forming structure includes a sealing flange utilizing a pressure assisted sealing mechanism. In use, the sealing flange can readily respond to a system positive pressure in the interior of the plenum chamber 3200 acting on its underside to urge it into tight sealing engagement with the face. The pressure assisted mechanism may act in conjunction with elastic tension in the positioning and stabilising structure.

In one form, the seal-forming structure 3100 comprises a sealing flange and a support flange. The sealing flange comprises a relatively thin member with a thickness of less than about 1 mm, for example about 0.25 mm to about 0.45 mm, which extends around the perimeter of the plenum chamber 3200. Support flange may be relatively thicker than the sealing flange. The support flange is disposed between the sealing flange and the marginal edge of the plenum chamber 3200, and extends at least part of the way around the perimeter. The support flange is or includes a spring-like element and functions to support the sealing flange from buckling in use.

In one form, the seal-forming structure may comprise a compression sealing portion or a gasket sealing portion. In use the compression sealing portion, or the gasket sealing portion is constructed and arranged to be in compression, e.g. as a result of elastic tension in the positioning and stabilising structure.

In one form, the seal-forming structure comprises a tension portion. In use, the tension portion is held in tension, e.g. by adjacent regions of the sealing flange.

In one form, the seal-forming structure comprises a region having a tacky or adhesive surface.

In certain forms of the present technology, a seal-forming structure may comprise one or more of a pressure-assisted sealing flange, a compression sealing portion, a gasket sealing portion, a tension portion, and a portion having a tacky or adhesive surface.

5.3.1.2 Nose Bridge or Nose Ridge Region

In one form, the non-invasive patient interface 3000 comprises a seal-forming structure that forms a seal in use on a nose bridge region or on a nose-ridge region of the patient's face.

In one form, the seal-forming structure includes a saddle-shaped region constructed to form a seal in use on a nose bridge region or on a nose-ridge region of the patient's face.

5.3.1.3 Upper Lip Region

In one form, the non-invasive patient interface 3000 comprises a seal-forming structure that forms a seal in use on an upper lip region (that is, the lip superior) of the patient's face.

In one form, the seal-forming structure includes a saddle-shaped region constructed to form a seal in use on an upper lip region of the patient's face.

5.3.1.4 Chin-Region

In one form the non-invasive patient interface 3000 comprises a seal-forming structure that forms a seal in use on a chin-region of the patient's face.

In one form, the seal-forming structure includes a saddle-shaped region constructed to form a seal in use on a chin-region of the patient's face.

5.3.1.5 Forehead Region

In one form, the seal-forming structure that forms a seal in use on a forehead region of the patient's face. In such a form, the plenum chamber may cover the eyes in use.

5.3.1.6 Nasal Pillows

In one form the seal-forming structure of the non-invasive patient interface 3000 comprises a pair of nasal puffs, or nasal pillows, each nasal puff or nasal pillow being constructed and arranged to form a seal with a respective naris of the nose of a patient. FIGS. 11A and 11B show a nasal cushion 3050 having a nasal seal-forming structure 3052 provided by a pillows cushion module. The pillows cushion module comprises a pair of nasal pillows 3165. In this example, the same positioning structure 3300 may be used to hold the pillows cushion module in sealing contact with the patient's nose. The same mouth cushion 3060 shown in other configuration (e.g., FIGS. 9A and 9B) could be coupled to the nasal cushion 3050 shown in FIGS. 11A and 11B.

Nasal pillows 3165 in accordance with an aspect of the present technology include: a frusto-cone, at least a portion of which forms a seal on an underside of the patient's nose, a stalk, a flexible region on the underside of the frusto-cone and connecting the frusto-cone to the stalk. In addition, the structure to which the nasal pillow of the present technology is connected includes a flexible region adjacent the base of the stalk. The flexible regions can act in concert to facilitate a universal joint structure that is accommodating of relative movement both displacement and angular of the frusto-cone and the structure to which the nasal pillow is connected. For example, the frusto-cone may be axially displaced towards the structure to which the stalk is connected.

5.3.2 Nasal Cushion and Mouth Cushion

The patient interface 3000 may be convertible between a nasal "under the nose" seal mask configuration and an oro-nasal mask configuration, depending on whether a nasal cushion 3050 and/or a mouth cushion 3060 is/are coupled to a headgear section. A nasal cushion 3050 may comprise a nasal seal-forming structure 3052 constructed and arranged to form a seal with a region of a patient's face surrounding the entrance to a patient's nares. A mouth cushion 3060 may comprise a mouth seal-forming structure 3062 constructed and arranged to form a seal with a region of a patient's face surrounding the entrance to a patient's mouth.

Examples of the present technology provide for independent sealing of the nose and mouth. A mouth seal-forming structure 3062 may be configured to form and/or adjust a seal with a region of a patient's face surrounding the entrance to a patient's mouth that is independent from a nasal seal-forming structure 3052 configured to form and/or adjust a seal with a region of a patient's face surrounding the entrance to a patient's nares. This configuration may overcome challenges associated with providing a geometry in one cushion that can effectively seal different portions of a patients face (e.g., on the corners of the nose and top lip of the patient), where it may be hardest to seal due to variabilities between patients. The interchangeability of the nasal cushion 3050 and the mouth cushion 3060 allows a patient to select a nasal cushion 3050 and mouth cushion 3060 that provide a comfortable fit and effective seal. In addition, examples of the present technology allows for movement of both the mouth seal-forming structure 3062 and the nasal seal-forming structure 3052 separate from one another to provide a comfortable fit and effective seal.

FIGS. 4A-12 show the seal-forming structure 3052 of the nasal cushion 3050 according to different examples of the present technology. The seal-forming structure 3052 may comprise a nasal cradle cushion and provide a flow of pressurised gas to the patient's nares by sealing against at least the underside of the patient's nose. The exemplary seal-forming structures 3052 will engage the patient's face below the bridge of the nose and some examples, depending on the size and shape of the patient's nose, may engage the patient's nose below the pronasale. Exemplary seal-forming structures 3052 may also engage the patient's face at least above the upper vermillion. Thus, exemplary seal-forming structures 3052 may seal against the patient's lip superior in use. Furthermore, the patient's mouth may remain uncovered by the seal-forming structure 3052 of the depicted examples such that the patient may breathe freely, i.e., directly to atmosphere, without interference from the seal-forming structure 3052. In some examples, the nasal seal-forming structure 3052 comprises a nasal cradle cushion, a nasal cushion or pillows adapted to form a seal relative to the entrance of a patient's nose.

The shape of the nasal seal-forming structure 3052 may be configured to match or closely follow the underside of the patient's nose, i.e. the profile and angle of the seal-forming structure may be substantially parallel to the patient's nasolabial angle. In one form of a nasal cradle cushion, the nasal seal-forming structure 3052 comprises a bridge portion 3055 defining two orifices 3054, each of which, in use, supplies air or breathable gas to a different one of the patient's nares. The bridge portion may be configured to contact or seal against the patient's columella in use. In some forms of the technology, the nasal seal-forming structure 3052 is configured to form a seal on an underside of the patient's nose without contacting a nasal bridge region of the patient's nose. The nasal cradle may be configured to be anchored on the superior part of the patient's upper lip, at or below the subnasale.

The exemplary nasal cradle cushion may include a superior saddle or concave region that has positive curvature across the cushion. Also, the nasal cradle cushion may be understood to have a single target seal forming region or surface, in contrast to a pillows cushion may have two target seal forming regions (one for each naris). Cradle cushions may also have a posterior wall that contacts the patient's lip superior and an upper, central, surface contacts the underside of the patient's nose. These two surfaces on the patient's face may form a nasolabial angle between them (see FIG. 2E). A cradle cushion may be shaped to have a nasolabial angle within the range of 90 degrees to 120 degrees.

In some examples, the exemplary nasal seal-forming structure 3052 may also be shaped and dimensioned such that no portion of the nasal seal-forming structure 3052 enters into the patient's nares during use.

FIGS. 9A and 9B show an exemplary nasal seal-forming structure 3052 according to one form of the present technology. The illustrated seal-forming structure 3052 includes two orifices 3054 formed through a medial region provided as a bridge portion 3055. The orifices 3054 are positioned to generally align with patient's corresponding naris to provide the flow of pressurised gas to the patient's nares for inhalation and for exhaled gas to be passed back into the nasal seal-forming structure 3052 for discharge to atmosphere via a vent 3400. In some example, the nasal seal-forming structure 3052 shown in FIGS. 9A and 9B may include a mouth cushion opening 3072 and/or a vent 3400 as shown, for example, in FIGS. 10A and 10B.

In one form of the present technology, the nasal seal-forming structure 3052 and/or mouth seal-forming structure 3062 may include a textured surface. FIG. 12 shows an exemplary nasal seal-forming structure 3052 according to one form of the present technology. The illustrated seal-forming structure 3052 includes a textured surface 3053 provided around orifices 3054.

FIGS. 6A-6D and 8A-12 show the seal-forming structures 3052 and 3062 of the nasal cushion 3050 and the mouth cushion 3060, respectively, according to different examples of the present technology. In some examples, the combined nasal cushion 3050 and mouth cushion 3060 may be referred to as a full face cushion or oro-nasal cushion. The mouth cushion 3060 may have a width to seal around the mouth between the patient's cheilion and naso-labial sulcus, a height to seal around the mouth on an inferior part of the upper lip and the junction between the supramenton and the lower lip, and/or a depth configured so as not to extend beyond the nasal cushion 3050 and/or the pronasale of the patient's nose.

FIGS. 9C, 9D and 10E show examples of a seal formed by a mouth cushion 3060 on a patient's face. FIGS. 9C and 9D show a mouth seal-forming structure 3062 of a mouth cushion shown in FIGS. 9A and 9B. FIG. 10E shows a mouth seal-forming structure 3062 of a mouth cushion shown in FIGS. 10A-10D. For simplicity, certain features (e.g., nasal cushion 3050, mouth cushion opening 3072, vent 3400 etc.) are now shown in FIGS. 9C, 9D and 10E. As shown in FIGS. 9C, 9D and 10E, the mouth seal-forming structure 3062 has a width to seal around the mouth between the patient's cheilion and naso-labial sulcus, and/or a height to seal around the mouth on an inferior part of the upper lip and the junction between the supramenton and the lower lip. In some examples of the present technology, the mouth seal-forming structure 3062 may touch or at least partially overlap the supramenton. The depth of the mouth cushion 3060 is shown not extending beyond the pronasale of the patient's nose. As shown in FIGS. 9C, 9D and 10E, the upper lip membrane of the mouth seal-forming structure 3062 occupies only a portion of the region between the upper lip and the subnasale in order to provide sufficient space for the nasal seal-forming structure 3052. In the illustrated example, the seal-forming structure 3062 may provide a flow of pressurized gas to the patient's mouth by sealing against at least a portion around the patient's mouth. The exemplary seal-forming structures 3062 will engage the patient's face around the mouth, such that air or breathable gas is supplied in use through separate orifices to the patient's nares and the patient's mouth. In some example, the seal-forming structures may also engage underside of the patient's nose and/or the patient's face below the bridge of the nose. An exemplary seal-forming structures 3062 may engage the patient's face above the upper lip vermillion and/or below the lower lip vermillion. Thus, an exemplary seal-forming structures 3062 of the mouth cushion may seal a portion of the patient's face around the mouth in use.

In one form of the present technology, the seal-forming structures 3062 may have a shape and size that seals around the patient's face without minimal displacement from the patients mouth. In one example, the mouth cushion 3060 and the seal-forming structures 3062 may be approximately 78-98 mm, e.g., 83-93, or about 88 mm wide, 35-55 mm, e.g., 40-50 mm, or 45 mm high and 25-45 mm, 30-40, or about 35 mm deep.

As shown in FIGS. 9A-12, the mouth cushion 3060 includes a front face 3074, a sealing lip (shown as seal-forming structure 3062) and a wall 3078 connecting the front face 3074 and the sealing lip. In some examples, the front face 3074, the sealing lip, and the wall 3078 may all be made of silicone. The mouth cushion 3060 may be completely flexible and/or made of the same flexible material. The wall 3078 and/or the sealing lip at a superior part of the corner-of-mouth portions of the mouth cushion 3060 may be more rigid than an inferior part of the corner of mouth portions of the mouth cushion 3060. The more rigid portions of the mouth cushion may allow for the mouth cushion 3060 to flex relative to the rigid portions due to movement of the patients mouth or jaw. Lateral sides 3090 of the mouth cushion 3060 may be flexible to allow the patient's jaw to drop while maintaining a seal.

In some forms of the present technology, one or more sides of the mouth seal-forming structure 3062 may include a structure allowing for a seal between the patient's face and mouth cushion 3060 to be maintained with movement of the patients mouth or jaw. For example, the seal-forming structure 3062 may expand in a vertical direction with movement of the patient's mouth or jaw in the vertical direction.

The mouth seal-forming structure 3062 may include an upper lip membrane 3076 configured to allow the mouth cushion to expand upwards when the patient's jaw opens. FIG. 9B shows the upper lip membrane 3076 including a central portion 3077 that is curved inwardly towards the plenum chamber 3200 of the mouth cushion 3060. In use, the curved central portion 3077 allows for the upper lip membrane 3076 to maintain a seal when the mouth is opened. In some examples, the curved central portion 3077 may allow for several millimetres of movement while maintaining engagement between the patient's face and the mouth seal-forming structure 3062. In this example, the mouth cushion 3060 may be set up while the patient's mouth is closed, allowing the mouth seal-forming structure 3062 to change shape from the shape shown in FIG. 9B when the mouth is opened.

In some examples, the upper lip membrane 3076 includes a central portion 3077 that is substantially linear or curved outwardly away from the mouth cushion plenum chamber 3200. In this example, the mouth cushion 3060 may be set up while the patient's mouth is open, and the upper lip membrane 3076 may change from the linear or curved outwardly shape to the shape shown in FIG. 9B when the mouth is closed.

The mouth seal-forming structure 3062 may include a lower lip membrane 3094 configured to allow the mouth cushion to expand downwards when the patient's jaw opens. FIG. 9B shows the lower lip membrane 3094 of the mouth seal-forming structure 3062 including a portion that is curved inwardly towards the plenum chamber 3200 of the mouth cushion 3060. In use, the curved portion allows for the lower lip membrane 3094 to maintain a seal when the mouth is opened or closed. In some examples, the lower lip membrane 3094 includes a central portion that is substantially linear or curved outwardly away from the mouth cushion plenum chamber 3200.

Examples of the present technology provide a membrane of the mouth seal-forming structure 3062 that may have a same structure along the perimeter (e.g., a lip area) of the mouth seal-forming structure 3062 or a different structure in one or more portions of the mouth seal-forming structure 3062.

The membrane of the mouth seal-forming structure 3062 may have a common width along the perimeter of the mouth seal-forming structure 3062. In other examples, the width of the seal-forming structure 3062 may be different at different locations of the patient's face. The width may be defined as the distance from an outside edge of the mouth seal-forming structure 3062 to a terminating portion of the mouth seal-forming structure 3062. The different width of seal-forming structure may be used when space is needed to accommodate the mouth seal-forming structure 3062 placed adjacent to the nasal seal-forming structure 3052.

When the modular mask takes on a full face mask configuration, the top lip region of the face needs to accommodate both the "body" from the nasal cradle or pillows, and the seal from the mouth cushion. In this configuration, the mouth cushion has to share the top lip area with the nasal component. As there is limited real estate on the top lip, the mouth cushion's seal in this region may need to be minimalistic.

Considering this limited room on the top lip, and that existing nasal cushion may need to be used (where no changes are possible to the nasal cushion), the mouth cushion may be designed to take-up as little space as possible to attain a seal. This may be achieved by placing a thin membrane seal along the top of the mouth cushion. The thin membrane seal may be allow the mouth cushion to adapt to any face shape without taking up much area/volume, produce an effective seal then pressurised and/or be comfortable.

In some examples, thin membrane seal along the top of the mouth cushion may mirror the amount of thin membrane that appears on the chin region of the mouth cushion. The thin membrane seal at the top of the mouth cushion may sufficiently form a seal on the remaining real estate available on the top lip once the nasal cushion is positioned for use.

In some examples, a width of the mouth seal-forming structure configured to seal against the patient's face above the mouth may be approximately the same as a width of the mouth seal-forming structure 3062 configured to seal against the patient's face below the mouth and/or on the sides of the mouth. This configuration is different from conventional seal-forming structure providing a wider above the mouth seal due to the above the mouth seal being formed by a combination of a continuous nasal and mouth seal forming structure.

The thin membrane on the top (and bottom) of the mouth seal-forming structure 3062 allows the mouth seal forming structure to flex and maintain seal with a mouth susceptible to jaw drop. This top and/or bottom membrane flexibility allows the cushion to absorb mouth movements and disturbances applied to the cushion itself. The flexible membranes may also "fill out" under pressure and expand in a longitudinal manner which helped fit mouths that are larger than cushion's moulded periphery height.

FIGS. 10F-10K illustrate back and cross sectional views of a mouth seal-forming structure 3062, according to an example of the present technology. Certain features are simplified or not shown (e.g., joint opening 3070 and/or the mouth cushion opening 3072) in FIGS. 10F-10K for simplicity.

In FIGS. 10F and 10G, the mouth seal-forming structure 3062 is shown in the relaxed position. In the relaxed position, the lip of the mouth seal-forming structure 3062 provides a mouth cushion opening that is W wide and H high. As shown in FIG. 10G, the top and bottom surfaces of the mouth cushion 3060 may be approximately parallel to each in the relaxed position.

FIGS. 10H and 10I illustrate the mouth seal-forming structure 3062 in a first use position. The first use position may be caused by one or more of the following: moving mouth, jaw drop, pressurised air, stretching by a larger mouth, and/or cushion compression and/or distortion against the face. In the first use position, the thin membrane on the top (and bottom) may allow for the opening to stretch in the vertical direction by a predetermined distance. In the example shown in FIG. 10H, the distance between the top and bottom membranes is increased by 2 h. The width of the mouth cushion opening in the first use position may be approximately equal to the width in the relaxed position due to lack of motion of the mouth in the horizontal direction. As shown in FIG. 10I, the mouth seal-forming structure 3062 may be compressed towards the patient's mouth in the first use position.

FIGS. 10J and 10K illustrate the mouth seal-forming structure 3062 in a second use position. In the second use position, the mouth seal-forming structure 3062 is vertically stretched and portions of the seal are partially inverted. Due to the flexibility of the thin membrane on the top (and bottom) of the mouth seal-forming structure 3062, the membrane of the mouth seal-forming structure 3062 can stretch and invert at the centre region and remain sealed. The inverted portions of the membrane can still hold pressure provided the headgear vectors are tightened to counteract the therapy pressure. The flexibility of the membrane does not cause discomfort by the inverted membrane. In the second use position, the mouth cushion opening in the vertical direction may extend beyond H+2 h, while the width may be approximately equal to the width in the first use position and/or the relaxed position.

The flexibility of the mouth cushion may allow for a one size fits all mouth cushion, which can be used with different nasal-seal forming structures 3052.

In some examples, a width of the mouth seal-forming structure configured to seal against the patient's face above the mouth may be smaller than a width of the mouth seal-forming structure 3062 configured to seal against the patient's face below the mouth and/or on the sides of the mouth (see e.g., FIGS. 10C, 10D and 11B). A width of the mouth seal-forming structure 3062 may need to be smaller above the mouth because the space above the mouth is shared by the nasal-seal forming structure 3052 and the mouth seal-forming structure 3062.

In some examples, the width of the seal forming structure may be between 3-15 mm, e.g., 5-10 mm, or 7 mm. In some examples, the width of the upper lip membrane may be half the width of the lower lip membrane. In some examples, the width of the upper lip membrane may be smaller than the width of the lateral side membrane and/or the lower lip membrane.

When a thin membrane is provided at the top and/or the bottom portions of the mouth cushion, the mouth cushion alone may lack stability. As discussed in more detail below, one or more thickened portions (e.g., thickened portion of silicone) may be provided to one or more regions of the seal-forming structure 3052 and/or 3062 to add support and stability to the one or more regions, e.g., to ensure cushion stability and seal performance. In some examples, additional stability may be "borrowed" from the attached nasal portion, vent 3400, and/or connection port 3600.

FIG. 10C shows a mouth seal-forming structure 3062 according to another example of the present technology. As shown in FIG. 10C, the mouth seal-forming structure 3062 includes an upper lip membrane 3076 and a lower lip membrane 3094, including linear central portions. The linear portions on the upper lip membrane 3076 and the lower lip membrane 3094 may be approximately in parallel to each other. The lateral sides 3090 may couple the upper lip membrane 3076 to the lower lip membrane 3094. The example shown in FIG. 10C may be a more basic shape as compared to the example shown in FIG. 9B due to the linear portions. In general, the more basic the shape, the easier it is to manufacture, the easier it is to seal, the easier it is to use textile seal membrane (no creasing) by bypassing the complex area where the nasal seal meets the mouth seal.

In one form of the present technology shown in FIG. 10C, the top half of the mouth seal-forming structure 3062 may be symmetrical to the bottom half of the mouth seal-forming structure 3062. In some examples, the top corners of the mouth seal-forming structure 3062 may be stiffer and/or thicker as compared to the lower corners to provide more force into the top lip below the nose. In addition or alternatively, a vector of the connectors (e.g., top portion of wishbone connector) may be positioned to provide a force into the top corners of the seal-forming structure 3062. As shown in FIGS. 9A, 10A, 10B, 11A and 11C, the connecting location for the upper arm 3066-1 and the lower arm 3066-2 is provided such that in use a force is applied towards the corners of the seal forming structure 3062.

Similar to the example shown in FIG. 9B, in use, the linear portion of the upper lip membrane 3076 may maintain a seal when the mouth is closed and opened. In some examples, the flexibility of the linear portion may allow for several millimetres of movement while maintaining engagement between the patient's face and the mouth seal-forming structure 3062.

In some examples of the present technology, a portion of the nasal seal-forming structure 3052 and/or the mouth seal-forming structure 3062 may be polished to improve grip between the seal-forming structure and the patient's face. For example, a central portion of the upper lip membrane 3076 and/or the upper lip membrane 3076 may be polished to provide a grip to the patient's lips. In some examples, only the central portion of the upper lip membrane 3076 and/or the upper lip membrane 3076 may be polished in the mouth seal-forming structure 3062.

In some examples, the central portion of the upper lip membrane 3076 and/or the upper lip membrane 3076 may have a membrane thickness that allows lots of flexibility in this region, enabling the cushion to maintain the seal when lips are moved (e.g., due to talking). For example, the central portion of the upper lip membrane 3076 and/or the upper lip membrane 3076 may have a thickness that is lower than other portions of the upper lip membrane 3076 and/or the upper lip membrane 3076. In one example, the central portion of the upper lip membrane 3076 and/or the upper lip membrane 3076 may have a thickness that is 0.25 mm to allow lots of flexibility, enabling the cushion to maintain the seal when lips are moved.

In some form of the present technology, a portion of the upper lip membrane 3076 may abut at least a portion of the nasal seal-forming structure 3052 or outer surface of the nasal cushion 3050.

In some forms of the present technology, the mouth cushion 3060 and the nasal cushion 3050 are releasably connected to one another via a joint 3068. In one form, the nasal cushion 3050 and mouth cushion 3060 are formed as separate components and are coupled by a joint 3068. In the jointed configuration, the mouth seal-forming structure 3062 and the nasal seal-forming structures 3052 provide separately sealed regions on the patient's face and provide a common plenum chamber 3200 connected by the joint 3068.

In an example, the exemplary seal-forming structure 3052 and/or 3062 may include at least two regions of different thickness. In an example, the differing thicknesses may be produced by extending regions of different thickness different distances into the interior of the seal-forming structures 3052 and/or 3062 such that the exterior surface of the seal-forming structure 3052 and 3062 are provided adjacent to each other and approximately even.

In an example, naris openings may be formed to generally align with patient's corresponding naris to provide the flow of pressurised gas to the patient's nares for inhalation.

In one form, the nasal cushion 3050 and/or the mouth cushion 3060 include a textile sealing surface mounted on a silicone body.

In an example, the seal-forming structure 3052 and/or 3062 may include two or more different sizes/shapes. For example, size dimensions and/or contours of the seal-forming structure may be varied to provide alternative seal forming surfaces for different patients.

In an example, one or more thickened portions (e.g., thickened portion of silicone) may be provided to one or more regions of the seal-forming structure 3052 and/or 3062 to add support and stability to the one or more regions, e.g., to ensure cushion stability and seal performance. The one or more thickened portions may be produced by increasing the thickness of the seal-forming structure 3052 and/or 3062 in one or more regions into the interior of the seal-forming structure 3052 and/or 3062 such that the exterior surface of the seal-forming structure 3052 and/or 3062 remains continuous and smooth.

In the example shown in FIGS. 4B and 4D, a thickened portion may be provided in regions 3066-4 around and/or under the lower headgear connector 3066, a region 3070-1 around the mouth cushion joint opening 3070, a region 3072-1 around the mouth cushion opening 3072, and/or regions 3066-4 around and/or under the upper arm 3066-1 and/or lower arm 3066-2. The thickened portion may be provided adjacent to or at the lateral sides 3090, the lower lip membrane 3094 and/or upper lip membrane 3076 (see FIG. 9B). A thickened portion along the upper lip membrane 3076 may provide structural support and avoid collapsing of the mouth cushion 3060 when positioning the mouth cushion 3060 against the nasal cushion 3050. In one example, the thickened portion is provided along opposite sides of the upper lip membrane 3076 but not along the central portion 3077 to allow more flexibility in area near the central portion 3077. The one or more thickened portions may include similar or different thicknesses relative to one another. In an example, the thickness of thickened portion(s) and/or the specific positioning of the thickened portion(s) along the seal-forming structure 3052 and/or 3062 may be at least partially dependent on the size of the seal-forming structure 3052 and/or 3062.

In some examples, the seal-forming structure 3052 and/or 3062 may comprise nasal cushion (e.g., a cradle cushion), mouth cushion and/or a seal forming structures as described in PCT Application No. PCT/AU2018/050289, filed Mar. 29, 2018, and PCT Patent Application Publication No. WO 2019/119058, filed Dec. 21, 2018, the entire contents of which are incorporated herein by reference.

In one form, the nasal cushion 3050 and mouth cushion 3060 are integrally formed as a single component. In other examples, discussed in more detail below, the nasal cushion 3050 and mouth cushion 3060 are formed as separate components and are coupled by a joint 3068.

In some forms of the present technology, the mouth cushion 3060 may contain no rigid structural features. This may allow for the mouth cushion's silicone material to readily contort and conform to the patient's shape for a seal around the whole periphery of the mouth. As discussed above, various thicknesses of silicone can be implemented for structural purposes while still providing flexibility and a good seal. The silicone material of the mouth cushion 3060 provides a fully flexible front portion, flexible top and side membrane supports that are positioned against a person's face around the mouth, and thin flexible bottom and/or top lip.

5.3.3 Plenum Chamber

The plenum chamber 3200 has a perimeter that is shaped to be complementary to the surface contour of the face of an average person in the region where a seal will form in use. In use, a marginal edge of the plenum chamber 3200 is positioned in close proximity to an adjacent surface of the face. Actual contact with the face is provided by the seal-forming structure 3100. The seal-forming structure 3100 may extend in use about the entire perimeter of the plenum chamber 3200. In some forms, the plenum chamber 3200 and the seal-forming structure 3100 are formed from a single homogeneous piece of material.

In certain forms of the present technology, common plenum chamber 3200 is provided by the plenum chamber in the nasal cushion 3050, the plenum chamber in the mouth cushion 3060, and chamber formed by the joint 3068 coupling the mouth cushion 3060 to the nasal cushion 3050.

In certain forms of the present technology, the plenum chamber 3200 does not cover the eyes of the patient in use. In other words, the eyes are outside the pressurised volume defined by the plenum chamber. Such forms tend to be less obtrusive and/or more comfortable for the wearer, which can improve compliance with therapy.

In certain forms of the present technology, the plenum chamber 3200 is constructed from a transparent material, e.g. a transparent polycarbonate. The use of a transparent material can reduce the obtrusiveness of the patient interface, and help improve compliance with therapy. The use of a transparent material can aid a clinician to observe how the patient interface is located and functioning.

In certain forms of the present technology, the plenum chamber 3200 is constructed from a translucent material. The use of a translucent material can reduce the obtrusiveness of the patient interface, and help improve compliance with therapy.

5.3.4 Positioning and Stabilising Structure

The seal-forming structure 3100 of the patient interface 3000 of the present technology may be held in sealing position in use by the positioning and stabilising structure 3300. Positioning and stabilising structure 3300 may be referred to as "headgear" since it engages the patient's head in order to hold the patient interface 3000 in a sealing position.

In one form the positioning and stabilising structure 3300 provides a retention force at least sufficient to overcome the effect of the positive pressure in the plenum chamber 3200 of the nasal cushion 3050 and/or the mouth cushion 3060 to lift off the face.

In one form the positioning and stabilising structure 3300 provides a retention force to overcome the effect of the gravitational force on the patient interface 3000.

In one form the positioning and stabilising structure 3300 provides a retention force as a safety margin to overcome the potential effect of disrupting forces on the patient interface 3000, such as from tube drag, or accidental interference with the patient interface.

In one form of the present technology, a positioning and stabilising structure 3300 is provided that is configured in a manner consistent with being worn by a patient while sleeping. In one example the positioning and stabilising structure 3300 has a low profile, or cross-sectional thickness, to reduce the perceived or actual bulk of the apparatus. In one example, the positioning and stabilising structure 3300 comprises at least one strap having a rectangular cross-section. In one example the positioning and stabilising structure 3300 comprises at least one flat strap.

In one form of the present technology, a positioning and stabilising structure 3300 is provided that is configured so as not to be too large and bulky to prevent the patient from lying in a supine sleeping position with a back region of the patient's head on a pillow.

In one form of the present technology, a positioning and stabilising structure 3300 is provided that is configured so as not to be too large and bulky to prevent the patient from lying in a side sleeping position with a side region of the patient's head on a pillow.

In one form of the present technology, a positioning and stabilising structure 3300 is provided with a decoupling portion located between an anterior portion of the positioning and stabilising structure 3300, and a posterior portion of the positioning and stabilising structure 3300. The decoupling portion does not resist compression and may be, e.g. a flexible or floppy strap. The decoupling portion is constructed and arranged so that when the patient lies with their head on a pillow, the presence of the decoupling portion prevents a force on the posterior portion from being transmitted along the positioning and stabilising structure 3300 and disrupting the seal.

In one form of the present technology, a positioning and stabilising structure 3300 comprises a strap constructed from a laminate of a fabric patient-contacting layer, a foam inner layer and a fabric outer layer. In one form, the foam is porous to allow moisture, (e.g., sweat), to pass through the strap. In one form, the fabric outer layer comprises loop material to engage with a hook material portion.

In certain forms of the present technology, a positioning and stabilising structure 3300 comprises a strap that is extensible, e.g. resiliently extensible. For example the strap may be configured in use to be in tension, and to direct a force to draw a seal-forming structure into sealing contact with a portion of a patient's face. In an example the strap may be configured as a tie.

In one form of the present technology, the positioning and stabilising structure comprises a first tie, the first tie being constructed and arranged so that in use at least a portion of an inferior edge thereof passes superior to an otobasion superior of the patient's head and overlays a portion of a parietal bone without overlaying the occipital bone.

In one form of the present technology suitable for a nasal-only mask or for a full-face mask, the positioning and stabilising structure includes a second tie, the second tie being constructed and arranged so that in use at least a portion of a superior edge thereof passes inferior to an otobasion inferior of the patient's head and overlays or lies inferior to the occipital bone of the patient's head.

In one form of the present technology suitable for a nasal-only mask or for a full-face mask, the positioning and stabilising structure includes a third tie that is constructed and arranged to interconnect the first tie and the second tie to reduce a tendency of the first tie and the second tie to move apart from one another.

In certain forms of the present technology, a positioning and stabilising structure 3300 comprises a strap that is bendable and e.g. non-rigid. An advantage of this aspect is that the strap is more comfortable for a patient to lie upon while the patient is sleeping.

In certain forms of the present technology, a positioning and stabilising structure 3300 comprises a strap constructed to be breathable to allow moisture vapour to be transmitted through the strap.

In certain forms of the present technology, a system is provided comprising more than one positioning and stabilizing structure 3300, each being configured to provide a retaining force to correspond to a different size and/or shape range. For example the system may comprise one form of positioning and stabilizing structure 3300 suitable for a large sized head, but not a small sized head, and another. suitable for a small sized head, but not a large sized head.

5.3.4.1 Headgear Conduits

In certain forms of the present technology, the positioning and stabilising structure 3300 comprises one or more hollow tubes configured to convey pressurized gas received from a conduit forming part of the air circuit 4170 at the therapeutic pressure to the nasal cushion 3050 and/or the mouth cushion 3060 for breathing by the patient.

In the form of the present technology, a common connecting element 3330 of the positioning and stabilizing structure 3300 may include a first headgear conduit 3010 (e.g., a left headgear tube) and a second headgear conduit 3020 (e.g., right headgear section), each adapted to pass along a patient's cheek under a patient's eye and between the patient's eye and ear towards a superior position at the rear of the patient's head. Each of the first and second headgear conduits 3010 and 3020 is adapted to extend towards the nasal cushion 3050 from a rear of the patient's head, e.g. a superior portion of the posterior of the patient's head, e.g., at or along the crown or parietal bones. Ends of the headgear conduits 3010 and 3020 near the patient's nose and mouth may be configured pass the pressurized gas to the nasal cushion 3050 while supporting the nasal cushion 3050 in position on the patient's face. The first and second headgear conduits 3010 and 3020 together with the nasal cushion 3050 form a loop.

In an example, the first headgear conduit 3010 may include a left cushion interface 3012 and the second headgear conduit 3020 may include a right cushion interface 3022 for removably or releasably coupling to and supporting the nasal cushion 3050. The left cushion interface 3012 and/or the right cushion interface 3022 may receive smaller protruding coupling sections (e.g., upper headgear connectors 3056) of the nasal cushion 3050 and secure the nasal cushion 3050 between ends of the first and second headgear conduits 3010 and 3020.

At each lateral side of the plenum chamber 3200 in the nasal cushion 3050 there may be a plenum chamber lateral end 3202 in the form of a hollow passageway. An each lateral side of the plenum chamber 3200, the upper headgear connectors 3056 extending laterally outward of the plenum chamber lateral end 3202. The upper headgear connectors 3056 may releasably connect to respective ends of the left and right cushion interfaces 3012 and 3022 of the first and second headgear conduits 3010 and 3020 of the positioning and stabilising structure 3300. In one form of the present technology, the nasal cushion may include plugs to close the opening provided by the plenum chamber lateral end 3202 and the upper headgear connectors 3056. The plugs may include connectors to connect to the nasal headgear strap 3310.

The headgear conduits 3010 and 3020 are provided as an integral part of the positioning and stabilising structure 3300 to position and stabilise the nasal cushion 3050 and/or the mouth cushion 3060 of the patient interface 3000 to the appropriate part of the patient's face (for example, the nose and/or mouth). This allows the conduit of air circuit 4170 providing the flow of pressurised air to connect to a connection port 3600 of the patient interface in a position other than in front of the patient's face which may be inconvenient and/or unsightly to some people. While a pair of conduits 3010, 3020 have some advantages, in some examples, the positioning and stabilising structure 3300 comprises only a single headgear conduit 3010 or 3020 configured to overlie the patient's head on one side. A strap or other stabilising component may be provided to the other side of the patient's head between the top end of the single headgear conduit 3010 or 3020 and the nasal cushion 3050, to provide balanced forces on the nasal cushion 3050.

Since air can be contained and passed through headgear conduits 3010, 3020 in order to deliver pressurised air from the air circuit 4170 to the patient's airways, the positioning and stabilising structure 3300 may be described as being inflatable. It will be understood that an inflatable positioning and stabilising structure 3300 does not require all components of the positioning and stabilising structure 3300 to be inflatable. For example, in the example shown in FIGS. 5A-6D, the positioning and stabilising structure 3300 comprises the headgear conduits 3010 and 3020, portions of which is inflatable, and the nasal headgear strap 3310, which is not inflatable.

Patient interfaces in which the connection port is not positioned in front of the patient's face may be advantageous as some patients find a conduit that connects to a patient interface in front of the face to be unsightly and obtrusive. For example, a conduit connecting to a patient interface in front of the face may be prone to being tangled up in bedclothes or bed linen, particularly if the conduit extends downwardly from the patient interface in use. Forms of the technology with a patient interface with a connection port positioned proximate the top of the patient's head in use may make it easier or more comfortable for a patient to lie or sleep in one or more of the following positions: in a side or lateral position; in a supine position (i.e. on their back, facing generally upwards); and in a prone position (i.e. on their front, facing generally downwards). Moreover, connecting a conduit to the front of a patient interface may exacerbate a problem known as tube drag, wherein the conduit may provide an undesired drag force upon the patient interface thereby causing dislodgement away from the face.

In the form of the present technology illustrated in FIGS. 6A-7D, the headgear conduits 3010 and 3020 are fluidly connected at their upper ends to each other and to connection port 3600. In one embodiment, the two headgear conduits 3010 and 3020 are integrally formed while in other embodiments the conduits are separate components that are connected together in use and may be disconnected, for example for cleaning or storage. Where separate conduits are used they may be indirectly connected together, for example each may be connected to a T-shaped conduit having two conduit arms each fluidly connectable to the headgear conduits 3010 and 3020 and a third conduit arm or opening acting as the connection port 3600. The connection port 3600 may comprise an elbow 3610 received in fluid connection opening at the centre of two integrally formed headgear conduits 3010 and 3020.

The headgear conduits 3010 and 3020 may be formed of a semi-rigid material such as an elastomeric material, e.g. silicone. For example, the headgear conduits 3010 and 3020 may have a natural, preformed shape and be able to be bent or moved into another shape if a force is applied to the tubes. For example, the headgear conduits may be generally arcuate or curved in a shape approximating the contours of a patient's head between the top of the head and the nasal or oral region.

As described in U.S. Pat. No. 6,044,844, the contents of which are incorporated herein, the headgear conduits may be crush resistant to avoid the flow of breathable gas through the tubes if either is crushed during use, for example if it is squashed between a patient's face and pillow. Crush resistant tubes may not be necessary in all cases as the pressurised gas in the tubes may act as a splint to prevent or at least restrict crushing of the headgear conduits during use. A crush resistant tube may be advantageous where only a single headgear conduits is present as if the single tube becomes blocked during use the flow of gas would be restricted and therapy will stop or reduce in efficacy.

In certain forms of the technology, one or more portions of the headgear conduits 3010 and/or 3020 may be rigidised by one or more rigidising or stiffening elements. Examples of rigidising elements include: sections of the headgear conduits 3010 and/or 3020 that are comparatively thicker than other sections; sections of the headgear conduits 3010 and/or 3020 that are formed from a material that is comparatively more rigid than the material forming other sections; and a rigid member attached to the inside, outside or embedded in a section of tube. The use of such rigidising elements helps to control how the positioning and stabilising structure 3300 will function in use, for example where the headgear conduits 3010 and/or 3020 is/are more likely to deform if forces are applied to them and where the shape of the headgear conduits 3010 and/or 3020 is more likely to be maintained if forces are applied. The selection of where such rigidising elements are positioned in the headgear conduits 3010 and/or 3020 can therefore help to promote comfort when the patient interface 3000 is worn and can help to maintain a good seal at the nasal seal-forming structure 3052 and/or the mouth seal-forming structure 3062 during use. Rigidising or stiffening elements may be in the positioning and stabilising structure 3300 which is configured to support relatively heavy seal-forming structures such as full face or oro-nasal cushion assemblies.

In certain forms of the technology, one or more portions of the headgear conduits 3010 and/or 3020 may include extendable sections. In some examples, an extendable tube section comprises an extendable concertina structure 3362. As shown in FIGS. 6A-7D, the superior portions of the headgear conduits 3010 and/or 3020 may include extendable tube sections each in the form of an extendable concertina structure 3362. Each extendable concertina structure 3362 may comprise a portion of the headgear conduit having one or more folding portions, pleats, corrugations or bellows to form an extendable portion of the headgear conduits 3010 and/or 3020.

5.3.4.2 Headgear Straps

In certain forms of the present technology, the positioning and stabilising structure 3300 comprises one or more headgear straps to position and/or support the mouth cushion 3060 and/or the nasal cushion 3050. The one or more headgear straps may act in addition to the one or more headgear conduits to position and stabilise the nasal cushion 3050 and/or the mouth cushion 3060 in sealing position at the entrance to the patient's airways. The one or more headgear straps form part of the positioning and stabilising structure 3300.

As shown in FIGS. 4A and 4C, different straps may be coupled to the headgear conduits 3010 and/or 3020 or the nasal cushion 3050. A nasal headgear strap 3310 may be coupled to the headgear conduits 3010 and/or 3020 or nasal cushion 350 when just the nasal cushion 3050 is used without the mouth cushion. An oro-nasal headgear strap 3320 may be coupled to the headgear conduits 3010 and/or 3020 or the nasal cushion when both the nasal cushion 3050 and mouth cushion 3060 are used.

The nasal headgear strap 3310 and the oro-nasal headgear strap 3320 may include different strap configurations to provide a therapeutically effective position and seal. With reference to FIG. 4A, the nasal headgear strap 3310 may include a single strap removably connected between the headgear conduits 3010 and/or 3020. The nasal headgear strap 3310 of the positioning and stabilising structure 3300 is connected between the two the headgear conduits 3010 and/or 3020 positioned on each side of the patient's head and passing around the back of the patient's head, for example overlying or lying inferior to the occipital bone of the patient's head in use. The nasal headgear strap 3310 connects to each tube above the patient's ears.

The oro-nasal headgear strap 3320 may include an upper strap 3322, which can be similar to the nasal headgear strap 3310 and one or more additional straps. As shown in FIGS. 4A and 4C, the oro-nasal headgear strap 3320 may include the upper strap 3322 removably connected between the headgear conduits 3010 and/or 3020, a lower strap 3326 including ends that are removably coupled to the mouth cushion 3060, and a coupling strap 3324 connecting the upper strap 3322 to the lower strap 3326.

The nasal headgear strap 3310 and the oro-nasal headgear strap 3320 are not limited to the specific number of straps and/or strap configurations shown in the figures and may include one or more further straps.

In certain forms of the technology, the positioning and stabilising structure 3300 comprises a mechanism for connecting the nasal headgear strap 3310 and the oro-nasal headgear strap 3320 to the headgear conduits 3010 and/or 3020, the nasal cushion 3050, and/or the mouth cushion 3060. The nasal headgear strap 3310 and/or the oro-nasal headgear strap 3320 may be connected directly or indirectly to the headgear conduits 3010 and/or 3020, the nasal cushion 3050, and/or the mouth cushion 3060. As shown in FIG. 4C the coupling strap 3324 may be detachable from the nasal headgear strap 3310. The coupling strap 3324 may attach to the nasal headgear strap 3310 via Velcro or another attaching mechanism.

In the case of the patient interface 3000 shown in FIGS. 4A and 6A-6D, the connecting elements 3980 are provided on each of the headgear conduits 3010 and/or 3020 is configured to connect the nasal headgear strap 3310 or the oro-nasal headgear strap 3320 to the headgear conduits 3010 and/or 3020. The connecting elements 3980 may comprise tabs protruding from the respective headgear conduit towards the rear of the patient's head. Each of the connecting elements 3980 may include one or more slots 3982 to threadedly receive ends of the nasal headgear strap 3310 or oro-nasal headgear strap 3320 in a length adjustable manner. The same slot or different slots (e.g., provided at different positions and/or angles) may be used for the nasal headgear strap 3310 and oro-nasal headgear strap 3320. In some examples, the connecting elements 3980 may include a magnet and/or a clip configured to removable engage a corresponding connecting element provided on the nasal headgear strap 3310 or oro-nasal headgear strap 3320.

In the examples illustrated in FIGS. 6A-6D and 8A-8D, the lower strap 3326 of the oro-nasal headgear strap 3320 may be adapted to pass under the patient's ears and/or include a pair of ends attachable to the mouth cushion 3060. Each end of the bottom strap section 3955 may include a connector 3328 including a magnet and/or a clip configured to removable engage a corresponding lower headgear connector 3066 on the mouth cushion 3060. The connector 3328 on the lower strap 3326 and corresponding lower headgear connector 3066, which may include a cushion clip or magnetic connection element, allow the oro-nasal headgear strap 3320 to be removable attached to the mouth cushion 3060.

In one example, the lower strap 3326 may include buckles 3360 near ends of the strap through which the ends of the strap are threaded to permit length adjustment of the lower strap 3326.

In some examples, the oro-nasal headgear strap 3320 includes the nasal headgear strap 3310 and a lower strap 3326 that is releasably connected (e.g., via a clip or connector) to the nasal headgear strap 3310.

In some forms of the present technology, the nasal headgear strap 3310 and/or the oro-nasal headgear strap 3320 are adjustable. The length of the nasal headgear strap 3310 and/or the oro-nasal headgear strap 3320 between the connecting elements 3980 may be adjusted by pulling more or less of the strap through one or both of the connecting elements 3980. The nasal headgear strap 3310 and/or the oro-nasal headgear strap 3320 may be secured to itself after passing through the slot 3982 in the connecting elements 3980, for example, with hook-and-loop fastening means.

The straps therefore are able to be adjusted to fit around different head sizes. In some forms of the technology the angle of the straps relative to the headgear conduits 3010 and/or 3020 or patient's head is able to be adjusted to fit around the patient's head at different locations. This adjustability assists the positioning and stabilising structure 3300 to accommodate different head shapes and sizes.

In some forms of the technology, nasal headgear strap 3310 and/or the oro-nasal headgear strap 3320 exert a force on the headgear conduits 3010 and 3020 to pull them in an at least partially posterior (e.g. rearwards) direction at the locations of the connecting elements 3980. The nasal headgear strap 3310 and/or the oro-nasal headgear strap 3320 may also exert a force on the headgear conduits 3010 and 3020 to pull them in an at least partially inferior (e.g. downwards) direction. The magnitude of this force may be adjusted by altering the length of the straps between connecting elements.

The nasal headgear strap 3310 and/or the oro-nasal headgear strap 3320 may comprise a rectangular cross-section along some or all of its length. Additionally, the nasal headgear strap 3310 and/or the oro-nasal headgear strap 3320 may have a profile with one or more rounded edges to provide greater comfort and to reduce the risk of headgear straps marking or irritating the patient. In certain forms of the present technology, a positioning and stabilising structure 3300 comprises a strap that is bendable and e.g. non-rigid. An advantage of this aspect is that the strap is more comfortable for a patient to lie upon while the patient is sleeping.

Examples of configurable and/or interchangeable nasal and/or oro-nasal headgear straps that may be used with the examples of the present disclosure are described in International Application No. PCT/AU2020/050959 filed on Sep. 10, 2020, which is hereby incorporated by reference in its entirety.

5.3.4.3 U-Shaped Headgear Connectors

In one form of the present technology illustrated in FIGS. 4D, 9A, 10A, 10B, and 11A, each of the lower headgear connectors 3066 on the mouth cushion 3060 includes a pair of arms having a wish-bone shape, each of the lower headgear connectors having an upper arm 3066-1 and a lower arm 3066-2 connected to a front face 3074 of the mouth cushion 3060, the upper arm 3066-1 being spaced from the lower arm 3066-2. The headgear connectors 3066 integrate with the flexible nature of the mouth cushion 3060. As the silicone's material characteristics are adequate for transferring (head gear) vector forces, the headgear connectors 3066 can be designed to be an integral part of the silicone mouth cushion.

The upper arm 3066-1 and the lower arm 3066-2 may be connected along vertical lines that are parallel to each other. In one example, the vertical connection of the upper arm 3066-1 and the vertical connection of the lower arm 3066-2 may be provided along a same vertical line. The connection of the upper arm 3066-1 and the lower arm 3066-2 may be integral (partially or fully) with the front surface of the mouth cushion 3060.

The arrangement of the upper arm 3066-1 and the lower arm 3066-2 may distribute support forces to different zones of the mouth cushion 3060. For example, the arrangement of the upper arm 3066-1 and the lower arm 3066-2 may distribute support forces, respectively, to a mid-zone and a lower zone of the mouth cushion 3060. In another example, the arrangement of the upper arm 3066-1 and the lower arm 3066-2 may distribute support forces, respectively, to an upper-zone and a lower zone of the mouth cushion 3060.

As shown in FIGS. 4D, 9A, 10A, 10B, and 11A, the upper arm 3066-1 may be coupled to the mouth cushion 3060 at or just above a mid-zone of the mouth cushion 3060 and the lower arm 3066-2 may be coupled to the mouth cushion 3060 near a lower zone of the mouth cushion. In some examples, the upper arm 3066-1 may be attached to a top of a front surface of the mouth cushion and the lower arm 3066-2 may be attached to a bottom of a front surface of the mouth cushion. This configuration may allow for the headgear connectors 3066 to equally split the headgear vector to the top and bottom of the cushion.

The upper arm 3066-1 and the lower arm 3066-2 may be attached (e.g., glued) to the front face of the mouth cushion 3060 at a position that is spaced inwards from the lateral edge of the mouth cushion 3060. In one example, one pair of upper arm 3066-1 and the lower arm 3066-2 may be attached along a vertical line crossing near an alar crest point of the patient on one side of the nose and the second pair of upper arm 3066-1 and the lower arm 3066-2 may be attached along a vertical line crossing near an alar crest point of the patient on an opposite side of the nose.

In some examples, the upper arm 3066-1 and the lower arm 3066-2 may have a uniform thickness (e.g., formed from a 1 mm silicone sheet) and be glued to the mouth cushion 3060 (e.g., via a silicone adhesive). In one form of the present technology, the upper arm 3066-1 and the lower arm 3066-2 may be moulded as one part with the cushion in the same material.

The upper arm 3066-1 and the lower arm 3066-2 may be movable and/or flexible to lie flush against the front face of the mouth cushion 3060. The pair of arms may conform to the shape of the mouth cushion 3060 as they extend from their attached points and towards the respective lateral edge of the mouth cushion 3060. The upper arm 3066-1 and the lower arm 3066-2 may deform in response to deformations applied to the mouth cushion 3060 (e.g., due to movement of patient's mouth). Each of the arms may be dimensioned and configured to straddle opposite sides of the patient's cheilion, thus applying forces against corners of the patient's mouth when the mouth cushion 3060 is worn by the patient and supported by the positioning and stabilizing structure 3300.

The upper arm 3066-1 and the lower arm 3066-2 may be provided in a U-shape or C-shape with ends coupled to the mouth cushion 3060. A connector 3066-3 including a clip or magnet may be provided in the middle section of the U-shape. The connector 3066-3 is removably coupled to a lower strap of the oro-nasal headgear strap 3320 (e.g., the strap 3326). In use, the upper arm 3066-1 and the lower arm 3066-2 apply a force to the front face of the mouth cushion 3060 due to tension applied to the lower strap, to anchor the mouth cushion into the corners surrounding the patient's mouth. As the force is applied, a portion of the upper arm 3066-1 and the lower arm 3066-2 near the connector 3066-3 may partially move away from the outer surface of the mouth cushion 3060, and a portion of the upper arm 3066-1 and the lower arm 3066-2 closer to the ends coupled to the mouth cushion 3060 may remain positioned against the mouth cushion 3060. The flexibility and elasticity of the upper arm 3066-1 and the lower arm 3066-2 allow for the mouth cushion 3060 to provide a sufficient seal between the seal-forming structure 3062 and the patient's face.

The arrangement of the upper arm 3066-1 and the lower arm 3066-2 may transfer the headgear vector force around towards periphery of the mouth cushion's seal. The headgear vector force travels through the connector 3066-3 (e.g., the magnetic coupling) and pulls the flexible connector "wing"

down onto the mouth cushion 3060. As a result, the flexible silicone connector 3066 distributes a force along it's underside unto and through the front surface of the mouth cushion 3060 to the cushion's sealing interface. Distribution of force from the headgear vectors through the flexible cushion's headgear connector "wing" and through the cushion may create a reaction seal against the face. FIG. 10L illustrates exemplary vector forces that may be distributed by the upper arm 3066-1 and the lower arm 3066-2 onto the mouth cushion 3060, mouth cushion 3060 reaction forces distributed onto a patient's face, and headgear action tension and headgear reaction forces.

The U-shape may be similar in size and/or shape to lateral side portions of the mouth cushion 3060. Each of the pair of arms may be flexible and conform to changes in the shape of the mouth cushion 3060 (e.g., due to expansion and/or deformation of the mouth cushion 3060).

While the pair of arms are shown as having a wish-bone shape other configuration of the two arms can be used to distribute the force applied to the connect 3066 to different portions of the mouth cushion 3060. For example, the upper arm and the lower arm may extend from the connector 3066—in a straight direction and be provided at an angle to each other.

The upper arm 3066-1 and the lower arm 3066-2 may be made of silicone or a material that is more rigid than silicone. The silicone of the pair of arms may be the same as the silicone of the front surface of the mouth cushion 3060.

5.3.5 Vent

In one form, the patient interface 3000 includes a vent 3400 constructed and arranged to allow for the washout of exhaled gases, e.g. carbon dioxide. In one form, the vent 3400 may be provided as part of an anti-asphyxia valve 3059.

In certain forms the vent 3400 is configured to allow a continuous vent flow from an interior of the plenum chamber 3200 to ambient whilst the pressure within the plenum chamber is positive with respect to ambient. The vent 3400 is configured such that the vent flow rate has a magnitude sufficient to reduce rebreathing of exhaled $CO_2$ by the patient while maintaining the therapeutic pressure in the plenum chamber in use. The vent 3400 may provide a continuous vent flow of gas from the interior of the plenum chamber 3200 to ambient throughout the patient's respiratory cycle.

One form of vent 3400 in accordance with the present technology comprises a plurality of holes, for example, about 20 to about 80 holes, or about 40 to about 60 holes, or about 45 to about 55 holes.

The vent 3400 may be located in the plenum chamber 3200. Alternatively, the vent 3400 is located in a decoupling structure, e.g., a swivel such as elbow 3610.

In one example, the patient interface 3000 comprises at least one vent 3400 in the nasal cushion 3050 (e.g., in the plenum chamber 3200), the mouth cushion 3060, and/or the joint 3068.

In the example shown in FIGS. 4A-8D, the patient interface 3000 comprises a plurality of vents 3400. In one example, the patient interface 3000 comprises at least one vent 3400 in the nasal cushion 3050 and at least one vent in the elbow 3610. In another example, the patient interface 3000 comprises at least one vent 3400 in the mouth cushion 3060 and at least one vent in the elbow 3610.

Each vent 3400 on the nasal cushion 3050, the mouth cushion 3060, and/or elbow 3610 may include an array of holes. The vent 3400 of the patient interface 3000 are sized and configured to provide sufficient gas washout throughout a range of therapeutic pressures.

The patient interface 3000 may comprise a diffuser configured to diffuse the flow of air though the vent to reduce vent noise and reduce jetting of air out of the vent holes. The diffuser may be provided to a cover over the vent holes. In some examples, the vent 3400 may comprise a vent module configured to be removed from the nasal cushion 3050, the mouth cushion 3060, and/or the elbow 3610.

While in the figures a vent 3400 is shown in specific locations, an anti-asphyxia valve 3059 including a vent 3400 may be provided in place of the illustrated vent. While the vent 3400 or the anti-asphyxia valve 3059 may be preferred in a specific configuration, the vent 3400 and the anti-asphyxia valve 3059 can be interchangeably used, and/or the anti-asphyxia valve 3059 may include the vent 3400. In some examples of the present technology, one or more features of the patient interface (e.g., nasal cushion 3050, mouth cushion 3060, and/or joint 3068) may be provided without the anti-asphyxia valve 3059 and/or the vent 3400 shown in the figures. For example, the anti-asphyxia valve 3059 shown in FIGS. 4A-4D, 8A, 8B, 9A, 10A, 11A and 13A, may be removed or replaced with a vent 3400. In another example, one or more of the vents 3400 shown in FIGS. 6A and 6B may be removed and/or replaced with an anti-asphyxia valve 3059.

5.3.6 Decoupling Structure(s)

In one form the patient interface 3000 includes at least one decoupling structure, for example, a swivel or a ball and socket. For example, the patient interface 3000 shown in FIGS. 4A-8D comprises an elbow 3610 configured the swivel with respect to the positioning and stabilising structure 3300. In this example the elbow 3610 is configured to swivel about an axis concentric with a circular opening in the positioning and stabilising structure 3300. In some examples of the present technology, the elbow 3610 may form part of a ball and socket joint to the positioning and stabilising structure 3300. For example, a ring having a partially spherical inner surface may be provided to the positioning and stabilising structure 3300 and may be configured to receive the elbow 3610. The elbow 3610 may have partially spherical outer surface complimentary to the partially spherical inner surface of the ring, thereby enabling the elbow 3610 to swivel with respect to the ring in a plurality of axes.

5.3.7 Connection Port

Connection port 3600 allows for connection to the air circuit 4170. In the exemplary patient interface 3000 shown in FIGS. 4D-8D, the elbow 3610 forms part of the connection port 3600. The elbow 3610, as a decoupling structure, decouples movement of the air circuit 4170 from the positioning and stabilising structure 3300 in order to reduce tube drag on the positioning and stabilising structure 3300. The elbow 3610 may be rotatable at one or more locations.

The patient interface 3000 shown in FIGS. 5A-6D may include a crown piece connecting sections of the positioning and stabilising structure 3300, the crown piece including an opening that receives the elbow 3610 and providing the connection port 3600.

The connection port 3600 and opening receiving the elbow 3610 is shown in FIGS. 4A-6D as being centered relative to the positioning and stabilising structure 3300. The connection port 3600 may be provided in other locations. For example, the connection port 3600 and/or rotatable elbow 3610 may be offset from a central portion of the positioning and stabilising structure 3300. In other examples shown in FIGS. 4C and 7A-8D, the connection port 3600 and/or rotatable elbow 3610 may be directly coupled to the nasal cushion 3050 or the mouth cushion 3060.

5.3.8 Forehead Support

In one form, the patient interface 3000 includes a forehead support 3700. In some examples, the patient interface 3000 may be provided without a forehead support. Advantageously, the exemplary patient interface 3000 shown in FIGS. 4D-8D comprises a positioning and stabilising structure 3300 that is able to hold the seal-forming structure 3052 in sealing position without connection to a forehead support or any frame or strap members that lie in front of the patient's face at eye level.

5.3.9 Anti-Asphyxia Valve

In one form, the patient interface 3000 includes an anti-asphyxia valve 3059. In some examples, the anti-asphyxia valve 3059 may include a vent 3400. In some examples, the patient interface 3000 includes a plurality of anti-asphyxia valves. In one form of the present technology the joint 3068 coupling a mouth cushion 3060 to a nasal cushion 3050 includes an anti-asphyxia valve 3059 provided on a front surface of the joint 3068. The anti-asphyxia valve 3059 may be provided on a top of the flexible joint near the nasal end of the joint 3068 (see FIG. 4A). While the vent 3400 or the anti-asphyxia valve 3059 may be preferred in a specific configuration, the vent 3400 and the anti-asphyxia valve 3059 can be interchangeably used, and/or the anti-asphyxia valve 3059 may include the vent 3400. In some examples of the present technology, one or more features of the patient interface (e.g., nasal cushion 3050, mouth cushion 3060, and/or joint 3068) may be provided without the anti-asphyxia valve 3059 and/or the vent 3400 shown in the figures.

5.3.10 Ports

In one form of the present technology, a patient interface 3000 includes one or more ports that allow access to the volume within the plenum chamber 3200. In one form this allows a clinician to supply supplementary oxygen. In one form, this allows for the direct measurement of a property of gases within the plenum chamber 3200, such as the pressure.

5.3.11 Modular Patient Interface

Examples of the present technology allow for a modular mask system allowing multiple mask configurations. For example, the modular nature of the mask system allows for a nasal mask configuration to transform into a full face mask configuration. Within each of these configurations there are also variants of each mask (e.g., variants in size, connection type, and/or material type). Beginning with an oral nasal configuration, the nasal component could be either a cradle or a pillows seal. Within the nasal cradle category, there are textile and silicone variants. In some example, the silicone and textile variants can extend to the mouth cushion. Material variants allow patients to setup a mask configuration based on their sealing and comfort preferences.

In addition, as discussed in more detail below, the air delivery can be configured to be either a conduit (tube-up) or a tube connected to the front of the mask (tube-down). The modular nature of the air delivery setup can further allow the patient to setup the mask system based on their sealing and comfort preferences.

As shown in FIGS. 4A-4D, the patient interface 3000 may be convertible between a nasal "under the nose" seal mask and an oro-nasal mask. The patient interface 3000 may include a common connecting element 3330 forming a part of the stabilising structure 3300 to which various components may be removably coupled to provide the nasal mask (shown in FIGS. 5A-5D and 7A-7D) or the oro-nasal mask (shown in FIGS. 6A-6D and 8A-8D). Different versions of nasal, mouth and/or oro-nasal masks can be used to provide the different configurations. As an example, the different versions may include cradle, pillows, crillows, textile version, or foam versions.

In use, breathable gas is supplied to the nasal cushion 3050 and/or the mouth cushion 3060 via a connection port 3600, and the nasal seal-forming structure 3052 and/or the mouth seal-forming structure 3062 are arranged to surround an entrance to the airways of the patient so as to facilitate the supply of the breathable gas at positive pressure to the patient's airways. The breathable gas may be supplied to the nasal cushion 3050 and/or the mouth cushion 3060 from the air circuit 4170 via a tube coupled in different configurations (e.g., a tube up or tube down configuration). For example, the connection port 3600 may be coupled to conduits, as shown in FIGS. 4A and 5A-6D, or a surface of the nasal cushion 3050 or mouth cushion 3060, as shown in FIGS. 4C and 7A-8D.

As discussed above, the modular mask system may provide for interchangeable components of the mask to be made of different material based on sealing and/or comfort preferences of the patient. In some examples, the nasal cushion 3050 and the mouth cushion 3060 can be made of the same material. For example, the nasal cushion 3050 and the mouth cushion 3060 may both be made of all silicone or all textile. In some examples, nasal cushion 3050 and the mouth cushion 3060 may both be made of a combination of materials (e.g., textile and silicone).

In other examples, the nasal cushion 3050 (or just sealing portion of the nasal cushion) may be made of a material that is different from material used in the mouth cushion 3060 (or sealing portion of the mouth cushion). For example, the nasal cushion 3050 may be made of all silicone and the mouth cushion 3060 may be made of all textile. In another example, the nasal cushion 3050 may be made of all textile and the mouth cushion 3060 may be made of all silicone. In another example, one of the nasal cushion 3050 and the mouth cushion 3060 may be made of a combination of materials while the other one of the nasal cushion 3050 and the mouth cushion 3060 may be made all of the same material.

In some examples, the modular mask system may provide the nasal cushion 3050, the mouth cushion 3060, the nasal seal-forming structure 3052 and/or the mouth seal-forming structure 3062 with two or more different sizes/shapes. For example, size dimensions and/or contours of the seal-forming structure may be varied to provide alternative seal forming surfaces for different patients. In some example, a same mouth cushion 3060 could be used with different nasal cushions and/or nasal seal-forming structures. In this example, the same mouth cushion 3060 may be designed to provide a sufficient seal for different patients, while the nasal cushions could be interchanged to provide desired sealing and comfort. The nasal cushion may be selected from a nasal cushion including: different size and/or shape seal-forming structures 3052, different size and/or shape orifices 3054, different size and/or shape nasal pillows 3165, and/or different materials used for a portion or the whole nasal cushion. As mentioned above, the nasal cushions may also include different type of materials used in the whole nasal cushions or a portion of the nasal cushion (e.g., in the nasal cradle and/or nasal pillows).

There are a number of different advantages provided by the modular mask system. The advantages include the individual components providing seal designs that target a specific region of the face (no compromises through the integration of seals) and/or decoupling between seal components (no destabilizing forces transferred from one sealing component to another). These advantages are particularly present in the full face mask configuration.

Splitting the seal components into separate nose and mouth components allows each component to have a seal design that targets a region of the face without compromise. There is no need to have transition regions where a seal transforms from a nose seal to a mouth seal.

Separate sealing components may also enable them to be decoupled and therefore result in one component having little to no disturbance on the other during fitting and adjusting. This allows the individual sealing component to be setup for comfort. In conventional oral-nasal full face masks, the lack of decoupling between seal components can result in situations where either the nose or mouth region needs to be over-tightened in order to attain a sufficient seal.

Decoupling the seals may also reduce the amount of disturbances that can transfer between the sealing components during sleeping movements. In conventional oral-nasal full face masks, these disturbance forces can often lead to leaks.

5.3.11.1 Modular Patient Interface Using Headgear Conduits

In the example shown in FIG. 4A, the modular patient interface is provided with tube-up configuration in which breathable gas is supplied via first and second headgear conduits 3010 and 3020 provided as part of the positioning and stabilizing structure 3300. The first and second headgear conduits 3010 and 3020 receive the breathable gas via the connection port 3600 coupled to the first and second headgear conduits 3010 and 3020.

In this example, to provide the nasal mask configuration (shown in FIGS. 5A-5D), a nasal cushion 3050 is coupled to the positioning and stabilizing structure 3300, which may be a first type of positioning and stabilizing structure. The first type of positioning and stabilizing structure 3300 may include a nasal headgear strap 3310 and a common connecting element 3330 including one or more conduits.

To provide the oro-nasal mask configuration (shown in FIGS. 6A-6D), the nasal cushion 3050 and a mouth cushion 3060 are coupled to the positioning and stabilizing structure 3300, which may be a second type of positioning and stabilizing structure. The second type of positioning and stabilizing structure 3300 may include an oro-nasal headgear strap 3320 and the common connecting element 3330 including one or more conduits. A joint 3068 is used to couple the mouth cushion 3060 to the nasal cushion 3050. In the oro-nasal mask configuration, the headgear straps and/or conduits, in combination with the nasal cushion 3050, provide support for the mouth cushion 3060. While FIGS. 6A and 6B are shown with vent holes 3400 provided in the joint 3068, examples of the present are not so limited. In some examples, the vent holes 3400 may be replaced with an anti-asphyxia valve 3059 (with or without vent holes).

In some examples, the same type of positioning and stabilizing structure 3300 (i.e., same common connecting element and/or headgear strap) may be used to provide the nasal mask or the oro-nasal mask, based on whether just the nasal cushion 3050 or both the nasal cushion 3050 and the mouth cushion 3060 are coupled to the positioning and stabilizing structure 3300.

The nasal cushion 3050 can be used in both the nasal mask and the oro-nasal mask configurations. The nasal cushion 3050 comprises a nasal seal-forming structure 3052 constructed and arranged to form a seal with a region of a patient's face surrounding the entrance to a patient's nares. The mouth cushion 3060 can be used only in the oro-nasal mask. The mouth cushion 3060 comprises a mouth seal-forming structure 3062 constructed and arranged to form a seal with a region of a patient's face surrounding the entrance to a patient's mouth. While the nasal seal-forming structure 3052 is shown as a nasal cradle in FIG. 4A, examples of the present technology are not so limited and may include other types of nasal seal-forming structures (e.g., including nasal pillows 3165).

FIGS. 9A and 9B show a nasal cushion 3050 and a mouth cushion 3060 configuration coupled by a joint 3068 that may receive breathable gas via first and second headgear conduits 3010 and 3020. In this example, the breathable gas is provided from the first and second headgear conduits 3010 and 3020 to the nasal cushion 3050 via the upper headgear connectors 3056 and from the nasal cushion 3050 to the mouth cushion 3060 via the joint 3068. As shown in FIGS. 9A and 9B, the joint 3068 may include an anti-asphyxia valve 3059 at the top of the joint 3068 (at the nasal end).

FIGS. 10A-10C and 11A-11B also show a nasal cushion 3050 and a mouth cushion 3060 configuration coupled by a joint 3068 that may receive breathable gas via first and second headgear conduits 3010 and 3020. In this example, a vent 3400 is provided in the mouth cushion opening. Similar to the example shown in FIGS. 9A and 9B, the breathable gas is provided from the first and second headgear conduits 3010 and 3020 to the nasal cushion 3050 via the upper headgear connectors 3056 and from the nasal cushion 3050 to the mouth cushion 3060 via the joint 3068.

While in FIGS. 4A and 4B the mouth cushion 3060 is shown including both a mouth cushion joint opening 3070 and a mouth cushion opening 3072, in some examples the mouth cushion 3060 may be provided without a mouth cushion opening 3072 (e.g., see mouth cushion 3060 shown in FIGS. 9A and 9B).

5.3.11.2 Modular Patient Interface with Connection Port Coupled to the Mouth Cushion or the Nasal Cushion In the example shown in FIG. 4C, the modular patient interface is provided with a tube-down configuration in which breathable gas is provided via a connection port 3600 coupled to a surface of the nasal cushion 3050 in the nasal mask configuration and coupled to a surface of the mouth cushion 3060 in the oro-nasal mask configuration. In the illustrated examples, the connection port 3600 is coupled to a front surface of the nasal cushion 3050 or the mouth cushion 3060.

To provide the nasal mask configuration, the nasal cushion 3050 is coupled to the positioning and stabilizing structure 3300 including a nasal headgear strap 3310. The nasal cushion 3050 includes a pair of upper headgear connectors 3056 for coupling the nasal cushion 3050 to the nasal headgear strap 3310. In the nasal mask configuration, the breathable gas is provided to the patient via the connection port 3600 coupled to a nasal cushion opening 3058 in a front surface of the nasal cushion 3050. While the nasal seal-forming structure 3052 is shown as a nasal cradle in FIG. 4A, examples of the present technology are not so limited and may include other types of nasal seal-forming structures (e.g., including nasal pillows 3165).

To provide the oro-nasal mask configuration, the nasal cushion 3050 and a mouth cushion 3060 are coupled to the positioning and stabilizing structure 3300 including the nasal headgear strap 3310 and the oro-nasal headgear strap 3320. The nasal cushion 3050 includes a pair of upper headgear connectors 3056 for coupling the nasal cushion 3050 to the nasal headgear strap 3310. The mouth cushion 3060 includes a pair of lower headgear connectors 3066 for coupling the mouth cushion 3060 to the oro-nasal headgear strap 3320.

A joint 3068 is configured to couple the mouth cushion 3060 to the nasal cushion 3050. To provide breathable gas to the patient in the oro-nasal mask configuration, the connection port 3600 is coupled to a mouth cushion opening 3072 in a front surface of the mouth cushion 3060. The breathable gas in the mouth cushion 3060 travels to the nasal cushion 3050 via the joint 3068.

In the example shown in FIG. 4C, the nasal headgear strap 3310 is provided as the common connecting element 3330 to which the different components are coupled to provide the nasal mask or the oro-nasal mask. The headgear straps, in combination with the nasal cushion 3050, provide support for the mouth cushion 3060.

FIG. 4D shows a modular patient interface according to one form of the present technology. In FIG. 4D, the mouth cushion 3060 is coupled to the nasal cushion 3050 via a joint 3068. The nasal cushion includes upper headgear connectors for coupling to conduits 3010 and 3020 or nasal headgear strap 3310. The joint 3068 is coupled to a nasal cushion opening 3058 in a front surface of the nasal cushion 3050. When the joint 3068 is not coupled to the nasal cushion opening 3058, a vent 3400 or a connection port 3600 may be connected to the nasal cushion opening 3058. The mouth cushion 3060 includes a mouth cushion opening 3072 to which a vent 3400 or a connection port 3600 may be connected. When the connection port 3600 is not connected to the mouth cushion 3060, the mouth cushion opening 3072 may be configured to receive a vent insert 3400 with one or more gas washout vents. The vent 3400 may be connected to the mouth cushion opening 3072 when the air is provided to the nasal cushion 3050 via conduits 3010 and 3020 and the connection port 3600 is connected when conduits 3010 and 3020 are not used. The size and shape of the nasal cushion opening 3058 and mouth cushion opening 3072 may be the same so that the same vent 3400 and/or connection port 3600 may be connected to either opening.

In the full face tube-down configuration shown in FIGS. 4D and 8A-8C, a single vent in the air delivery tube (e.g., the elbow of the connection port 3600) may not be sufficient to remove the build-up of CO2 in the mask, particularly in the nasal chamber. Some examples of the present technology, may include one or more additional vents in the full face tube-down configuration. In some examples, extra venting may be added at the extremities of the nasal chamber to extract CO2. This can be implemented by adding venting on the tube-down headgear at the plugs that connects to either nasal cushions.

FIG. 16 illustrates a vent connector 6000 including vent holes 6010 according to an example of the present technology. The vent connector 6000 may be disposed between the nasal cushion 3050 and a nasal headgear strap 3310. The vent connector 6000 may be made entirely of silicone. In one example, the vent connector 6000 may be a silicone over-moulded connector. As shown in FIG. 16, the vent connector 6000 includes a plurality of holes 6010 provided on one side of the connector. In some examples, the vent holes may be provided on additional surfaces of the vent connector 6000.

A first end 6020 of the vent connector 6000 may be configured to engage the end of the nasal headgear strap 3310. In one examples, the first end 6020 of the vent connector 6000 may include a male portion configured to engage a textile sleeve of the nasal headgear strap 3310. In this example, the first end 6020 may include a rigidizer on one or more sides of the first end 6020. A second end 6030 of the vent connector 6000 may be configured to engage upper headgear connectors 3056 of the nasal cushion 3050.

As shown in FIG. 16, the second end 6030 may include a female portion configured to accept the upper headgear connectors 3056.

FIGS. 10D and 11C show a nasal cushion 3050 and a mouth cushion 3060 configuration coupled by a joint 3068 that may receive breathable gas via an air circuit 4170 coupled to a front surface of the mouth cushion 3060. In this example, the breathable gas is provided from the air circuit 4170 to the mouth cushion 3060 via a connection port 3600 coupled to a front of the mouth cushion 3060, and from the mouth cushion 3060 to the nasal cushion 3050 via the joint 3068. In this example, upper headgear connectors 3056 or the air inlet port in the positioning and stabilizing structure 3300 would be blocked. Alternatively, a different nasal cushion 3050 (e.g., without upper headgear connectors 3056 that allow air flow) could be used in these examples.

5.3.11.3 Joint Coupling the Mouth Cushion to the Nasal Cushion

The nasal cushion 3050 and the mouth cushion 3060 may be removably coupled using a joint 3068 to provide an oro-nasal cushion forming a nasal and mouth seal-forming structure. The joint 3068 may be removably coupled to the nasal cushion 3050 and/or the mouth cushion 3060. In some examples, the joint 3068 may be removably coupled only to the nasal cushion 3050.

The joint 3068 allows for the nasal and mouth sealing components to be pneumatically connected, while maximising the sealing and comfort benefits of separated components and minimizing any transferrable disturbances that may be caused by the nasal cushion 3050 or the mouth cushion 3060.

Conventional oral nasal full face masks "stack" the nasal seal on top of the mouth cushion such that the plenum chamber is a single large chamber. As a result, any force or displacement from one component will transfer through to the other relatively easily, as there is no buffer between these seals. Examples of the present technology provide a joint 3068 that provides a link that physically couples the components together and supports them correctly for set-up and sealing activities. The joint 3068 also decouples the components sufficiently such that one component does not shunt the other during use. The joint 3068 allows for sealing components to be joined together through an extended pathway while at the same time allowing for an effective decoupling mechanism.

The joint 3068 provides a pneumatic bridge at the front of the mask which connects the nasal cushion chamber to the mouth cushion chamber producing an extended pathway for air flow. In some examples, the joint 3068 provides a fixed feature of the mouth cushion which extends upwards towards the nasal cushion. The flexibility of the joint 3068 allows for the nasal cushion to move with respect to the mouth cushion in a plurality of directions. For example, the joint 3068 provides a flexible bridge allowing the nasal seal to flex side to side, back and forth and rotate (yaw rotation) with minimal transferal of force to the mouth cushion (see FIG. 14F illustrating the yaw rotation about a central axis of the joint 3068). Conversely, forces from the mouth cushion have minimal effect on the nasal seal due to the force absorbing characteristics of the flexible bridge connection.

Traditionally, a user attached a nasal cushion 3050 to a positioning and stabilizing structure 3300 when a nasal mask is desired, and the user replaced the nasal cushion 3050 with a full-face mask cushion or oro-nasal mask cushion when an oro-nasla mask is desired. The joint 3068 allows for the same nasal cushion 3050 to be used in both the nasal mask and the oro-nasal mask configurations. The joint 3068 also provides for independent sealing of the nose and mouth with the mouth seal-forming structure 3062 providing a seal with a region of a patient's face surrounding the entrance to a patient's mouth that independent from a nasal seal-forming structure 3052 providing a seal with a region of a patient's face surrounding the entrance to a patient's nares. The joint 3068 also provides for adjusting relative positioning between the nasal cushion 3050 and the mouth cushion 3060 to provide a better fit between the patient's face and the nasal cushion 3050 and/or the mouth cushion 3060.

In the oro-nasal mask configuration, the mouth cushion 3060 is attached to the nasal cushion 3050 using a joint 3068. The joint 3068 according to the present technology allows for the relative positioning between the nasal cushion 3050 and the mouth cushion 3060 to be adjustable to obtain a good seal between the nasal and mouth cushions and the user's face and/or to obtain a more comfortable positioning of the nasal and/or mouth cushion. The ability to position and adjust the nasal cushion 3050 and the mouth cushion 3060, according to the present technology, reduces the need to use full-face mask cushion or oro-nasal mask having discrete sizes (e.g., small, medium and large size). Forcing a patient to choose between discrete sizes may cause some patients to be unable to achieve a "perfect" fit.

FIGS. 13A-13D show a joint 3068 coupled to a mouth cushion 3060 according to different examples of the present technology. In FIGS. 13A-13D, the mouth cushion 3060 is shown according to one form of the present technology including a mouth cushion opening 3072 for receiving a vent 3400 or a connection port 3600. While FIGS. 13C and 13D illustrate the mouth cushion 3060 including a mouth cushion opening 3072, the mouth cushion 3060 according to one form of the present technology may be provided without a mouth cushion opening 3072. In FIG. 13D, the mouth cushion 3060 is shown having a central portion 3077 that is curved inwardly towards the plenum chamber 3200.

The joint 3068 may have a hollow interior and connect to the nasal cushion 3050 on a nasal cushion end 3082 and to the mouth cushion 3060 on a mouth cushion end 3084. In one example, the joint 3068 may be detachably connected to the nasal cushion 3050 and the mouth cushion 3060. In another example, the joint 3068 may be detachably connected to the nasal cushion 3050 and permanently connected to the mouth cushion 3060. FIGS. 14A-14B show a joint 3068 without being coupled to the nasal cushion 3050 and the mouth cushion 3060. The mouth cushion 3060 and the joint 3068 may form a one piece construction made of the same material. The joint 3068 may include a flexible structure to allow for independent adjustment of the nasal cushion 3050 and the mouth cushion 3060 position. The flexible structure may allow for the end of the joint 3068 including the flange 3096 to flex side to side, back and forth and rotate (yaw rotation) with minimal transferal of force to the mouth cushion (see FIG. 14F illustrating the yaw rotation about a central axis of the joint 3068).

As shown by arrows in FIGS. 14A and 14B, the breathable gas may flow into and out of the nasal cushion end 3082 and the mouth cushion end 3084 of the joint 3068. The breathable gas may flow into and out of the nasal cushion end 3082 in a horizontal direction and flow into and out of the mouth cushion end 3084 in a vertical direction. In one example, breathable gas may flow into and out of the mouth cushion end 3084 in angled direction towards the patient's mouth and/or in a horizontal direction.

The nasal cushion 3050 includes a nasal seal-forming structure 3052 constructed and arranged to form a seal with a region of a patient's face surrounding the entrance to a patient's nares, and a nasal cushion opening 3058 configured to receive a nasal cushion end 3082 of the flexible joint 3068. The nasal cushion opening 3058 may be provided on a side of the nasal cushion 3050 that is opposite to the side including the nasal seal-forming structure 3052. When the joint 3068 is not connected to the nasal cushion 3050, the nasal cushion opening 3058 may be configured to receive a vent insert 3400 with one or more gas washout vents, or a connection port 3600.

The mouth cushion 3060 includes a mouth seal-forming structure 3062 constructed and arranged to form a seal with a region of a patient's face surrounding the entrance to a patient's mouth, and a mouth cushion joint opening 3070 to receive the mouth cushion end 3084 of the joint 3068. The mouth cushion joint opening 3070 may be provided on a side of the mouth cushion 3060 that is opposite to the side including the mouth seal-forming structure 3062 (e.g., a front surface 3074). The mouth cushion end 3084 may be attached to the mouth cushion 3060 at a position that is at or above a horizontal medial plane of the mouth cushion.

The nasal cushion opening 3058 and the mouth cushion joint opening 3070 may have the same shape and/or size to allow for the same vent insert and/or connecting port to be used in either opening. In the nasal cushion therapy mode, the nasal cushion opening 3058 may include the vent insert, and in the oro-nasal cushion therapy mode the nasal cushion opening 3058 may be coupled to the joint 3068 and the other mouth cushion opening (e.g., opening 3072) may include the vent insert. In some examples, an anti-asphyxia valve 3059 and/or a vent 3400 may be provided in a surface of the joint 3068. As an example, the anti-asphyxia valve 3059 and/or vent 3400 may be provided in a front surface of the joint 3068 or surface of the joint 3068 between the front surface and the flange 3096 (e.g., see slanted surface shown in FIGS. 14A and 14B).

The joint 3068 may include a connecting portion (e.g. a circular or oval flange 3096) at the nasal cushion end 3082 to engage corresponding connecting portion in the nasal cushion opening 3058 or mouth cushion opening 3072. In some examples the flange 3096 may provide a u-shaped retaining mechanism configured to engage corresponding connecting portion (e.g., a male portion) in the nasal or mouth cushion opening. In some examples, the flange 3096 may be configured to engage a u-shaped retaining mechanism provided in an opening of the nasal or mouth cushion.

The engagement between the flange 3096 and the groove in the nasal or mouth cushion opening may provide an air tight seal. In some examples, the flange 3096 may be inserted inside of the mouth cushion opening 3072 and abut against the thickened portion around the mouth cushion opening 3072.

As shown in FIGS. 10A-13C the mouth cushion joint opening 3070 may be provided adjacent to the mouth cushion opening 3072. The mouth cushion opening 3072 may include a thickened portion along the perimeter of the mouth cushion opening 3072. The mouth cushion joint opening 3070 may abut the thickened portion of the mouth cushion opening 3072 and/or the mouth cushion opening 3072. In one example, the mouth cushion joint opening 3070 and the mouth cushion opening 3072 may be provided on a front surface 3074 such that the mouth cushion joint opening 3070 is provided above a horizontal central plane of the mouth cushion 3060 and the mouth cushion opening 3072 is provided below the horizontal central plane of the mouth cushion 3060 (e.g., see FIG. 10C).

In some examples, the nasal cushion opening 3058, the mouth cushion joint opening 3070, and/or the mouth cushion opening 3072 may have the same shape and/or size to allow for the same vent or tube connector (e.g., connection port 3600 coupled to the air circuit 4170) to be connected. In the nasal cushion therapy mode, the nasal cushion opening 3058 may include the tube connector, and in the oronasal cushion therapy mode, the mouth cushion opening 3072 may include the tube connector.

In some examples, one or more ends of the joint 3068, the connection port 3600, and/or the vent 3400 may have a coupling mechanism having a same shape and/or size. In some examples, one or more ends of the joint 3068, the connection port 3600, and/or the vent 3400 may be identical. The coupling mechanism may be configured to engage the nasal cushion opening 3058, the mouth cushion joint opening 3070, and/or the mouth cushion opening 3072. FIG. 15 an example of a vent 3400 including a coupling mechanism 3410 that may correspond to the coupling mechanism provided in the joint 3068 and/or the connection port 3600.

As shown in FIG. 15, the coupling mechanism of the vent 3400 may include a U-shaped channel extending around at least a portion of the perimeter of the vent 3400. In some examples, the coupling mechanism may include a continuous u-section around its entire periphery of the vent 3400. The coupling mechanism may provide a female engaging portion on the rigid vent 3400 configured to engage a male engaging portion on the flexible mouth or nasal cushion. The engagement of the two portions may provide an air-tight seal. Furthermore, positioning of the rigid coupling mechanism in the flexible mouth or nasal cushion may increase stability of the mouth or nasal cushion. FIGS. 13A-14B and 15 show the coupling mechanism 3410 of the vent 3400 corresponds to the coupling mechanism of the joint 3068 including the flange 3096.

The common coupling mechanism of the openings in the nasal and mouth cushions allow for the vent 3400 and/or connecting port 3600 to be repurposed in different portions of the mask system depending on the configuration or the modular mask system. The vent 3400 on the nasal portion can be repurposed into a mouth cushion connector when configured into a full face mask, can be located to another region of the mask. Similarly, to the vent 3400 being repurposed on the nasal cushion, the vent 3400 on the mouth cushion (in the tube-up position) can be repurposed as the connector for the air tube in the tube-down full face mask configuration. The air tube in the tube-down configuration may contain the female portion of the coupling mechanism so that it can attach securely to the mouth cushion. The vent 3400 that is repurposed on the mouth cushion connector when configured into a tube-down full face mask, can be relocated to the elbow region of the connecting port 3600.

Examples of a vent that can be used with the examples of the present disclosure are described in International Application No. PCT/AU2020/050959 filed on Sep. 10, 2020, which is hereby incorporated by reference in its entirety.

In use, pressurised air is provided to the nasal cushion 3050 (e.g., via headgear conduits 3010 and 3020) or to the mouth cushion 3060 (e.g., via an air circuit 4170 coupled to the mouth cushion 3060). The joint 3068 provides a path for pressurised air to travel between the plenum chamber of the nasal cushion 3050 and the plenum chamber of the mouth cushion 3060. In some examples, the mouth cushion end 3084 of the joint 3068 may direct or receive the flow of pressurized gas into or from the mouth cushion plenum chamber in a direction that is substantially perpendicular to the patient's Frankfurt horizontal. In some examples, the nasal cushion end 3082 may direct or receive the flow of pressurized breathable gas into or from the nasal plenum chamber in a direction that is substantially parallel to the patient's Frankfurt horizontal.

The cross-sectional shape of the joint 3068 may be circular, elliptical, oval, D-shaped or a rounded rectangle. A side of the joint 3068 that faces the patient's face may have a shape that closely conforms to a shape of the nasal cushion 3050 and/or mouth cushion 3060. FIGS. 14D and 14E show example cross-sectional shapes of the joint 3068.

The joint 3068 may be a flexible joint connecting the mouth cushion 3060 to the nasal cushion 3050. The flexibility of the joint 3068 may allow the patient to adjust the position of the mouth cushion 3060 in one or more directions relative to the nasal cushion 3050. In some examples, the flexible joint is configured to allow the mouth cushion 3060 to move relative to the nasal cushion 3050 to adjust for the patient's supramenton angle (see FIG. 14F). The joint 3068 may be constructed entirely or partially from a soft, flexible, resilient material such as silicone, which may be the same or different material as the material of the nasal cushion 3050 and the mouth cushion 3060. The joint 3068 may include an interior surface and/or an exterior surface that is smooth. In some example, the interior surface and/or the exterior surface of the joint 3068 may include one or more ridges 3092 extending at least partially around the joint 3068 to provide structural support to the joint 3068. As shown in FIGS. 13A and 13B, one or more ridges 3092 may be provided on a front surface and side surface of the joint 3068, while a back side of the joint 3068 includes a smooth surface.

In some examples, the joint 3068 may include a concertina section 3080 including one or more folds, pleats, corrugations or bellows to form a flexible and/or an extendable portion of the joint 3068 in a portion of the joint 3068 between one end 3082 of the joint 3068 and an opposite end 3084 of the joint 3068. In some example, a joint 3068 may be provided without a concertina section 3080. The concertina section 3080 may allow positioning of the mouth cushion 3060 to be adjustable in one or more directions relative to the nasal cushion 3050. In some examples, concertina section 3080 allows the mouth cushion 3060 to move relative to the nasal cushion 3050 in an axial direction and/or as a curved direction to accommodate the patient's supramenton angle. The concertina section 3080 may allow for a length of the joint 3068 to be adjusted in an axial direction of the joint 3068.

The concertina section 3080 may include a plurality of ridges 3086 and/or a plurality of grooves 3088, as shown in FIGS. 14A and 14C. FIG. 14B shows a joint 3068 without the plurality of ridges 3086 and/or a plurality of grooves 3088, according to one form of the present technology. The ridges 3086 and grooves 3088 may be alternatingly formed into the wall of the concertina section 3080. An alternating series of ridges and grooves will be understood to refer to a series in which a groove is provided between each pair of ridges and a ridge is provided between each pair of grooves (e.g. ridge, groove, ridge, groove and so on).

The alternating ridges 3086 and grooves 3088 may function like folds or bellows able to fold and unfold independently or in concert to shorten or lengthen the concertina section 3080. A large groove depth (or ridge height) may provide for a more extendable joint 3068. When tension is applied to the joint 3068, the ridges 3086 and grooves 3088 of the concertina section 3080 may be pulled away from each other which straightens out the joint wall, lengthening the joint 3068. The concertina section 3080 may be biased to an original (e.g. unextended) length.

In addition to facilitating a change in the length, the ridges 3086 and grooves 3088 may also facilitate a change in shape of the concertina section 3080. In some examples of the present technology, a first series of alternating ridges 3086 and grooves 3088 is provided to a first side of the joint 3068 (e.g. a patient's face-contacting side), while a second series of alternating ridges 3087 and grooves 3089 is provided to a second, opposite, side of the joint 3068 (e.g. a non-contacting side). The concertina section 3080 may facilitate bending of the joint 3068 as the ridges and grooves are able to move with respect to each other by differing degrees on the different sides of the joint 3068. For example, on the first side of the joint 3068 the ridges 3086 and grooves 3088 may contract while on the second side of the joint 3068 the ridges 3087 and grooves 3089 may expand, with the result being that the joint 3068 bends in the concertina section 3080. This configuration of the concertina section 3080 may allow for the same mouth cushion 3060 to be adaptable to large number of different face sizes and shapes.

In some examples, the first alternating series of ridges 3086 and grooves 3088 may have a lesser extension stiffness (e.g. a lesser force required to achieve a change in unit length) than the second alternating series of ridges 3087 and grooves 3089. The reduced extension stiffness in the non-patient-contacting side of the concertina section 3080 may advantageously facilitate bending/curvature in the joint 3068.

In some examples, the folds forming the concertina section 3080 may also form ridges and grooves interior to the joint 3068 (e.g. as a result of the folds forming a wavelike shape in the joint 3068, such as a sinusoidal shape, square wave or other waveform). FIG. 14B shows a particular wavelike shape formed in the joint wall. As shown in FIG. 14B, the concertina section 3080 comprises folds forming interior ridges and interior grooves.

The present technology allows for the mouth cushion 3060 to flex away from the nasal cushion 3050 so as to not interfere with the initial positioning of the nasal cushion 3050 on the patient's face. When suspended freely for set-up, the flexible joint 3068 may have enough rigidity to hold the mouth cushion in the correct orientation relative to the nasal cushion 3050. This configuration allows for the nasal cushion 3050 to be positioned on the patient's face such that nasal cushion 3050 provides a comfortable and good seal, before the mouth cushion 3060 is positioned on the patient's face. After the nasal cushion 3050 is positioned on the patient's face, the patient can position the mouth cushion 3060 on the patient's face such that the mouth cushion 3060 provides a comfortable and good seal.

In one example, the flexible joint 3068 and/or the mouth cushion 3060 are configured to move towards the patient's supramenton due to a spring bias of the flexible joint 3068 and/or the introduction of the flow of pressurized breathable gas through the mouth cushion and/or the flexible joint.

The spring bias of the flexible joint 3068 may be provided by the concertina section 3080. For example, one or more folds of the concertina may be provided on a surface of the joint 3068 closer to the patient's face and omitted on an opposite side of the joint 3068. In this example, on or more folds may go around the joint 3068 and one or more folds may partially encircle the joint 3068.

In some examples, the mouth cushion 3060 may include a gusset that causes the mouth cushion to move towards the patient's mouth upon application of the flow of pressurized gas. In use, the gusset may expand/compress/tilt to enhance the range of adjustability of the mouth cushion 3060. In some examples, the joint 3068 may include a gusset that causes the mouth cushion to move towards the patient's mouth upon application of the flow of pressurized gas.

The flexible joint 3068 may have a neutral position and a curved position oriented towards the patient's supramenton. The flexible joint may be configured to resist movement from the neutral position to a position away from the patient's face. The neutral position may be provided when the joint 3068 is decoupled or coupled to the nasal cushion 3050 and the mouth cushion 3060 without flow of pressurized gas supplied to the nasal cushion 3050 and/or the mouth cushion 3060. The curved position may be provided when the joint 3068 is coupled to the nasal cushion 3050 and the mouth cushion 3060 with flow of pressurized gas supplied to the nasal cushion 3050 and/or the mouth cushion 3060. Supplying the flow of pressurized gas in the joint 3068 and/or the mouth cushion 3060 may expand portions of the joint 3068 and/or the mouth cushion 3060 (e.g., the gusset portion) so that the joint 3068 moves from the neutral position to the curved position oriented towards the patient's supramenton. In some examples, the folds in the concertina section 3080 may provide the neutral portion without pressurized gas, and curved position upon pressurized gas filling one or more folds on an interior surface of the joint 3068.

In one form of the present technology, the flow of pressurized gas in the joint 3068 and/or the mouth cushion 3060 helps to provide and maintain a seal between the mouth cushion 3060 and the patient's face. The mouth cushion 3060 may be configured to expand in one or more directions due to flow of pressurized gas in the mouth cushion 3060. For example, the pressurized gas in the mouth cushion 3060 may expand portions of the mouth cushion 3060 outwards, upwards and/or downwards. In some examples, the pressurized gas in the mouth cushion 3060 may expand upper and lower portions of the mouth cushion 3060 outwards. The outward expansion of the upper and lower portions may increase an outward force applied to the joint 3068 by the mouth cushion 3060, which causes the mouth cushion 3060 to move inward relative to the joint 3068, for the mouth seal-forming structure 3062 to move towards the patient's face and provide a seal between the seal-forming structure 3062 and the patients' face.

One or more of the expanding seal-forming structure 3062, expanding mouth cushion 3060, and/or the flexible joint 3068, allows the mouth cushion 3060 coupled to the nasal cushion 3050 via a joint 3068 to provide and maintain a sufficient seal between the seal-forming structure 3062 and the patient's face.

5.3.11.4 Method for Using Patient Interface with a Joint Coupling the Mouth and Nasal Cushions Fitting an oro-nasal mask on a patient according to one form of the present technology may include first fitting the nasal cushion 3050 and then attaching the mouth cushion 3060 to the nasal cushion 3050 via the joint 3068. The nasal cushion 3050 can be properly adjusted before the mouth cushion 3060 is attached. During setup, the mouth cushion 3060 may flex away from the nasal cushion 3050, to not interfere with the initial positioning of the nasal cushion 3050.

The flexibility of the joint 3068 allows for the mouth cushion 3060 to be attached and adjusted independent of needing to make further adjustments to the nasal cushion 3050. The flexibility of the joint 3068 and/or the configuration of the mouth seal-forming structure 3062, allows for the setup of the oro-nasal mask to occur while the mouth is closed but provide a good seal during use even when the mouth opens. As discussed above, the soft membrane on top of the mouth seal-forming structure 3062 allows for the mouth cushion 3060 to expand upwards when the mouth opens, and the soft membrane on the bottom of the mouth seal-forming structure 3062 allows for the mouth cushion 3060 to expand downwards when the mouth opens.

Fitting the nasal cushion 3050 and the mouth cushion 3060 may provide for an auto positioning of the mouth cushion 3060. The nasal cushion 3050 may be positioned first and then the mouth cushion 3060 is lifted upwards until a top part of the mouth cushion 3060 abuts a lower section of the nasal cushion 3050. In some examples, the top part of the mouth cushion 3060, which may include at least a portion of the mouth seal-forming structure 3062, may abut at least portion of nasal seal-forming structure 3052 and/or a portion of nasal cushion 3050 adjacent to the nasal seal-forming structure 3052. The top part of the mouth cushion 3060 may include a complementary shape to a shape of the lower section of the nasal cushion 3050. As the mouth cushion 3060 is brought closer to the nasal cushion 3050, the complementary shape of the nasal cushion lower section may help centre and guide the mouth cushion 3060 into position. The flexible joint 3068 may be attached to the nasal cushion 3050 before the mouth cushion 3060 abuts the nasal cushion 3050 and adjust in size and/or shape as the mouth cushion 3060 is guided into positioned against the nasal cushion 3050.

According to one form of the present technology the method of fitting an oro-nasal mask on a patient includes, providing a nasal cushion 3050 forming at least part of a nasal cushion plenum chamber pressurizable to a therapeutic pressure, wherein the nasal cushion 3050 comprises a nasal seal-forming structure 3052 constructed and arranged to form a seal with a region of a patient's face surrounding an entrance to a patient's nares, and providing a mouth cushion 3060 forming at least part of a mouth cushion plenum chamber pressurizable to the therapeutic pressure, wherein the mouth cushion 3060 comprises a seal-forming structure 3062 constructed and arranged to form a seal with a region of a patient's face surrounding the entrance to a patient's mouth. The nasal cushion 3050 and the mouth cushion 3060 are connected with a flexible joint 3068.

The nasal and mouth seal-forming structures in a therapeutically effective position on a patient's head is held by: placing the nasal cushion 3050 under the patient's nose and engaging a superior portion of the patient's upper lip, whilst the mouth cushion 3060 is connected to the nasal cushion 3050, securing the nasal cushion 3050 on the patient's head using upper headgear conduits or straps, adjusting the length and/or position of the upper headgear conduits or straps, positioning an upper membrane of the mouth cushion 3060 on an inferior portion of the patient's upper lip, below the nasal cushion 3050, allowing engagement between the mouth cushion 3060 and the nasal cushion 3050, securing the mouth cushion 3060 on the patient's head using lower headgear straps, and adjusting the length and/or position of the lower headgear straps. The adjustment of the upper headgear conduits or straps can be substantially independent of adjustment of the lower headgear straps.

5.4 Air Circuit

An air circuit 4170 in accordance with an aspect of the present technology is a conduit or a tube constructed and arranged to allow, in use, a flow of air to travel between two components such as RPT device 4000 and the patient interface 3000.

In particular, the air circuit 4170 may be in fluid connection with the outlet of the pneumatic block of the RPT device 4000 and the patient interface. The air circuit may be referred to as an air delivery tube. In some cases there may be separate limbs of the circuit for inhalation and exhalation. In other cases a single limb is used.

In some forms, the air circuit 4170 may comprise one or more heating elements configured to heat air in the air circuit, for example to maintain or raise the temperature of the air. The heating element may be in a form of a heated wire circuit, and may comprise one or more transducers, such as temperature sensors. In one form, the heated wire circuit may be helically wound around the axis of the air circuit 4170. The heating element may be in communication with a controller such as a central controller. One example of an air circuit 4170 comprising a heated wire circuit is described in U.S. Pat. No. 8,733,349, which is incorporated herewithin in its entirety by reference.

5.4.1 Oxygen Delivery

In one form of the present technology, supplemental oxygen may be delivered to one or more points in the pneumatic path, such as upstream of the pneumatic block, to the air circuit 4170 and/or to the patient interface 3000.

5.5 Glossary

For the purposes of the present technology disclosure, in certain forms of the present technology, one or more of the following definitions may apply. In other forms of the present technology, alternative definitions may apply.

5.5.1 General

Air: In certain forms of the present technology, air may be taken to mean atmospheric air, and in other forms of the present technology air may be taken to mean some other combination of breathable gases, e.g. atmospheric air enriched with oxygen.

Ambient. In certain forms of the present technology, the term ambient will be taken to mean (i) external of the treatment system or patient, and (ii) immediately surrounding the treatment system or patient.

For example, ambient humidity with respect to a humidifier may be the humidity of air immediately surrounding the humidifier, e.g. the humidity in the room where a patient is sleeping. Such ambient humidity may be different to the humidity outside the room where a patient is sleeping.

In another example, ambient pressure may be the pressure immediately surrounding or external to the body.

In certain forms, ambient (e.g., acoustic) noise may be considered to be the background noise level in the room where a patient is located, other than for example, noise generated by an RPT device or emanating from a mask or patient interface. Ambient noise may be generated by sources outside the room.

Automatic Positive Airway Pressure (APAP) therapy: CPAP therapy in which the treatment pressure is automatically adjustable, e.g. from breath to breath, between minimum and maximum limits, depending on the presence or absence of indications of SDB events.

Continuous Positive Airway Pressure (CPAP) therapy: Respiratory pressure therapy in which the treatment pressure is approximately constant through a respiratory cycle of a patient. In some forms, the pressure at the entrance to the airways will be slightly higher during exhalation, and slightly lower during inhalation. In some forms, the pressure will vary between different respiratory cycles of the patient, for example, being increased in response to detection of indications of partial upper airway obstruction, and decreased in the absence of indications of partial upper airway obstruction.

Flow rate: The volume (or mass) of air delivered per unit time. Flow rate may refer to an instantaneous quantity. In some cases, a reference to flow rate will be a reference to a scalar quantity, namely a quantity having magnitude only. In other cases, a reference to flow rate will be a reference to a vector quantity, namely a quantity having both magnitude and direction. Flow rate may be given the symbol Q. 'Flow rate' is sometimes shortened to simply 'flow' or 'airflow'.

In the example of patient respiration, a flow rate may be nominally positive for the inspiratory portion of a breathing cycle of a patient, and hence negative for the expiratory portion of the breathing cycle of a patient. Total flow rate, Qt, is the flow rate of air leaving the RPT device. Vent flow rate, Qv, is the flow rate of air leaving a vent to allow washout of exhaled gases. Leak flow rate, Ql, is the flow rate of leak from a patient interface system or elsewhere. Respiratory flow rate, Qr, is the flow rate of air that is received into the patient's respiratory system.

Humidifier: The word humidifier will be taken to mean a humidifying apparatus constructed and arranged, or configured with a physical structure to be capable of providing a therapeutically beneficial amount of water ($H_2O$) vapour to a flow of air to ameliorate a medical respiratory condition of a patient.

Leak: The word leak will be taken to be an unintended flow of air. In one example, leak may occur as the result of an incomplete seal between a mask and a patient's face. In another example leak may occur in a swivel elbow to the ambient.

Noise, conducted (acoustic): Conducted noise in the present document refers to noise which is carried to the patient by the pneumatic path, such as the air circuit and the patient interface as well as the air therein. In one form, conducted noise may be quantified by measuring sound pressure levels at the end of an air circuit.

Noise, radiated (acoustic): Radiated noise in the present document refers to noise which is carried to the patient by the ambient air. In one form, radiated noise may be quantified by measuring sound power/pressure levels of the object in question according to ISO 3744.

Noise, vent (acoustic): Vent noise in the present document refers to noise which is generated by the flow of air through any vents such as vent holes of the patient interface.

Patient. A person, whether or not they are suffering from a respiratory condition.

Pressure: Force per unit area. Pressure may be expressed in a range of units, including $cmH_2O$, g-f/cm$^2$ and hectopascal. 1 $cmH_2O$ is equal to 1 g-f/cm$^2$ and is approximately 0.98 hectopascal. In this specification, unless otherwise stated, pressure is given in units of $cmH_2O$.

The pressure in the patient interface is given the symbol Pm, while the treatment pressure, which represents a target value to be achieved by the mask pressure Pm at the current instant of time, is given the symbol Pt.

Respiratory Pressure Therapy (RPT): The application of a supply of air to an entrance to the airways at a treatment pressure that is typically positive with respect to atmosphere.

Ventilator: A mechanical device that provides pressure support to a patient to perform some or all of the work of breathing.

5.5.1.1 Materials

Silicone or Silicone Elastomer: A synthetic rubber. In this specification, a reference to silicone is a reference to liquid silicone rubber (LSR) or a compression moulded silicone rubber (CMSR). One form of commercially available LSR is SILASTIC (included in the range of products sold under this trademark), manufactured by Dow Corning. Another manufacturer of LSR is Wacker. Unless otherwise specified to the contrary, an exemplary form of LSR has a Shore A (or Type A) indentation hardness in the range of about 35 to about 45 as measured using ASTM D2240.

Polycarbonate: a thermoplastic polymer of Bisphenol-A Carbonate.

5.5.1.2 Mechanical Properties

Resilience: Ability of a material to absorb energy when deformed elastically and to release the energy upon unloading.

Resilient: Will release substantially all of the energy when unloaded. Includes e.g. certain silicones, and thermoplastic elastomers.

Hardness: The ability of a material per se to resist deformation (e.g. described by a Young's Modulus, or an indentation hardness scale measured on a standardised sample size).

'Soft' materials may include silicone or thermo-plastic elastomer (TPE), and may, e.g. readily deform under finger pressure. 'Hard' materials may include polycarbonate, polypropylene, steel or aluminium, and may not e.g. readily deform under finger pressure.

Stiffness (or rigidity) of a structure or component: The ability of the structure or component to resist deformation in response to an applied load. The load may be a force or a moment, e.g. compression, tension, bending or torsion. The structure or component may offer different resistances in different directions.

Floppy structure or component: A structure or component that will change shape, e.g. bend, when caused to support its own weight, within a relatively short period of time such as 1 second.

Rigid structure or component: A structure or component that will not substantially change shape when subject to the loads typically encountered in use. An example of such a use may be setting up and maintaining a patient interface in sealing relationship with an entrance to a patient's airways, e.g. at a load of approximately 20 to 30 $cmH_2O$ pressure.

As an example, an I-beam may comprise a different bending stiffness (resistance to a bending load) in a first direction in comparison to a second, orthogonal direction. In another example, a structure or component may be floppy in a first direction and rigid in a second direction.

5.5.2 Respiratory Cycle

Apnea: According to some definitions, an apnea is said to have occurred when flow falls below a predetermined threshold for a duration, e.g. 10 seconds. An obstructive apnea will be said to have occurred when, despite patient effort, some obstruction of the airway does not allow air to flow. A central apnea will be said to have occurred when an apnea is detected that is due to a reduction in breathing effort, or the absence of breathing effort, despite the airway being patent. A mixed apnea occurs when a reduction or absence of breathing effort coincides with an obstructed airway.

Breathing rate: The rate of spontaneous respiration of a patient, usually measured in breaths per minute.

Duty cycle: The ratio of inhalation time, Ti to total breath time, Ttot.

Effort (breathing): The work done by a spontaneously breathing person attempting to breathe.

Expiratory portion of a breathing cycle: The period from the start of expiratory flow to the start of inspiratory flow.

Flow limitation: Flow limitation will be taken to be the state of affairs in a patient's respiration where an increase in effort by the patient does not give rise to a corresponding increase in flow. Where flow limitation occurs during an inspiratory portion of the breathing cycle it may be described as inspiratory flow limitation. Where flow limitation occurs during an expiratory portion of the breathing cycle it may be described as expiratory flow limitation.

Types of flow limited inspiratory waveforms:

(3072) Flattened: Having a rise followed by a relatively flat portion, followed by a fall.

(ii) M-shaped: Having two local peaks, one at the leading edge, and one at the trailing edge, and a relatively flat portion between the two peaks.

(iii) Chair-shaped: Having a single local peak, the peak being at the leading edge, followed by a relatively flat portion.

(iv) Reverse-chair shaped: Having a relatively flat portion followed by single local peak, the peak being at the trailing edge.

Hypopnea: According to some definitions, a hypopnea is taken to be a reduction in flow, but not a cessation of flow. In one form, a hypopnea may be said to have occurred when there is a reduction in flow below a threshold rate for a duration. A central hypopnea will be said to have occurred when a hypopnea is detected that is due to a reduction in breathing effort. In one form in adults, either of the following may be regarded as being hypopneas:

(3072) a 30% reduction in patient breathing for at least 10 seconds plus an associated 4% desaturation; or (ii) a reduction in patient breathing (but less than 50%) for at least 10 seconds, with an associated desaturation of at least 3% or an arousal.

Hyperpnea: An increase in flow to a level higher than normal.

Inspiratory portion of a breathing cycle: The period from the start of inspiratory flow to the start of expiratory flow will be taken to be the inspiratory portion of a breathing cycle.

Patency (airway): The degree of the airway being open, or the extent to which the airway is open. A patent airway is open. Airway patency may be quantified, for example with a value of one (1) being patent, and a value of zero (0), being closed (obstructed).

Positive End-Expiratory Pressure (PEEP): The pressure above atmosphere in the lungs that exists at the end of expiration.

Peak flow rate (Qpeak): The maximum value of flow rate during the inspiratory portion of the respiratory flow waveform.

Respiratory flow rate, patient airflow rate, respiratory airflow rate (Qr): These terms may be understood to refer to the RPT device's estimate of respiratory flow rate, as opposed to "true respiratory flow rate" or "true respiratory flow rate", which is the actual respiratory flow rate experienced by the patient, usually expressed in litres per minute.

Tidal volume (Vt): The volume of air inhaled or exhaled during normal breathing, when extra effort is not applied. In principle the inspiratory volume Vi (the volume of air inhaled) is equal to the expiratory volume Ve (the volume of air exhaled), and therefore a single tidal volume Vt may be defined as equal to either quantity. In practice the tidal volume Vt is estimated as some combination, e.g. the mean, of the inspiratory volume Vi and the expiratory volume Ve.

(inhalation) Time (Ti): The duration of the inspiratory portion of the respiratory flow rate waveform.

(exhalation) Time (Te): The duration of the expiratory portion of the respiratory flow rate waveform.

(total) Time (Ttot): The total duration between the start of one inspiratory portion of a respiratory flow rate waveform and the start of the following inspiratory portion of the respiratory flow rate waveform.

Typical recent ventilation: The value of ventilation around which recent values of ventilation Vent over some predetermined timescale tend to cluster, that is, a measure of the central tendency of the recent values of ventilation.

Upper airway obstruction (UAO): includes both partial and total upper airway obstruction. This may be associated with a state of flow limitation, in which the flow rate increases only slightly or may even decrease as the pressure difference across the upper airway increases (Starling resistor behaviour).

Ventilation (Vent): A measure of a rate of gas being exchanged by the patient's respiratory system. Measures of ventilation may include one or both of inspiratory and expiratory flow, per unit time. When expressed as a volume per minute, this quantity is often referred to as "minute ventilation". Minute ventilation is sometimes given simply as a volume, understood to be the volume per minute.

5.5.3 Ventilation

Adaptive Servo-Ventilator (ASV): A servo-ventilator that has a changeable, rather than fixed target ventilation. The changeable target ventilation may be learned from some characteristic of the patient, for example, a respiratory characteristic of the patient.

Backup rate: A parameter of a ventilator that establishes the minimum breathing rate (typically in number of breaths per minute) that the ventilator will deliver to the patient, if not triggered by spontaneous respiratory effort.

Cycled: The termination of a ventilator's inspiratory phase. When a ventilator delivers a breath to a spontaneously breathing patient, at the end of the inspiratory portion of the breathing cycle, the ventilator is said to be cycled to stop delivering the breath.

Expiratory positive airway pressure (EPAP): a base pressure, to which a pressure varying within the breath is added to produce the desired mask pressure which the ventilator will attempt to achieve at a given time.

End expiratory pressure (EEP): Desired mask pressure which the ventilator will attempt to achieve at the end of the expiratory portion of the breath. If the pressure waveform template $\Pi(\Phi)$ is zero-valued at the end of expiration, i.e. $\Pi(\Phi)=0$ when $\Phi=1$, the EEP is equal to the EPAP.

Inspiratory positive airway pressure (IPAP): Maximum desired mask pressure which the ventilator will attempt to achieve during the inspiratory portion of the breath.

Pressure support: A number that is indicative of the increase in pressure during ventilator inspiration over that during ventilator expiration, and generally means the difference in pressure between the maximum value during inspiration and the base pressure (e.g., PS=IPAP−EPAP). In some contexts pressure support means the difference which the ventilator aims to achieve, rather than what it actually achieves.

Servo-ventilator: A ventilator that measures patient ventilation, has a target ventilation, and which adjusts the level of pressure support to bring the patient ventilation towards the target ventilation.

Spontaneous/Timed (S/T): A mode of a ventilator or other device that attempts to detect the initiation of a breath of a spontaneously breathing patient. If however, the device is unable to detect a breath within a predetermined period of time, the device will automatically initiate delivery of the breath.

Swing: Equivalent term to pressure support.

Triggered: When a ventilator delivers a breath of air to a spontaneously breathing patient, it is said to be triggered to do so at the initiation of the respiratory portion of the breathing cycle by the patient's efforts.

5.5.4 Anatomy 5.5.4.1 Anatomy of the Face

Ala: the external outer wall or "wing" of each nostril (plural: alar)

Alar angle:

Alare: The most lateral point on the nasal ala.

Alar curvature (or alar crest) point: The most posterior point in the curved base line of each ala, found in the crease formed by the union of the ala with the cheek.

Auricle: The whole external visible part of the ear.

(nose) Bony framework: The bony framework of the nose comprises the nasal bones, the frontal process of the maxillae and the nasal part of the frontal bone.

(nose) Cartilaginous framework: The cartilaginous framework of the nose comprises the septal, lateral, major and minor cartilages.

Columella: the strip of skin that separates the nares and which runs from the pronasale to the upper lip.

Columella angle: The angle between the line drawn through the midpoint of the nostril aperture and a line drawn perpendicular to the Frankfort horizontal while intersecting subnasale.

Frankfort horizontal plane: A line extending from the most inferior point of the orbital margin to the left tragion. The tragion is the deepest point in the notch superior to the tragus of the auricle.

Glabella: Located on the soft tissue, the most prominent point in the midsagittal plane of the forehead.

Lateral nasal cartilage: A generally triangular plate of cartilage. Its superior margin is attached to the nasal bone and frontal process of the maxilla, and its inferior margin is connected to the greater alar cartilage.

Lip, lower (labrale inferius):

Lip, upper (labrale superius):

Greater alar cartilage: A plate of cartilage lying below the lateral nasal cartilage. It is curved around the anterior part of the naris. Its posterior end is connected to the frontal process of the maxilla by a tough fibrous membrane containing three or four minor cartilages of the ala.

Nares (Nostrils): Approximately ellipsoidal apertures forming the entrance to the nasal cavity. The singular form of nares is naris (nostril). The nares are separated by the nasal septum.

Naso-labial sulcus or Naso-labial fold: The skin fold or groove that runs from each side of the nose to the corners of the mouth, separating the cheeks from the upper lip.

Naso-labial angle: The angle between the columella and the upper lip, while intersecting subnasale.

Otobasion inferior: The lowest point of attachment of the auricle to the skin of the face.

Otobasion superior: The highest point of attachment of the auricle to the skin of the face.

Pronasale: the most protruded point or tip of the nose, which can be identified in lateral view of the rest of the portion of the head.

Philtrum: the midline groove that runs from lower border of the nasal septum to the top of the lip in the upper lip region.

Pogonion: Located on the soft tissue, the most anterior midpoint of the chin.

Ridge (nasal): The nasal ridge is the midline prominence of the nose, extending from the Sellion to the Pronasale.

Sagittal plane: A vertical plane that passes from anterior (front) to posterior (rear). The midsagittal plane is a sagittal plane that divides the body into right and left halves.

Sellion: Located on the soft tissue, the most concave point overlying the area of the frontonasal suture.

Septal cartilage (nasal): The nasal septal cartilage forms part of the septum and divides the front part of the nasal cavity.

Subalare: The point at the lower margin of the alar base, where the alar base joins with the skin of the superior (upper) lip.

Subnasal point: Located on the soft tissue, the point at which the columella merges with the upper lip in the midsagittal plane.

Supramenton: The point of greatest concavity in the midline of the lower lip between labrale inferius and soft tissue pogonion 5.5.4.2 Anatomy of the Skull Frontal bone: The frontal bone includes a large vertical portion, the squama frontalis, corresponding to the region known as the forehead.

Mandible: The mandible forms the lower jaw. The mental protuberance is the bony protuberance of the jaw that forms the chin.

Maxilla: The maxilla forms the upper jaw and is located above the mandible and below the orbits. The frontal process of the maxilla projects upwards by the side of the nose, and forms part of its lateral boundary.

Nasal bones: The nasal bones are two small oblong bones, varying in size and form in different individuals; they are placed side by side at the middle and upper part of the face, and form, by their junction, the "bridge" of the nose.

Nasion: The intersection of the frontal bone and the two nasal bones, a depressed area directly between the eyes and superior to the bridge of the nose.

Occipital bone: The occipital bone is situated at the back and lower part of the cranium. It includes an oval aperture, the foramen magnum, through which the cranial cavity communicates with the vertebral canal. The curved plate behind the foramen magnum is the squama occipitalis.

Orbit: The bony cavity in the skull to contain the eyeball.

Parietal bones: The parietal bones are the bones that, when joined together, form the roof and sides of the cranium.

Temporal bones: The temporal bones are situated on the bases and sides of the skull, and support that part of the face known as the temple.

Zygomatic bones: The face includes two zygomatic bones, located in the upper and lateral parts of the face and forming the prominence of the cheek.

5.5.4.3 Anatomy of the Respiratory System

Diaphragm: A sheet of muscle that extends across the bottom of the rib cage. The diaphragm separates the thoracic cavity, containing the heart, lungs and ribs, from the abdominal cavity. As the diaphragm contracts the volume of the thoracic cavity increases and air is drawn into the lungs.

Larynx: The larynx, or voice box houses the vocal folds and connects the inferior part of the pharynx (hypopharynx) with the trachea.

Lungs: The organs of respiration in humans. The conducting zone of the lungs contains the trachea, the bronchi, the bronchioles, and the terminal bronchioles. The respiratory zone contains the respiratory bronchioles, the alveolar ducts, and the alveoli.

Nasal cavity: The nasal cavity (or nasal fossa) is a large air filled space above and behind the nose in the middle of the face. The nasal cavity is divided in two by a vertical fin called the nasal septum. On the sides of the nasal cavity are three horizontal outgrowths called nasal conchae (singular "concha") or turbinates. To the front of the nasal cavity is the nose, while the back blends, via the choanae, into the nasopharynx.

Pharynx: The part of the throat situated immediately inferior to (below) the nasal cavity, and superior to the oesophagus and larynx. The pharynx is conventionally divided into three sections: the nasopharynx (epipharynx) (the nasal part of the pharynx), the oropharynx (mesopharynx) (the oral part of the pharynx), and the laryngopharynx (hypopharynx).

5.5.5 Patient Interface

Anti-asphyxia valve (AAV): The component or sub-assembly of a mask system that, by opening to atmosphere in a failsafe manner, reduces the risk of excessive $CO_2$ rebreathing by a patient.

Elbow: An elbow is an example of a structure that directs an axis of flow of air travelling therethrough to change direction through an angle. In one form, the angle may be approximately 90 degrees. In another form, the angle may be more, or less than 90 degrees. The elbow may have an approximately circular cross-section. In another form the elbow may have an oval or a rectangular cross-section. In certain forms an elbow may be rotatable with respect to a mating component, e.g. about 360 degrees. In certain forms an elbow may be removable from a mating component, e.g. via a snap connection. In certain forms, an elbow may be assembled to a mating component via a one-time snap during manufacture, but not removable by a patient.

Frame: Frame will be taken to mean a mask structure that bears the load of tension between two or more points of connection with a headgear. A mask frame may be a non-airtight load bearing structure in the mask. However, some forms of mask frame may also be air-tight.

Headgear: Headgear will be taken to mean a form of positioning and stabilizing structure designed for use on a head. For example the headgear may comprise a collection of one or more struts, ties and stiffeners configured to locate and retain a patient interface in position on a patient's face for delivery of respiratory therapy. Some ties are formed of a soft, flexible, elastic material such as a laminated composite of foam and fabric.

Membrane: Membrane will be taken to mean a typically thin element that has, preferably, substantially no resistance to bending, but has resistance to being stretched.

Plenum chamber: a mask plenum chamber will be taken to mean a portion of a patient interface having walls at least partially enclosing a volume of space, the volume having air therein pressurised above atmospheric pressure in use. A shell may form part of the walls of a mask plenum chamber.

Seal: May be a noun form ("a seal") which refers to a structure, or a verb form ("to seal") which refers to the effect. Two elements may be constructed and/or arranged to 'seal' or to effect 'sealing' therebetween without requiring a separate 'seal' element per se.

Shell: A shell will be taken to mean a curved, relatively thin structure having bending, tensile and compressive stiffness. For example, a curved structural wall of a mask may be a shell. In some forms, a shell may be faceted. In some forms a shell may be airtight. In some forms a shell may not be airtight.

Stiffener: A stiffener will be taken to mean a structural component designed to increase the bending resistance of another component in at least one direction.

Strut: A strut will be taken to be a structural component designed to increase the compression resistance of another component in at least one direction.

Swivel (noun): A subassembly of components configured to rotate about a common axis, preferably independently, preferably under low torque. In one form, the swivel may be constructed to rotate through an angle of at least 360 degrees. In another form, the swivel may be constructed to rotate through an angle less than 360 degrees. When used in the context of an air delivery conduit, the sub-assembly of components preferably comprises a matched pair of cylindrical conduits. There may be little or no leak flow of air from the swivel in use.

Tie (noun): A structure designed to resist tension.

Vent: (noun): A structure that allows a flow of air from an interior of the mask, or conduit, to ambient air for clinically effective washout of exhaled gases. For example, a clinically effective washout may involve a flow rate of about 10 litres per minute to about 100 litres per minute, depending on the mask design and treatment pressure.

5.5.6 Shape of Structures

Products in accordance with the present technology may comprise one or more three-dimensional mechanical structures, for example a mask cushion or an impeller. The three-dimensional structures may be bounded by two-dimensional surfaces. These surfaces may be distinguished using a label to describe an associated surface orientation, location, function, or some other characteristic. For example a structure may comprise one or more of an anterior surface, a posterior surface, an interior surface and an exterior surface. In another example, a seal-forming structure may comprise a face-contacting (e.g. outer) surface, and a separate non-face-contacting (e.g. underside or inner) surface. In another example, a structure may comprise a first surface and a second surface.

To facilitate describing the shape of the three-dimensional structures and the surfaces, we first consider a cross-section through a surface of the structure at a point, p. See FIG. 3B to FIG. 3F, which illustrate examples of cross-sections at point p on a surface, and the resulting plane curves. FIGS. 3B to 3F also illustrate an outward normal vector at p. The outward normal vector at p points away from the surface. In some examples we describe the surface from the point of view of an imaginary small person standing upright on the surface.

5.5.6.1 Curvature in One Dimension

The curvature of a plane curve at p may be described as having a sign (e.g. positive, negative) and a magnitude (e.g. 1/radius of a circle that just touches the curve at p).

Positive curvature: If the curve at p turns towards the outward normal, the curvature at that point will be taken to be positive (if the imaginary small person leaves the point p they must walk uphill). See FIG. 3B (relatively large positive curvature compared to FIG. 3C) and FIG. 3C (relatively small positive curvature compared to FIG. 3B). Such curves are often referred to as concave.

Zero curvature: If the curve at p is a straight line, the curvature will be taken to be zero (if the imaginary small person leaves the point p, they can walk on a level, neither up nor down). See FIG. 3D.

Negative curvature: If the curve at p turns away from the outward normal, the curvature in that direction at that point will be taken to be negative (if the imaginary small person leaves the point p they must walk downhill). See FIG. 3E (relatively small negative curvature compared to FIG. 3F) and FIG. 3F (relatively large negative curvature compared to FIG. 3E). Such curves are often referred to as convex.

5.5.6.2 Curvature of Two Dimensional Surfaces

A description of the shape at a given point on a two-dimensional surface in accordance with the present technology may include multiple normal cross-sections. The multiple cross-sections may cut the surface in a plane that includes the outward normal (a "normal plane"), and each cross-section may be taken in a different direction. Each cross-section results in a plane curve with a corresponding curvature. The different curvatures at that point may have the same sign, or a different sign. Each of the curvatures at that point has a magnitude, e.g. relatively small. The plane curves in FIGS. 3B to 3F could be examples of such multiple cross-sections at a particular point.

Principal curvatures and directions: The directions of the normal planes where the curvature of the curve takes its maximum and minimum values are called the principal directions. In the examples of FIG. 3B to FIG. 3F, the maximum curvature occurs in FIG. 3B, and the minimum occurs in FIG. 3F, hence FIG. 3B and FIG. 3F are cross sections in the principal directions. The principal curvatures at p are the curvatures in the principal directions.

Region of a surface: A connected set of points on a surface. The set of points in a region may have similar characteristics, e.g. curvatures or signs.

Saddle region: A region where at each point, the principal curvatures have opposite signs, that is, one is positive, and the other is negative (depending on the direction to which the imaginary person turns, they may walk uphill or downhill).

Dome region: A region where at each point the principal curvatures have the same sign, e.g. both positive (a "concave dome") or both negative (a "convex dome").

Cylindrical region: A region where one principal curvature is zero (or, for example, zero within manufacturing tolerances) and the other principal curvature is non-zero.

Planar region: A region of a surface where both of the principal curvatures are zero (or, for example, zero within manufacturing tolerances).

Edge of a surface: A boundary or limit of a surface or region.

Path: In certain forms of the present technology, 'path' will be taken to mean a path in the mathematical—topological sense, e.g. a continuous space curve from f(0) to f(1) on a surface. In certain forms of the present technology, a 'path' may be described as a route or course, including e.g. a set of points on a surface. (The path for the imaginary person is where they walk on the surface, and is analogous to a garden path).

Path length: In certain forms of the present technology, 'path length' will be taken to mean the distance along the surface from f(0) to f(1), that is, the distance along the path on the surface. There may be more than one path between two points on a surface and such paths may have different path lengths. (The path length for the imaginary person would be the distance they have to walk on the surface along the path).

Straight-line distance: The straight-line distance is the distance between two points on a surface, but without regard to the surface. On planar regions, there would be a path on the surface having the same path length as the straight-line distance between two points on the surface. On non-planar surfaces, there may be no paths having the same path length as the straight-line distance between two points. (For the imaginary person, the straight-line distance would correspond to the distance 'as the crow flies'.)

5.5.6.3 Space Curves

Space curves: Unlike a plane curve, a space curve does not necessarily lie in any particular plane. A space curve may be closed, that is, having no endpoints. A space curve may be considered to be a one-dimensional piece of three-dimensional space. An imaginary person walking on a strand of the DNA helix walks along a space curve. A typical human left ear comprises a helix, which is a left-hand helix, see FIG. 3Q. A typical human right ear comprises a helix, which is a right-hand helix, see FIG. 3R. FIG. 3S shows a right-hand helix. The edge of a structure, e.g. the edge of a membrane or impeller, may follow a space curve. In general, a space curve may be described by a curvature and a torsion at each point on the space curve. Torsion is a measure of how the curve turns out of a plane. Torsion has a sign and a magnitude. The torsion at a point on a space curve may be characterised with reference to the tangent, normal and binormal vectors at that point.

Tangent unit vector (or unit tangent vector): For each point on a curve, a vector at the point specifies a direction from that point, as well as a magnitude. A tangent unit vector is a unit vector pointing in the same direction as the curve at that point. If an imaginary person were flying along the curve and fell off her vehicle at a particular point, the direction of the tangent vector is the direction she would be travelling.

Unit normal vector: As the imaginary person moves along the curve, this tangent vector itself changes. The unit vector pointing in the same direction that the tangent vector is changing is called the unit principal normal vector. It is perpendicular to the tangent vector.

Binormal unit vector. The binormal unit vector is perpendicular to both the tangent vector and the principal normal vector. Its direction may be determined by a right-hand rule (see e.g. FIG. 3P), or alternatively by a left-hand rule (FIG. 3O).

Osculating plane: The plane containing the unit tangent vector and the unit principal normal vector. See FIGS. 3O and 3P.

Torsion of a space curve: The torsion at a point of a space curve is the magnitude of the rate of change of the binormal unit vector at that point. It measures how much the curve deviates from the osculating plane. A space curve which lies in a plane has zero torsion. A space curve which deviates a relatively small amount from the osculating plane will have a relatively small magnitude of torsion (e.g. a gently sloping helical path). A space curve which deviates a relatively large amount from the osculating plane will have a relatively large magnitude of torsion (e.g. a steeply sloping helical path). With reference to FIG. 3S, since T2>T1, the magnitude of the torsion near the top coils of the helix of FIG. 3S is greater than the magnitude of the torsion of the bottom coils of the helix of FIG. 3S With reference to the right-hand rule of FIG. 3P, a space curve turning towards the direction of the right-hand binormal may be considered as having a right-hand positive torsion (e.g. a right-hand helix as shown in FIG. 3S). A space curve turning away from the direction of the right-hand binormal may be considered as having a right-hand negative torsion (e.g. a left-hand helix).

Equivalently, and with reference to a left-hand rule (see FIG. 3O), a space curve turning towards the direction of the left-hand binormal may be considered as having a left-hand positive torsion (e.g. a left-hand helix). Hence left-hand positive is equivalent to right-hand negative. See FIG. 3T.

5.5.6.4 Holes

A surface may have a one-dimensional hole, e.g. a hole bounded by a plane curve or by a space curve. Thin structures (e.g. a membrane) with a hole, may be described as having a one-dimensional hole. See for example the one dimensional hole in the surface of structure shown in FIG. 3I, bounded by a plane curve.

A structure may have a two-dimensional hole, e.g. a hole bounded by a surface. For example, an inflatable tyre has a two dimensional hole bounded by the interior surface of the tyre. In another example, a bladder with a cavity for air or gel could have a two-dimensional hole. See for example the cushion of FIG. 3L and the example cross-sections therethrough in FIG. 3M and FIG. 3N, with the interior surface bounding a two dimensional hole indicated. In a yet another example, a conduit may comprise a one-dimension hole (e.g. at its entrance or at its exit), and a two-dimension hole bounded by the inside surface of the conduit. See also the two dimensional hole through the structure shown in FIG. 3K, bounded by a surface as shown.

5.6 Other Remarks

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated herein by reference in their entirety to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

The terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

5.7 Reference Signs List

| Feature Item | Number |
| --- | --- |
| patient | 1000 |
| bed partner | 1100 |
| patient interface | 3000 |
| headgear conduit | 3010 |
| cushion interface | 3012 |
| headgear conduit | 3020 |
| cushion interface | 3022 |
| nasal cushion | 3050 |
| nasal seal-forming structure | 3052 |
| textured surface | 3053 |
| orifices | 3054 |
| bridge portion | 3055 |
| upper headgear connectors | 3056 |
| nasal cushion opening | 3058 |
| mouth cushion | 3060 |
| mouth seal-forming structure | 3062 |
| lower headgear connector | 3066 |
| joint | 3068 |
| mouth cushion joint opening | 3070 |
| region | 3070-1 |
| mouth cushion opening | 3072 |
| region | 3072-1 |
| front face | 3074 |
| upper lip membrane | 3076 |
| central portion | 3077 |
| wall | 3078 |
| concertina section | 3080 |
| nasal cushion end | 3082 |
| mouth cushion end | 3084 |
| ridges | 3086 |
| ridges | 3087 |
| grooves | 3088 |
| grooves | 3089 |
| lateral sides | 3090 |
| ridges | 3092 |
| lip membrane | 3094 |
| nasal pillows | 3165 |
| plenum chamber | 3200 |
| plenum chamber lateral end | 3202 |
| chord | 3210 |
| superior point | 3220 |
| inferior point | 3230 |
| positioning and stabilising structure | 3300 |

-continued

| Feature Item | Number |
|---|---|
| nasal headgear strap | 3310 |
| oro-nasal headgear strap | 3320 |
| upper strap | 3322 |
| coupling strap | 3324 |
| strap | 3326 |
| connector | 3328 |
| common connecting element | 3330 |
| buckles | 3360 |
| extendable concertina structure | 3362 |
| vent | 3400 |
| coupling mechanism | 3410 |
| connection port | 3600 |
| elbow | 3610 |
| forehead support | 3700 |
| section | 3955 |
| elements | 3980 |
| slot | 3982 |
| flange | 3096 |
| air circuit | 4170 |
| humidifier | 5000 |
| vent connector | 6000 |
| vent holes | 6010 |
| first end | 6020 |
| second end | 6030 |
| upper arm | 3066-1 |
| lower arm | 3066-2 |
| connector | 3066-3 |
| region | 3066-4 |

The invention claimed is:

1. A patient interface kit to deliver a flow of air at a positive pressure with respect to ambient air pressure to an entrance to a patient's airways including at least the entrance of a patient's nares while the patient is sleeping, to ameliorate sleep disordered breathing, the patient interface comprising:

a nasal cushion forming at least part of a nasal cushion plenum chamber pressurizable to a therapeutic pressure, wherein the nasal cushion comprises a nasal seal-forming structure configured to form a seal with a region of a patient's face surrounding the entrance to the patient's nares, the nasal cushion having a nasal cushion opening;

a mouth cushion forming at least part of a mouth cushion plenum chamber pressurizable to the therapeutic pressure, wherein the mouth cushion comprises a mouth seal-forming structure configured to form a seal with a region of a patient's face surrounding the entrance to a patient's mouth, the mouth cushion having a mouth cushion opening, the mouth cushion including a flexible joint, extending from another opening in the mouth cushion positioned above the mouth cushion opening, to selectively connect the nasal cushion to the mouth cushion; and a positioning and stabilizing structure configured to provide a force to hold the nasal seal-forming structure and/or the mouth seal-forming structure in a therapeutically effective position on a patient's head, the positioning an stabilizing structure including a nasal headgear including upper straps or upper conduits and a mouth headgear including lower straps, the mouth headgear being selectively connected to the nasal headgear, wherein each of the nasal cushion opening and the mouth cushion opening is configured to receive a vent insert with one or more gas washout vents, and in the alternative, a tube connector configured to connect to an air delivery tube, the nasal cushion opening and the mouth cushion opening having the same size, wherein the nasal cushion opening is additionally and alternatively configured to receive a nasal cushion end of the flexible joint, wherein the patient interface kit is configured to allow the patient to select a nasal cushion therapy mode or a combined nasal cushion and mouth cushion therapy mode, the nasal cushion therapy mode including a nasal assembly having the nasal cushion and the nasal headgear and not the mouth cushion or the mouth headgear, the nasal cushion including the vent insert and/or the tube connection received in the nasal cushion opening, the combined nasal cushion and mouth cushion therapy mode including an oro-nasal assembly including the nasal cushion and the mouth cushion being connected by inserting the nasal cushion end of the flexible joint into the nasal cushion opening, the nasal headgear connected to nasal connectors of the nasal cushion, the mouth headgear connected to mouth connectors of the mouth cushion, the mouth headgear being detachably connected to the nasal headgear, the mouth cushion including the vent insert or the tube connector received in the mouth cushion opening.

2. The patient interface kit of claim 1, wherein the nasal headgear includes the upper conduits to deliver flow of breathable gas to the nasal cushion.

3. The patient interface kit of claim 1, wherein, in the nasal cushion therapy mode, the nasal cushion opening includes the vent insert, and wherein in the nasal cushion and mouth cushion therapy mode the mouth cushion opening includes the vent insert.

4. The patient interface kit of claim 1, wherein the nasal headgear includes the upper straps to connect with the nasal cushion.

5. The patient interface kit of claim 1, wherein, in the nasal cushion therapy mode, the nasal cushion opening includes the tube connector, and wherein in the nasal cushion and mouth cushion therapy mode, the mouth cushion opening includes the tube connector.

6. The patient interface kit of claim 1, wherein the nasal cushion includes ports to receive pressurized gas, the nasal cushion including plugs to close the ports, the plugs including connectors to connect to the upper straps.

7. The patient interface kit of claim 1, wherein the tube connector includes at least one vent hole for gas washout.

8. The patient interface kit of claim 1, wherein the flexible joint comprises a concertina section having at least one fold.

9. The patient interface kit of claim 8, wherein the concertina allows the mouth cushion to move relative to the nasal cushion in an axial direction, as well as a curved direction to accommodate the patient's supramenton angle.

10. The patient interface kit of claim 1, wherein the flexible joint and/or the mouth cushion are configured to move towards the patient's supramenton due to a spring bias of the flexible joint and/or introduction of the flow of breathable gas through the mouth cushion and/or the flexible joint.

11. The patient interface kit of claim 1, wherein the flexible joint has a neutral position and a curved position oriented towards the patient's supramenton, and wherein the flexible joint resists movement from the neutral position to a position away from the patient's face.

12. The patient interface kit of claim 1, wherein the nasal cushion end is configured to direct or receive the flow of pressurized breathable gas into or from the nasal plenum chamber in a direction that is substantially parallel to the patient's Frankfurt horizontal.

13. The patient interface kit of claim 1, wherein the flexible joint is attached to the mouth cushion at a position that is above a horizontal medial plane of the mouth cushion.

14. The patient interface kit of claim 1, wherein the nasal cushion includes a pair of upper headgear connectors, the mouth cushion includes a pair of lower headgear connectors, the nasal headgear is configured to connect to the upper headgear connectors, and the mouth headgear is configured to connect to the lower headgear connectors.

15. The patient interface kit of claim 14, wherein each of the lower headgear connectors includes a magnetic connection element.

16. The patient interface kit of claim 1, wherein the lower headgear connectors each include a pair of arms having a wish-bone shape, each of the lower headgear connectors having an upper arm and a lower arm connected to a front face of the mouth cushion, the upper arm being spaced from the lower arm.

17. The patient interface kit of claim 16, wherein the upper arm and the lower arm distribute support forces, respectively, to a mid-zone and a lower zone of the mouth cushion.

18. The patient interface kit of claim 16, wherein each of the pair of arms is flexible and has a U-shape.

19. The patient interface kit of claim 18, wherein the U-shape is similar in size and/or shape to lateral side portions of the mouth cushion.

20. The patient interface kit of claim 16, wherein each of the pair of arms is made of silicone or a material that is more rigid than silicone.

21. The patient interface kit of claim 16, wherein each of the pair of arms is connected to the front face of the mouth cushion made of silicone.

22. The patient interface kit of claim 16, wherein each of the arms is attached to the front face of the mouth cushion at a position that is spaced inwards from a lateral edge of the mouth cushion.

23. The patient interface kit of claim 16, wherein each of the arms is dimensioned and configured to straddle opposite sides of the patient's cheilion, thus applying forces against corners of the patient's mouth when worn by the patient and supported by the positioning and stabilizing structure.

24. The patient interface kit of claim 16, wherein each of the arms is movable or flexible to lie flush against the front face of the mouth cushion.

25. The patient interface kit of claim 16, wherein the arms apply a force to the front face of the mouth cushion due to tension applied to the lower straps coupled to the arms, to anchor the mouth cushion into corners surrounding the patient's mouth.

26. The patient interface kit of claim 1, wherein the mouth cushion and/or the nasal cushion includes a textile sealing surface mounted on a silicone body.

27. The patient interface kit of claim 1, wherein the mouth cushion includes a front face, a sealing lip and a wall connecting the front face and the sealing lip, all made of silicone, wherein the wall and/or the sealing lip at a superior part of the corner-of-mouth portions of the mouth cushion is more rigid than an inferior part of the corner-of-mouth portions of the mouth cushion.

28. The patient interface kit of claim 1, wherein the mouth cushion has a depth configured so as not to extend beyond the nasal cushion and/or the pronasale of the patient's nose.

29. The patient interface kit of claim 1, wherein the mouth seal-forming structure includes an upper lip membrane configured to allow the mouth cushion to expand upwards when the patient's jaw opens.

30. The patient interface kit of claim 29, wherein the upper lip membrane includes a central portion that is curved inwardly towards the mouth cushion plenum chamber.

31. The patient interface kit of claim 30, wherein the upper lip membrane includes a central portion that is substantially linear or curved outwardly away from the mouth cushion plenum chamber.

32. The patient interface kit of claim 1, wherein the mouth seal-forming structure includes a lower lip membrane configured to allow the mouth cushion to expand downwards when the patient's jaw opens.

33. The patient interface kit of claim 1, wherein the mouth cushion is configured to expand due to flow of pressurized gas to hold upper portion and/or lower portion of the mouth cushion outwards from lateral sides of the mouth cushion.

34. The patient interface kit of claim 1, wherein the flexible joint includes an anti-asphyxia valve.

35. The patient interface kit of claim 1, wherein the mouth cushion is made of a first type of material and the nasal cushion is made of a second type of material different from the first type of material.

36. The patient interface kit of claim 1, wherein the mouth cushion includes a sealing surface made of a first type of material and the nasal cushion includes a sealing surface of a second type of material different from the first type of material.

37. The patient interface kit of claim 35, wherein one of the first type of material and the second type of material is silicone and the other one of the first type of material and the second type of material is textile.

38. The patient interface kit of claim 1, further comprising a pair of vent connectors including a plurality of holes, the pair of vent connectors configured to couple the nasal headgear to the nasal connectors of the nasal cushion.

39. A patient interface kit to deliver a flow of air at a positive pressure with respect to ambient air pressure to an entrance to a patient's airways including at least the entrance of a patient's nares while the patient is sleeping, to ameliorate sleep disordered breathing, the patient interface comprising:

a nasal cushion forming at least part of a nasal cushion plenum chamber pressurizable to a therapeutic pressure, wherein the nasal cushion comprises a nasal seal-forming structure configured to form a seal with a region of a patient's face surrounding the entrance to the patient's nares, the nasal cushion having a nasal cushion opening;

a mouth cushion forming at least part of a mouth cushion plenum chamber pressurizable to the therapeutic pressure, wherein the mouth cushion comprises a mouth seal-forming structure configured to form a seal with a region of a patient's face surrounding the entrance to a patient's mouth, the mouth cushion having a mouth cushion opening, the mouth cushion including a flexible joint, extending from another opening in the mouth cushion positioned above the mouth cushion opening, to selectively connect the nasal cushion to the mouth cushion; and a positioning and stabilizing structure configured to provide a force to hold the nasal seal-forming structure and/or the mouth seal-forming structure in a therapeutically effective position on a patient's head, the positioning an stabilizing structure including a nasal headgear including upper conduits and a mouth headgear including lower straps, the mouth headgear being selectively connected to the nasal headgear, wherein each of the nasal cushion opening and the mouth cushion opening is configured to receive a vent insert with one or more gas washout vents, and in the alternative, a tube connector configured to connect to an air delivery tube, the nasal cushion opening and the mouth cushion opening having the same size, wherein the nasal cushion opening is additionally and alternatively configured to receive a nasal cushion end of the flexible joint, wherein the patient interface kit is configured to allow the patient to select a nasal cushion therapy mode or a combined nasal cushion and mouth cushion therapy mode, the nasal cushion therapy mode including a nasal assembly having the nasal cushion and the upper conduits and not the mouth cushion, the mouth headgear or the tube connector, the nasal cushion including the vent insert received in the nasal cushion opening, the combined nasal cushion and mouth cushion therapy mode including an oro-nasal assembly including the nasal cushion and the mouth cushion being connected by inserting the nasal cushion end of the flexible joint into the nasal cushion opening, the upper conduits being connected to hollow nasal connectors of the nasal cushion, the mouth headgear connected to mouth connectors of the mouth cushion, the mouth headgear being detachably connected to the nasal headgear, the mouth cushion including the vent insert received in the mouth cushion opening.

40. A method of fitting an oro-nasal mask on a patient, the oro-nasal mask configured to deliver a flow of air at a positive pressure with respect to ambient air pressure to the patient's while the patient is sleeping, to ameliorate sleep disordered breathing, the method comprising:

provided a nasal cushion forming at least part of a nasal cushion plenum chamber pressurizable to a therapeutic pressure, wherein the nasal cushion comprises a nasal seal-forming structure configured to form a seal with a region of a patient's face surrounding an entrance to a patient's nares;

providing a mouth cushion forming at least part of a mouth cushion plenum chamber pressurizable to the therapeutic pressure, wherein the mouth cushion comprises a mouth seal-forming structure configured to form a seal with a region of a patient's face surrounding the entrance to a patient's mouth, the mouth cushion having a mouth cushion opening;

connecting the nasal cushion and the mouth cushion with a flexible joint extending from another opening in the mouth cushion positioned above the mouth cushion opening; and holding the nasal seal-forming structure and the mouth seal-forming structure in a therapeutically effective position on a patient's head by:

placing the nasal cushion under the patient's nose and engaging a superior portion of the patient's upper lip, whilst the mouth cushion is connected to the nasal cushion, securing the nasal cushion on the patient's head using upper headgear conduits or straps, adjusting a length and/or position of the upper headgear conduits or straps, positioning an upper membrane of the mouth cushion on an inferior portion of the patient's upper lip, below the nasal cushion, allowing engagement between the mouth cushion and the nasal cushion, securing the mouth cushion on the patient's head using lower headgear straps, adjusting a length and/or position of the lower headgear straps, wherein the adjustment of the upper headgear conduits or straps is substantially independent of adjustment of the lower headgear straps.

* * * * *